US008992936B2

(12) United States Patent
Luft et al.

(10) Patent No.: US 8,992,936 B2
(45) Date of Patent: Mar. 31, 2015

(54) ALTERED OSPA OF *BORRELIA BURGDORFERI*

(71) Applicants: Brookhaven Sciences Associates, LLC, Upton, NY (US); University of Rochester, Rochester, NY (US); Research Foundation of the State University of New York, Stony Brook, NY (US)

(72) Inventors: Benjamin J. Luft, Riverhead, NY (US); John J. Dunn, Bellport, NY (US); Shohei Koide, Chicago, IL (US); Catherine L. Lawson, Piscataway, NJ (US)

(73) Assignees: Research Foundation of the State University of New York, Stony Brook, NY (US); Brookhaven Sciences Associates, LLC, Upton, NY (US); University of Rochester, Rochester, NY (US)

( * ) Notice: Subject to any disclaimer, the term of this patent is extended or adjusted under 35 U.S.C. 154(b) by 0 days.

(21) Appl. No.: 13/944,078

(22) Filed: Jul. 17, 2013

(65) Prior Publication Data

US 2014/0030285 A1 Jan. 30, 2014

Related U.S. Application Data

(60) Division of application No. 12/313,443, filed on Nov. 19, 2008, which is a continuation of application No. 10/369,339, filed on Feb. 18, 2003, now abandoned, which is a continuation of application No. PCT/US01/25852, filed on Aug. 17, 2001.

(60) Provisional application No. 60/226,484, filed on Aug. 18, 2000.

(51) Int. Cl.
*C07K 14/20* (2006.01)
*A61K 39/02* (2006.01)
*A61K 38/00* (2006.01)

(52) U.S. Cl.
USPC ......................... 424/190.1; 530/806; 530/350

(58) Field of Classification Search
CPC ... A61K 39/0225; A61K 38/164; C07K 14/20
See application file for complete search history.

(56) References Cited

U.S. PATENT DOCUMENTS

| | | | |
|---|---|---|---|
| 5,217,872 | A | 6/1993 | Dorward et al. |
| 5,470,712 | A | 11/1995 | Simpson et al. |
| 5,523,089 | A | 6/1996 | Bergstrom et al. |
| 5,571,718 | A | 11/1996 | Dunn et al. |
| 5,620,862 | A | 4/1997 | Padula |
| 5,688,512 | A | 11/1997 | Bergstrom et al. |
| 5,747,294 | A | 5/1998 | Flavell et al. |
| 5,777,095 | A | 7/1998 | Barbour et al. |
| 5,780,041 | A | 7/1998 | Simpson et al. |
| 6,113,914 | A | 9/2000 | Lobet et al. |
| 6,197,301 | B1 | 3/2001 | Flavell et al. |
| 6,210,676 | B1 | 4/2001 | Callister et al. |
| 6,248,562 | B1 | 6/2001 | Dunn et al. |
| 8,680,236 | B2 | 3/2014 | Luft et al. |
| 2004/0023325 | A1 | 2/2004 | Luft et al. |
| 2004/0033236 | A1 | 2/2004 | Dattwyler et al. |

FOREIGN PATENT DOCUMENTS

| | | |
|---|---|---|
| EP | 0 418 827 A1 | 3/1991 |
| EP | 0 465 204 A2 | 1/1992 |
| EP | 0 492 964 A2 | 7/1992 |
| EP | 0 522 560 A2 | 1/1993 |
| EP | 0 540 457 A1 | 5/1993 |
| EP | 0 643 974 B1 | 3/1995 |
| EP | 0 711 563 A1 | 5/1996 |
| EP | 0598 816 B1 | 6/1999 |
| EP | 1 016 416 A2 | 7/2000 |
| EP | 1 311 540 B1 | 5/2003 |
| WO | WO 90/04411 | 5/1990 |
| WO | WO 91/09870 | 7/1991 |
| WO | WO 91/13630 | 9/1991 |
| WO | WO 92/00055 | 1/1992 |
| WO | WO 93/04175 | 3/1993 |
| WO | WO 93/08286 | 4/1993 |
| WO | WO 93/08299 | 4/1993 |
| WO | WO 93/10237 | 5/1993 |
| WO | WO 94/19697 | 9/1994 |

(Continued)

OTHER PUBLICATIONS

Wallich, R. et al., "DNA Vaccines Expressing a Fusion Product of Outer Surface Proteins A and C from *Borrelia burgdorferi* Induce Protective Antibodies Suitable for Prophylaxis but Not for Resolution of Lyme Disease," Infect. Immun., 69(4):2130-2136 (Apr. 2001).

Kalish, R.S., et al., "Lyme Disease: Human T-cell Response to OspA and OspC *Borrelia* Lipoproteins Includes Both CD8+ and CD4+ T-Cells," J. Invest. Dermatol., 114(4):836 Abstract 523 (2000) (month not available).

Luft, B.J., et al., "A New Multi-Target OspA-OspC Vaccine for Lyme Disease," Abstracts of the Interscience Conference on Antimicrobial Agents and Chemotherapy, 40:248 Abstract 1932 (Sep. 2000).

Gomes-Solecki, M.J.C., et al., "Recombinant Chimeric *Borrelia* Proteins for Diagnosis of Lyme Disease," J. Clin. Microbiol., 38(7):2530-2535 (Jul. 2000).

Bakken, L.L., et al., "Interlaboratory Comparison of Test Results for Detection of Lyme Disease by 516 Participants in the Wisconsin State Laboratory of Hygiene/College of American Pathologists Proficiency Testing Program," J. Clin. Microbiol., 35(3):537-543 (Mar. 1997).

(Continued)

*Primary Examiner* — Maria Marvich
(74) *Attorney, Agent, or Firm* — Hamilton Brook Smith & Reynolds, PC

(57) ABSTRACT

Provided herein are OspA polypeptides from Lyme Disease-causing *Borrelia* having certain alteration(s). In one embodiment, the alteration(s) increase the conformational stability of the OspA polypeptide containing the alteration(s) while maintaining at least some of the antigenicity of the corresponding unaltered OspA polypeptide. In another embodiment, the altered OspA polypeptide has reduced cross-reactivity to hLFA-1, as compared to the corresponding unaltered OspA polypeptide.

6 Claims, 138 Drawing Sheets

(56) References Cited

FOREIGN PATENT DOCUMENTS

| | | |
|---|---|---|
| WO | WO 94/20536 | 9/1994 |
| WO | WO 94/25596 | 11/1994 |
| WO | WO 95/12676 | 5/1995 |
| WO | WO 96/40290 | 12/1996 |
| WO | WO 96/49718 | 12/1996 |
| WO | WO 97/42221 | 11/1997 |
| WO | WO 98/00549 | 1/1998 |
| WO | WO 99/14345 | 3/1999 |
| WO | WO 00/06745 | 2/2000 |
| WO | WO02/16421 | 2/2002 |

OTHER PUBLICATIONS

Balmelli, T., et al., "Association Between Different Clinical Manifestations of Lyme Disease and of *Borrelia burgdorferi* Sensu Lato," Res. Microbiol. 146:329-340 (1995).

Chang, Y-F., et al., "Expression and Secretion of Outer Surface Protein (OSP-A) of *Borrelia burgdorferi* From *Escherichia coli*," FEMS Microbiol. Lett. 109:297-301 (Mar. 1993).

De, B.K., et al., "Purification and Characterization of *Streptococcus pneumoniae* Palmitoylated Pneumococcal Surface Adhesion A Expressed in *Escherichia coli*," Vaccine, 18:1811-1821 (2000) (month not available).

de Silva, A.M., et al., "*Borrelia burgdorferi* OspA is an Arthropod-Specific Transmission-Blocking Lyme Disease Vaccine," J. Exp. Med. 183(1):271-275 (Jan. 1996).

de Silva, A.M. and E. Fikrig, "Arthopod- and Host-Specific Gene Expression by *Borrelia burgdorferi*," J. Clin. Invest. 99(3):377-379 (Feb. 1997).

Fingerle, V., et al., "Expression of Outer Surface Proteins A and C of *Borrelia burgdorferi* in *Ixodes ricinus* Ticks Removed from Humans," Med. Microbiol. Immunol. 187(2):121-126 (Jul. 1998).

Dykhuizen, D.E., et al., "*Borrelia burgdorferi* is Clonal: Implications for Taxonomy and Vaccine Development," Proc. Natl. Acad. Sci. USA 90:10163-10167 (Jul. 1993).

Eiffert, H., et al., "Nucleotide Sequence of the ospAB Operon of a *Borrelia burgdorferi* Strain Expressing OspA but not OspB," Infection and Immunity, 60(5): 1864-1868 (May 1992).

Gilmore, R.D., Jr., et al., "Outer Surface Protein C (OspC), but Not P39, Is a Protective Immunogen Against a Tick-Transmitted *Borrelia burgdorferi* Challenge: Evidence for a Conformational Protective Epitope in OspC," Infect. Immun. (64)6:2234-2239 (Jun. 1996).

Guo, H.H., et al., Protein Tolerance to Random Amino Acid Change, PNAS, 101(25):9205-9210 (2004).

Lesk, A.M., et al., "Prediction of Protein Function from Protein Sequence and Structure," p. 27 and 28, downloaded Sep. 16, 2007.

Montgomery, R.R., et al., "Direct Demonstration of Antigenic Substitution of *Borrelia burgdorferi* Ex Vivo: Exploration of the Paradox of the Early Immune Response to Outer Surface Proteins A and C in Lyme Disease," J. Exp. Med. 183 (1):261-269 (Jan. 1996).

Probert, W.S. and R.B. LeFebvre, "Protection of C3H/HeN Mice from Challenge with *Borrelia burgdorferi* through Active Immunization with OspA, OspB, or OspC, but Not OspD or the 83-Kilodalton Antigen," Infect. Immun. 62(5):1920-1926 (Mar. 1994).

Probert, W.S., et al., "Immunization with Outer Surface Protein (Osp) A, but Not OspC, Provides Cross-Protection of Mice Challenged with North American Isolates of *Borrelia burgdorferi*," J. Infect. Dis. 175(2):400-405 (1997) (month not available).

Schwan, T.G., et al., "Induction of an Outer Surface Protein on *Borrelia burgdorferi* During Tick Feeding," Proc. Natl. Acad. Sci. USA 92:2909-2913 (Mar. 1995).

Simon, M.M., et al., "Protective Immunization with Plasmid DNA Containing the Outer Surface Lipoprotein A Gene of *Borrelia burgdorferi* is Independent of an Eukaryotic Promoter," Eur. J. Immunol. 26(12):2831-2840 (Aug. 1996).

Simon, M.M., et al., "Lyme Disease: Pathogenesis and Vaccine Development," Zent.bl. Bakteriol. 289:690-695 (1999) (month not available).

Solé, M., et al., "*Borrelia burgdorferi* Escape Mutants That Survive in the Presence of Antiserum to the OspA Vaccine Are Killed When Complement is Also Present," Infect. Immun. 66(6):2540-2546 (Jun. 1998).

Steigbigel, R.T. and J.L. Benach, "Immunization Against Lyme Disease—An Important First Step," N. Engl. J. Med. 339(4):263-264 (Jul. 1998).

Stover, C.K., et al., "Protective Immunity Elicited by rBCG Vaccines," Dev. Biol. Stand. 82:163-170 (1994) (month not available).

Thanassi, W.T. and R.T. Schoen, "The Lyme Disease Vaccine: Conception, Development, and Implementation," Ann. Intern. Med. 132:661-668 (2000) (month not available).

Wahlberg, P., "Vaccination Against Lyme borreliosis," Ann. Med. 31:233-235 (1999) (month not available).

Wang, I-N., et al., "Genetic Diversity of ospC in a Local Population of *Borrelia burgdorferi* sensu stricto," Genetics 151:15-30 (Jan. 1999).

Wieneke, C.A., et al., "Evaluation of Whole-Cell and OspC Enzyme-Linked Immunosorbent Assays for Discrimination of Early Lyme Borreliosis from OspA Vaccination," J. Clin. Microbio., 38(1):313-317 (Jan. 2000).

Willett, T.A., et al., An Effective Second-Generation Outer Surface Protein A-Derived Lyme Vaccine That Eliminates a Potentially Autoreactive T Cell Epitope, PNAS, 101(5): 1303-1308 (Feb. 2004).

Wilske, B., et al., "Diversity of OspA and OspC among Cerebrospinal Fluid Isolates of *Borrelia burgdorferi* sensu lato from Patients with Neuroborreliosis in Germany," Med. Microbiol. Immunol. 184:195-201 (1996) (month not available).

Wilske, B., et al., "Immunological and Molecular Variability of OspA and OspC. Implications for *Borrelia* Vaccine Development," Infection 24(2):208-212 (1996) (month not available).

Wilske, B., at al, "Immunological and Molecular Polymomhisms of OspC, an Immunodominant Major Outer Surface Protein of *Borrelia burgdorferi*," Infect. Immun. 61(5):2182-2191 (May 1993).

Zhong, W. et al., "Therapeutic Passive Vaccination Against Chronic Lyme Disease in Mice," Proc. Natl. Acad. Sci. USA 94:12533-12538 (Nov. 1997).

Zhong, W. et al., "Resolution of Experimental and Tick-borne *Borrelia burgdorferi* Infection in Mice by Passive, But Not Active Immunization Using Recombinant OspC," Eur. J. Immunol. 29:946-957 (1999) (month not available).

Fikrig, E., et al., "Selection of Variant *Borrelia burgdorferi* Isolates From Mice Immunized With Outer Surface Protein A or B," Infect. Immun., 63(5):1658-1662 (May 1995).

Sellati, T.J., et al., "Outer Surface Lipoproteins of *Borrelia burgdorferi* Activate Vascular Endothelium in Vitro," Infect. Immun. 64(8):3180-3187 (Aug. 1996).

Zhang, Y-Q., et al., "*Borrelia burgdorferi* Enzyme-Linked Immunosorbent Assay for Discrimination of OspA Vaccination from Spirochete Infection," J. Clin. Microbiol., 35(1):233-238 (Jan. 1997).

Bunikis, J., et al., "Access of Antibody or Trypsin to an Integral Outer Membrane Protein (P66) of *Borrelia burgdorferi* is Hindered by Osp Lipoproteins," Infect. Immun., 67(6):2874-2883 (Jun. 1999).

Hughes, C.A.N., et al., "Protective Immunity is Induced by a *Borrelia burgdorferi* Mutant That Lacks OspA and OspB," Infect. Immun. 61(12):5115-5122 (Dec. 1993).

Wallich, R., et al., "A Recombinant Vaccine for Lyme Disease," Behring Inst. Mitt., 95:106-108 (1994) (month not available).

Rosa, P.A., et al., "Recombination Between Genes Encoding Major Outer Surface Proteins A and B of *Borrelia burgdorferi*," Mol. Microbiol., 6(20):3031-3040 (Jul. 1992).

Stover, C.K., et al., "Protective Immunity Elicited by Recombinant Bacille Calmette-Guerin (BCG) Expressing Outer Surface Protein A (OspA) Lipoprotein: A Candidate Lyme Disease Vaccine," J. Exp. Med., 178:197-209 (Jul. 1993).

Schwan, T.G., et al., "Distribution and Molecular Analysis of Lyme Disease Spirochetes, *Borrelia burgdorferi*, Isolated From Ticks Throughout California," J. Clin. Microbiol., 31(12):3096-3108 (Dec. 1993).

Hu, C.M., et al., "Comparison in the Immunological Properties of *Borrelia burgdorferi* Isolates from Ixodes Ricinus Derived From Three Endemic Areas in Switzerland," Epidemiol. Infect., 112:533-542 (Jan. 1994).

(56) References Cited

OTHER PUBLICATIONS

Schubach, W.H., et al., "Mapping Antibody-Binding Domains of the Major Outer Surface Membrane Protein (OspA) of *Borrelia burgdorferi*," Infect. Immun. 59(6):1911-1915 (Jun. 1991).
Kitten, T., et al., "Intragenic Recombination and a Chimeric Outer Membrane Protein in the Relapsing Fever Agent *Borrelia hermsii*", J. Bacteriol., 175(9):2516-2522 (May 1993).
McGrath, B.C., et al., "Biochemical and Biophysical Characterization of the Major Outer Surface Protein from North American and European Isolates of *Borrelia burgdorferi*", Vaccines 93:365-370 (1993) (month not available).
France, L.L., et al., "Evidence for an ÿ-Helical Epitope on Outer Surface Protein A From the Lyme Disease Spirochete, *Borrelia burgdorferi*: An Application of Steady-State and Time-Resolved Fluorescence Quenching Techniques," Biochim. Biophys. Acta., 1202:287-296 (May 1993).
Kantor, F.S., "Disarming Lyme Disease," Sci. Am. 271(3):34-39 (Sep. 1994).
McGrath, B.C., et al., "Identification of an Immunologically Important Hypervariable Domain of Major Outer Surface Protein A of *Borrelia burgdorferi*," Infect. Immun., 63(4):1356-1361 (Apr. 1995).
Wilske, B., et al., "An OspA Serotyping System for *Borrelia burgdorferi* Based on Reactivity With Monoclonal Antibodies and OspA Sequence Analysis," J. Clin. Microbiol., 31(2):340-350 (Feb. 1993).
Marconi, R.T., et al., "Variability of osp Genes and Gene Products Among Species of Lyme Disease Spirochetes," Infect. Immun., 61(6):2611-2617 (Jun. 1993).
Fikrig, E., et al., "*Borrelia burgdorferi* Strain 25015: Characterization of Outer Surface Protein A and Vaccination Against Infection," J. Immunol. 148(7):2256-2260 (1992) (month not available).
Schaible, U., et al., "Immune Sera to Individual *Borrelia burgdorferi* Isolates or Recombinant OspA Thereof Protect SCID Mice Against Infection With Homologous Strains but Only Partially or Not at All Against Those of Different OspA/OspB Genotype," Vaccine 11(10):1049-1054 (1993) (month not available).
Masuzawa, T., et al., "Protective Activity of Antisera Against Isolates of *Borrelia burgdorferi* From Various Geographical Origins," Microbiol. Immunol., 37(1):79-83 (1993) (month not available).
Wallich, R., et al., "Evaluation of Genetic Divergence Among *Borrelia burgdorferi* Isolates by Use of OspA, fla, HSP60, and HSP70 Gene Probes," Infect. Immun., 60(11):4856-4866 (Nov. 1992).
Simon, M.M., et al., "A Mouse Model for *Borrelia burgdorferi* Infection: Approach to a Vaccine Against Lyme Disease," Immunol. Today, 12(1):11-16 (1991) (month not available).
Schaible, U.E., et al., "Monoclonal Antibodies Specific for the Outer Surface Protein A (OspA) of *Borrelia burgdorferi* Prevent Lyme Borreliosis in Severe combined Immunodeficiency, (scid) Mice," Proc. Natl. Acad. Sci. USA, 87:3768-3772 (May 1990).
Preac-Mursic, V., et al., "Active Immunization With pC Protein of *Borrelia burgdorferi* Protects Gerbils Against *B. burgdorferi* Infection," Infection, 20(6):342-349 (Oct. 1992).
Simon, M., et al., "Spirochetes: Vaccines, Animal Models and Diagnostics," Res. Microbiol., 143:641-647 (1992) (month not available).
Simon, M.M., et al., "Recombinant Outer Surface Protein A from *Borrelia burgdorferi* Induces Antibodies Protective against Spirochetal Infection in Mice," J. Infect. Dis., 164:123-132 (Feb. 1991).
Howe, T.R., et al., "A Single Recombinant Plasmid Expressing Two Major Outer Surface Proteins of the Lyme Disease Spirochete," Science, 227:645-46 (Feb. 1985).
Johnson, R.C., et al., "Experimental Infection of the Hamster with *Borrelia burgdorferi*," Ann. N.Y. Acad. Sci., 539:258-263 (1988) (month not available).
France, L.L., et al., "Structural Analysis of an Outer Surface Protein From the Lyme Disease Spirochete, *Borrelia burgdorferi*, Using Circular Dichroism and Fluorescence Spectroscopy," Biochim. Biophys. Acta, 1120:59-68 (1992) (month not available).
Howe, T.R., et al., "Organization of Genes Encoding Two Outer Membrane Proteins of the Lyme Disease Agent *Borrelia burgdorferi* within a Single Transcriptional Unit," Infect. Immun , 54(1):207-212 (Oct. 1986).
Johnson, R.C., et al., "Vaccination of Hamsters Against Experimental Infection with *Borrelia burgdorferi*," Zbl. Bakt. Hyg. A, 263:45-48 (1986) (month not available).
Johnson, R.C., et al., "Passive Immunization of Hamsters Against Experimental Infection with the Lyme Disease Spirochete," Infect. and Immun., 53(3):713-714 (Sep. 1986).
Johnson, R.C., et al., "Active Immunization of Hamsters Against Experimental Infection with *Borrelia burgdorferi*," Infect. Immun , 54(3):897-898 (Dec. 1986).
Fikrig, E., et al., "Elimination of *Borrelia burgdorferi* from Vector Ticks Feeding on OspA-Immunized Mice," Proc. Natl. Acad. Sci. USA, 89:5418-5421 (Jun. 1992).
Fikrig, E., et al., "Long-Term Protection of Mice From Lyme Disease by Vaccination with OspA," Infect. Immun., 60(3):773-777 (Mar. 1992).
Fikrig, E., et al., "Protection of Mice Against the Lyme Disease Agent by Immunizing with Recombinant OspA," Science, 250:553-556 (Oct. 1990).
Erdile, L. F. et al., "Role of Attached Lipid in Immunogenicity of *Borrelia burgdorferi* OspA," Infect. Immun., 61(1):81-90 (Jan. 1993).
Bockenstedt, L.K., et al., "Inability of Truncated Recombinant Osp A Proteins to Elicit Protective Immunity to *Borrelia burgdorferi* in Mice," J. Immun., 151(2):900-906 (Jul. 1993).
Lovrich, S.D., et al., "Seroprotective Groups Among Isolates of *Borrelia burgdorferi*," Infect. Immun., 61(10):4367-4374 (Oct. 1993).
Wilske, B., et al., "Molecular Analysis of the Outer Surface Protein A (OspA) of *Borrelia burgdorferi* for Conserved and Variable Antibody Binding Domains," Med. Microbiol. Immunol., 181:191-207 (May 1992).
Sears, J.E., et al., "Molecular Mapping of Osp-A Mediated Immunity Against *Borrelia burgdorferi*, The Agent of Lyme Disease," J. Immunol., 147(6):1995-2000 (Sep. 1991).
Lovrich, S.D., et al., "Seroprotective Groups of Lyme Borreliosis Spirochetes from North America and Europe," J. Infect. Dis. 170:115-121 (Feb. 1994).
Gern, L., et al., "Immunization With a Polyvalent OspA Vaccine Protects Mice Against *Ixodes ricinus* Tick Bites Infected by *Borrelia burgdorferi* ss, *Borrelia garinii* and *Borrelia afzelli*," Vaccine 15(14):1551-1557 (Mar. 1997).
Golde, W.T., et al., "The Lyme Disease Vaccine Candidate Outer Surface Protein A (OspA) in a Formulation Compatible With Human Use Protects Mice Against Natural Tick Transmission of *B. burgdorferi*," Vaccine 13(5):435-441 (1995) (month not available).
Masuzawa, T., et al., "Negative Finding in Cross-Protective Activity of Japanese *Borrelia* Isolates Against Infection with Three Species of Lyme Disease *Borrelia* in Outbred Mice," Microbiol. Immunol., 41(9):733-736 (Jun. 1997).
Bowie, J.U., et al., "Deciphering the Message in Protein Sequences: Tolerance to Amino acid Substitutions," Science, 247:1306-1310 (Mar. 1990).
Li, H., et al., "Crystal Structure of Lyme Disease Antigen Outer Surface Protein A Complexed With an Fab," Proc. Natl. Acad. Sci. USA, 94:3584-3589 (Apr. 1997).
Gross, D.M., et al., "Identification of LFA-1 as a Candidate Autoantigen in Treatment-Resistant Lyme Arthritis," Science, 281:703-706 (Jul. 1998).
Kumaran, D., et al., "Crystal Structure of Outer Surface Protein C (OspC) From the Lyme Disease Spirochete, *Borrelia burgdorferi*," EMBO J., 20(5):971-978 (2001) (month not available).
Golde, W.T., et al., "T Cell Antigen Reactivity to Recombinant OspA and the Homologous Self Peptide of LFA-1 in Patients with Lyme Disease," FASEB J., 14(6):A950 (Apr. 2000).
Malawista, S.E., et al., "Geographic Clustering of an Outer Surface Protein A Mutant of *Borrelia burgdorferi*. Possible Implications of Multiple Variants for Lyme Disease Persistence," Rheumatology 39(5):537-541 (May 2000).

(56) References Cited

OTHER PUBLICATIONS

Huang, X., et al., "Formation of the Single-Layer ÿ-Sheet of *Borrelia burgdorferi* OspA in the Absence of the C-Terminal Capping Globular Domain," J. Mol. Biol. 308:367-375 (2001) (month not available).

Koide, S., et al., "Design of Single-Layer ÿ-Sheets without a Hydrophobic Core," Nature 403(6768):456-460 (Jan. 2000).

Barbour, A.G., et al., "Lyme Disease Spirochetes and Ixodid Tick Spirochetes Share a Common Surface Antigenic Determinant Defined by a Monoclonal Antibody," Infect. Immun. 41(2):795-804 (Aug. 1983).

Koide, S., et al., "Structure-Based Design of a Second-Generation Lyme Disease Vaccine Based on a C-Terminal Fragment of *Borrelia burgdorferi* OspA," J. Mol. Biol., 350:290-299 (Jul. 2005).

Purcell, A.W., et al., "Dissecting the Role of Peptides in the Immune Response: Theory, Practice and the Application to Vaccine Design," *J. Pept. Sci.* 9(5): 255-281 (2003) (month not available).

Ding, W., et al., "Structural Identification of a Key Protective B-Cell Epitope in Lyme Disease Antigen OspA," *J. Mol. Biol.* 302(5): 1153-1164 (2000) (month not available).

Richards, F.M., "Protein Stability: Still an Unsolved Problem," *Cell. Mol. Life Sci.* 53(10):790-802 (1997) (month not available).

Domain 1

| | 34 | 35 | 36 | 37 | 38 | 39 | 40 | 41 | |
|---|---|---|---|---|---|---|---|---|---|
| A-B31 | L | P | G | E | M | K | V | L | SEQ ID NO:131 |
| A-TRo | L | P | G | E | M | K | V | L | SEQ ID NO:132 |
| A-K48 | L | P | G | G | M | T | V | L | SEQ ID NO:133 |
| A-DK29 | L | P | G | G | M | T | V | L | SEQ ID NO:134 |
| A-P/Gau | L | P | G | E | M | K | V | L | SEQ ID NO:135 |
| A-PKo | L | P | G | E | M | K | V | L | SEQ ID NO:136 |
| A-IP3 | L | P | G | E | I | K | V | L | SEQ ID NO:137 |
| A-IP90 | L | P | G | G | M | G | V | L | SEQ ID NO:138 |
| A-25015 | L | P | G | E | M | K | V | L | SEQ ID NO:139 |

FIG. 2A

Domain 2

| | 65 | 66 | 67 | 68 | 69 | 70 | 71 | 72 | 73 | 74 | 75 | |
|---|---|---|---|---|---|---|---|---|---|---|---|---|
| A-B31 | G | T | S | D | K | N | N | G | S | G | V | SEQ ID NO:140 |
| A-TRo | G | T | S | D | K | S | N | G | S | G | T | SEQ ID NO:141 |
| A-K48 | G | T | S | D | K | N | N | G | S | G | T | SEQ ID NO:142 |
| A-DK29 | G | T | S | D | K | N | N | G | S | G | T | SEQ ID NO:143 |
| A-P/Gau | G | T | S | D | K | D | N | G | S | G | T | SEQ ID NO:144 |
| A-PKo | G | T | S | D | K | D | N | G | S | G | T | SEQ ID NO:145 |
| A-IP3 | G | T | S | D | K | D | N | G | S | G | V | SEQ ID NO:146 |
| A-IP90 | G | T | S | D | K | N | N | G | S | G | T | SEQ ID NO:147 |
| A-25015 | G | T | S | D | K | N | N | G | S | G | V | SEQ ID NO:148 |

FIG. 2B

Domain 3

| | 190 200 210 220 | |
|---|---|---|
| A-B31 | NISKSGEVSVELNDTDSSAATKKTAAWNSGT | SEQ ID NO:149 |
| A-TRo | HIPNSGEITVELNDSNSTQATKKTGKWDSNT | SEQ ID NO:150 |
| A-K48 | NILKSGEITVALDDSDTTQATKKTGKWDSKT | SEQ ID NO:151 |
| A-DK29 | NILKSGEITAALDDSDTTRATKKTGKWDSKT | SEQ ID NO:152 |
| A-P/Gau | EIAKSGEVTVALNDTNTTQATKKTGAWDSKT | SEQ ID NO:153 |
| A-PKo | EIAKSGEVTVALNDTNTTQATKKTGAWDSKT | SEQ ID NO:154 |
| A-IP3 | EIAKSGEVTVALNDTNTTQATKKTGAWDSKT | SEQ ID NO:155 |
| A-IP90 | HISNSGEITVELNDSDTTQATKKTGTWDSKT | SEQ ID NO:156 |
| A-25015 | HISKSGEVTAELNDTDSTQATKKTGKWDAGT | SEQ ID NO:157 |

FIG. 2C

Domain 4

| | 250 260 270 | |
|---|---|---|
| A-B31 | SNGTKLEGSAVEITKLDEIKN | SEQ ID NO:158 |
| A-TRo | SAGTNLEGNAVEIKTLDELKN | SEQ ID NO:159 |
| A-K48 | SAGTNLEGKAVEITTLKELKN | SEQ ID NO:160 |
| A-DK29 | SAGTNLEGKAVEITTLKELKN | SEQ ID NO:161 |
| A-P/Gau | SAGTNLEGTAVEIKTLDELKN | SEQ ID NO:162 |
| A-PKo | SAGTNLEGTAVEIKTLDELKN | SEQ ID NO:163 |
| A-IP3 | SAGTNLEGTAVEIKTLDELKN | SEQ ID NO:164 |
| A-IP90 | SAGTNLEGKAVEITTLKELKN | SEQ ID NO:165 |
| A-25015 | SAGTNLEGTAVEIKTLDEIKN | SEQ ID NO:166 |

FIG. 2D

Protein sequence of OspAs from B31, K48 and site-directed mutants from amino acids 200-220

↓

| | | |
|---|---|---|
| B31: | ELNDTDSSAATKKTAAWNSGT | (SEQ ID NO:167) |
| K48: | ALDDSDTTQATKKTGKWDSKT | (SEQ ID NO:168) |
| 613: | ELNDSDTSAATKKTAAWNSGT | (SEQ ID NO:169) |
| 625: | ELNDTDSSAATKKTGKWNSGT | (SEQ ID NO:170) |
| 640: | ELNDTDSSAATKKTAAWDSKT | (SEQ ID NO:171) |
| 613/625: | ELNDSDTSAATKKTGKWNSGT | (SEQ ID NO:172) |
| 613/640: | ELNDSDTSAATKKTAAWDSKT | (SEQ ID NO:173) |

FIG. 4

```
        10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

     150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

           250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 6A

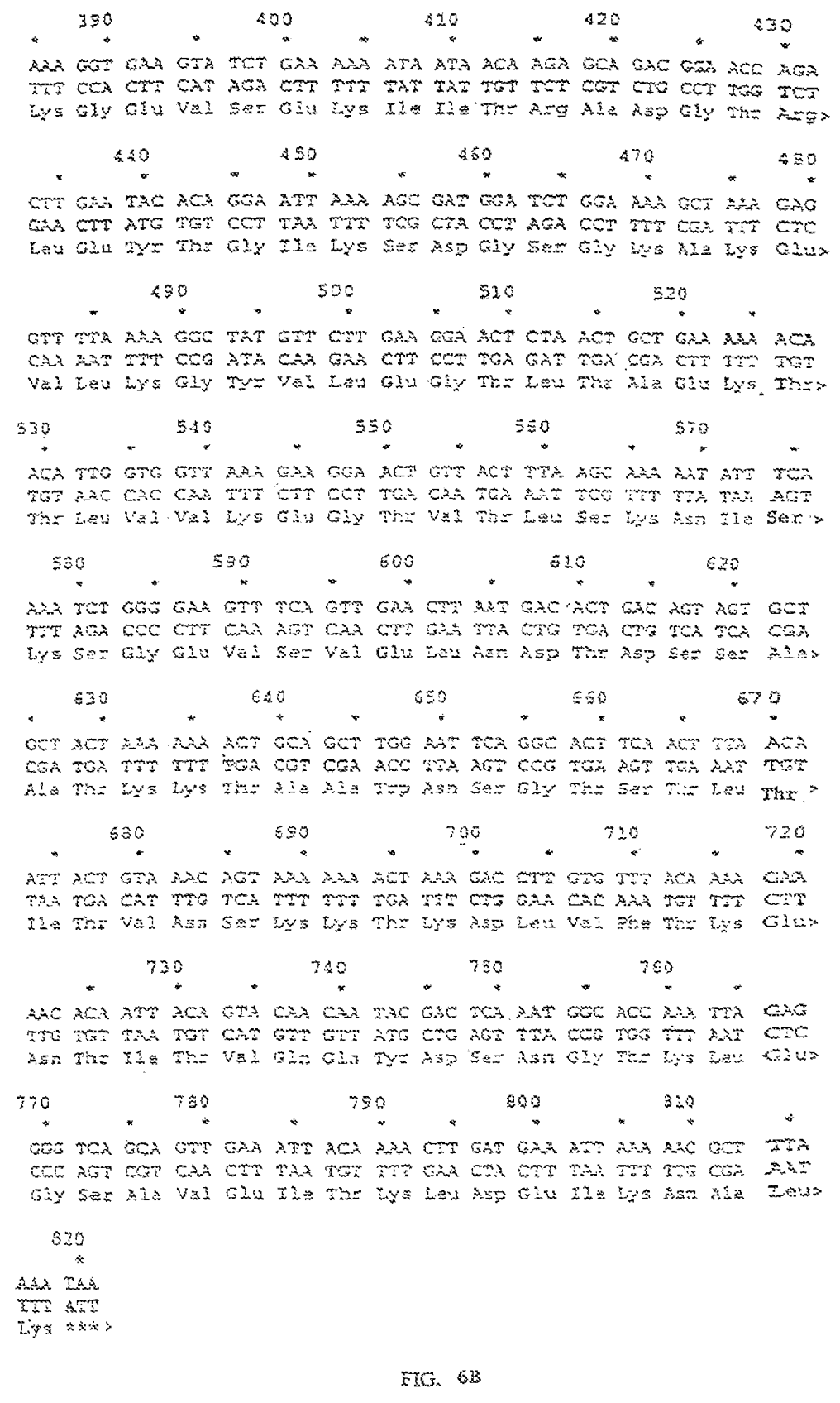

```
      390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

      680         690         700         710         720
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

        730         740         750         760
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

  820
AAA TAA
TTT ATT
Lys ***>
```

FIG. 6B

ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CG'
Met Lys Lys Tyr Leu Leu Gly Ile Gly Leu Ile Leu Ala Leu Ile Ala>

50 60 70 80 90
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

100 110 120 130 140
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

150 160 170 180 190
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

200 210 220 230 240
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

250 260 270 280
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290 300 310 320 330
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

340 350 360 370 380
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>

FIG. 7A

```
     390          400          410          420          430
*     *      *      *      *      *      *      *      *      *
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

        440          450          460          470          480
   *      *      *      *      *      *      *      *      *      *
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

          490          500          510          520
      *      *      *      *      *      *      *      *      *
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530          540          550          560          570
 *      *      *      *      *      *      *      *      *      *
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

  580          590          600          610          620
    *      *      *      *      *      *      *      *      *
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

     630          640          650          660          670
*     *      *      *      *      *      *      *      *      *
CAG GCT ACT AAA AAA ACT GGA AAA TGG GAT TCA AAA ACT TCC ACT TTA
GTC CGA TGA TTT TTT TGA CCT TTT ACC CTA AGT TTT TGA AGG TGA AAT
Gln Ala Thr Lys Lys Thr Gly Lys Trp Asp Ser Lys Thr Ser Thr Leu>

        680          690          700          710          720
   *      *      *      *      *      *      *      *      *      *
ACA ATT AGT GTG AAT AGC CAA AAA ACC AAA AAC CTT GTA TTC ACA AAA
TGT TAA TCA CAC TTA TCG GTT TTT TGG TTT TTG GAA CAT AAG TGT TTT
Thr Ile Ser Val Asn Ser Gln Lys Thr Lys Asn Leu Val Phe Thr Lys>

          730          740          750          760
      *      *      *      *      *      *      *      *      *
GAA GAC ACA ATA ACA GTA CAA AAA TAC GAC TCA GCA GGC ACC AAT CTA
CTT CTG TGT TAT TGT CAT GTT TTT ATG CTG AGT CGT CCG TGG TTA GAT
Glu Asp Thr Ile Thr Val Gln Lys Tyr Asp Ser Ala Gly Thr Asn Leu>
```

FIG. 7B

```
770          780          790          800          810
 *      *      *      *      *      *      *      *      *      *
GAA GGC AAA GCA GTC GAA ATT ACA ACA CTT AAA GAA CTT AAA AAC GCT
CTT CCG TTT CGT CAG CTT TAA TGT TGT GAA TTT CTT GAA TTT TTG CGA
Glu Gly Lys Ala Val Glu Ile Thr Thr Leu Lys Glu Leu Lys Asn Ala>
```

```
  820
   *      *
TTA AAA TAA
AAT TTT ATT
Leu Lys ***>
```

FIG. 7C 10 20 30 40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50 60 70 80 90
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

100 110 120 130 140
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

150 160 170 180 190
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

200 210 220 230 240
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

250 260 270 280
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290 300 310 320 330
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

340 350 360 370 380
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>

FIG. 8A 390 400 410 420 430
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

440 450 460 470 480
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

490 500 510 520
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

530 540 550 560 570
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

580 590 600 610 620
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

630 640 650 660 670
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

680 690 700 710 720
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

730 740 750 760
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>

FIG. 8B

```
770         780         790         800         810
 *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

  820
   *
AAA TAA
TTT ATT
Lys ***>
```

FIG. 8C

```
                 10               20               30               40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

 50              60               70               80               90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

   100              110              120              130              140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

     150              160              170              180              190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200              210              220              230              240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

           250              260              270              280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290              300              310              320              330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

   340              350              360              370              380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 9A

```
     390          400          410          420          430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440          450          460          470          480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

           490          500          510          520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530          540          550          560          570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580          590          600          610          620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630          640          650          660          670
GCT ACT AAA AAA ACT GCA GCT TGG AAT GCA GGC ACT TCA ACT TTA ACA
CGA TGA TTT TTT TGA CGT CGA ACC TTA CGT CCG TGA AGT TGA AAT TGT
Ala Thr Lys Lys Thr Ala Ala Trp Asn Ala Gly Thr Ser Thr Leu Thr>

        680          690          700          710          720
ATT ACT GTA AAC AAC AAA AAA ACT AAA GCC CTT GTA TTT ACA AAA CAA
TAA TGA CAT TTG TTG TTT TTT TGA TTT CGG GAA CAT AAA TGT TTT GTT
Ile Thr Val Asn Asn Lys Lys Thr Lys Ala Leu Val Phe Thr Lys Gln>

           730          740          750          760
GAC ACA ATT ACA TCA CAA AAA TAC GAC TCA GCA GGA ACC AAC TTG GAA
CTG TGT TAA TGT AGT GTT TTT ATG CTG AGT CGT CCT TGG TTG AAC CTT
Asp Thr Ile Thr Ser Gln Lys Tyr Asp Ser Ala Gly Thr Asn Leu Glu>

     OSPA 25015
770          780          790          800          810
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

FIG. 9B

```
          10          20          30          40
     *     *     *     *     *     *     *     *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
 *     *     *     *     *     *     *     *     *     *
TGT AAG CAA AAT GTT AGC AGC CTT GAT GAA AAA-AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

  100         110         120         130         140
   *     *     *     *     *     *     *     *     *
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

    150         160         170         180         190
*     *     *     *     *     *     *     *     *     *
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

       200         210         220         230         240
  *     *     *     *     *     *     *     *     *     *
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

         250         260         270         280
     *     *     *     *     *     *     *     *     *
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290         300         310         320         330
 *     *     *     *     *     *     *     *     *     *
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

  340         350         360         370         380
   *     *     *     *     *     *     *     *     *
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 10A

```
     390            400           410           420            430
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

        440           450           460           470           480
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

           490           500           510           520
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530           540           550           560           570
ACA ACA TTG AAA GTT ACA GAA GGC ACT GTT GTT TTA AGC AAG AAC ATT
TGT TGT AAC TTT CAA TGT CTT CCG TGA CAA CAA AAT TCG TTC TTG TAA
Thr Thr Leu Lys Val Thr Glu Gly Thr Val Val Leu Ser Lys Asn Ile>

   580           590           600           610           620
TTA AAA TCC GGA GAA ATA ACA GTT GCA CTT GAT GAC TCT GAC ACT ACT
AAT TTT AGG CCT CTT TAT TGT CAA CGT GAA CTA CTG AGA CTG TGA TGA
Leu Lys Ser Gly Glu Ile Thr Val Ala Leu Asp Asp Ser Asp Thr Thr>

     630           640           650           660            670
CAG GCT ACT AAA AAA ACT GGA AAA TGG GAT TCA AAA ACT TCT ACT TTA
GTC CGA TGA TTT TTT TGA CCT TTT ACC CTA AGT TTT TGA AGA TGA AAT
Gln Ala Thr Lys Lys Thr Gly Lys Trp Asp Ser Lys Thr Ser Thr Leu>

        680           690           700           710           720
ACA ATT AGT GTT AAC AGC AAA AAA ACT ACA CAA CTT GTG TTT ACT AAA
TGT TAA TCA CAA TTG TCG TTT TTT TGA TGT GTT GAA CAC AAA TGA TTT
Thr Ile Ser Val Asn Ser Lys Lys Thr Thr Gln Leu Val Phe Thr Lys>

           730           740           750           760
CAA TAC ACA ATA ACT GTA AAA CAA TAC GAC TCC GCA GGT ACC AAT TTA
GTT ATG TGT TAT TGA CAT TTT GTT ATG CTG AGG CGT CCA TGG TTA AAT
Gln Tyr Thr Ile Thr Val Lys Gln Tyr Asp Ser Ala Gly Thr Asn Leu>
```

FIG. 10B

```
770        780        790        800        810
 *     *     *     *     *     *     *     *     *     *
GAA GGC ACA GCA GTC GAA ATT AAA ACA CTT GAT GAA CTT AAA AAC GCT
CTT CCG TGT CGT CAG CTT TAA TTT TGT GAA CTA CTT GAA TTT TTG CGA
Glu Gly Thr Ala Val Glu Ile Lys Thr Leu Asp Glu Leu Lys Asn Ala>

  820
   *     *
TTA AAA TAA
AAT TTT ATT
Leu Lys ***>
```

FIG. 10C

```
            10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGC AAG CAA AAT GTT AGC AGC CTT GAT GAA AAA AAC AGC GCT TCA GTA
ACG TTC GTT TTA CAA TCG TCG GAA CTA CTT TTT TTG TCG CGA AGT CAT
Cys Lys Gln Asn Val Ser Ser Leu Asp Glu Lys Asn Ser Ala Ser Val>

  100         110         120         130         140
GAT TTG CCT GGT GAG ATG AAA GTT CTT GTA AGT AAA GAA AAA GAC AAA
CTA AAC GGA CCA CTC TAC TTT CAA GAA CAT TCA TTT CTT TTT CTG TTT
Asp Leu Pro Gly Glu Met Lys Val Leu Val Ser Lys Glu Lys Asp Lys>

    150         160         170         180         190
GAC GGT AAG TAC AGT CTA AAG GCA ACA GTA GAC AAG ATT GAG CTA AAA
CTG CCA TTC ATG TCA GAT TTC CGT TGT CAT CTG TTC TAA CTC GAT TTT
Asp Gly Lys Tyr Ser Leu Lys Ala Thr Val Asp Lys Ile Glu Leu Lys>

        200         210         220         230         240
GGA ACT TCT GAT AAA GAC AAT GGT TCT GGA GTG CTT GAA GGT ACA AAA
CCT TGA AGA CTA TTT CTG TTA CCA AGA CCT CAC GAA CTT CCA TGT TTT
Gly Thr Ser Asp Lys Asp Asn Gly Ser Gly Val Leu Glu Gly Thr Lys>

            250         260         270         280
GAT GAC AAA AGT AAA GCA AAA TTA ACA ATT GCT GAC GAT CTA AGT AAA
CTA CTG TTT TCA TTT CGT TTT AAT TGT TAA CGA CTG CTA GAT TCA TTT
Asp Asp Lys Ser Lys Ala Lys Leu Thr Ile Ala Asp Asp Leu Ser Lys>

290         300         310         320         330
ACC ACA TTC GAA CTT TTA AAA GAA GAT GGC AAA ACA TTA GTG TCA AGA
TGG TGT AAG CTT GAA AAT TTT CTT CTA CCG TTT TGT AAT CAC AGT TCT
Thr Thr Phe Glu Leu Leu Lys Glu Asp Gly Lys Thr Leu Val Ser Arg>

  340         350         360         370         380
AAA GTA AGT TCT AGA GAC AAA ACA TCA ACA GAT GAA ATG TTC AAT GAA
TTT CAT TCA AGA TCT CTG TTT TGT AGT TGT CTA CTT TAC AAG TTA CTT
Lys Val Ser Ser Arg Asp Lys Thr Ser Thr Asp Glu Met Phe Asn Glu>
```

FIG. 11A

```
         390          400          410          420          430
          *   *    *    *    *    *    *    *    *    *
AAA GGT GAA TTG TCT GCA AAA ACC ATG ACA AGA GAA AAT GGA ACC AAA
TTT CCA CTT AAC AGA CGT TTT TGG TAC TGT TCT CTT TTA CCT TGG TTT
Lys Gly Glu Leu Ser Ala Lys Thr Met Thr Arg Glu Asn Gly Thr Lys>

         440          450          460          470          480
          *   *    *    *    *    *    *    *    *    *
CTT GAA TAT ACA GAA ATG AAA AGC GAT GGA ACC GGA AAA GCT AAA GAA
GAA CTT ATA TGT CTT TAC TTT TCG CTA CCT TGG CCT TTT CGA TTT CTT
Leu Glu Tyr Thr Glu Met Lys Ser Asp Gly Thr Gly Lys Ala Lys Glu>

         490          500          510          520
          *   *    *    *    *    *    *    *    *
GTT TTA AAA AAG TTT ACT CTT GAA GGA AAA GTA GCT AAT GAT AAA GTA
CAA AAT TTT TTC AAA TGA GAA CTT CCT TTT CAT CGA TTA CTA TTT CAT
Val Leu Lys Lys Phe Thr Leu Glu Gly Lys Val Ala Asn Asp Lys Val>

 530         540          550          560          570
  *   *    *    *    *    *    *    *    *    *
ACA TTG GAA GTA AAA GAA GGA ACC GTT ACT TTA AGT AAG GAA ATT GCA
TGT AAC CTT CAT TTT CTT CCT TGG CAA TGA AAT TCA TTC CTT TAA CGT
Thr Leu Glu Val Lys Glu Gly Thr Val Thr Leu Ser Lys Glu Ile Ala>

         580          590          600          610          620
          *   *    *    *    *    *    *    *    *    *
AAA TCT GGA GAA GTA ACA GTT GCT CTT AAT GAC ACT AAC ACT ACT CAG
TTT AGA CCT CTT CAT TGT CAA CGA GAA TTA CTG TGA TTG TGA TGA GTC
Lys Ser Gly Glu Val Thr Val Ala Leu Asn Asp Thr Asn Thr Thr Gln>

         630          640          650          660          670
          *   *    *    *    *    *    *    *    *    *
GCT ACT AAA AAA ACT GGC GCA TGG GAT TCA AAA ACT TCT ACT TTA ACA
CGA TGA TTT TTT TGA CCG CGT ACC CTA AGT TTT TGA AGA TGA AAT TGT
Ala Thr Lys Lys Thr Gly Ala Trp Asp Ser Lys Thr Ser Thr Leu Thr>

         680          690          700          710          720
          *   *    *    *    *    *    *    *    *    *
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
Ile Ser Val Asn Ser Lys Lys Thr Thr Gln Leu Val Phe Thr Lys Gln>

         730          740          750          760
          *   *    *    *    *    *    *    *    *
TAC ACA ATA ACT GTA AAA CAA TAC GAC TCC GCA GGT ACC AAT TTA GAA
ATG TGT TAT TGA CAT TTT GTT ATG CTG AGG CGT CCA TGG TTA AAT CTT
Tyr Thr Ile Thr Val Lys Gln Tyr Asp Ser Ala Gly Thr Asn Leu Glu>
```

FIG. 11B

```
770         780         790         800         810
 *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

   820
     *
AAA TAA
TTT ATT
Lys ***>
```

FIG. 11C

```
            10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>

    390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>
```

FIG. 12A

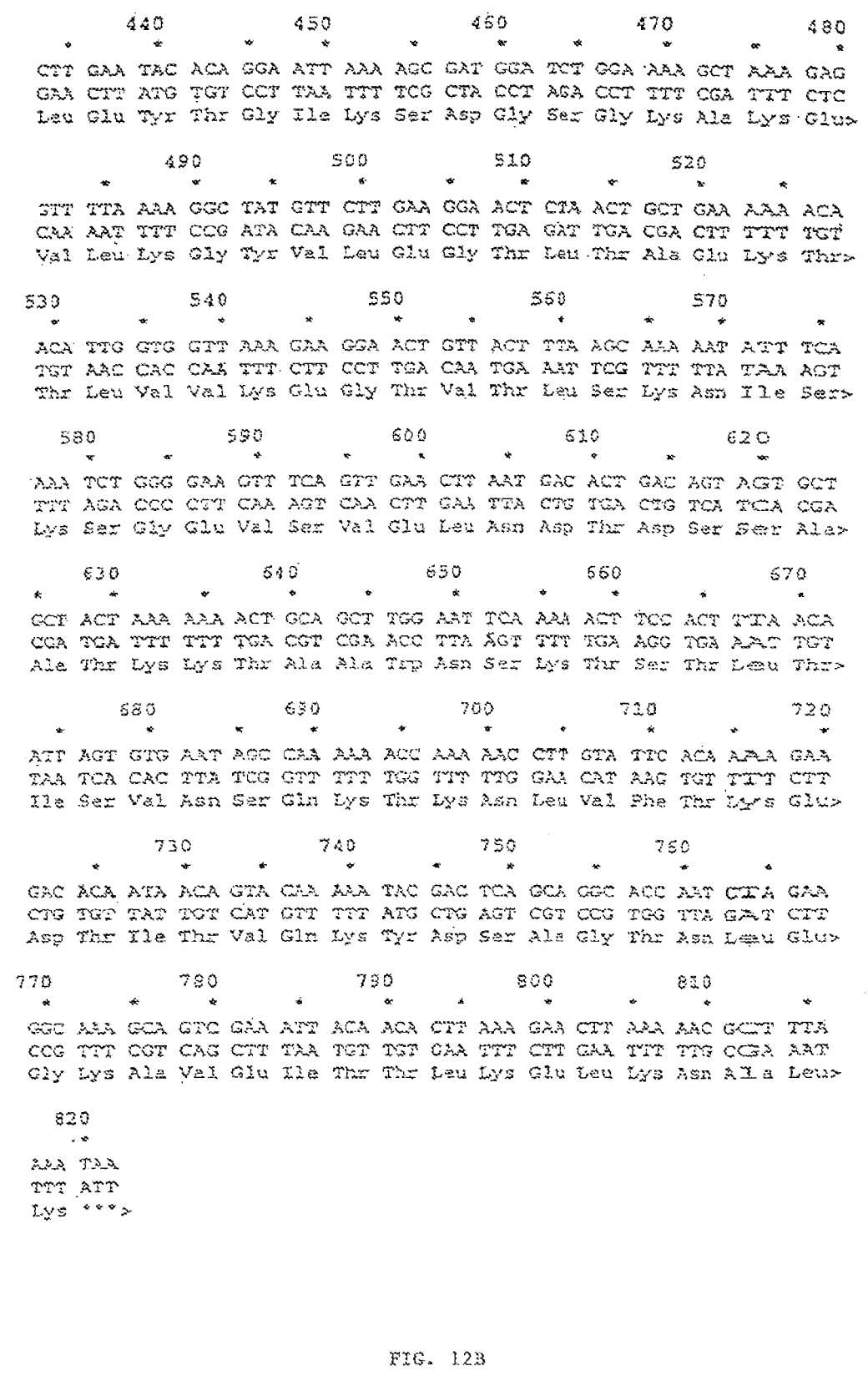

```
        440         450         460         470         480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

           490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630         640         650         660         670
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

        680         690         700         710         720
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

           730         740         750         760
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>

770         780         790         800         810
GGC AAA GCA GTC GAA ATT ACA ACA CTT AAA GAA CTT AAA AAC GCT TTA
CCG TTT CGT CAG CTT TAA TGT TGT GAA TTT CTT GAA TTT TTG CGA AAT
Gly Lys Ala Val Glu Ile Thr Thr Leu Lys Glu Leu Lys Asn Ala Leu>

  820
AAA TAA
TTT ATT
Lys ***>
```

FIG. 12B

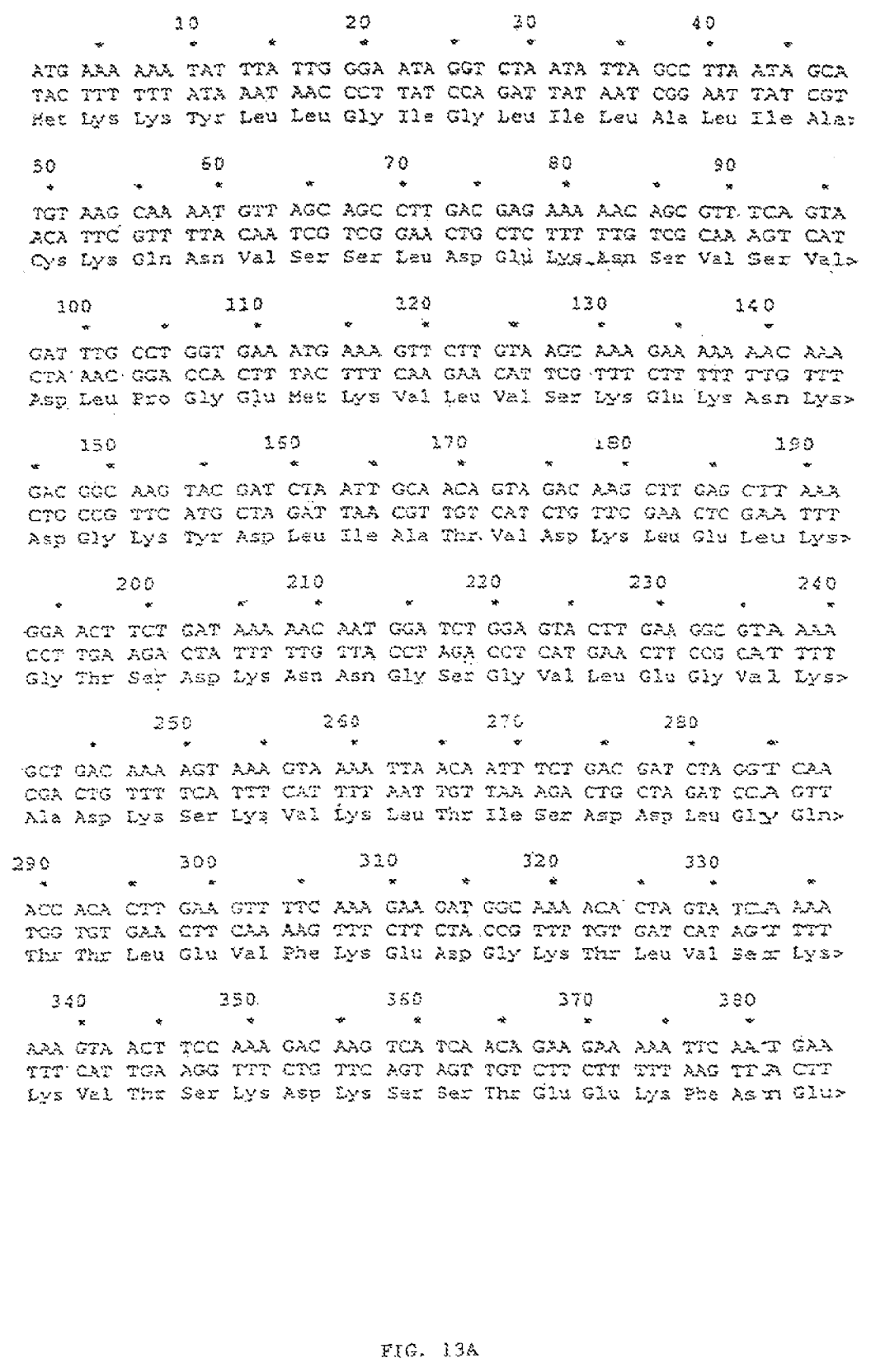

```
            10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

            250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 13A

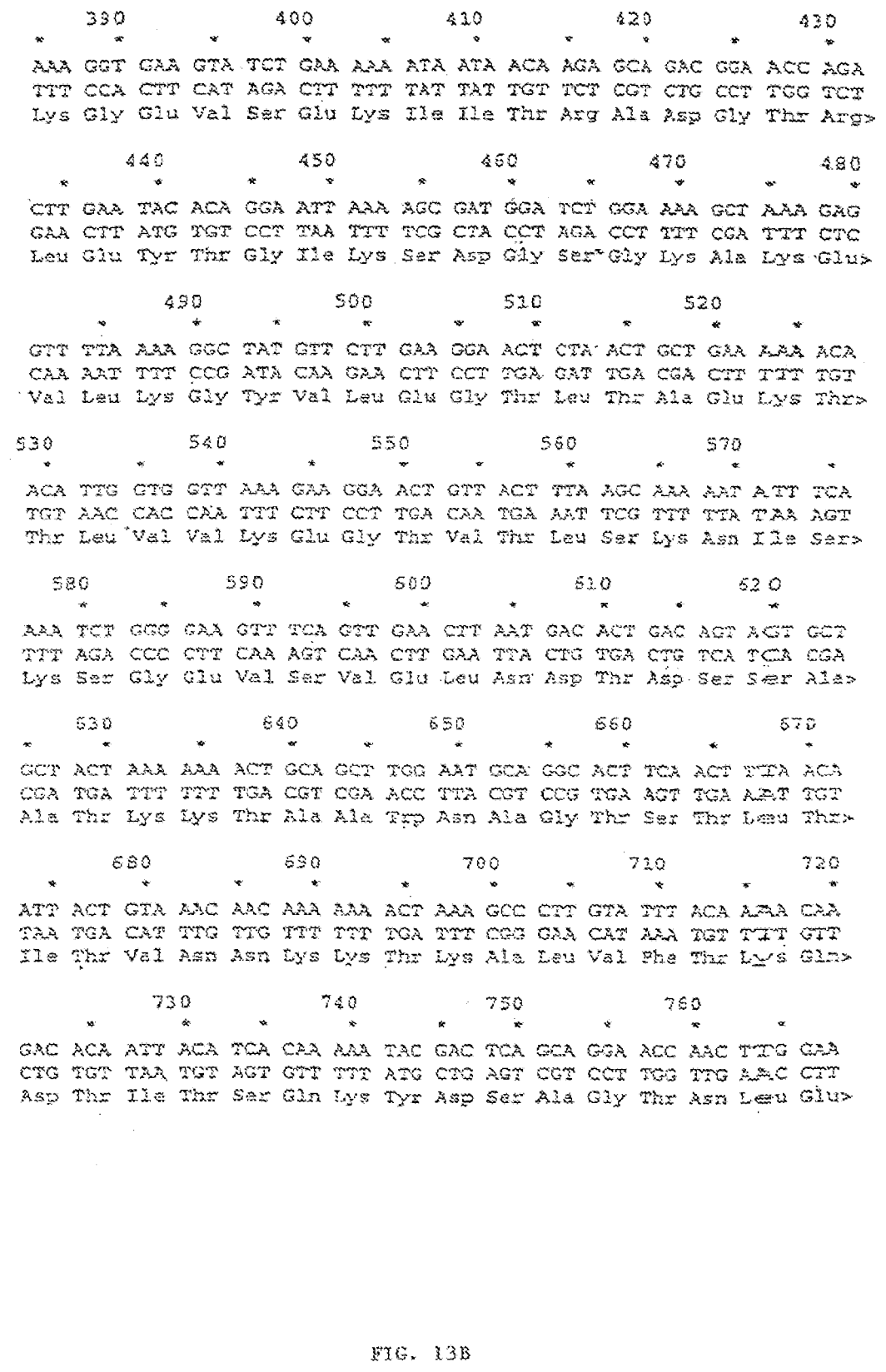

```
    390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

            490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
GCT ACT AAA AAA ACT GCA GCT TGG AAT GCA GGC ACT TCA ACT TTA ACA
CGA TGA TTT TTT TGA CGT CGA ACC TTA CGT CCG TGA AGT TGA AAT TGT
Ala Thr Lys Lys Thr Ala Ala Trp Asn Ala Gly Thr Ser Thr Leu Thr>

        680         690         700         710         720
ATT ACT GTA AAC AAC AAA AAA ACT AAA GCC CTT GTA TTT ACA AAA CAA
TAA TGA CAT TTG TTG TTT TTT TGA TTT CGG GAA CAT AAA TGT TTT GTT
Ile Thr Val Asn Asn Lys Lys Thr Lys Ala Leu Val Phe Thr Lys Gln>

            730         740         750         760
GAC ACA ATT ACA TCA CAA AAA TAC GAC TCA GCA GGA ACC AAC TTG GAA
CTG TGT TAA TGT AGT GTT TTT ATG CTG AGT CGT CCT TGG TTG AAC CTT
Asp Thr Ile Thr Ser Gln Lys Tyr Asp Ser Ala Gly Thr Asn Leu Glu>
```

FIG. 13B

```
770          780          790          800          810
 *     *     *     *     *     *     *     *     *     *
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
Gly Thr Ala Val Glu Ile Lys Thr Leu Asp Glu Leu Lys Asn Ala Leu>

AGA
TCT
Arg>
```

FIG. 13C

```
          10         20         30         40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

  100        110        120        130        140
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

    150        160        170        180        190
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

      200        210        220        230        240
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

        250        260        270        280
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290        300        310        320        330
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

  340        350        360        370        380
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 14A

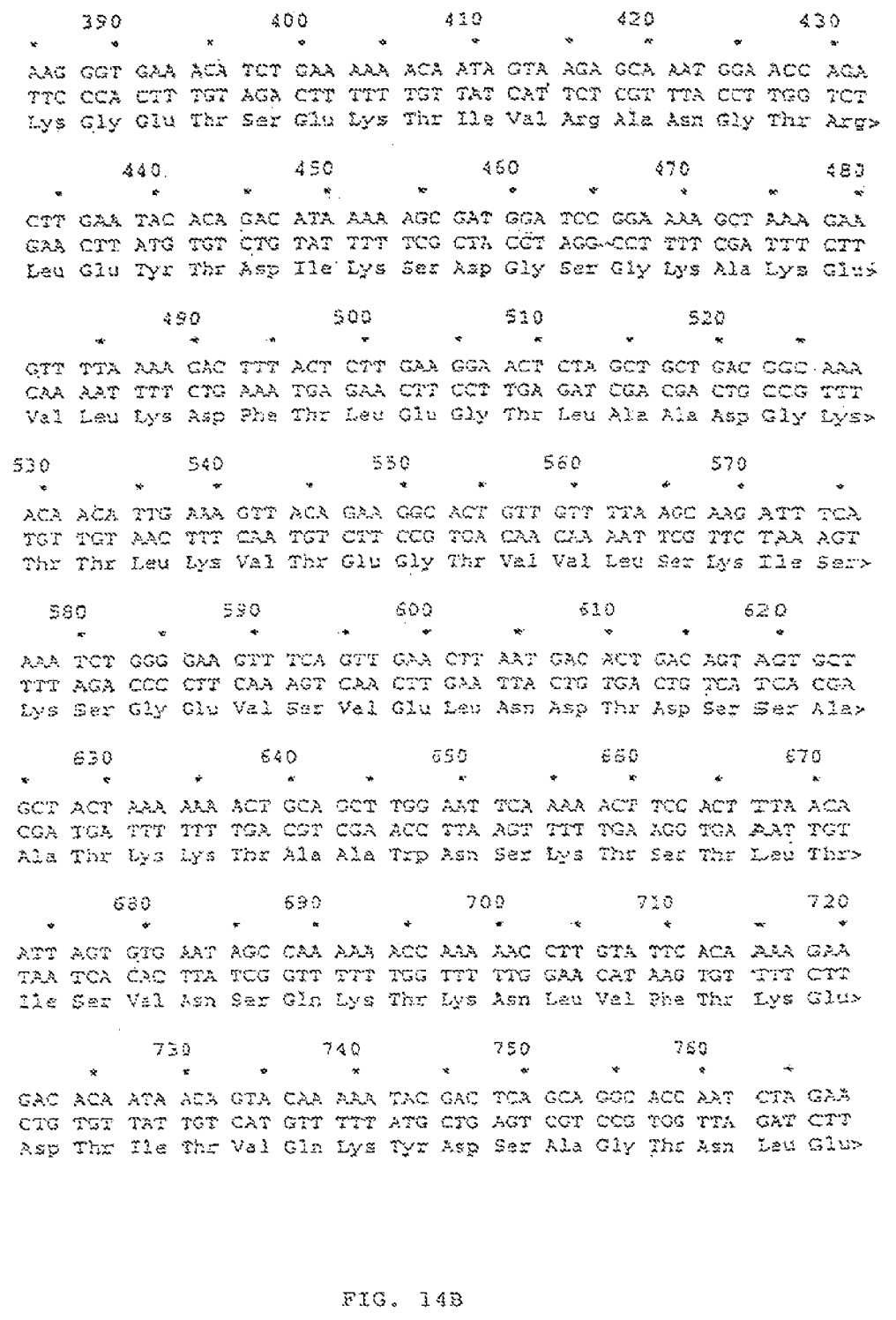

```
     390        400        410        420        430
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

       440        450        460        470        480
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

         490        500        510        520
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530        540        550        560        570
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

  580        590        600        610        620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630        640        650        660        670
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

       680        690        700        710        720
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

         730        740        750        760
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

FIG. 14B

```
      770          780          790          800          810
       *     *      *     *      *     *      *     *      *     *
      GGC  AAA  GCA  GTC  GAA  ATT  ACA  ACA  CTT  AAA  GAA  CTT  AAA  AAC  GCT  TTA
      CCG  TTT  CGT  CAG  CTT  TAA  TGT  TGT  GAA  TTT  CTT  GAA  TTT  TTG  CGA  AAT
      Gly  Lys  Ala  Val  Glu  Ile  Thr  Thr  Leu  Lys  Glu  Leu  Lys  Asn  Ala  Leu>

       820
        *
      AAA  TAA
      TTT  ATT
      Lys  ***>
```

FIG. 14C

```
         10         20         30         40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
TGT AAG CAA AAT GTT AGC AGC CTT GAT GAA AAA AAT AGC GTT TCA GTA
ACA TTC GTT TTA CAA TCG TCG GAA CTA CTT TTT TTA TCG CAA AGT CAT
Cys Lys Gln Asn Val Ser Ser Leu Asp Glu Lys Asn Ser Val Ser Val>

 100        110        120        130        140
GAT TTA CCT GGT GGA ATG ACA GTT CTT GTA AGT AAA GAA AAA GAC AAA
CTA AAT GGA CCA CCT TAC TGT CAA GAA CAT TCA TTT CTT TTT CTG TTT
Asp Leu Pro Gly Gly Met Thr Val Leu Val Ser Lys Glu Lys Asp Lys>

   150        160        170        180        190
GAC GGT AAA TAC AGT CTA GAG GCA ACA GTA GAC AAG CTT GAG CTT AAA
CTG CCA TTT ATG TCA GAT CTC CGT TGT CAT CTG TTC GAA CTC GAA TTT
Asp Gly Lys Tyr Ser Leu Glu Ala Thr Val Asp Lys Leu Glu Leu Lys>

      200        210        220        230        240
GGA ACT TCT GAT AAA AAC AAC GGT TCT GGA ACA CTT GAA GGT GAA AAA
CCT TGA AGA CTA TTT TTG TTG CCA AGA CCT TGT GAA CTT CCA CTT TTT
Gly Thr Ser Asp Lys Asn Asn Gly Ser Gly Thr Leu Glu Gly Glu Lys>

         250        260        270        280
ACT GAC AAA AGT AAA GTA AAA TTA ACA ATT GCT GAT GAC CTA AGT CAA
TGA CTG TTT TCA TTT CAT TTT AAT TGT TAA CGA CTA CTG GAT TCA GTT
Thr Asp Lys Ser Lys Val Lys Leu Thr Ile Ala Asp Asp Leu Ser Gln>

290        300        310        320        330
ACT AAA TTT GAA ATT TTC AAA GAA GAT GCC AAA ACA TTA GTA TCA AAA
TGA TTT AAA CTT TAA AAG TTT CTT CTA CGG TTT TGT AAT CAT AGT TTT
Thr Lys Phe Glu Ile Phe Lys Glu Asp Ala Lys Thr Leu Val Ser Lys>

 340        350        360        370        380
AAA GTA ACC CTT AAA GAC AAG TCA TCA ACA GAA GAA AAA TTC AAC GAA
TTT CAT TGG GAA TTT CTG TTC AGT AGT TGT CTT CTT TTT AAG TTG CTT
Lys Val Thr Leu Lys Asp Lys Ser Ser Thr Glu Glu Lys Phe Asn Glu>
```

FIG. 15A

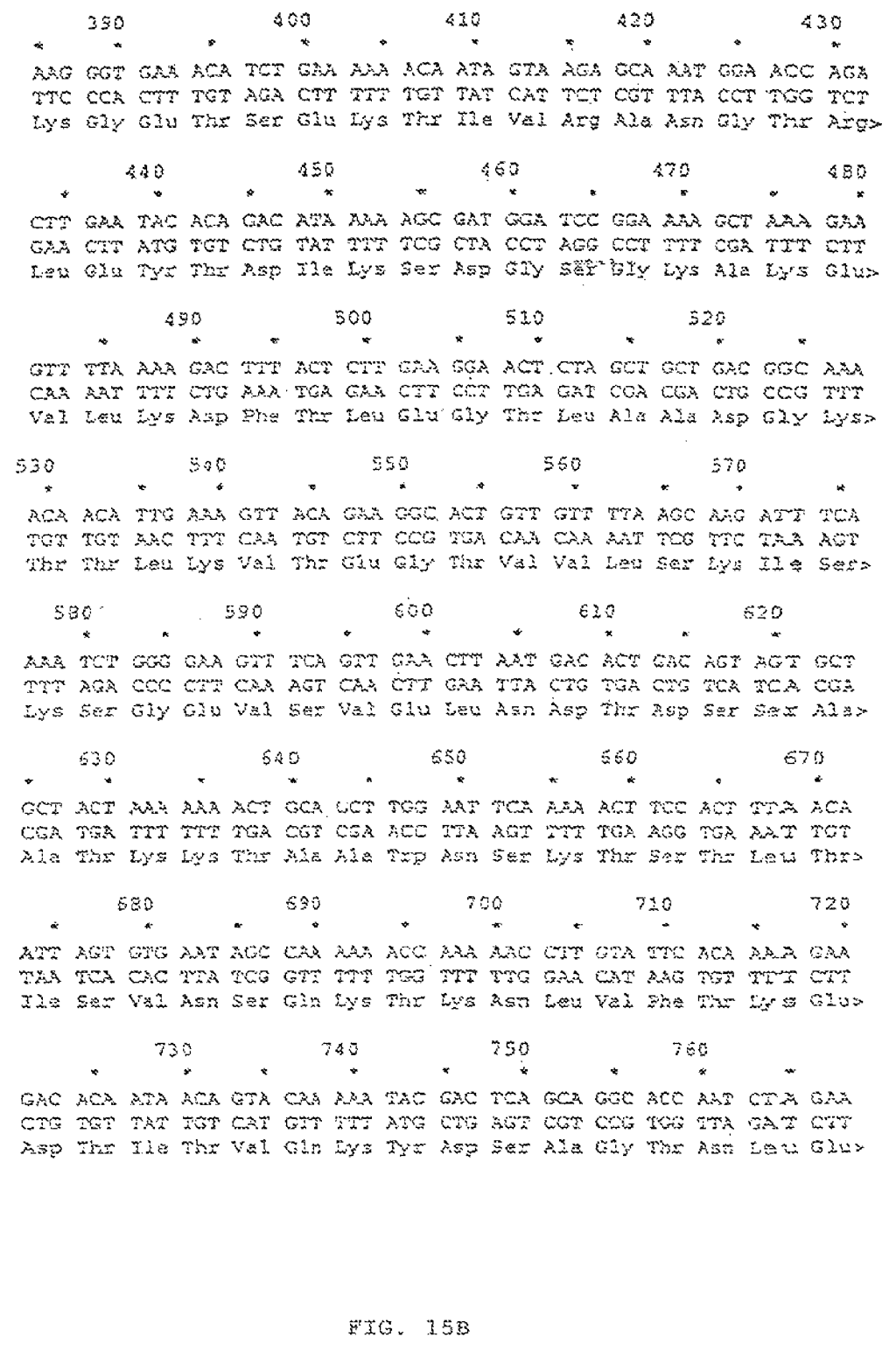

```
      390            400            410            420            430
AAG GGT GAA ACA TCT GAA AAA ACA ATA GTA AGA GCA AAT GGA ACC AGA
TTC CCA CTT TGT AGA CTT TTT TGT TAT CAT TCT CGT TTA CCT TGG TCT
Lys Gly Glu Thr Ser Glu Lys Thr Ile Val Arg Ala Asn Gly Thr Arg>

        440            450            460            470            480
CTT GAA TAC ACA GAC ATA AAA AGC GAT GGA TCC GGA AAA GCT AAA GAA
GAA CTT ATG TGT CTG TAT TTT TCG CTA CCT AGG CCT TTT CGA TTT CTT
Leu Glu Tyr Thr Asp Ile Lys Ser Asp Gly Ser Gly Lys Ala Lys Glu>

           490            500            510            520
GTT TTA AAA GAC TTT ACT CTT GAA GGA ACT CTA GCT GCT GAC GGC AAA
CAA AAT TTT CTG AAA TGA GAA CTT CCT TGA GAT CGA CGA CTG CCG TTT
Val Leu Lys Asp Phe Thr Leu Glu Gly Thr Leu Ala Ala Asp Gly Lys>

530            540            550            560            570
ACA ACA TTG AAA GTT ACA GAA GGC ACT GTT GTT TTA AGC AAG ATT TCA
TGT TGT AAC TTT CAA TGT CTT CCG TGA CAA CAA AAT TCG TTC TAA AGT
Thr Thr Leu Lys Val Thr Glu Gly Thr Val Val Leu Ser Lys Ile Ser>

   580            590            600            610            620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

      630            640            650            660            670
GCT ACT AAA AAA ACT GCA GCT TGG AAT TCA AAA ACT TCC ACT TTA ACA
CGA TGA TTT TTT TGA CGT CGA ACC TTA AGT TTT TGA AGG TGA AAT TGT
Ala Thr Lys Lys Thr Ala Ala Trp Asn Ser Lys Thr Ser Thr Leu Thr>

         680            690            700            710            720
ATT AGT GTG AAT AGC CAA AAA ACC AAA AAC CTT GTA TTC ACA AAA GAA
TAA TCA CAC TTA TCG GTT TTT TGG TTT TTG GAA CAT AAG TGT TTT CTT
Ile Ser Val Asn Ser Gln Lys Thr Lys Asn Leu Val Phe Thr Lys Glu>

            730            740            750            760
GAC ACA ATA ACA GTA CAA AAA TAC GAC TCA GCA GGC ACC AAT CTA GAA
CTG TGT TAT TGT CAT GTT TTT ATG CTG AGT CGT CCG TGG TTA GAT CTT
Asp Thr Ile Thr Val Gln Lys Tyr Asp Ser Ala Gly Thr Asn Leu Glu>
```

FIG. 15B

```
     770         780         790         800         810
      *           *           *           *           *
 GGC AAA GCA GTC GAA ATT ACA ACA CTT AAA GAA CTT AAA AAC GCT TTA
 CCG TTT CGT CAG CTT TAA TGT TGT GAA TTT CTT GAA TTT TTG CGA AAT
 Gly Lys Ala Val Glu Ile Thr Thr Leu Lys Glu Leu Lys Asn Ala Leu>

     820
      *
 AAA TAA
 TTT ATT
 Lys ***>
```

FIG. 15C

```
        10         20         30         40
         *     *     *     *     *     *     *     *     *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

 50         60         70         80         90
  *     *     *     *     *     *     *     *     *     *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100        110        120        130        140
   *     *     *     *     *     *     *     *     *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150        160        170        180        190
 *     *     *     *     *     *     *     *     *     *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200        210        220        230        240
  *     *     *     *     *     *     *     *     *     *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

         250        260        270        280
     *     *     *     *     *     *     *     *     *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290        300        310        320        330
 *     *     *     *     *     *     *     *     *     *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340        350        360        370        380
   *     *     *     *     *     *     *     *     *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 16A

```
    390          400          410          420          430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

       440          450          460          470          480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490          500          510          520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530          540          550          560          570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580          590          600          610          620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630          640          650          660          670
GCT ACT AAA AAA ACT GCA GCT TGG AAT GAC AGT ACT AGC ACT TTA ACA
CGA TGA TTT TTT TGA CGT CGA ACC TTA CTG TCA TGA TCG TGA AAT TGT
Ala Thr Lys Lys Thr Ala Ala Trp Asn Asp Ser Thr Ser Thr Leu Thr>

        680          690          700          710          720
ATT AGT GCT GAC AGC AAA AAA ACT AAA GAT TTG GTG TTC TTA ACA GAT
TAA TCA CGA CTG TCG TTT TTT TGA TTT CTA AAC CAC AAG AAT TGT CTA
Ile Ser Ala Asp Ser Lys Lys Thr Lys Asp Leu Val Phe Leu Thr Asp>

           730          740          750          760
GGT ACA ATT ACA GTA CAA CAA TAC AAC ACA GCT GGA ACC AGC CTA GAA
CCA TGT TAA TGT CAT GTT GTT ATG TTG TGT CGA CCT TGG TCG GAT CTT
Gly Thr Ile Thr Val Gln Gln Tyr Asn Thr Ala Gly Thr Ser Leu Glu>
```

FIG. 16B

```
770         780         790         800         810
 *     *     *     *     *     *     *     *     *     *
GGA TCA GCA AGT GAA ATT AAA AAT CTT TCA GAG CTT AAA AAC GCT TTA
CCT AGT CGT TCA CTT TAA TTT TTA GAA AGT CTC GAA TTT TTG CGA AAT
Gly Ser Ala Ser Glu Ile Lys Asn Leu Ser Glu Leu Lys Asn Ala Leu>

    820
     *
AAA TAA
TTT ATT
Lys ***>
```

FIG. 16C

```
Sequence Range: 1 to 822

                       10         20         30         40
               *       *      *      *      *     *      *       *
OspA-B31     ATG AAA AAA TAT TTA TTG GGA ATA GGT CTA ATA TTA GCC TTA ATA GCA
             TAC TTT TTT ATA AAT AAC CCT TAT CCA GAT TAT AAT CGG AAT TAT CGT

OspA-B31               10         20         30         40
[ 3298 ]     ... ... ... ... ... ... ... ... ... ... ... ... ... ... ... ...>

OspA-KA                10         20         30         40
[ 3288 ]     ... ... ... ... ... ... ... ... ... ... ... ... ... ... ... ...>

OspA-N40               10         20         30         40
[ 3276 ]     ... ... ... ... ... ... ... ... ... ... ... ... ... ... ... ...>

OspA-ZS7               10         20         30         40
[ 3264 ]     ... ... ... ... ... ... ... ... ... ... ... ... ... ... ... ...>

OspA-2S015             10         20         30         40
[ 2802 ]     ... ... ... ... ... ... ... ... ... ... ... ... ... ..t ... ...>

OspA-TRO               10         20         30         40
[ 2648 ]     ... ... ... ... ... ... ... ... ... ... ... ... ... ... ... ...>

OspA-K48               10         20         30         40
[ 2584 ]     ... ... ... ... ... ... ... ... ... ... ... ... ... ... ... ...>

OspA-HE 11             10         20         30         40
[ 2580 ]     ... ... ... ... ... ... ... ... ... ... ... ... ... ... ... ...>

OspA-DK29              10         20         30         40
[ 2566 ]     ... ... ... ... ... ... ... ... ... ... ... ... ... ... ... ...>

OspA-Ip90              10         20         30         40
[ 2562 ]     ... ... ... ... ... ... ... ... ... ... ... ... ... ..a ... ...>

OspA-BO                10         20         30         40
[ 2558 ]     ... ... ... ... ... ... ... ... ... ... ... ... ... ... ... ...>

OSPA-IP3               10         20         30         40
[ 2558 ]     ... ... ... ... ... ... ... ... ... ... ... ... ... ... ... ...>

OspA-PKO               10         20         30         40
[ 2558 ]     ... ... ... ... ... ... ... ... ... ... ... ... ... ... ... ...>

OspA-ACAI              10         20         30         40
[ 2556 ]     ... ... ... ... ... ... ... ... ... ... ... ... ... ... ... ...>

OspA-P-GAU             10         20         30         40
[ 2544 ]     ... ... ... ... ... ... ... ... ... ... ... ... ... ... ... ...>

             50         60         70         80         90
             *     *    *     *     *     *     *     *     *     *
OspA-B31     TGT AAG CAA AAT GTT AGC AGC CTT GAC GAG AAA AAC AGC GTT TCA GTA
             ACA TTC GTT TTA CAA TCG TCG GAA CTG CTC TTT TTG TCG CAA AGT CAT
```

FIG. 17A

```
OspA-B31      50          60            70           80           90
[ 3288 ]      ... ... ... ... ... ... ... ... ... ... ... ... ... ... ... ...>

OspA-KA       50          60            70           80           90
[ 3288 ]      ... ... ... ... ... ... ... ... ... ... ... ... ... ... ... ...>

OspA-N40      50          60            70           80           90
[ 3276 ]      ... ... ... ... ... ... ... ... ... ... ... ... ... ... ... ...>

OspA-ZS7      50          60            70           80           90
[ 3264 ]      ... ... ... ... ... ... ... ... ... ... ... ... ... ... ... ...>

OspA-25015    50          60            70           80           90
[ 2802 ]      ... ... ... ... ... ... ... ... ... ... ... ... ... ... ... ...>

OspA-TRO      50          60            70           80           90
[ 2648 ]      ... ... ... ... ... ... ... ... ..t ... ... ... ... ... ... ...>

OspA-K48      50          60            70           80           90
[ 2584 ]      ... ... ... ... ... ... ... ... ..t ..a ... ..t ... ... ... ...>

OspA-HE 11    50          60            70           80           90
[ 2580 ]      ... ... ... ... ... ... ... ... ..t ..a ... ..t ... ... ... ...>

OspA-DK29     50          60            70           80           90
[ 2566 ]      ... ... ... ... ... ... ... ... ..t ..a ... ..t ... ... ... ...>

OspA-Ip90     50          60            70           80           90
[ 2563 ]      ... ... ... ... ... ... ... ... ..t ..a ... ..t ... ... ... ...>

OspA-BO       50          60            70           80           90
[ 2558 ]      ..c ... ... ... ... ... ... ... ..t ..a ... ... ... .c. ... ...>

OSPA-IP3      50          60            70           80           90
[ 2558 ]      ..c ... ... ... ... ... ... ... ..t ..a ... ... ... .c. ... ...>

OspA-PKO      50          60            70           80           90
[ 2559 ]      ..c ... ... ... ... ... ... ... ..t ... ... ... ... .c. ... ...>

OspA-ACAI     50          60            70           80           90
[ 2556 ]      ..c ... ... ... ... ... ... ... ..t ..a ... ... ... .c. ... ...>

ospA-P-GAU    50          50            70           80           90
[ 2544 ]      ..c ... ... ... ... ... ... ... ..t ..a ... ... ... .c. ... ...>

                100          110          120          130          140
                 *     *      *      *     *     *     *     *      *
OspA-B31      GAT TTG CCT GGT GAA ATG AAA GTT CTT GTA AGC AAA GAA AAA AAC AAA
              CTA AAC GGA CCA CTT TAC TTT CAA GAA CAT TCG TTT CTT TTT TTG TTT

OspA-B31        100          110          120          130          140
[ 3288 ]      ... ... ... ... ... ... ... ... ... ... ... ... ... ... ... ...>

OspA-KA         100          110          120          130          140
[ 3288 ]      ... ... ... ... ... ... ... ... ... ... ... ... ... ... ... ...>

OspA-N40        100          110          120          130          140
```

```
[ 3276 ]      ... ... ... ... ... ... ..c ... ... ... ... ... ... ...  ... ...>

OspA-ZS7      100            110            120            130            140
[ 3264 ]      ... ... ... ... ... ... ..c ... ... ... ... ... ... ...  ... ...>

OspA-25015    100            110            120            130            140
[ 2802 ]      ... ... ... ... ... ... ... ... ... ... ... ... ... ...  g.. ...>

OspA-TRO      100            110            120            130            140
[ 2548 ]      ... ..a ... ... ... ... ... ... ... ... ... ... ... ...  g.. ...>

OspA-K48      100            110            120            130            140
[ 2584 ]      ... ..a ... ... .g. ... .c. ... ... ... ..t ... ... ...  g.. ...>

OspA-HE 11    100            110            120            130            140
[ 2580 ]      ... ..a ... ... .g. ... ... ... ... ... ..t ... ... ...  g.. ...>

OspA-DK29     100            110            120            130            140
[ 2566 ]      ... ..a ... ... .g. ... .c. ... ... ... ..t ... ... ...  g.. ...>

OspA-Ip90     100            110            120            130            140
[ 2562 ]      ... ..a ... ... .g. ... c.. ... ... ... ..t ... ... ...  g.. ...>

OspA-SO       100            110            120            130            140
[ 2558 ]      ... ... ... ... ..g ... ... ... ... ... ..t ... ... ...  g.. ...>

OSPA-IP3      100            110            120            130            140
[ 2558 ]      ... ... ... ... ..g ..t ... ... ... ... ..t ... ... ...  g.. ...>

OspA-PKO      100            110            120            130            140
[ 2558 ]      ... ... ... ... ..g ... ... ... ... ... ..t ... ... ...  g.. ...>

OspA-ACAI     100            110            120            130            140
[ 2556 ]      ... ... ... ... ..g ... ... ... ... ... ..t ... ... ...  g.. ...>

ospA-P-GAU    100            110            120            130            140
[ 2544 ]      ... ... ... ... ..g ... ... ... ... ... ..t ... ... ...  g.. ...>

                  150            160            170            180            190
               *   *       *       *       *       *       *       *       *       *
OspA-B31      GAC GGC AAG TAC GAT CTA ATT GCA ACA GTA GAC AAG CTT GAG  CTT AAA
              CTG CCG TTC ATG CTA GAT TAA CGT TGT CAT CTG TTC GAA CTC  GAA TTT

OspA-B31          150            160            170            180            190
[ 3288 ]      ... ... ... ... ... ... ... ... ... ... ... ... ... ...  ... ...>

OspA-KA           150            160            170            180            190
[ 3288 ]      ... ... ... ... ... ... ... ... ... ... ... ... ... ...  ... ...>

OspA-N40          150            160            170            180            190
[ 3276 ]      ... ... ... ... ... ... ... ... ... ... ... ... ... ...  ... ...>

OspA-ZS7          150            160            170            180            190
[ 3264 ]      ... ... ... ... ... ... ... ... ... ... ... ... ... ...  ... ...>

OspA-25015        150            160            170            180            190
[ 2802 ]      ... ... ... ... ag. ... ..g ... ... ... ... ... ... ...  ... ...>
```

FIG. 17C

```
OspA-TRO          150            160            170            180            190
[ 2648 ]     ..t ..t ..a ... ag. ... ..g ... ... ... ... ... ..a ... ... ...>

OspA-K48          150            160            170            180            190
[ 2584 ]     ... ..t ..a ... ag. ... gag ... ... ... ... ... ... ... ... ...>

OspA-HD 11        150            160            170            180            190
[ 2580 ]     ..t ..t ..a ... ag. ... ..g ... ... ... ..a ... ... ... ... ...>

OspA-DK29         150            160            170            180            190
[ 2556 ]     ... ..t ..a ... ag. ... gag ... ... ... ... ... ... ... ... ...>

OspA-Ip90         150            160            170            180            190
[ 2562 ]     ..t ..t ..a ... ag. ... ..g ... ... ... ... ... ... ... ... ...>

OspA-BO           150            160            170            180            190
[ 2558 ]     ... ..t ... ... ag. ... .ag ... ... ... ... ... a.. ... ..a ...>

OSPA-IP3          150            160            170            180            190
[ 2558 ]     ... ..t ... ... ag. ... .ag ... ... ... ... ... a.. ... ..a ...>

OspA-PKO          150            160            170            180            190
[ 2558 ]     ... ..t ... ... ag. ... .ag ... ... ... ... ... a.. ... ..a ...>

OspA-ACAI         150            160            170            180            190
[ 2556 ]     ... ..t ... ... ag. ... .ag ... ... ... ... ... a.. ... ..a ...>

ospA-P-GAU        150            160            170            180            190
[ 2544 ]     ... ..t ... ... ag. ... .ag ... ... ... ... ... a.. ... ..a ...>

                  200            210            220            230            240
              *       *       *       *       *       *       *       *       *   *
OspA-B31     GGA ACT TCT GAT AAA AAC AAT GGA TCT GGA GTA CTT GAA GGC GTA AAA
             CCT TGA AGA CTA TTT TTG TTA CCT AGA CCT CAT GAA CTT CCG CAT TTT

OspA-B31          200            210            220            230            240
[ 3288 ]     ... ... ... ... ... ... ... ... ... ... ... ... ... ... ... ...>

OspA-KA           200            210            220            230            240
[ 3288 ]     ... ... ... ... ... ... ... ... ... ... ... ... ... ... ... ...>

OspA-N40          200            210            220            230            240
[ 3276 ]     ... ... ... ... ... ... ... ... ... ... ... ... ... ... ... ...>

OspA-ZS7          200            210            220            230            240
[ 3264 ]     ... ... ... ... ... ... ... ... ... ... ... ... ... ... ... ...>

OspA-25015        200            210            220            230            240
[ 2802 ]     ... ..a ... ... ... ... ... ... ... ..g ..g ... ... ... ... ...>

OspA-TRO          200            210            220            230            240
[ 2648 ]     ... ... ... ... ... .g. ..c ..t ... ... ac. ... ... ..t .a. ...>

OspA-K48          200            210            220            230            240
[ 2584 ]     ... ... ... ... ... ... ..c ..t ... ... ac. ... ... ..t .a. ...>
```

FIG. 17D

```
OspA-HE 11          200         210          220         230         240
[ 2580 ]      ... ... ... ... ... ... ..c ..t ... ... ac. ... ... ..t .a. ...>

OspA-DK29           200         210          220         230         240
[ 2566 ]      ... ... ... ... ... ... ..c ..t ... ... ac. ... ... ..t .a. ...>

OspA-Ip90           200         210          220         230         240
[ 2562 ]      ... ... ... ... ... ... ..c ..t ... ... ac. ... ... ..t .a. ...>

OspA-BO             200         210          220         230         240
[ 2558 ]      ... ... ... ... ... g.. ... ..t ... ..g ..g ... ... ..t ac. ...>

OSPA-IP3            200         210          220         230         240
[ 2558 ]      ... ... ... ... ... g.. ... ..t ... ... ..g ... ... ..t ac. ...>

OspA-PKO            200         210          220         230         240
[ 2558 ]      ... ... ... ... ... g.. ... ..t ... ..g ..g ... ... ..t ac. ...>

OspA-ACAI           200         210          220         230         240
[ 2556 ]      ... ... ... ... ... g.. ... ..t ... ... ..g ... ... ..t ac. ...>

OspA-P-GAU          200         210          220         230         240
[ 2544 ]      ... ... ... ... ... g.. ... ..t ... ... ..g ... ... ..t ac. ...>


                        250          250          270          280
                     *     *     *     *     *     *     *     *     *
OspA-B31      GCT GAC AAA AGT AAA GTA AAA TTA ACA ATT TCT GAC GAT CTA GGT CAA
              CGA CTG TTT TCA TTT CAT TTT AAT TGT TAA AGA CTG CTA GAT CCA GTT

OspA-B31                250          260          270          280
[ 3288 ]      ... ... ... ... ... ... ... ... ... ... ... ... ... ... ... ...>

OspA-KA                 250          250          270          280
[ 3283 ]      ... ... ... ... ... ... ... ... ... ... ... ... ... ... ... ...>

OspA-N40                250          250          270          280
[ 3276 ]      ... ... ... ... ... ... ... ... ... ... ... ... ... ... ... ...>

OspA-ZS7                250          250          270          280
[ 3254 ]      ... ... ... ... ... ... ... ... ... ... ... ... ... ... ... ...>

OspA-25015              250          250          270          280
[ 2802 ]      ... ... ... ..c ... ... ... ... ... g.. ... ... ... ... a.c ac.>

OspA-TRO                250          250          270          280
[ 2648 ]      t.. ... ... ... ... .c. ... ... ... ... ... ..a ... ... a.. a..>

OspA-K48                250          250          270          280
[ 2584 ]      a.. ... ... ... ... ... ... ... ... ... g.. ..c ..c ... a.. ...>

OspA-HE 11              250          250          270          280
[ 2580 ]      a.. ... ... ... ... ... ... ... ... ... g.. ..g ... ... a.. a..>

OspA-DK29               250          250          270          280
[ 2566 ]      a.. ... ... ... ... ... ... .c. ... ... g.. ..c ..c ... a.. ...>

OspA-Ip90               250          260          270          280
```

FIG. 17E

```
[ 2562 ]       a.. ... ... ... ... .c. ... ... ... ... g.. ..g ... ...  a.. a..>
OspA-BO            250           260           270           280
[ 2558 ]       .a. ... ... ... ... .c. ... ... ... ... g.. ... ... ...  ... a..>
OSPA-IP3           250           260           270           280
[ 2558 ]       .a. ... ... ... ... .c. ... ... ... ... g.. ... ... ...  a.. a..>
OspA-PKO           250           260           270           280
[ 2558 ]       .a. ... ... ... ... .c. ... ... ... ... g.. ... ... ...  ... a..>
OspA-ACAI          250           260           270           280
[ 2558 ]       .a. ... ... ... ... .c. ... ... ... ... g.. ... ... ...  a.. a..>
ospA-P-GAU         250           260           270           280
[ 2544 ]       .a. ... ... ... ... .c. ... ... ... ... g.. ... ... ...  a.. a..>

               290        300           310          320          330
                *    *     *     *     *     *     *     *     *    *     *
OspA-B31       ACC ACA CTT GAA GTT TTC AAA GAA GAT GGC AAA ACA CTA GTA  TCA AAA
               TGG TGT GAA CTT CAA AAG TTT CTT CTA CCG TTT TGT GAT CAT  AGT TTT

OspA-B31       290        300           310          320          330
[ 3288 ]       ... ... ... ... ... ... ... ... ... ... ... ... ... ...  ... ...>
OspA-KA        290        300           310          320          330
[ 3283 ]       ... ... ... ... ... ... ... ... ... ... ... ... ... ...  ... ...>
OspA-N40       290        300           310          320          330
[ 3276 ]       ... ... ... ... ... ... ... ... ... ... ... ... ... ...  ... ...>
OspA-ZS7       290        300           310          320          330
[ 3264 ]       ... ... ... ... ... ... ... ... ... ... ... ... ... ...  ... ...>
OspA-25015     290        300           310          320          330
[ 2802 ]       ... ... ... ... ... ..a ... ... ... ... ... ... t.. ..g  ... ...>
OspA-TRO       290        300           310          320          330
[ 2648 ]       ... ... t.. ... a.. ... ... ... ... ... ... ... t.. ...  ... ...>
OspA-K48       290        300           310          320          330
[ 2584 ]       ..t .a. t.. ... a.. ... ... ... ... .c. ... ... t.. ...  ... ...>
OspA-HE 11     290        300           310          320          330
[ 2580 ]       ... ... t.. ... a.c ... ... ... ... ... ... ... t.. ...  ..g ...>
OspA-DK29      290        300           310          320          330
[ 2566 ]       ..t .a. t.. ... a.. ... ... ... ... ... ... ... t.. ...  ... ...>
OspA-Ip90      290        300           310          320          330
[ 2562 ]       ... ... t.. ... a.c ... ... ... ... ... ... ... t.. ...  ... ...>
OspA-BO        290        300           310          320          330
[ 2558 ]       ... ... t.c ... c.. ... ... ... ... ... ... ... t.. ..g  ... .g.>
OSPA-IP3       290        300           310          320          330
[ 2558 ]       ... ... t.c ... c.. ... ... ... ... ... ... ... t.. ..g  ... .g.>
```

FIG. 17F

```
OspA-PKO    290          300          310          320          330
[ 2558 ]    ... ... t.c ... c.. ... ... ... ... ... ... ... t.. ..g ... .g.>

OspA-ACA1   290          300          310          320          330
[ 2556 ]    ... ... t.c ... c.. ... ... ... ... ... ... ... t.. ..g ... .g.>

ospA-P-GAU  290          300          310          320          330
[ 2544 ]    ... ... t.c ... c.. ..a ... ... ... ... ... ... t.. ..g ... .g.>

                340          350          360          370          380
                  *     *     *     *     *     *     *     *     *
OspA-B31    AAA GTA ACT TCC AAA GAC AAG TCA TCA ACA GAA GAA AAA TTC AAT GAA
            TTT CAT TGA AGG TTT CTG TTC AGT AGT TGT CTT CTT TTT AAG TTA CTT

OspA-B31     340          350          360          370          380
[ 3288 ]    ... ... ... ... ... ... ... ... ... ... ... ... ... ...  ... ...>

OspA-KA      340          350          360          370          380
[ 3288 ]    ... ... ... ... ... ... ... ... ... ... ... ... ... ...  ... ...>

OspA-N40     340          350          360          370          380
[ 3276 ]    ... ... ... ... ... ... ... ... ... ... ... ... ... ...  ... ...>

OspA-ZS7     340          350          360          370          380
[ 3264 ]    ... ... ... ... ... ... ... ... ... ... ... ... ... ...  ... ...>

OspA-25015   340          350          360          370          380
[ 2802 ]    ... ag. ... ..t ... ..t ... ... ... ... ... ... ..g ...  ... ...>

OspA-TRO     340          350          360          370          380
[ 2648 ]    ... ... .a. ..t ... ..t ... ... ... .t. ... ... ... ...  ..c .c.>

OspA-K48     340          350          360          370          380
[ 2584 ]    ... ... ..c ctt ... ... ... ... ... ... ... ... ... ...  ..c ...>

OspA-HB 11   340          350          360          370          380
[ 2590 ]    ... ... ..c ctt ... ... ... ... ... ... ... ... ... ...  ..t ...>

OspA-DK29    340          350          360          370          380
[ 2566 ]    ... ... ..c ctt ... ... ... ... ... ... ... ... ... ...  ..c .g.>

OspA-Ip90    340          350          360          370          380
[ 2562 ]    ... ... ..c ctt ... ... ... ... ... ... ... ... ... ...  ..c .c.>

OspA-PO      340          350          360          370          380
[ 2553 ]    ... ... .g. ..t ... ... ..a a.. ... ... ..t ... .tg ...  ... ...>

OSPA-IP3     340          350          360          370          380
[ 2553 ]    ... ... .g. ..t ... ... ..a a.. ... ... ..t ... .tg ...  ... ...>

OspA-PKO     340          350          360          370          380
[ 2558 ]    ... ... .g. ..t ... ... ..a a.. ... ... ..t ... .tg ...  ... ...>

OspA-ACA1    340          350          360          370          380
[ 2556 ]    ... ... .g. ..t ... ... ..a a.. ... ... ..t ... .tg ...  ... ...>
```

FIG. 17G

```
OspA-P-GAU     340           350           360            370          380
[ 2544 ]     ... ... .g. ..t .g. ... ..a a.. ... ... ..t ... .tg ... ... ...>

                     390           400           410           420           430
              *   *     *   *     *   *     *     *     *     *
OspA-B31     AAA GTT GAA GTA TCT GAA AAA ATA ATA ACA AGA GCA GAC GGA ACC AGA
             TTT CCA CTT CAT AGA CTT TTT TAT TAT TGT TCT CGT CTG CCT TGG TCT

OspA-B31         390           400           410           420           430
[ 3288 ]     ... ... ... ... ... ... ... ... ... ... ... ... ... ... ... ...>

OspA-KA          390           400           410           420           430
[ 3289 ]     ... ... ... ... ... ... ... ... ... ... ... ... ... ... ... ...>

OspA-N40         390           400           410           420           430
[ 3276 ]     ... ... ... ... ... ... ... ... ... ... ... ... ... ... ... ...>

OspA-ZS7         390           400           410           420           430
[ 3264 ]     ... ... ... ... ... ... ... ... ... ... ... ... ... ... ... ...>

OspA-25015       390           400           410           420           430
[ 2902 ]     ... ..c ... t.. gc. ... ... ... ..g g.. ... ... a.. ... ... .t.>

OspA-TRO         390           400           410           420           430
[ 2648 ]     ... ... ... t.. ... ... ... .c. ... ct. ... ... a.. ... ... ..g>

OspA-K48         390           400           410           420           430
[ 2584 ]     ..g ... ... ac. ... ... ... .c. ... gt. ... ... a.t ... ... ...>

OspA-HE 11       390           400           410           420           430
[ 2580 ]     ..g t.. ... a.. ... ... ... .c. ... gt. ... ... a.t ... ... ...>

OspA-DK29        390           400           410           420           430
[ 2566 ]     ..g ... ... ac. ... ... ... .c. ... gt. ... ... a.t ... ... ...>

OspA-Ip90        390           400           410           420           430
[ 2562 ]     ..g ... ... .c. ... ... ... .c. ... gt. ... ... a.t ... ... ...>

OspA-BO          390           400           410           420           430
[ 2558 ]     ... ... ... t.g ... .c. ... .cc ..g ... ... .a. a.t ... ... .a.>

OspA-IP3         390           400           410           420           430
[ 2558 ]     ... ... ... t.g ... .c. ... .cc ..g ... ... .a. a.t ... ... .a.>

OspA-PKO         390           400           410           420           430
[ 2558 ]     ... ... ... t.g ... .c. ... .cc ..g ... ... .a. a.t ... ... .a.>

OspA-ACA1        390           400           410           420           430
[ 2556 ]     ... ... ... t.g ... .c. ... .cc ..g ... ... .a. a.t ... ... .a.>

OspA-P-GAU       390           400           410           420           430
[ 2544 ]     ... ... ... t.g ... .c. ... .cc ..g ... ... .a. a.t ... ... .a.>

                 440           450           460           470           480
              *   *     *   *     *     *   *     *     *   *
OspA-B31     CTT GAA TAC ACA GGA ATT AAA AGC GAT GGA TCT GGA AAA GCT AAA GAG
```

FIG. 17B

```
              GAA CTT ATG TGT CCT TAA TTT TCG CTA CCT AGA CCT TTT CGA TTT CTC
OspA-B31           440         450         460         470         480
[ 3283 ]      ... ... ... ... ... ... ... ... ... ... ... ... ... ... ... ...>

OspA-KA            440         450         460         470         480
[ 3286 ]      ... ... ... ... ... ... ... ... ... ... ... ... ... ... ... ...>

OspA-N40           440         450         460         470         480
[ 3276 ]      ... ... ... ... .a. ... ... ... ... ... ... ... ... ... ... ...>

OspA-ZS7           440         450         450         470         480
[ 3354 ]      ... ... ... ... .a. ... ... ... ... ... ... ... ... ... ... ...>

OspA-25015         440         450         460         470         480
[ 2802 ]      ... ... ... ... ... ... ... ... ... ... ..c ... ... ... ... ..a>

OspA-TRO           440         450         460         470         480
[ 2548 ]      ... ... ... ... .a. ..a ... ... ... ... a.c ... ... ... ... ..a>

OspA-K48           440         450         460         470         480
[ 2584 ]      ... ... ... ... .ac ..a ... ... ... ... ..c ... ... ... ... ..a>

OspA-HB 11         440         450         460         470         480
[ 2580 ]      ... ... ... ... .ac ..a ... ... ... aa. a.c ... ... ... ... ..a>

OspA-DK29          440         450         460         470         480
[ 2565 ]      ... ... ... ... .ac ..a ... ... ... ... ..c ... ... ... ... ..a>

OspA-Ip90          440         450         460         470         480
[ 2562 ]      ... ... ... ... .ac ..a ... ... ... aa. a.c ... ... ... ... ..a>

OspA-BO            440         450         460         470         480
[ 2558 ]      ... ... ..t ... .a. ..g ... ... ... ... a.c ... ... ... ... ..a>

OSPA-IP3           440         450         460         470         480
[ 2558 ]      ... ... ..t ... .a. ..g ... ... ... ... a.c ... ... ... ... ..a>

OspA-PKO           440         450         450         470         480
[ 2558 ]      ... ... ..t ... .a. ..g ... ... ... ... a.c ... ... ... ... ..a>

OspA-ACAI          440         450         460         470         490
[ 2556 ]      ... ... ..t ... .a. ..g ... ... ... ... a.c ... ... ... ... ..a>

ospA-P-GAU         440         450         460         470         480
[ 2544 ]      ... ... ..t ... .a. ..g ... ... ... ... a.c ... ... ... ... ..a>

                   490         500         510         520
               *    *    *    *    *    *    *    *    *
OspA-B31      GTT TTA AAA GCC TAT GTT CTT GAA GGA ACT CTA ACT GCT GAA AAA ACA
              CAA AAT TTT CGG ATA CAA GAA CTT CCT TGA GAT TGA CGA CTT TTT TGT

OspA-B31           490         500         510         520
[ 3283 ]      ... ... ... ... ... ... ... ... ... ... ... ... ... ... ... ...>

OspA-KA            490         500         510         520
[ 3288 ]      ... ... ... ... ... ... ... ... ... ... ... ... ... ... ... ...>
```

FIG. 17I

```
OspA-N40            490         500         510         520
[ 3276 ]   ... ... ... ... ... ... ... ... ... ... ... ... ... ... ... ...>

OspA-ZS7            490         500         510         520
[ 3264 ]   ... ... ... a.. ... ... ... ... ... ... t.. ... ... ... ... ...>

OspA-25015          490         500         510         520
[ 2802 ]   ac. ... ... .aa ... ... ... ... ... ... ... ... ... ... ... g..>

OspA-TRO.           490         500         510         520
[ 2548 ]   .c. .t. ... .a. .t. .c. ... ... ... ... ... g.. ..c ..c ... ...>

                                                          cgg
                                                           |
OspA-K48            490         500         510         520|      530
[ 2584 ]   ... ... ... .a. .t. ac. ... ... ... ... ... g.. ... ..c ... ...>

                                                          cgg
                                                           |
OspA-HB 11          490         500         510         520|      530
[ 2590 ]   ... ... ... .a. .t. ac. ... ... ... ... ... g.. ... ..c ... ...>

                                                          cgg
                                                           |
OspA-DK29           490         500         510         520|      530
[ 2566 ]   ... ... ... .a. .t. ac. ... ... ... ... ... g.. ... ..c ... ...>

                                                          cgg
                                                           |
OspA-Ip90           490         500         510         520|      530
[ 2562 ]   ... ... ... .a. .t. .c. ... ... ... ... ... g.. ... ..c ... ...>

OspA-20             490         500         510         520
[ 2558 ]   ... ... ... aa. .t. ac. ... ... ... .aa g.. g.. aa. ..t ... gt.>

OSPA-IP3            490         500         510         520
[ 2558 ]   ... ... ... aa. .t. ac. ... ... ... .aa g.. g.. aa. ..t ... gt.>

OspA-PKO            490         500         510         520
[ 2558 ]   ... ... ... aa. .t. ac. ... ... ... .aa g.. g.. aa. ..t ... gt.>

OspA-ACAI           490         500         510         520
[ 2556 ]   ... ... ... aa. .t. ac. ... ... ... .aa g.. g.. aa. ..t ... gt.>

ospA-F-GAU          490         500         510         520
[ 2544 ]   ... ... ... aag .t. ac. ... ... ... .aa g.. g.. aa. ..t ... gt.>

           530         540         550         560         570
            *     *     *     *     *     *     *     *     *     *
OspA-B31   ACA TTC GTG GTT AAA GAA GGA ACT GTT ACT TTA AGC AAA AAT ATT TCA
           TGT AAG CAC CAA TTT CTT CCT TGA CAA TGA AAT TCG TTT TTA TAA AGT

OspA-B31   530         540         550         560         570
[ 3238 ]   ... ... ... ... ... ... ... ... ... ... ... ... ... ... ... ...>

OspA-KA    530         540         550         560         570
```

```
[ 3288 ]          ... ... ... ... ... ... ... ... ... ... ... ... ... ... ... ...>

OspA-N40     530            540           550           560           570
[ 3276 ]          ... ... ... ... ... ... ... ... ... ... ... ... ... ... ... ...>

OspA-ZS7     530            540           550           560           570
[ 3264 ]          ... ... ... ... ... ... ... ... ... ... ... ... ... ... ... ...>

OspA-25015   530            540           550           560           570
[ 2802 ]          ... ... ... ... ... ... ... ... ... ... ... ..t ..g c.c ... ...>

OspA-TRO     530            540           550           560           570
[ 2648 ]          ... ... aaa ... .c. ... ..c ... ... gt. ... ... ... c.c ... c..>

OspA-K48                540           550           560-          570
[ 2584 ]          ... ... aaa ... .c. ... ..c ... ... gt. ... ... ..g ..c ... .t.>

OspA-HB 11              540           550           560           570
[ 2580 ]          ... ... aaa ... .c. ..g ..c ... ... ... ... ... ..g ..c ... ...>

OspA-DK29               540           550           560           570
[ 2566 ]          ... ... aaa ... .c. ... ..c ... ... gt. ... ... ..g ..c ... .t.>

OspA-Ip90               540           550           560           570
[ 2562 ]          ... ..a aaa ... .c. ... ..c ... ... gt. ... ... ... c.c ... ...>

OspA-BO      530            540           550           560           570
[ 2558 ]          ... ... .aa ..a ... ... ... ..c ... ... ... ..t ..g g.a ... g..>

OSPA-IF3     530            540           550           560           570
[ 2558 ]          ... ... .aa ..a ... ... ... ..c ... ... ... ..t ..g g.a ... g..>

OspA-PKO     530            540           550           560           570
[ 2558 ]          ... ... .aa ..a ... ... ... ..c ... ... ... ..t ..g g.a ... g..>

OspA-ACA I   530            540           550           560           570
[ 2556 ]          ... ... .aa ..a ... ... ... ..c ... ... ... ..t ..g g.a ... g..>

ospA-P-GAU   530            540           550           560           570
[ 2544 ]          ... ... .aa ..a ... ... ... ..c ... ... ... ..t ..g g.a ... g..>


                   580           590           600           610           620
                    *     *     *      *     *     *     *     *     *
OspA-B31          AAA TCT GGG GAA GTT TCA GTT GAA CTT AAT GAC ACT GAC AGT AGT GCT
                  TTT AGA CCC CTT CAA AGT CAA CTT GAA TTA CTG TGA CTG TCA TCA CGA

OspA-B31           580           590           600           610           620
[ 3288 ]          ... ... ... ... ... ... ... ... ... ... ... ... ... ... ... ...>

OspA-KA            580           590           600           610           620
[ 3298 ]          ... ... ... ... ... ... ... ... ... ... ... ... ... ... ... ...>

OspA-N40           580           590           600           610           620
[ 3276 ]          ... ... ... ... ... ... ... ... ... ... ... ... ... ... ... ...>

OspA-ZS7           580           590           600           610           620
[ 3264 ]          ... ... ... ... ... ... ... ... ... ... ... ... ... ... ... ...>
```

FIG. 17K

```
OspA-25015    580         590         600          610        620
[ 2802 ]      ... ... ..a ... ..a a.. .c. ... ... ... ... ... ... ... .c. caa>

OspA-TRO      580         590 .       600          610        620
[ 2648 ]      ..c ... ..a ... a.a a.. ... ..g ... ... ... t.. a.. tc. .c. cag>

OspA-K48  580         590         600          610        620
[ 2584 ]      ... ..c ..a ... a.a a.. ... .c. ... g.. ... t.. ... .c. .c. cag>

OspA-HB 11580         590         600          610        620
[ 2380 ]      ... ..c ..a ... a.a a.. ... .c. ... g.. ... ... ... tc. .-- ..g>

OspA-DK29 580         590         600          610        620
[ 2566 ]      ... ..c ..a ... a.a a.. .c. .c. ... g.- ---t-- ... .c. .c. cgg>

OspA-Ip90 580         590         600          610        620
[ 2562 ]      ..c ... ..a ... a.a a.. ... ..g ... ... ... t.. ... .c. .c. cag>

OspA-BO       580         590         600          610        620
[ 2558 ]      ... ... ..a ... ..a a.. ... .ct ... ... ... ... a.. .c. .c. cag>

OSPA-IP3      580         590         600          610        620
[ 2558 ]      ... ... ..a ... ..a a.. ... .ct ... ... ... ... a.. .c. .c. cag>

OspA-PKO      580         590         600          610        620
[ 2558 ]      ... ... ..a ... ..a a.. ... .ct ... ... ... ... a.. .c. .c. cag>

OspA-ACAI     580         590         600          610        620
[ 2556 ]      ... ... ..a ... ..a a.. ... .ct ... ... ... ... a.. .c. .c. cag>

OspA-P-GAU    580         590         600          610        620
[ 2544 ]      ... ... ..a ... ..a a.. ... .ct ... ... ... ... a.. .c. .c. cag>


                  630         640         650         660         670
              *   *   *   *   *   *   *   *   *   *
OspA-B31      GCT ACT AAA AAA ACT GCA GCT TGG AAT TCA GGC ACT TCA ACT TTA ACA
              CGA TGA TTT TTT TGA CGT CGA ACC TTA AGT CCG TGA AGT TGA AAT TGT

OspA-B31          630         640         650         660         670
[ 3283 ]      ... ... ... ... ... ... ... ... ... ... ... ... ... ... ... ...>

OspA-KA           630         640         650         660         670
[ 3288 ]      ... ... ... ... ... ... ... ... ... ... ... ... ... ... ... ...>

OspA-N40          630         640         650         660         670
[ 3276 ]      ... ... ... ... ... ... ... ... ... ... ... ... ... ... ... ...>

OspA-ZS7          630         640         650         660         670
[ 3264 ]      ... ... ... ... ... ... ... ... ... ... ... ... ... ... ... ...>

OspA-25015        630         640         650         660         670
[ 2802 ]      ... ... ... ... ... .gg aaa ... g.. g.. ... ... ... ... ... ...>

OspA-TRO          630         640         650         660         670
[ 2648 ]      ... ... ... ... ... .g. aaa ... g.. ... aat ... ..c ... ... ...>
```

FIG. 17L

```
OspA-K48       630        640        650        660        670
[ 2584 ]       ... ... ... ... ... .g. aaa ... g.. ... aaa ... ..c ... ... ...>

OspA-HE 11      630        640        650        660        670
[ 2580 ]       ... .a. ... ... t.c .g. a.a ... g.. ... ..t ... ..t ... ... ...>

OspA-DK29      630        640        650        660        670
[ 2556 ]       ... ... ... ... ... .g. aaa ... g.. ... aag ... ..c ... ... ...>

OspA-Ip90      630        640        650        660        670
[ 2562 ]       ... ... ... ... ... .g. a.a ... g.. ... aag ... ..c ... ... ...>

OspA-BO         630        640        650        660        670
[ 2558 ]       ... ... ... ... ... .gc ..a ... g.. ... aaa ... ..t ... ... ...>

OSPA-IP3        630        640        650        660        670
[ 2558 ]       ... ... ... ... ... .gc ..a ... g.. ... aaa ... ..t ... ... ...>

OspA-PKO        630        640        650        660        670
[ 2558 ]       ... ... ... ... ... .gc ..a ... g.. ... aaa ... ..t ... ... ...>

OspA-ACAI       630        640        650        660        670
[ 2556 ]       ... ... ... ... ... .gc ..a ... g.. ... aaa ... ..t ... ... ...>

OspA-P-GAU      630        640        650        660        670
[ 2544 ]       ... ... ... ... ... .gc ..a ... g.. ... aaa ... ..t ... ... ...>

                   680        690        700        710        720
                *     *     *     *     *     *     *     *
OspA-B31       ATT ACT GTA AAC AGT AAA AAA ACT AAA GAC CTT GTG TTT ACA AAA GAA
               TAA TGA CAT TTG TCA TTT TTT TGA TTT CTG GAA CAC AAA TGT TTT CTT

OspA-B31           680        690        700        710        720
[ 3288 ]       ... ... ... ... ... ... ... ... ... ... ... ... ... ... ... ...>

OspA-KA            680        690        700        710        720
[ 3288 ]       ... ... ... ... ... ... ... ... ... ... ... ... ... ... ... ...>

OspA-N40           680        690        700        710        720
[ 3276 ]       ... ... ... ... ... ... ... ... ... ... ... ... ... ... ... ...>

OspA-ZS7           680        690        700        710        720
[ 3264 ]       ... ... ... ... ... ... ... ... ... ... ... ... ... ... ... ...>

OspA-25015         680        690        700        710        720
[ 2802 ]       ... ... ... ... .ac ... ... ... ... .c. ... ..a ... ... ... c..>

OspA-TRO           680        690        700        710        720
[ 2648 ]       ... .g. ..g ..t ..c ... ... ... ... a.. a.. ..a ... ... ... ...>

OspA-K48        680        690        700        710        720
[ 2584 ]       ... .g. ..g ..t ..c c.. ... ..c ... a.. ... ..a ..c ... ... ...>

OspA-HE 11         680        690        700        710        720
[ 2580 ]       ... .g. aa. ... ..a c.. ... ... ... c.a ... ..a ..c ... ... ...>

OspA-DK29       680        690        700        710        720
```

```
[ 2566 ]     ... .g. ..g ..t ..c c.. ... ..c ... a.. ... ..a ..c ... ... ...>

OspA-Ip90        680          690           700         710           720
[ 2562 ]     ... .g. ..g ..t ..c cg. ... ..c ... a.. ... ..a ..c ... ... ...>

OspA-BO            680          690           700         710            720
[ 2558 ]     ... .g. ..t ... ..c ... ... ... .c. c.a ... ... ... ..t ... c..>

OSPA-IP3           680          690           700         710            720
[ 2558 ]     ... .g. ..t ... ... ... ... ... .c. c.a ... ... ... ..t ... c..>

OspA-PKO           680          690           700         710            720
[ 2558 ]     ... .g. ..t ... ..c ... ... ... .c. c.a ... ... ... ..t ... c..>

OspA-ACA1          680          690           700         710            720
[ 2556 ]     ... .g. ..t ... ..c ... ... ... .c. c.a ... ... ... ..t ... c..>

ospA-P-GAU         680          690           700         710            720
[ 2544 ]     ... .g. ..t ... ..c ... ... ... .c. c.a ... ... ... ..t ... c..>

                       730           740           750           760
                   *       *       *       *       *       *       *       *       *
OspA-B31     AAC ACA ATT ACA GTA CAA CAA TAC GAC TCA AAT GGC ACC AAA TTA GAG
             TTG TGT TAA TGT CAT GTT GTT ATG CTG AGT TTA CCG TGG TTT AAT CTC

OspA-B31               730           740           750           760
[ 3288 ]     ... ... ... ... ... ... ... ... ... ... ... ... ... ... ... ...>

OspA-KA                730           740           750           760
[ 3288 ]     ... ... ... ... ... ... ... ... ... ... ... ... ... ... ... ...>

OspA-N40               730           740           750           760
[ 3276 ]     ... ... ... ... ... ... ... ... ... ... ... ... ... ... ... ...>

OspA-ZS7               730           740           750           760
[ 3264 ]     ... ... ... ... ... ... ... ... ... ... ... ... ... ... ... ...>

OspA-25015             730           740           750           760
[ 2802 ]     g.. ... ... ... tc. ... a.. ... ... ... gca ..a ... ..c ..g ..a>

OspA-TRO               730           740           750           760
[ 2648 ]     g.. ... ..a ... ... ... a.. ... ... ... gca ... ... ..t c.. ..a>

OspA-K48           730           740           750           760           770
[ 2584 ]     g.. ... ..a ... ... ... a.. ... ... ... gca ... ... ..t c.. ..a>

OspA-HE 11             730           740           750           760
[ 2580 ]     g.. ... ..a ... ... ... a.c ... ... ... gca ... ... ..t c.. ..a>

OspA-DK29          730           740           750           760           770
[ 2565 ]     g.. ... ..a ... ... ... ag. ... ... ... gca ... ... ..t c.. ..a>

OspA-Ip90          730           740           750           760           770
[ 2562 ]     g.. ... ..a ... ... ... a.. ... ... ... gca ... ... ..t c.. ..a>

OspA-BO                730           740           750           760
[ 2558 ]     g.. ... ..a ..t ... ... a.. ... ... ..c gca ..t ... ..t ... ..a>
```

FIG. 17N

```
OSPA-IP3              730          740          750            760
[ 2558 ]   g.. ... ..a ..t ... ... a.. ... ... ..c gca ..t ... ..t ... ..a>

OspA-PKO              730          740          750            760
[ 2558 ]   g.. ... ..a ..t ... ... a.. ... ... ..c gca ..t ... ..t ... ..a>

OspA-ACAI             730          740          750            760
[ 2556 ]   g.. ... ..a ..t ... ... a.. ... ... ..c gca ..t ... ..t ... ..a>

ospA-P-GAD            730          740          750            760
[ 2544 ]   t.. ... ..a ..t ... a.. ... ... ... ..c gca ..t ... ..t ... ..a>

           770.         780          790          800          810
            *       *    *      *      *     *     *      *     *     *
OspA-B31    GGG TCA GCA GTT GAA ATT ACA AAA CTT GAT GAA ATT AAA AAC GCT TTA
            CCC AGT CGT CAA CTT TAA TGT TTT GAA CTA CTT TAA TTT TTG CGA AAT

OspA-B31   770          780          790          800          810
[ 3288 ]    ... ... ... ... ... ... ... ... ... ... ... ... ... ... ... ...>

OspA-KA    770          780          790          800          810
[ 3288 ]    ... ... ... ... ... ... ... ... ... ... ... ... ... ... ... ...>

OspA-N40   770          780          790          800          810
[ 3276 ]    ... ... ... ... ... ... ... ... ... ... ... ... ... ... ... ...>

OspA-ZS7   770          780          790          800          810
[ 3264 ]    ... ... ... ... ... ... ... ... ... ... ... ... ... ... ... ...>

OspA-25015 770          780          790          800          810
[ 2802 ]    ..c a.. ... ..c ... ... .a. .c. ... ... ... c.. ... ... ... ...>

OspA-TRO   770          780          790          800          810
[ 2543 ]    ..c aac ... ..c ... ... .a. .c. ... ... ... c.. ... ... ... ...>

OspA-K48                780          790          800          810
[ 2584 ]    ..c aa. ... ..c ... ... ... .c. ... a.a ... c.. ... ... ... ...>

OspA-HE 11 770          780          790          800          810
[ 2590 ]    ..c aa. ... ..c ... ... ... .c. ... a.a ... c.. ... ... ... ...>

OspA-DK29               780          790          800          810
[ 2566 ]    ..c aa. ... ..c ... ... ... .c. ... a.a ... c.. ... ... ... ...>

OspA-Ip90               780          790          800          810
[ 2562 ]    ..c aa. ... ..c ... ... ... .cg ... a.a ... c.. ... g.t ... ...>

OspA-DO    770          780          790          800          810
[ 2558 ]    ..c a.. ... ..c ... ... .a. .c. ... ... ... c.. ... ... ... ...>

OSPA-IP3   770          780          790          800          810
[ 2558 ]    ..c a.. ... ..c ... ... .a. .c. ... ... ... c.. ... ... ... ...>

OspA-PKO   770          780          790          800          810
[ 2558 ]    ..c a.. ... ..c ... ... .a. .c. ... ... ... c.. ... ... ... ...>
```

FIG. 17O

```
OspA-ACAI  770          780           790          800          810
[ 2556 ]    ..c a.. ... ..c ... ... .a. .c. ... ... ... c.. ... ... ... ..g>

ospA-P-GAU 770          780           790          800          810
[ 2544 ]    ..c a.. ... ..c ... ... .a. .c. ... ... ... c.. ... ... ... ...>


              820
               *
OspA-B31     AAA TAA
             TTT ATT

OspA-B31      820
[ 3288 ]     ... ...>

OspA-KA       820
[ 3288 ]     ... ...>

OspA-N40      820
[ 3276 ]     ... ...>

OspA-ZS7      820
[ 3264 ]     ... ...>

OspA-25015
[ 2802 ]     .g.>

OspA-TRO      820
[ 2648 ]     ... ..>

OspA-K48  820
[ 2584 ]     ... ...>

OspA-HE 11    820
[ 2580 ]     ... ..>

OspA-DK29 820
[ 2566 ]     ... ...>

OspA-Ip90 820
[ 2562 ]     ... ..>

OspA-BO       820
[ 2558 ]     ... ..>

OSPA-IP3      820
[ 2558 ]     ... ..>

OspA-FKO      820
[ 2558 ]     ... ..>

OspA-ACAI     820
[ 2556 ]     ... ...>

ospA-P-GAU    820
[ 2544 ]     ... ...>
```

FIG. 17P

```
                10                  20                  30                  40
     *           *        *          *        *          *        *          *        *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

     50                  60                  70                  80                  90
     *           *        *          *        *          *        *          *        *
GCA TGT AAG CAA AAT GTT AGC AGC CTT GAT GAA AAA AAT AGC GTT
CGT ACA TTC GTT TTA CAA TCG TCG GAA CTA CTT TTT TTA TCG CAA

                100                 110                 120                 130
     *           *        *          *        *          *        *          *        *
TCA GTA GAT TTA CCT GGT GGA ATG ACA GTT CTT GTA AGT AAA GAA
AGT CAT CTA AAT GGA CCA CCT TAC TGT CAA GAA CAT TCA TTT CTT

     140                 150                 160                 170                 180
     *           *        *          *        *          *        *          *        *
AAA GAC AAA GAC GGT AAA TAC AGT CTA GAG GCA ACA GTA GAC AAG
TTT CTG TTT CTG CCA TTT ATG TCA GAT CTC CGT TGT CAT CTG TTC

                190                 200                 210                 220
     *           *        *          *        *          *        *          *        *
CTT GAG CTT AAA GGA ACT TCT GAT AAA AAC AAC GGT TCT GGA ACA
GAA CTC GAA TTT CCT TGA AGA CTA TTT TTG TTG CCA AGA CCT TGT

     230                 240                 250                 260                 270
     *           *        *          *        *          *        *          *        *
CTT GAA GGT GAA AAA ACT GAC AAA AGT AAA GTA AAA TTA ACA ATT
GAA CTT CCA CTT TTT TGA CTG TTT TCA TTT CAT TTT AAT TGT TAA

                280                 290                 300                 310
     *           *        *          *        *          *        *          *        *
GCT GAT GAC CTA AGT CAA ACT AAA TTT GAA ATT TTC AAA GAA GAT
CGA CTA CTG GAT TCA GTT TGA TTT AAA CTT TAA AAG TTT CTT CTA

     320                 330                 340                 350                 360
     *           *        *          *        *          *        *          *        *
GCC AAA ACA TTA GTA TCA AAA AAA GTA ACC CTT AAA GAC AAG TCA
CGG TTT TGT AAT CAT AGT TTT TTT CAT TGG GAA TTT CTG TTC AGT

                370                 380                 390                 400
     *           *        *          *        *          *        *          *        *
TCA ACA GAA GAA AAA TTC AAC GAA AAG GGT GAA ACA TCT GAA AAA
AGT TGT CTT CTT TTT AAG TTG CTT TTC CCA CTT TGT AGA CTT TTT

     410                 420                 430                 440                 450
     *           *        *          *        *          *        *          *        *
ACA ATA GTA AGA GCA AAT GGA ACC AGA CTT GAA TAC ACA GAC ATA
TGT TAT CAT TCT CGT TTA CCT TGG TCT GAA CTT ATG TGT CTG TAT

                460                 470                 480                 490
     *           *        *          *        *          *        *          *        *
AAA AGC GAT GGA TCC GGA AAA GCT AAA GAA GTT TTA AAA GAC TTT
TTT TCG CTA CCT AGG CCT TTT CGA TTT CTT CAA AAT TTT CTG AAA

     500                 510                 520                 530                 540
     *           *        *          *        *          *        *          *        *
ACT CTT GAA GGA ACT CTA GCT GCT GAC GGC AAA ACA ACA TTG AAA
TGA GAA CTT CCT TGA GAT CGA CGA CTG CCG TTT TGT TGT AAC TTT

                550                 560                 570                 580
     *           *        *          *        *          *        *          *        *
GTT ACA GAA GGC ACT GTT GTT TTA AGC AAG AAC ATT TTA AAA TCC
```

Fig. 18A

```
CAA TGT CTT CCG TGA CAA CAA AAT TCG TTC TTG TAA AAT TTT AGG

   590           600           610           620           630
    *     *     *     *     *     *     *     *     *     *
GGA GAA ATA ACA GTT GCA CTT GAT GAC TCT GAC ACT ACT CAG GCT
CCT CTT TAT TGT CAA CGT GAA CTA CTG AGA CTG TGA TGA GTC CGA

         640           650           660           670
    *     *     *     *     *     *     *     *     *
ACT AAA AAA ACT GGA AAA TGG GAT TCA AAT ACT TCC ACT TTA ACA
TGA TTT TTT TGA CCT TTT ACC CTA AGT TTA TGA AGG TGA AAT TGT

   680           690           700           710           720
    *     *     *     *     *     *     *     *     *
ATT AGT GTG AAT AGC AAA AAA ACT AAA AAC ATT GTA TTT ACA AAA
TAA TCA CAC TTA TCG TTT TTT TGA TTT TTG TAA CAT AAA TGT TTT

         730           740           750           760
    *     *     *     *     *     *     *     *     *
GAA GAC ACA ATA ACA GTA CAA AAA TAC GAC TCA GCA GGC ACC AAT
CTT CTG TGT TAT TGT CAT GTT TTT ATG CTG AGT CGT CCG TGG TTA

   770           780           790           800           810
    *     *     *     *     *     *     *     *     *
CTA GAA GGC AAC GCA GTC GAA ATT AAA ACA CTT GAT GAA CTT AAA
GAT CTT CCG TTG CGT CAG CTT TAA TTT TGT GAA CTA CTT GAA TTT

         820
    *     *     *
AAC GCT TTA AAA TAG
TTG CGA AAT TTT ATC
```

FIG. 18B

```
             10          20          30          40
     *        *     *     *     *     *     *     *     *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

     50          60          70          80          90
     *     *     *     *     *     *     *     *     *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA

            100         110         120         130
     *     *     *     *     *     *     *     *     *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT

    140         150         160         170         180
     *     *     *     *     *     *     *     *     *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC

            190         200         210         220
     *     *     *     *     *     *     *     *     *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC

    230         240         250         260         270
     *     *     *     *     *     *     *     *     *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA

            280         290         300         310
     *     *     *     *     *     *     *     *     *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA

    320         330         340         350         360
     *     *     *     *     *     *     *     *     *
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT

            370         380         390         400
     *     *     *     *     *     *     *     *     *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT

    410         420         430         440         450
     *     *     *     *     *     *     *     *     *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC

            460         470         480         490
     *     *     *     *     *     *     *     *     *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA

    500         510         520         530         540
     *     *     *     *     *     *     *     *     *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT

            550         560         570         580
     *     *     *     *     *     *     *     *     *
AAA GAA GGA ACC GTT ACT TTA AGT AAG GAA ATT GCA AAA TCT GGA
```

FIG. 19A

```
TTT CTT CCT TGG CAA TGA AAT TCA TTC CTT TAA CGT TTT AGA CCT

    590         600         610         620         630
     *     *     *     *     *     *     *     *     *
GAA GTA ACA GTT GCT CTT AAT GAC ACT AAC ACT ACT CAG GCT ACT
CTT CAT TGT CAA CGA GAA TTA CTG TGA TTG TGA TGA GTC CGA TGA

          640         650         660         670
     *     *     *     *     *     *     *     *     *
AAA AAA ACT GGC GCA TGG GAT TCA AAA ACT TCT ACT TTA ACA ATT
TTT TTT TGA CCG CGT ACC CTA AGT TTT TGA AGA TGA AAT TGT TAA

    680         690         700         710         720
     *     *     *     *     *     *     *     *     *
AGT GTT AAC AGC AAA AAA ACT ACA CAA CTT GTG TTT ACT AAA CAA
TCA CAA TTG TCG TTT TTT TGA TGT GTT GAA CAC AAA TGA TTT GTT

          730         740         750         760
     *     *     *     *     *     *     *     *     *
GAC ACA ATA ACT GTA CAA AAA TAC GAC TCC GCA GGT ACC AAT TTA
CTG TGT TAT TGA CAT GTT TTT ATG CTG AGG CGT CCA TGG TTA AAT

    770         780         790         800         810
     *     *     *     *     *     *     *     *     *
GAA GGC ACA GCA GTC GAA ATT AAA ACA CTT GAT GAA CTT AAA AAC
CTT CCG TGT CGT CAG CTT TAA TTT TGT GAA CTA CTT GAA TTT TTG

          820
     *     *
GCT TTA AAA TAG
CGA AAT TTT ATC
```

FIG. 19B

```
          10          20          30          40
 *     *     *     *     *     *     *     *     *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

    50          60          70          80          90
 *     *     *     *     *     *     *     *     *
GCA TGT AAG CAA AAT GTT AGC AGC CTT GAC GAG AAA AAC AGC GTT
CGT ACA TTC GTT TTA CAA TCG TCG GAA CTG CTC TTT TTG TCG CAA

         100         110         120         130
 *     *     *     *     *     *     *     *     *
TCA GTA GAT TTG CCT GGT GAA ATG AAA GTT CTT GTA AGC AAA GAA
AGT CAT CTA AAC GGA CCA CTT TAC TTT CAA GAA CAT TCG TTT CTT

   140         150         160         170         180
 *     *     *     *     *     *     *     *     *
AAA AAC AAA GAC GGC AAG TAC GAT CTA ATT GCA ACA GTA GAC AAG
TTT TTG TTT CTG CCG TTC ATG CTA GAT TAA CGT TGT CAT CTG TTC

         190         200         210         220
 *     *     *     *     *     *     *     *     *
CTT GAG CTT AAA GGA ACT TCT GAT AAA AAC AAT GGA TCT GGA GTA
GAA CTC GAA TTT CCT TGA AGA CTA TTT TTG TTA CCT AGA CCT CAT

   230         240         250         260         270
 *     *     *     *     *     *     *     *     *
CTT GAA GGC GTA AAA GCT GAC AAA AGT AAA GTA AAA TTA ACA ATT
GAA CTT CCG CAT TTT CGA CTG TTT TCA TTT CAT TTT AAT TGT TAA

         280         290         300         310
 *     *     *     *     *     *     *     *     *
TCT GAC GAT CTA GGT CAA ACC ACA CTT GAA GTT TTC AAA GAA GAT
AGA CTG CTA GAT CCA GTT TGG TGT GAA CTT CAA AAG TTT CTT CTA

   320         330         340         350         360
 *     *     *     *     *     *     *     *     *
GGC AAA ACA CTA GTA TCA AAA AAA GTA ACT TCC AAA GAC AAG TCA
CCG TTT TGT GAT CAT AGT TTT TTT CAT TGA AGG TTT CTG TTC AGT

         370         380         390         400
 *     *     *     *     *     *     *     *     *
TCA ACA GAA GAA AAA TTC AAT GAA AAA GGT GAA GTA TCT GAA AAA
AGT TGT CTT CTT TTT AAG TTA CTT TTT CCA CTT CAT AGA CTT TTT

   410         420         430         440         450
 *     *     *     *     *     *     *     *     *
ATA ATA ACA AGA GCA AAT GGA ACC AAA CTT GAA TAT ACA GAA ATG
TAT TAT TGT TCT CGT TTA CCT TGG TTT GAA CTT ATA TGT CTT TAC

         460         470         480         490
 *     *     *     *     *     *     *     *     *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA

   500         510         520         530         540
 *     *     *     *     *     *     *     *     *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT

         550         560         570         580
 *     *     *     *     *     *     *     *     *
AAA GAA GGA ACC GTT ACT TTA AGT AAG GAA ATT TCA AAA TCT GGG
```

FIG. 20A

```
TTT CTT CCT TGG CAA TGA AAT TCA TTC CTT TAA AGT TTT AGA CCC

    590         600         610         620         630
     *     *     *     *     *     *     *     *     *
GAA GTT TCA GTT GAA CTT AAT GAC ACT GAC AGT AGT GCT GCT ACT
CTT CAA AGT CAA CTT GAA TTA CTG TGA CTG TCA TCA CGA CGA TGA

            640         650         660         670
     *     *     *     *     *     *     *     *     *
AAA AAA ACT GCA GCT TGG AAT TCA AAA ACT TCC ACT TTA ACA ATT
TTT TTT TGA CGT CGA ACC TTA AGT TTT TGA AGG TGA AAT TGT TAA

    680         690         700         710         720
     *     *     *     *     *     *     *     *     *
AGT GTG AAT AGC CAA AAA ACC AAA AAC CTT GTA TTC ACA AAA GAA
TCA CAC TTA TCG GTT TTT TGG TTT TTG GAA CAT AAG TGT TTT CTT

            730         740         750         760
     *     *     *     *     *     *     *     *     *
GAC ACA ATA ACA GTA CAA AAA TAC GAC TCA GCA GGC ACC AAT CTA
CTG TGT TAT TGT CAT GTT TTT ATG CTG AGT CGT CCG TGG TTA GAT

    770         780         790         800         810
     *     *     *     *     *     *     *     *     *
GAA GGC AAA GCA GTC GAA ATT ACA ACA CTT AAA GAA CTT AAA AAC
CTT CCG TTT CGT CAG CTT TAA TGT TGT GAA TTT CTT GAA TTT TTG

            820
     *     *
GCT TTA AAA TAA
CGA AAT TTT ATT
```

FIG. 20B

```
                 10          20          30          40
         *        *     *     *     *     *     *     *     *
ATG AAA AAA TAT TTA TTG GGA ATA GGT CTA ATA TTA GCC TTA ATA
TAC TTT TTT ATA AAT AAC CCT TAT CCA GAT TAT AAT CGG AAT TAT

     50          60          70          80          90
      *     *     *     *     *     *     *     *     *
GCA TGC AAG CAA AAT GTT AGC AGC CTT GAT GAA AAA AAC AGC GCT
CGT ACG TTC GTT TTA CAA TCG TCG GAA CTA CTT TTT TTG TCG CGA

                100         110         120         130
         *        *     *     *     *     *     *     *     *
TCA GTA GAT TTG CCT GGT GAG ATG AAA GTT CTT GTA AGT AAA GAA
AGT CAT CTA AAC GGA CCA CTC TAC TTT CAA GAA CAT TCA TTT CTT

    140         150         160         170         180
      *     *     *     *     *     *     *     *     *
AAA GAC AAA GAC GGT AAG TAC AGT CTA AAG GCA ACA GTA GAC AAG
TTT CTG TTT CTG CCA TTC ATG TCA GAT TTC CGT TGT CAT CTG TTC

                190         200         210         220
         *        *     *     *     *     *     *     *     *
ATT GAG CTA AAA GGA ACT TCT GAT AAA GAC AAT GGT TCT GGA GTG
TAA CTC GAT TTT CCT TGA AGA CTA TTT CTG TTA CCA AGA CCT CAC

    230         240         250         260         270
      *     *     *     *     *     *     *     *     *
CTT GAA GGT ACA AAA GAT GAC AAA AGT AAA GCA AAA TTA ACA ATT
GAA CTT CCA TGT TTT CTA CTG TTT TCA TTT CGT TTT AAT TGT TAA

                280         290         300         310
         *        *     *     *     *     *     *     *     *
GCT GAC GAT CTA AGT AAA ACC ACA TTC GAA CTT TTA AAA GAA GAT
CGA CTG CTA GAT TCA TTT TGG TGT AAG CTT GAA AAT TTT CTT CTA

    320         330         340         350         360
      *     *     *     *     *     *     *     *     *
GGC AAA ACA TTA GTG TCA AGA AAA GTA AGT TCT AGA GAC AAA ACA
CCG TTT TGT AAT CAC AGT TCT TTT CAT TCA AGA TCT CTG TTT TGT

                370         380         390         400
         *        *     *     *     *     *     *     *     *
TCA ACA GAT GAA ATG TTC AAT GAA AAA GGT GAA TTG TCT GCA AAA
AGT TGT CTA CTT TAC AAG TTA CTT TTT CCA CTT AAC AGA CGT TTT

    410         420         430         440         450
      *     *     *     *     *     *     *     *     *
ACC ATG ACA AGA GAA AAT GGA ACC AAA CTT GAA TAT ACA GAA ATG
TGG TAC TGT TCT CTT TTA CCT TGG TTT GAA CTT ATA TGT CTT TAC

                460         470         480         490
         *        *     *     *     *     *     *     *     *
AAA AGC GAT GGA ACC GGA AAA GCT AAA GAA GTT TTA AAA AAG TTT
TTT TCG CTA CCT TGG CCT TTT CGA TTT CTT CAA AAT TTT TTC AAA

    500         510         520         530         540
      *     *     *     *     *     *     *     *     *
ACT CTT GAA GGA AAA GTA GCT AAT GAT AAA GTA ACA TTG GAA GTA
TGA GAA CTT CCT TTT CAT CGA TTA CTA TTT CAT TGT AAC CTT CAT

                550         560         570         580
         *        *     *     *     *     *     *     *     *
AAA GAA GGA ACC GTT ACT TTA AGT AAG GAA ATT TCA AAA TCT GGG
```

FIG. 21A

```
TTT CTT CCT TGG CAA TGA AAT TCA TTC CTT TAA AGT TTT AGA CCC

    590         600             610             620         630
     *       *   *       *       *     *       *       *     *
GAA GTT TCA GTT GAA CTT AAT GAC ACT GAC AGT AGT GCT GCT ACT
CTT CAA AGT CAA CTT GAA TTA CTG TGA CTG TCA TCA CGA CGA TGA

            640         650             660             670
     *       *   *       *       *     *       *       *     *
AAA AAA ACT GCA GCT TGG AAT TCA AAA ACT TCC ACT TTA ACA ATT
TTT TTT TGA CGT CGA ACC TTA AGT TTT TGA AGG TGA AAT TGT TAA

    680         690             700             710         720
     *       *   *       *       *     *       *       *     *
AGT GTG AAT AGC CAA AAA ACC AAA AAC CTT GTA TTC ACA AAA GAA
TCA CAC TTA TCG GTT TTT TGG TTT TTG GAA CAT AAG TGT TTT CTT

            730         740             750             760
     *       *   *       *       *     *       *       *     *
GAC ACA ATA ACA GTA CAA AAA TAC GAC TCA GCA GGC ACC AAT CTA
CTG TGT TAT TGT CAT GTT TTT ATG CTG AGT CGT CCG TGG TTA GAT

    770         780             790             800         810
     *       *   *       *       *     *       *       *     *
GAA GGC AAA GCA GTC GAA ATT ACA ACA CTT AAA GAA CTT AAA AAC
CTT CCG TTT CGT CAG CTT TAA TGT TGT GAA TTT CTT GAA TTT TTG

            820
     *       *
GCT TTA AAA TAA
CGA AAT TTT ATT
```

FIG. 21B

```
           10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

      200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

         250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

   390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

      440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

         490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 30A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
K P S M A K Q N V S S L D E K N>

630 640 650 660 670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
S V S V D L P G E M K V L V S K>

680 690 700 710 720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
E K N K D G K Y D L I A T V D K>

730 740 750 760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
L E L K G T S D K N N G S G V L>

770 780 790 800 810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
E G V K A D K S K V K L T I S D>

820 830 840 850 860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
D L G Q T T L E V F K E D G K T>

870 880 890 900 910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
L V S K K V T S K D K S S T E E>

920 930 940 950 960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
K F N E K G E V S E K I I T R A>

970 980 990 1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
D G T R L E Y T G I K S D G S G>

1010 1020 1030 1040 1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
K A K E V L K G Y V L E G T L T>

1060 1070 1080 1090 1100
GCT GAA AAA ACA ACA TTG GTG GTT AAA GAA GGA ACT GTT ACT TTA AGC

FIG. 30B

```
 CGA CTT TTT TGT TGT AAC CAC CAA TTT CTT CCT TGA CAA TGA AAT TCG
A    E   K   T   T   L   V   V   K   E   G   T   V   T   L   S>

  1110          1120          1130          1140          1150
 AAA AAT ATT TCA AAA TCT GGG GAA GTT TCA GTT GAA CTT AAT GAC ACT
 TTT TTA TAA AGT TTT AGA CCC CTT CAA AGT CAA CTT GAA TTA CTG TGA
 K   N   I   S   K   S   G   E   V   S   V   E   L   N   D   T>

     1160          1170          1180          1190          1200
 GAC AGT AGT GCT GCT ACT AAA AAA ACT GCA GCT TGG AAT TCA GGC ACT
 CTG TCA TCA CGA CGA TGA TTT TTT TGA CGT CGA ACC TTA AGT CCG TGA
 D   S   S   A   A   T   K   K   T   A   A   W   N   S   G   T>

         1210          1220          1230          1240
 TCA ACT TTA ACA ATT ACT GTA AAC AGT AAA AAA ACT AAA GAC CTT GTG
 AGT TGA AAT TGT TAA TGA CAT TTG TCA TTT TTT TGA TTT CTG GAA CAC
 S   T   L   T   I   T   V   N   S   K   K   T   K   D   L   V>

1250         1260          1270          1280          1290
 TTT ACA AAA GAA AAC ACA ATT ACA GTA CAA CAA TAC GAC TCA AAT GGC
 AAA TGT TTT CTT TTG TGT TAA TGT CAT GTT GTT ATG CTG AGT TTA CCG
 F   T   K   E   N   T   I   T   V   Q   Q   Y   D   S   N   G>

 1300          1310          1320          1330          1340
 ACC AAA TTA GAG GGG TCA GCA GTT GAA ATT ACA AAA CTT GAT GAA ATT
 TGG TTT AAT CTC CCC AGT CGT CAA CTT TAA TGT TTT GAA CTA CTT TAA
 T   K   L   E   G   S   A   V   E   I   T   K   L   D   E   I>

   1350          1360
 AAA AAC GCT TTA AAA TAA
 TTT TTG CGA AAT TTT ATT
 K   N   A   L   K   *>
```

FIG. 30C

```
                10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50              60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

100             110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

            250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290             300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

340             350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

        440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

            490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 31A

```
530         540           550          560          570
 AAT TCA GTT AAA GAG CTT ACA AGC CCT GTT GTG GCA GAA AGT CCA GCC
 TTA AGT CAA TTT CTC GAA TGT TCG GGA CAA CAC CGT CTT TCA GGT CGG
 N   S   V   K   E   L   T   S   P   V   V   A   E   S   P   A>

  580         590          600          610          620
 ATG GCC AAG CAA AAT GTT AGC AGC CTT GAC GAG AAA AAC AGC GTT TCA
 TAC CGG TTC GTT TTA CAA TCG TCG GAA CTG CTC TTT TTG TCG CAA AGT
 M   A   K   Q   N   V   S   S   L   D   E   K   N   S   V   S>

   630         640          650          660           670
 GTA GAT TTG CCT GGT GAA ATG AAA GTT CTT GTA AGC AAA GAA AAA AAC
 CAT CTA AAC GGA CCA CTT TAC TTT CAA GAA CAT TCG TTT CTT TTT TTG
 V   D   L   P   G   E   M   K   V   L   V   S   K   E   K   N>

     680         690          700          710          720
 AAA GAC GGC AAG TAC GAT CTA ATT GCA ACA GTA GAC AAG CTT GAG CTT
 TTT CTG CCG TTC ATG CTA GAT TAA CGT TGT CAT CTG TTC GAA CTC GAA
 K   D   G   K   Y   D   L   I   A   T   V   D   K   L   E   L>

       730         740          750          760
 AAA GGA ACT TCT GAT AAA AAC AAT GGA TCT GGA GTA CTT GAA GGC GTA
 TTT CCT TGA AGA CTA TTT TTG TTA CCT AGA CCT CAT GAA CTT CCG CAT
 K   G   T   S   D   K   N   N   G   S   G   V   L   E   G   V>

770         780          790          800          810
 AAA GCT GAC AAA AGT AAA GTA AAA TTA ACA ATT TCT GAC GAT CTA GGT
 TTT CGA CTG TTT TCA TTT CAT TTT AAT TGT TAA AGA CTG CTA GAT CCA
 K   A   D   K   S   K   V   K   L   T   I   S   D   D   L   G>

 820         830          840          850          860
 CAA ACC ACA CTT GAA GTT TTC AAA GAA GAT GGC AAA ACA CTA GTA TCA
 GTT TGG TGT GAA CTT CAA AAG TTT CTT CTA CCG TTT TGT GAT CAT AGT
 Q   T   T   L   E   V   F   K   E   D   G   K   T   L   V   S>

   870         880          890          900          910
 AAA AAA GTA ACT TCC AAA GAC AAG TCA TCA ACA GAA GAA AAA TTC AAT
 TTT TTT CAT TGA AGG TTT CTG TTC AGT AGT TGT CTT CTT TTT AAG TTA
 K   K   V   T   S   K   D   K   S   S   T   E   E   K   F   N>

      920         930          940          950          960
 GAA AAA GGT GAA GTA TCT GAA AAA ATA ATA ACA AGA GCA GAC GGA ACC
 CTT TTT CCA CTT CAT AGA CTT TTT TAT TAT TGT TCT CGT CTG CCT TGG
 E   K   G   E   V   S   E   K   I   I   T   R   A   D   G   T>

       970         980          990          1000
 AGA CTT GAA TAC ACA GGA ATT AAA AGC GAT GGA TCT GGA AAA GCT AAA
 TCT GAA CTT ATG TGT CCT TAA TTT TCG CTA CCT AGA CCT TTT CGA TTT
 R   L   E   Y   T   G   I   K   S   D   G   S   G   K   A   K>

1010        1020         1030         1040         1050
 GAG GTT TTA AAA GGC TAT GTT CTT GAA GGA ACT CTA ACT GCT GAA AAA
 CTC CAA AAT TTT CCG ATA CAA GAA CTT CCT TGA GAT TGA CGA CTT TTT
 E   V   L   K   G   Y   V   L   E   G   T   L   T   A   E   K>

 1060        1070         1080         1090         1100
 ACA ACA TTG GTG GTT AAA GAA GGA ACT GTT ACT TTA AGC AAA AAT ATT
```

FIG. 31B

```
 TGT TGT AAC CAC CAA TTT CTT CCT TGA CAA TGA AAT TCG TTT TTA TAA
 T   T   L   V   V   K   E   G   T   V   T   L   S   K   N   I>

  1110            1120            1130            1140            1150
 TCA AAA TCT GGG GAA GTT TCA GTT GAA CTT AAT GAC ACT GAC AGT AGT
 AGT TTT AGA CCC CTT CAA AGT CAA CTT GAA TTA CTG TGA CTG TCA TCA
 S   K   S   G   E   V   S   V   E   L   N   D   T   D   S   S>

      1160            1170            1180            1190            1200
 GCT GCT ACT AAA AAA ACT GCA GCT TGG AAT TCA GGC ACT TCA ACT TTA
 CGA CGA TGA TTT TTT TGA CGT CGA ACC TTA AGT CCG TGA AGT TGA AAT
 A   A   T   K   K   T   A   A   W   N   S   G   T   S   T   L>

          1210            1220            1230            1240
 ACA ATT ACT GTA AAC AGT AAA AAA ACT AAA GAC CTT GTG TTT ACA AAA
 TGT TAA TGA CAT TTG TCA TTT TTT TGA TTT CTG GAA CAC AAA TGT TTT
 T   I   T   V   N   S   K   K   T   K   D   L   V   F   T   K>

1250          1260            1270            1280            1290
 GAA AAC ACA ATT ACA GTA CAA CAA TAC GAC TCA AAT GGC ACC AAA TTA
 CTT TTG TGT TAA TGT CAT GTT GTT ATG CTG AGT TTA CCG TGG TTT AAT
 E   N   T   I   T   V   Q   Q   Y   D   S   N   G   T   K   L>

 1300           1310            1320            1330            1340
 GAG GGG TCA GCA GTT GAA ATT ACA AAA CTT GAT GAA ATT AAA AAC GCT
 CTC CCC AGT CGT CAA CTT TAA TGT TTT GAA CTA CTT TAA TTT TTG CGA
 E   G   S   A   V   E   I   T   K   L   D   E   I   K   N   A>

  1350
TTA AAA TAA
AAT TTT ATT
L   K   *>
```

FIG. 31C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

  150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

      200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

          250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

 340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

   390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

      440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

          490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 32A

```
530          540          550          560          570
  GCT AAT TCA GTT AAA GAG CTT ACA AGC CCT GTT GTC CAT GGC AAG CAA
  CGA TTA AGT CAA TTT CTC GAA TGT TCG GGA CAA CAG GTA CCG TTC GTT
  A   N   S   V   K   E   L   T   S   P   V   V   H   G   K   Q>

   580          590          600          610          620
  AAT GTT AGC AGC CTT GAC GAG AAA AAC AGC GTT TCA GTA GAT TTG CCT
  TTA CAA TCG TCG GAA CTG CTC TTT TTG TCG CAA AGT CAT CTA AAC GGA
  N   V   S   S   L   D   E   K   N   S   V   S   V   D   L   P>

     630          640          650          660          670
  GGT GAA ATG AAA GTT CTT GTA AGC AAA GAA AAA AAC AAA GAC GGC AAG
  CCA CTT TAC TTT CAA GAA CAT TCG TTT CTT TTT TTG TTT CTG CCG TTC
  G   E   M   K   V   L   V   S   K   E   K   N   K   D   G   K>

        680          690          700          710          720
  TAC GAT CTA ATT GCA ACA GTA GAC AAG CTT GAG CTT AAA GGA ACT TCT
  ATG CTA GAT TAA CGT TGT CAT CTG TTC GAA CTC GAA TTT CCT TGA AGA
  Y   D   L   I   A   T   V   D   K   L   E   L   K   G   T   S>

           730          740          750          760
  GAT AAA AAC AAT GGA TCT GGA GTA CTT GAA GGC GTA AAA GCT GAC AAA
  CTA TTT TTG TTA CCT AGA CCT CAT GAA CTT CCG CAT TTT CGA CTG TTT
  D   K   N   N   G   S   G   V   L   E   G   V   K   A   D   K>

770          780          790          800          810
  AGT AAA GTA AAA TTA ACA ATT TCT GAC GAT CTA GGT CAA ACC ACA CTT
  TCA TTT CAT TTT AAT TGT TAA AGA CTG CTA GAT CCA GTT TGG TGT GAA
  S   K   V   K   L   T   I   S   D   D   L   G   Q   T   T   L>

   820          830          840          850          860
  GAA GTT TTC AAA GAA GAT GGC AAA ACA CTA GTA TCA AAA AAA GTA ACT
  CTT CAA AAG TTT CTT CTA CCG TTT TGT GAT CAT AGT TTT TTT CAT TGA
  E   V   F   K   E   D   G   K   T   L   V   S   K   K   V   T>

     870          880          890          900          910
  TCC AAA GAC AAG TCA TCA ACA GAA GAA AAA TTC AAT GAA AAA GGT GAA
  AGG TTT CTG TTC AGT AGT TGT CTT CTT TTT AAG TTA CTT TTT CCA CTT
  S   K   D   K   S   S   T   E   E   K   F   N   E   K   G   E>

        920          930          940          950          960
  GTA TCT GAA AAA ATA ATA ACA AGA GCA GAC GGA ACC AGA CTT GAA TAC
  CAT AGA CTT TTT TAT TAT TGT TCT CGT CTG CCT TGG TCT GAA CTT ATG
  V   S   E   K   I   I   T   R   A   D   G   T   R   L   E   Y>

           970          980          990          1000
  ACA GGA ATT AAA AGC GAT GGA TCT GGA AAA GCT AAA GAG GTT TTA AAA
  TGT CCT TAA TTT TCG CTA CCT AGA CCT TTT CGA TTT CTC CAA AAT TTT
  T   G   I   K   S   D   G   S   G   K   A   K   E   V   L   K>

1010         1020         1030         1040         1050
  GGC TAT GTT CTT GAA GGA ACT CTA ACT GCT GAA AAA ACA ACA TTG GTG
  CCG ATA CAA GAA CTT CCT TGA GAT TGA CGA CTT TTT TGT TGT AAC CAC
  G   Y   V   L   E   G   T   L   T   A   E   K   T   T   L   V>

   1060         1070         1080         1090         1100
  GTT AAA GAA GGA ACT GTT ACT TTA AGC AAA AAT ATT TCA AAA TCT GGG
```

FIG. 32B

```
CAA TTT CTT CCT TGA CAA TGA AAT TCG TTT TTA TAA AGT TTT AGA CCC
V   K   E   G   T   V   T   L   S   K   N   I   S   K   S   G>

  1110        1120        1130        1140        1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
E   V   S   V   E   L   N   D   T   D   S   S   A   A   T   K>

    1160        1170        1180        1190        1200
AAA ACT GCA GCT TGG AAT TCA GGC ACT TCA ACT TTA ACA ATT ACT GTA
TTT TGA CGT CGA ACC TTA AGT CCG TGA AGT TGA AAT TGT TAA TGA CAT
K   T   A   A   W   N   S   G   T   S   T   L   T   I   T   V>

        1210        1220        1230        1240
AAC AGT AAA AAA ACT AAA GAC CTT GTG TTT ACA AAA GAA AAC ACA ATT
TTG TCA TTT TTT TGA TTT CTG GAA CAC AAA TGT TTT CTT TTG TGT TAA
N   S   K   K   T   K   D   L   V   F   T   K   E   N   T   I>

1250        1260        1270        1280        1290
ACA GTA CAA CAA TAC GAC TCA AAT GGC ACC AAA TTA GAG GGG TCA GCA
TGT CAT GTT GTT ATG CTG AGT TTA CCG TGG TTT AAT CTC CCC AGT CGT
T   V   Q   Q   Y   D   S   N   G   T   K   L   E   G   S   A>

1300        1310        1320        1330        1340
GTT GAA ATT ACA AAA CTT GAT GAA ATT AAA AAC GCT TTA AAA TAA
CAA CTT TAA TGT TTT GAA CTA CTT TAA TTT TTG CGA AAT TTT ATT
V   E   I   T   K   L   D   E   I   K   N   A   L   K   *>
```

FIG. 32C

```
          10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50          60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

  150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

      200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

        250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

  390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

     440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

        490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 33A

```
530         540         550         560         570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
 N   S   V   K   E   L   T   S   P   V   V   A   E   S   P   K>

 580         590         600         610         620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
 K   P   S   M   A   K   Q   N   V   S   S   L   D   E   K   N>

   630         640         650         660         670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
 S   V   S   V   D   L   P   G   E   M   K   V   L   V   S   K>

      680         690         700         710         720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
 E   K   N   K   D   G   K   Y   D   L   I   A   T   V   D   K>

         730         740         750         760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
 L   E   L   K   G   T   S   D   K   N   N   G   S   G   V   L>

770         780         790         800         810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
 E   G   V   K   A   D   K   S   K   V   K   L   T   I   S   D>

 820         830         840         850         860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
 D   L   G   Q   T   T   L   E   V   F   K   E   D   G   K   T>

   870         880         890         900         910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
 L   V   S   K   K   V   T   S   K   D   K   S   S   T   E   E>

      920         930         940         950         960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
 K   F   N   E   K   G   E   V   S   E   K   I   I   T   R   A>

         970         980         990         1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
 D   G   T   R   L   E   Y   T   G   I   K   S   D   G   S   G>

1010        1020        1030        1040        1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
 K   A   K   E   V   L   K   G   Y   V   L   E   G   T   L   T>

 1060        1070        1080        1090        1100
GCT GAA AAA ACA ACA TTG GTG GTT AAA GAA GGA ACT GTT ACT TTA AGC
```

FIG. 33B

```
 CGA CTT TTT TGT TGT AAC CAC CAA TTT CTT CCT TGA CAA TGA AAT TCG
 A   E   K   T   T   L   V   V   K   E   G   T   V   T   L   S>

   1110        1120        1130        1140        1150
 AAA AAT ATT TCA AAA TCT GGG GAA GTT TCA GTT GAA CTT AAT GAC ACT
 TTT TTA TAA AGT TTT AGA CCC CTT CAA AGT CAA CTT GAA TTA CTG TGA
 K   N   I   S   K   S   G   E   V   S   V   E   L   N   D   T>

      1160        1170        1180        1190        1200
 GAC AGT AGT GCT GCT ACT AAA AAA ACT GCA GCT TGG AAT TCA AAA ACT
 CTG TCA TCA CGA CGA TGA TTT TTT TGA CGT CGA ACC TTA AGT TTT TGA
 D   S   S   A   A   T   K   K   T   A   A   W   N   S   K   T>

         1210        1220        1230        1240
 TCC ACT TTA ACA ATT AGT GTG AAT AGC CAA AAA ACC AAA AAC CTT GTA
 AGG TGA AAT TGT TAA TCA CAC TTA TCG GTT TTT TGG TTT TTG GAA CAT
 S   T   L   T   I   S   V   N   S   Q   K   T   K   N   L   V>

1250       1260        1270        1280        1290
 TTC ACA AAA GAA GAC ACA ATA ACA GTA CAA AAA TAC GAC TCA GCA GGC
 AAG TGT TTT CTT CTG TGT TAT TGT CAT GTT TTT ATG CTG AGT CGT CCG
 F   T   K   E   D   T   I   T   V   Q   K   Y   D   S   A   G>

 1300       1310        1320        1330        1340
 ACC AAT CTA GAA GGC AAA GCA GTC GAA ATT ACA ACA CTT AAA GAA CTT
 TGG TTA GAT CTT CCG TTT CGT CAG CTT TAA TGT TGT GAA TTT CTT GAA
 T   N   L   E   G   K   A   V   E   I   T   T   L   K   E   L>

   1350        1360
 AAA AAC GCT TTA AAA TAA
 TTT TTG CGA AAT TTT ATT
 K   N   A   L   K   *>
```

FIG. 33C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

            250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

 340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

    390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

        440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

            490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 34A

```
530        540        550        560        570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
A   N   S   V   K   E   L   T   S   P   V   V   H   G   K   Q>

580        590        600        610        620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
N   V   S   S   L   D   E   K   N   S   V   S   V   D   L   P>

630        640        650        660        670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
G   E   M   K   V   L   V   S   K   E   K   N   K   D   G   K>

680        690        700        710        720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
Y   D   L   I   A   T   V   D   K   L   E   L   K   G   T   S>

730        740        750        760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
D   K   N   N   G   S   G   V   L   E   G   V   K   A   D   K>

770        780        790        800        810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
S   K   V   K   L   T   I   S   D   D   L   G   Q   T   T   L>

820        830        840        850        860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
E   V   F   K   E   D   G   K   T   L   V   S   K   K   V   T>

870        880        890        900        910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
S   K   D   K   S   S   T   E   E   K   F   N   E   K   G   E>

920        930        940        950        960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
V   S   E   K   I   I   T   R   A   D   G   T   R   L   E   Y>

970        980        990        1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
T   G   I   K   S   D   G   S   G   K   A   K   E   V   L   K>

1010       1020       1030       1040       1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
G   Y   V   L   E   G   T   L   T   A   E   K   T   T   L   V>

1060       1070       1080       1090       1100
GTT AAA GAA GGA ACT GTT ACT TTA AGC AAA AAT ATT TCA AAA TCT GGG
```

FIG. 34B

```
CAA TTT CTT CCT TGA CAA TGA AAT TCG TTT TTA TAA AGT TTT AGA CCC
V   K   E   G   T   V   T   L   S   K   N   I   S   K   S   G>

 1110            1120             1130             1140             1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
E   V   S   V   E   L   N   D   T   D   S   S   A   A   T   K>

     1160             1170             1180             1190             1200
AAA ACT GCA GCT TGG AAT TCA AAA ACT TCC ACT TTA ACA ATT AGT GTG
TTT TGA CGT CGA ACC TTA AGT TTT TGA AGG TGA AAT TGT TAA TCA CAC
K   T   A   A   W   N   S   K   T   S   T   L   T   I   S   V>

         1210             1220             1230             1240
AAT AGC CAA AAA ACC AAA AAC CTT GTA TTC ACA AAA GAA GAC ACA ATA
TTA TCG GTT TTT TGG TTT TTG GAA CAT AAG TGT TTT CTT CTG TGT TAT
N   S   Q   K   T   K   N   L   V   F   T   K   E   D   T   I>

1250            1260             1270             1280             1290
ACA GTA CAA AAA TAC GAC TCA GCA GGC ACC AAT CTA GAA GGC AAA GCA
TGT CAT GTT TTT ATG CTG AGT CGT CCG TGG TTA GAT CTT CCG TTT CGT
T   V   Q   K   Y   D   S   A   G   T   N   L   E   G   K   A>

1300             1310             1320             1330             1340
GTC GAA ATT ACA ACA CTT AAA GAA CTT AAA AAC GCT TTA AAA TAA
CAG CTT TAA TGT TGT GAA TTT CTT GAA TTT TTG CGA AAT TTT ATT
V   E   I   T   T   L   K   E   L   K   N   A   L   K   *>
```

FIG. 34C

```
                 10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                 60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290                 300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

        440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

            490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 35A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTT AGC AGC CTT GAC GAG AAA AAC
TTT GGA AGG TAC CGG TTC GTT TTA CAA TCG TCG GAA CTG CTC TTT TTG
K P S M A K Q N V S S L D E K N>

630 640 650 660 670
AGC GTT TCA GTA GAT TTG CCT GGT GAA ATG AAA GTT CTT GTA AGC AAA
TCG CAA AGT CAT CTA AAC GGA CCA CTT TAC TTT CAA GAA CAT TCG TTT
S V S V D L P G E M K V L V S K>

680 690 700 710 720
GAA AAA AAC AAA GAC GGC AAG TAC GAT CTA ATT GCA ACA GTA GAC AAG
CTT TTT TTG TTT CTG CCG TTC ATG CTA GAT TAA CGT TGT CAT CTG TTC
E K N K D G K Y D L I A T V D K>

730 740 750 760
CTT GAG CTT AAA GGA ACT TCT GAT AAA AAC AAT GGA TCT GGA GTA CTT
GAA CTC GAA TTT CCT TGA AGA CTA TTT TTG TTA CCT AGA CCT CAT GAA
L E L K G T S D K N N G S G V L>

770 780 790 800 810
GAA GGC GTA AAA GCT GAC AAA AGT AAA GTA AAA TTA ACA ATT TCT GAC
CTT CCG CAT TTT CGA CTG TTT TCA TTT CAT TTT AAT TGT TAA AGA CTG
E G V K A D K S K V K L T I S D>

820 830 840 850 860
GAT CTA GGT CAA ACC ACA CTT GAA GTT TTC AAA GAA GAT GGC AAA ACA
CTA GAT CCA GTT TGG TGT GAA CTT CAA AAG TTT CTT CTA CCG TTT TGT
D L G Q T T L E V F K E D G K T>

870 880 890 900 910
CTA GTA TCA AAA AAA GTA ACT TCC AAA GAC AAG TCA TCA ACA GAA GAA
GAT CAT AGT TTT TTT CAT TGA AGG TTT CTG TTC AGT AGT TGT CTT CTT
L V S K K V T S K D K S S T E E>

920 930 940 950 960
AAA TTC AAT GAA AAA GGT GAA GTA TCT GAA AAA ATA ATA ACA AGA GCA
TTT AAG TTA CTT TTT CCA CTT CAT AGA CTT TTT TAT TAT TGT TCT CGT
K F N E K G E V S E K I I T R A>

970 980 990 1000
GAC GGA ACC AGA CTT GAA TAC ACA GGA ATT AAA AGC GAT GGA TCT GGA
CTG CCT TGG TCT GAA CTT ATG TGT CCT TAA TTT TCG CTA CCT AGA CCT
D G T R L E Y T G I K S D G S G>

1010 1020 1030 1040 1050
AAA GCT AAA GAG GTT TTA AAA GGC TAT GTT CTT GAA GGA ACT CTA ACT
TTT CGA TTT CTC CAA AAT TTT CCG ATA CAA GAA CTT CCT TGA GAT TGA
K A K E V L K G Y V L E G T L T>

1060 1070 1080 1090 1100
GCT GAA AAA ACA ACA TTG GTG GTT AAA GAA GGA ACT GTT ACT TTA AGC

FIG. 35B

```
CGA CTT TTT TGT TGT AAC CAC CAA TTT CTT CCT TGA CAA TGA AAT TCG
A   E   K   T   T   L   V   V   K   E   G   T   V   T   L   S>

  1110        1120        1130        1140        1150
AAA AAT ATT TCA AAA TCT GGG GAA GTT TCA GTT GAA CTT AAT GAC ACT
TTT TTA TAA AGT TTT AGA CCC CTT CAA AGT CAA CTT GAA TTA CTG TGA
K   N   I   S   K   S   G   E   V   S   V   E   L   N   D   T>

     1160        1170        1180        1190        1200
GAC AGT AGT GCT GCT ACT AAA AAA ACT GCA GCT TGG AAT TCA AAA ACT
CTG TCA TCA CGA CGA TGA TTT TTT TGA CGT CGA ACC TTA AGT TTT TGA
D   S   S   A   A   T   K   K   T   A   A   W   N   S   K   T>

        1210        1220        1230        1240
TCT ACT TTA ACA ATT AGT GTT AAC AGC AAA AAA ACT ACA CAA CTT GTG
AGA TGA AAT TGT TAA TCA CAA TTG TCG TTT TTT TGA TGT GTT GAA CAC
S   T   L   T   I   S   V   N   S   K   K   T   T   Q   L   V>

1250        1260        1270        1280        1290
TTT ACT AAA CAA GAC ACA ATA ACT GTA CAA AAA TAC GAC TCC GCA GGT
AAA TGA TTT GTT CTG TGT TAT TGA CAT GTT TTT ATG CTG AGG CGT CCA
F   T   K   Q   D   T   I   T   V   Q   K   Y   D   S   A   G>

1300        1310        1320        1330        1340
ACC AAT TTA GAA GGC ACA GCA GTC GAA ATT AAA ACA CTT GAT GAA CTT
TGG TTA AAT CTT CCG TGT CGT CAG CTT TAA TTT TGT GAA CTA CTT GAA
T   N   L   E   G   T   A   V   E   I   K   T   L   D   E   L>

  1350        1360
AAA AAC GCT TTA AAA TAA
TTT TTG CGA AAT TTT ATT
K   N   A   L   K   *>
```

FIG. 35C

```
          10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50          60              70              80              90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

 100         110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150             160             170             180             190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200             210             220             230             240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

            250             260             270             280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290         300             310             320             330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

 340         350             360             370             380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

   390             400             410             420             430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

        440             450             460             470             480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

            490             500             510             520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 36A

```
530          540          550          560          570
GCT AAT TCA GTT AAA GAG CTT ACA AGC CCT GTT GTC CAT GGC AAG CAA
CGA TTA AGT CAA TTT CTC GAA TGT TCG GGA CAA CAG GTA CCG TTC GTT
A   N   S   V   K   E   L   T   S   P   V   V   H   G   K   Q>

580          590          600          610          620
AAT GTT AGC AGC CTT GAC GAG AAA AAC AGC GTT TCA GTA GAT TTG CCT
TTA CAA TCG TCG GAA CTG CTC TTT TTG TCG CAA AGT CAT CTA AAC GGA
N   V   S   S   L   D   E   K   N   S   V   S   V   D   L   P>

630          640          650          660          670
GGT GAA ATG AAA GTT CTT GTA AGC AAA GAA AAA AAC AAA GAC GGC AAG
CCA CTT TAC TTT CAA GAA CAT TCG TTT CTT TTT TTG TTT CTG CCG TTC
G   E   M   K   V   L   V   S   K   E   K   N   K   D   G   K>

680          690          700          710          720
TAC GAT CTA ATT GCA ACA GTA GAC AAG CTT GAG CTT AAA GGA ACT TCT
ATG CTA GAT TAA CGT TGT CAT CTG TTC GAA CTC GAA TTT CCT TGA AGA
Y   D   L   I   A   T   V   D   K   L   E   L   K   G   T   S>

730          740          750          760
GAT AAA AAC AAT GGA TCT GGA GTA CTT GAA GGC GTA AAA GCT GAC AAA
CTA TTT TTG TTA CCT AGA CCT CAT GAA CTT CCG CAT TTT CGA CTG TTT
D   K   N   N   G   S   G   V   L   E   G   V   K   A   D   K>

770          780          790          800          810
AGT AAA GTA AAA TTA ACA ATT TCT GAC GAT CTA GGT CAA ACC ACA CTT
TCA TTT CAT TTT AAT TGT TAA AGA CTG CTA GAT CCA GTT TGG TGT GAA
S   K   V   K   L   T   I   S   D   D   L   G   Q   T   T   L>

820          830          840          850          860
GAA GTT TTC AAA GAA GAT GGC AAA ACA CTA GTA TCA AAA AAA GTA ACT
CTT CAA AAG TTT CTT CTA CCG TTT TGT GAT CAT AGT TTT TTT CAT TGA
E   V   F   K   E   D   G   K   T   L   V   S   K   K   V   T>

870          880          890          900          910
TCC AAA GAC AAG TCA TCA ACA GAA GAA AAA TTC AAT GAA AAA GGT GAA
AGG TTT CTG TTC AGT AGT TGT CTT CTT TTT AAG TTA CTT TTT CCA CTT
S   K   D   K   S   S   T   E   E   K   F   N   E   K   G   E>

920          930          940          950          960
GTA TCT GAA AAA ATA ATA ACA AGA GCA GAC GGA ACC AGA CTT GAA TAC
CAT AGA CTT TTT TAT TAT TGT TCT CGT CTG CCT TGG TCT GAA CTT ATG
V   S   E   K   I   I   T   R   A   D   G   T   R   L   E   Y>

970          980          990          1000
ACA GGA ATT AAA AGC GAT GGA TCT GGA AAA GCT AAA GAG GTT TTA AAA
TGT CCT TAA TTT TCG CTA CCT AGA CCT TTT CGA TTT CTC CAA AAT TTT
T   G   I   K   S   D   G   S   G   K   A   K   E   V   L   K>

1010         1020         1030         1040         1050
GGC TAT GTT CTT GAA GGA ACT CTA ACT GCT GAA AAA ACA ACA TTG GTG
CCG ATA CAA GAA CTT CCT TGA GAT TGA CGA CTT TTT TGT TGT AAC CAC
G   Y   V   L   E   G   T   L   T   A   E   K   T   T   L   V>

1060         1070         1080         1090         1100
GTT AAA GAA GGA ACT GTT ACT TTA AGC AAA AAT ATT TCA AAA TCT GGG
```

FIG. 36B

```
CAA TTT CTT CCT TGA CAA TGA AAT TCG TTT TTA TAA AGT TTT AGA CCC
 V   K   E   G   T   V   T   L   S   K   N   I   S   K   S   G>

     1110        1120        1130        1140        1150
GAA GTT TCA GTT GAA CTT AAT GAC ACT GAC AGT AGT GCT GCT ACT AAA
CTT CAA AGT CAA CTT GAA TTA CTG TGA CTG TCA TCA CGA CGA TGA TTT
 E   V   S   V   E   L   N   D   T   D   S   S   A   A   T   K>

     1160        1170        1180        1190        1200
AAA ACT GCA GCT TGG AAT TCA AAA ACT TCT ACT TTA ACA ATT AGT GTT
TTT TGA CGT CGA ACC TTA AGT TTT TGA AGA TGA AAT TGT TAA TCA CAA
 K   T   A   A   W   N   S   K   T   S   T   L   T   I   S   V>

     1210        1220        1230        1240
AAC AGC AAA AAA ACT ACA CAA CTT GTG TTT ACT AAA CAA TAC ACA ATA
TTG TCG TTT TTT TGA TGT GTT GAA CAC AAA TGA TTT GTT ATG TGT TAT
 N   S   K   K   T   T   Q   L   V   F   T   K   Q   Y   T   I>

1250        1260        1270        1280        1290
ACT GTA AAA CAA TAC GAC TCC GCA GGT ACC AAT TTA GAA GGC ACA GCA
TGA CAT TTT GTT ATG CTG AGG CGT CCA TGG TTA AAT CTT CCG TGT CGT
 T   V   K   Q   Y   D   S   A   G   T   N   L   E   G   T   A>

     1300        1310        1320        1330        1340
GTC GAA ATT AAA ACA CTT GAT GAA CTT AAA AAC GCT TTA AAA TAA
CAG CTT TAA TTT TGT GAA CTA CTT GAA TTT TTG CGA AAT TTT ATT
 V   E   I   K   T   L   D   E   L   K   N   A   L   K   *>
```

FIG. 36C

```
             10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
 M   A   C   N   N   S   G   K   D   G   N   T   S   A   N   S>

50                 60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
 A   D   E   S   V   K   G   P   N   L   T   E   I   S   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
 I   T   D   S   N   A   V   L   L   A   V   K   E   V   E   A>

   150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
 L   L   S   S   I   D   E   I   A   A   K   A   I   G   K   K>

      200                 210                 220                 230                 240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
 I   H   Q   N   N   G   L   D   T   E   Y   N   H   N   G   S>

         250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
 L   L   A   G   A   Y   A   I   S   T   L   I   K   Q   K   L>

290          300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
 D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
 K   C   S   E   T   F   T   N   K   L   K   E   K   H   T   D>

   390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
 L   G   K   E   G   V   T   D   A   D   A   K   E   A   I   L>

      440                 450                 460                 470                 480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
 K   T   N   G   T   K   T   K   G   A   E   E   L   G   K   L>

         490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
 F   E   S   V   E   V   L   S   K   A   A   K   E   M   L   A>
```

FIG. 37A

```
530         540         550         560         570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

 580         590         600         610         620
AAA CCT TCC ATG GCC AAG CAA AAT GTT AGC AGC CTT GAT GAA AAA AAT
TTT GGA AGG TAC CGG TTC GTT TTA CAA TCG TCG GAA CTA CTT TTT TTA
K   P   S   M   A   K   Q   N   V   S   S   L   D   E   K   N>

    630         640         650         660         670
AGC GTT TCA GTA GAT TTA CCT GGT GGA ATG ACA GTT CTT GTA AGT AAA
TCG CAA AGT CAT CTA AAT GGA CCA CCT TAC TGT CAA GAA CAT TCA TTT
S   V   S   V   D   L   P   G   G   M   T   V   L   V   S   K>

        680         690         700         710         720
GAA AAA GAC AAA GAC GGT AAA TAC AGT CTA GAG GCA ACA GTA GAC AAG
CTT TTT CTG TTT CTG CCA TTT ATG TCA GAT CTC CGT TGT CAT CTG TTC
E   K   D   K   D   G   K   Y   S   L   E   A   T   V   D   K>

            730         740         750         760
CTT GAG CTT AAA GGA ACT TCT GAT AAA AAC AAC GGT TCT GGA ACA CTT
GAA CTC GAA TTT CCT TGA AGA CTA TTT TTG TTG CCA AGA CCT TGT GAA
L   E   L   K   G   T   S   D   K   N   N   G   S   G   T   L>

770         780         790         800         810
GAA GGT GAA AAA ACT GAC AAA AGT AAA GTA AAA TTA ACA ATT GCT GAT
CTT CCA CTT TTT TGA CTG TTT TCA TTT CAT TTT AAT TGT TAA CGA CTA
E   G   E   K   T   D   K   S   K   V   K   L   T   I   A   D>

 820         830         840         850         860
GAC CTA AGT CAA ACT AAA TTT GAA ATT TTC AAA GAA GAT GCC AAA ACA
CTG GAT TCA GTT TGA TTT AAA CTT TAA AAG TTT CTT CTA CGG TTT TGT
D   L   S   Q   T   K   F   E   I   F   K   E   D   A   K   T>

    870         880         890         900         910
TTA GTA TCA AAA AAA GTA ACC CTT AAA GAC AAG TCA TCA ACA GAA GAA
AAT CAT AGT TTT TTT CAT TGG GAA TTT CTG TTC AGT AGT TGT CTT CTT
L   V   S   K   K   V   T   L   K   D   K   S   S   T   E   E>

        920         930         940         950         960
AAA TTC AAC GAA AAG GGT GAA ACA TCT GAA AAA ACA ATA GTA AGA GCA
TTT AAG TTG CTT TTC CCA CTT TGT AGA CTT TTT TGT TAT CAT TCT CGT
K   F   N   E   K   G   E   T   S   E   K   T   I   V   R   A>

            970         980         990         1000
AAT GGA ACC AGA CTT GAA TAC ACA GAC ATA AAA AGC GAT GGA TCC GGA
TTA CCT TGG TCT GAA CTT ATG TGT CTG TAT TTT TCG CTA CCT AGG CCT
N   G   T   R   L   E   Y   T   D   I   K   S   D   G   S   G>

1010        1020        1030        1040        1050
AAA GCT AAA GAA GTT TTA AAA GAC TTT ACT CTT GAA GGA ACT CTA GCT
TTT CGA TTT CTT CAA AAT TTT CTG AAA TGA GAA CTT CCT TGA GAT CGA
K   A   K   E   V   L   K   D   F   T   L   E   G   T   L   A>

1060        1070        1080        1090        1100
GCT GAC GGC AAA ACA ACA TTG AAA GTT ACA GAA GGC ACT GTT GTT TTA
```

FIG. 37B

```
    CGA CTG CCG TTT TGT TGT AAC TTT CAA TGT CTT CCG TGA CAA CAA AAT
     A   D   G   K   T   T   L   K   V   T   E   G   T   V   V   L>

        1110        1120        1130        1140        1150
    AGC AAG AAC ATT TTA AAA TCC GGA GAA ATA ACA GTT GCA CTT GAT GAC
    TCG TTC TTG TAA AAT TTT AGG CCT CTT TAT TGT CAA CGT GAA CTA CTG
     S   K   N   I   L   K   S   G   E   I   T   V   A   L   D   D>

        1160        1170        1180        1190        1200
    TCT GAC ACT ACT CAG GCT ACT AAA AAA ACT GGA AAA TGG GAT TCA AAT
    AGA CTG TGA TGA GTC CGA TGA TTT TTT TGA CCT TTT ACC CTA AGT TTA
     S   D   T   T   Q   A   T   K   K   T   G   K   W   D   S   N>

        1210        1220        1230        1240
    ACT TCC ACT TTA ACA ATT AGT GTG AAT AGC AAA AAA ACT AAA AAC ATT
    TGA AGG TGA AAT TGT TAA TCA CAC TTA TCG TTT TTT TGA TTT TTG TAA
     T   S   T   L   T   I   S   V   N   S   K   K   T   K   N   I>

1250        1260        1270        1280        1290
    GTA TTT ACA AAA GAA GAC ACA ATA ACA GTA CAA AAA TAC GAC TCA GCA
    CAT AAA TGT TTT CTT CTG TGT TAT TGT CAT GTT TTT ATG CTG AGT CGT
     V   F   T   K   E   D   T   I   T   V   Q   K   Y   D   S   A>

        1300        1310        1320        1330        1340
    GGC ACC AAT CTA GAA GGC AAC GCA GTC GAA ATT AAA ACA CTT GAT GAA
    CCG TGG TTA GAT CTT CCG TTG CGT CAG CTT TAA TTT TGT GAA CTA CTT
     G   T   N   L   E   G   N   A   V   E   I   K   T   L   D   E>

        1350        1360
    CTT AAA AAC GCT TTA AAA TAG
    GAA TTT TTG CGA AAT TTT ATC
     L   K   N   A   L   K   *>
```

FIG. 37C

```
          10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50          60          70          80          90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

 100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150         160         170         180         190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200         210         220         230         240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

           250         260         270         280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290          300         310         320         330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

 340         350         360         370         380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

   390         400         410         420         430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

       440         450         460         470         480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

          490         500         510         520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 38A

```
530           540           550           560           570
 GCT AAT TCA GTT AAA GAG CTT ACA AGC CCT GTT GTC CAT GGC AAG CAA
 CGA TTA AGT CAA TTT CTC GAA TGT TCG GGA CAA CAG GTA CCG TTC GTT
 A   N   S   V   K   E   L   T   S   P   V   V   H   G   K   Q>

  580           590           600           610           620
 AAT GTT AGC AGC CTT GAT GAA AAA AAT AGC GTT TCA GTA GAT TTA CCT
 TTA CAA TCG TCG GAA CTA CTT TTT TTA TCG CAA AGT CAT CTA AAT GGA
 N   V   S   S   L   D   E   K   N   S   V   S   V   D   L   P>

    630           640           650           660           670
 GGT GGA ATG ACA GTT CTT GTA AGT AAA GAA AAA GAC AAA GAC GGT AAA
 CCA CCT TAC TGT CAA GAA CAT TCA TTT CTT TTT CTG TTT CTG CCA TTT
 G   G   M   T   V   L   V   S   K   E   K   D   K   D   G   K>

      680           690           700           710           720
 TAC AGT CTA GAG GCA ACA GTA GAC AAG CTT GAG CTT AAA GGA ACT TCT
 ATG TCA GAT CTC CGT TGT CAT CTG TTC GAA CTC GAA TTT CCT TGA AGA
 Y   S   L   E   A   T   V   D   K   L   E   L   K   G   T   S>

          730           740           750           760
 GAT AAA AAC AAC GGT TCT GGA ACA CTT GAA GGT GAA AAA ACT GAC AAA
 CTA TTT TTG TTG CCA AGA CCT TGT GAA CTT CCA CTT TTT TGA CTG TTT
 D   K   N   N   G   S   G   T   L   E   G   E   K   T   D   K>

770           780           790           800           810
 AGT AAA GTA AAA TTA ACA ATT GCT GAT GAC CTA AGT CAA ACT AAA TTT
 TCA TTT CAT TTT AAT TGT TAA CGA CTA CTG GAT TCA GTT TGA TTT AAA
 S   K   V   K   L   T   I   A   D   D   L   S   Q   T   K   F>

  820           830           840           850           860
 GAA ATT TTC AAA GAA GAT GCC AAA ACA TTA GTA TCA AAA AAA GTA ACC
 CTT TAA AAG TTT CTT CTA CGG TTT TGT AAT CAT AGT TTT TTT CAT TGG
 E   I   F   K   E   D   A   K   T   L   V   S   K   K   V   T>

    870           880           890           900           910
 CTT AAA GAC AAG TCA TCA ACA GAA GAA AAA TTC AAC GAA AAG GGT GAA
 GAA TTT CTG TTC AGT AGT TGT CTT CTT TTT AAG TTG CTT TTC CCA CTT
 L   K   D   K   S   S   T   E   E   K   F   N   E   K   G   E>

      920           930           940           950           960
 ACA TCT GAA AAA ACA ATA GTA AGA GCA AAT GGA ACC AGA CTT GAA TAC
 TGT AGA CTT TTT TGT TAT CAT TCT CGT TTA CCT TGG TCT GAA CTT ATG
 T   S   E   K   T   I   V   R   A   N   G   T   R   L   E   Y>

          970           980           990           1000
 ACA GAC ATA AAA AGC GAT GGA TCC GGA AAA GCT AAA GAA GTT TTA AAA
 TGT CTG TAT TTT TCG CTA CCT AGG CCT TTT CGA TTT CTT CAA AAT TTT
 T   D   I   K   S   D   G   S   G   K   A   K   E   V   L   K>

1010          1020          1030          1040          1050
 GAC TTT ACT CTT GAA GGA ACT CTA GCT GCT GAC GGC AAA ACA ACA TTG
 CTG AAA TGA GAA CTT CCT TGA GAT CGA CGA CTG CCG TTT TGT TGT AAC
 D   F   T   L   E   G   T   L   A   A   D   G   K   T   T   L>

 1060          1070          1080          1090          1100
 AAA GTT ACA GAA GGC ACT GTT GTT TTA AGC AAG AAC ATT TTA AAA TCC
```

FIG. 38B

```
TTT CAA TGT CTT CCG TGA CAA CAA AAT TCG TTC TTG TAA AAT TTT AGG
K   V   T   E   G   T   V   V   L   S   K   N   I   L   K   S>

  1110            1120           1130           1140           1150
GGA GAA ATA ACA GTT GCA CTT GAT GAC TCT GAC ACT ACT CAG GCT ACT
CCT CTT TAT TGT CAA CGT GAA CTA CTG AGA CTG TGA TGA GTC CGA TGA
G   E   I   T   V   A   L   D   D   S   D   T   T   Q   A   T>

     1160           1170           1180           1190          1200
AAA AAA ACT GGA AAA TGG GAT TCA AAT ACT TCC ACT TTA ACA ATT AGT
TTT TTT TGA CCT TTT ACC CTA AGT TTA TGA AGG TGA AAT TGT TAA TCA
K   K   T   G   K   W   D   S   N   T   S   T   L   T   I   S>

         1210           1220           1230           1240
GTG AAT AGC AAA AAA ACT AAA AAC ATT GTA TTT ACA AAA GAA GAC ACA
CAC TTA TCG TTT TTT TGA TTT TTG TAA CAT AAA TGT TTT CTT CTG TGT
V   N   S   K   K   T   K   N   I   V   F   T   K   E   D   T>

1250        1260           1270           1280           1290
ATA ACA GTA CAA AAA TAC GAC TCA GCA GGC ACC AAT CTA GAA GGC AAC
TAT TGT CAT GTT TTT ATG CTG AGT CGT CCG TGG TTA GAT CTT CCG TTG
I   T   V   Q   K   Y   D   S   A   G   T   N   L   E   G   N>

1300          1310           1320           1330           1340
GCA GTC GAA ATT AAA ACA CTT GAT GAA CTT AAA AAC GCT TTA AAA TAG
CGT CAG CTT TAA TTT TGT GAA CTA CTT GAA TTT TTG CGA AAT TTT ATC
A   V   E   I   K   T   L   D   E   L   K   N   A   L   K   *>
```

FIG. 38C 10 20 30 40
ATG GCT TGT AAT AAT TCA GGA AAA GAT GGG AAT ACA TCT GCA AAT TCT
TAC CGA ACA TTA TTA AGT CCT TTT CTA CCC TTA TGT AGA CGT TTA AGA
M A C N N S G K D G N T S A N S>

50 60 70 80 90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A D E S V K G P N L T E I S K K>

100 110 120 130 140
ATT ACA GAA TCT AAC GCA GTT GTT CTG GCT GTG AAA GAA ATT GAA ACT
TAA TGT CTT AGA TTG CGT CAA CAA GAC CGA CAC TTT CTT TAA CTT TGA
I T E S N A V V L A V K E I E T>

150 160 170 180 190
TTG CTT GCA TCT ATA GAT GAA CTT GCT ACT AAA GCT ATT GGT AAA AAA
AAC GAA CGT AGA TAT CTA CTT GAA CGA TGA TTT CGA TAA CCA TTT TTT
L L A S I D E L A T K A I G K K>

200 210 220 230 240
ATA CAA CAA AAT GGT GGT TTA GCT GTC GAA GCG GGG CAT AAT GGA ACA
TAT GTT GTT TTA CCA CCA AAT CGA CAG CTT CGC CCC GTA TTA CCT TGT
I Q Q N G G L A V E A G H N G T>

250 260 270 280
TTG TTA GCA GGT GCT TAT ACA ATA TCA AAA CTA ATA ACA CAA AAA TTA
AAC AAT CGT CCA CGA ATA TGT TAT AGT TTT GAT TAT TGT GTT TTT AAT
L L A G A Y T I S K L I T Q K L>

290 300 310 320 330
GAT GGA TTG AAA AAT TCA GAA AAA TTA AAG GAA AAA ATT GAA AAT GCT
CTA CCT AAC TTT TTA AGT CTT TTT AAT TTC CTT TTT TAA CTT TTA CGA
D G L K N S E K L K E K I E N A>

340 350 360 370 380
AAG AAA TGT TCT GAA GAT TTT ACT AAA AAA CTA GAA GGA GAA CAT GCG
TTC TTT ACA AGA CTT CTA AAA TGA TTT TTT GAT CTT CCT CTT GTA CGC
K K C S E D F T K K L E G E H A>

390 400 410 420 430
CAA CTT GGA ATT GAA AAT GTT ACT GAT GAG AAT GCA AAA AAA GCT ATT
GTT GAA CCT TAA CTT TTA CAA TGA CTA CTC TTA CGT TTT TTT CGA TAA
Q L G I E N V T D E N A K K A I>

440 450 460 470 480
TTA ATA ACA GAT GCA GCT AAA GAT AAG GGC GCT GCA GAG CTT GAA AAG
AAT TAT TGT CTA CGT CGA TTT CTA TTC CCG CGA CGT CTC GAA CTT TTC
L I T D A A K D K G A A E L E K>

490 500 510 520
CTA TTT AAA GCA GTA GAA AAC TTG GCA AAA GCA GCT AAA GAG ATG CTT
GAT AAA TTT CGT CAT CTT TTG AAC CGT TTT CGT CGA TTT CTC TAC GAA
L F K A V E N L A K A A K E M L>

FIG. 39A

```
530              540              550              560              570
  GCT AAT TCA GTT AAA GAG CTT ACA AGT CCT ATT GTG CAT GGC GTT TCA
  CGA TTA AGT CAA TTT CTC GAA TGT TCA GGA TAA CAC GTA CCG CAA AGT
  A   N   S   V   K   E   L   T   S   P   I   V   H   G   V   S>

   580              590              600              610              620
  GTA GAT TTG CCT GGT GAA ATG AAA GTT CTT GTA AGC AAA GAA AAA AAC
  CAT CTA AAC GGA CCA CTT TAC TTT CAA GAA CAT TCG TTT CTT TTT TTG
  V   D   L   P   G   E   M   K   V   L   V   S   K   E   K   N>

     630              640              650              660              670
  AAA GAC GGC AAG TAC GAT CTA ATT GCA ACA GTA GAC AAG CTT GAG CTT
  TTT CTG CCG TTC ATG CTA GAT TAA CGT TGT CAT CTG TTC GAA CTC GAA
  K   D   G   K   Y   D   L   I   A   T   V   D   K   L   E   L>

        680              690              700              710              720
  AAA GGA ACT TCT GAT AAA AAC AAT GGA TCT GGA GTA CTT GAA GGC GTA
  TTT CCT TGA AGA CTA TTT TTG TTA CCT AGA CCT CAT GAA CTT CCG CAT
  K   G   T   S   D   K   N   N   G   S   G   V   L   E   G   V>

           730              740              750              760
  AAA GCT GAC AAA AGT AAA GTA AAA TTA ACA ATT TCT GAC GAT CTA GGT
  TTT CGA CTG TTT TCA TTT CAT TTT AAT TGT TAA AGA CTG CTA GAT CCA
  K   A   D   K   S   K   V   K   L   T   I   S   D   D   L   G>

770              780              790              800              810
  CAA ACC ACA CTT GAA GTT TTC AAA GAA GAT GGC AAA ACA CTA GTA TCA
  GTT TGG TGT GAA CTT CAA AAG TTT CTT CTA CCG TTT TGT GAT CAT AGT
  Q   T   T   L   E   V   F   K   E   D   G   K   T   L   V   S>

   820              830              840              850              860
  AAA AAA GTA ACT TCC AAA GAC AAG TCA TCA ACA GAA GAA AAA TTC AAT
  TTT TTT CAT TGA AGG TTT CTG TTC AGT AGT TGT CTT CTT TTT AAG TTA
  K   K   V   T   S   K   D   K   S   S   T   E   E   K   F   N>

     870              880              890              900              910
  GAA AAA GGT GAA GTA TCT GAA AAA ATA ATA ACA AGA GCA GAC GGA ACC
  CTT TTT CCA CTT CAT AGA CTT TTT TAT TAT TGT TCT CGT CTG CCT TGG
  E   K   G   E   V   S   E   K   I   I   T   R   A   D   G   T>

        920              930              940              950              960
  AGA CTT GAA TAC ACA GGA ATT AAA AGC GAT GGA TCT GGA AAA GCT AAA
  TCT GAA CTT ATG TGT CCT TAA TTT TCG CTA CCT AGA CCT TTT CGA TTT
  R   L   E   Y   T   G   I   K   S   D   G   S   G   K   A   K>

           970              980              990              1000
  GAG GTT TTA AAA AAA TTT ACT CTT GAA GGA AAA GTA GCT AAT GAT AAA
  CTC CAA AAT TTT TTT AAA TGA GAA CTT CCT TTT CAT CGA TTA CTA TTT
  E   V   L   K   K   F   T   L   E   G   K   V   A   N   D   K>

1010             1020             1030             1040             1050
  GTA ACA TTG GAA GTA AAA GAA GGA ACC GTT ACT TTA AGT AAG AAC ATT
  CAT TGT AAC CTT CAT TTT CTT CCT TGG CAA TGA AAT TCA TTC TTG TAA
  V   T   L   E   V   K   E   G   T   V   T   L   S   K   N   I>

  1060             1070             1080             1090             1100
  TCA AAA TCT GGG GAA GTT TCA GTT GAA CTT AAT GAC ACT GAC AGT AGT
```

FIG. 39B

```
                                    AGT TTT AGA CCC CTT CAA AGT CAA CTT GAA TTA CTG TGA CTG TCA TCA
                                     S   K   S   G   E   V   S   V   E   L   N   D   T   D   S   S>

           1110        1120        1130        1140        1150
        GCT GCT ACT AAA AAA ACT GCA GCT TGG AAT TCA GGC ACT TCA ACT TTA
        CGA CGA TGA TTT TTT TGA CGT CGA ACC TTA AGT CCG TGA AGT TGA AAT
         A   A   T   K   K   T   A   A   W   N   S   G   T   S   T   L>

           1160        1170        1180        1190        1200
        ACA ATT ACT GTA AAC AGT AAA AAA ACT AAA GAC CTT GTG TTT ACA AAA
        TGT TAA TGA CAT TTG TCA TTT TTT TGA TTT CTG GAA CAC AAA TGT TTT
         T   I   T   V   N   S   K   K   T   K   D   L   V   F   T   K>

                    1210        1220        1230        1240
        GAA AAC ACA ATT ACA GTA CAA CAA TAC GAC TCA AAT GGC ACC AAA TTA
        CTT TTG TGT TAA TGT CAT GTT GTT ATG CTG AGT TTA CCG TGG TTT AAT
         E   N   T   I   T   V   Q   Q   Y   D   S   N   G   T   K   L>

1250        1260        1270        1280        1290
GAG GGG TCA GCA GTT GAA ATT ACA AAA CTT GAT GAA ATT AAA AAC GCT
CTC CCC AGT CGT CAA CTT TAA TGT TTT GAA CTA CTT TAA TTT TTG CGA
 E   G   S   A   V   E   I   T   K   L   D   E   I   K   N   A>

1300
TTA AAA TAA
AAT TTT ATT
 L   K   *>
```

FIG. 39C 10 20 30 40
ATG GCT TGT AGT AAT TCA GGG AAA GGT GGG GAT TCT GCA TCT ACT AAT
TAC CGA ACA TCA TTA AGT CCC TTT CCA CCC CTA AGA CGT AGA TGA TTA
M A C S N S G K G G D S A S T N>

50 60 70 80 90
CCT GCT GAC GAG TCT GCG AAA GGG CCT AAT CTT ACA GAA ATA AGC AAA
GGA CGA CTG CTC AGA CGC TTT CCC GGA TTA GAA TGT CTT TAT TCG TTT
P A D E S A K G P N L T E I S K>

100 110 120 130 140
AAA ATT ACA GAT TCT AAT GCA TTT GTA CTT GCT GTT AAA GAA GTT GAG
TTT TAA TGT CTA AGA TTA CGT AAA CAT GAA CGA CAA TTT CTT CAA CTC
K I T D S N A F V L A V K E V E>

150 160 170 180 190
ACT TTG GTT TTA TCT ATA GAT GAA CTT GCT AAG AAA GCT ATT GGT CAA
TGA AAC CAA AAT AGA TAT CTA CTT GAA CGA TTC TTT CGA TAA CCA GTT
T L V L S I D E L A K K A I G Q>

200 210 220 230 240
AAA ATA GAC AAT AAT AAT GGT TTA GCT GCT TTA AAT AAT CAG AAT GGA
TTT TAT CTG TTA TTA TTA CCA AAT CGA CGA AAT TTA TTA GTC TTA CCT
K I D N N N G L A A L N N Q N G>

250 260 270 280
TCG TTG TTA GCA GGA GCC TAT GCA ATA TCA ACC CTA ATA ACA GAA AAA
AGC AAC AAT CGT CCT CGG ATA CGT TAT AGT TGG GAT TAT TGT CTT TTT
S L L A G A Y A I S T L I T E K>

290 300 310 320 330
TTG AGT AAA TTG AAA AAT TTA GAA GAA TTA AAG ACA GAA ATT GCA AAG
AAC TCA TTT AAC TTT TTA AAT CTT CTT AAT TTC TGT CTT TAA CGT TTC
L S K L K N L E E L K T E I A K>

340 350 360 370 380
GCT AAG AAA TGT TCC GAA GAA TTT ACT AAT AAA CTA AAA AGT GGT CAT
CGA TTC TTT ACA AGG CTT CTT AAA TGA TTA TTT GAT TTT TCA CCA GTA
A K K C S E E F T N K L K S G H>

390 400 410 420 430
GCA GAT CTT GGC AAA CAG GAT GCT ACC GAT GAT CAT GCA AAA GCA GCT
CGT CTA GAA CCG TTT GTC CTA CGA TGG CTA CTA GTA CGT TTT CGT CGA
A D L G K Q D A T D D H A K A A>

440 450 460 470 480
ATT TTA AAA ACA CAT GCA ACT ACC GAT AAA GGT GCT AAA GAA TTT AAA
TAA AAT TTT TGT GTA CGT TGA TGG CTA TTT CCA CGA TTT CTT AAA TTT
I L K T H A T T D K G A K E F K>

490 500 510 520
GAT TTA TTT GAA TCA GTA GAA GGT TTG TTA AAA GCA GCT CAA GTA GCA
CTA AAT AAA CTT AGT CAT CTT CCA AAC AAT TTT CGT CGA GTT CAT CGT
D L F E S V E G L L K A A Q V A>

FIG. 40A

```
530          540          550          560          570
 CTA ACT AAT TCA GTT AAA GAA CTT ACA AGT CCT GTT GTA GCA GAA AGT
 GAT TGA TTA AGT CAA TTT CTT GAA TGT TCA GGA CAA CAT CGT CTT TCA
 L   T   N   S   V   K   E   L   T   S   P   V   V   A   E   S>

  580          590          600          610          620
 CCA AAA AAA CCT TCC ATG GCC GTT TCA GTA GAT TTG CCT GGT GAA ATG
 GGT TTT TTT GGA AGG TAC CGG CAA AGT CAT CTA AAC GGA CCA CTT TAC
 P   K   K   P   S   M   A   V   S   V   D   L   P   G   E   M>

   630          640          650          660          670
 AAA GTT CTT GTA AGC AAA GAA AAA AAC AAA GAC GGC AAG TAC GAT CTA
 TTT CAA GAA CAT TCG TTT CTT TTT TTG TTT CTG CCG TTC ATG CTA GAT
 K   V   L   V   S   K   E   K   N   K   D   G   K   Y   D   L>

      680          690          700          710          720
 ATT GCA ACA GTA GAC AAG CTT GAG CTT AAA GGA ACT TCT GAT AAA AAC
 TAA CGT TGT CAT CTG TTC GAA CTC GAA TTT CCT TGA AGA CTA TTT TTG
 I   A   T   V   D   K   L   E   L   K   G   T   S   D   K   N>

         730          740          750          760
 AAT GGA TCT GGA GTA CTT GAA GGC GTA AAA GCT GAC AAA AGT AAA GTA
 TTA CCT AGA CCT CAT GAA CTT CCG CAT TTT CGA CTG TTT TCA TTT CAT
 N   G   S   G   V   L   E   G   V   K   A   D   K   S   K   V>

770          780          790          800          810
 AAA TTA ACA ATT TCT GAC GAT CTA GGT CAA ACC ACA CTT GAA GTT TTC
 TTT AAT TGT TAA AGA CTG CTA GAT CCA GTT TGG TGT GAA CTT CAA AAG
 K   L   T   I   S   D   D   L   G   Q   T   T   L   E   V   F>

  820          830          840          850          860
 AAA GAA GAT GGC AAA ACA CTA GTA TCA AAA AAA GTA ACT TCC AAA GAC
 TTT CTT CTA CCG TTT TGT GAT CAT AGT TTT TTT CAT TGA AGG TTT CTG
 K   E   D   G   K   T   L   V   S   K   K   V   T   S   K   D>

   870          880          890          900          910
 AAG TCA TCA ACA GAA GAA AAA TTC AAT GAA AAA GGT GAA GTA TCT GAA
 TTC AGT AGT TGT CTT CTT TTT AAG TTA CTT TTT CCA CTT CAT AGA CTT
 K   S   S   T   E   E   K   F   N   E   K   G   E   V   S   E>

      920          930          940          950          960
 AAA ATA ATA ACA AGA GCA GAC GGA ACC AGA CTT GAA TAC ACA GGA ATT
 TTT TAT TAT TGT TCT CGT CTG CCT TGG TCT GAA CTT ATG TGT CCT TAA
 K   I   I   T   R   A   D   G   T   R   L   E   Y   T   G   I>

         970          980          990          1000
 AAA AGC GAT GGA TCT GGA AAA GCT AAA GAG GTT TTA AAA AAA TTT ACT
 TTT TCG CTA CCT AGA CCT TTT CGA TTT CTC CAA AAT TTT TTT AAA TGA
 K   S   D   G   S   G   K   A   K   E   V   L   K   K   F   T>

1010         1020         1030         1040         1050
 CTT GAA GGA AAA GTA GCT AAT GAT AAA GTA ACA TTG GAA GTA AAA GAA
 GAA CTT CCT TTT CAT CGA TTA CTA TTT CAT TGT AAC CTT CAT TTT CTT
 L   E   G   K   V   A   N   D   K   V   T   L   E   V   K   E>

  1060         1070         1080         1090         1100
 GGA ACC GTT ACT TTA AGT AAG AAT ATT TCA AAA TCT GGG GAA GTT TCA
```

FIG. 40B

```
           CCT TGG CAA TGA AAT TCA TTC TTA TAA AGT TTT AGA CCC CTT CAA AGT
            G   T   V   T   L   S   K   N   I   S   K   S   G   E   V   S>

                1110        1120        1130        1140        1150
           GTT GAA CTT AAT GAC ACT GAC AGT AGT GCT GCT ACT AAA AAA ACT GCA
           CAA CTT GAA TTA CTG TGA CTG TCA TCA CGA CGA TGA TTT TTT TGA CGT
            V   E   L   N   D   T   D   S   S   A   A   T   K   K   T   A>

                1160        1170        1180        1190        1200
           GCT TGG AAT TCA AAA ACT TCC ACT TTA ACA ATT AGT GTG AAT AGC CAA
           CGA ACC TTA AGT TTT TGA AGG TGA AAT TGT TAA TCA CAC TTA TCG GTT
            A   W   N   S   K   T   S   T   L   T   I   S   V   N   S   Q>

                1210        1220        1230        1240
           AAA ACC AAA AAC CTT GTA TTC ACA AAA GAA GAC ACA ATA ACA GTA CAA
           TTT TGG TTT TTG GAA CAT AAG TGT TTT CTT CTG TGT TAT TGT CAT GTT
            K   T   K   N   L   V   F   T   K   E   D   T   I   T   V   Q>

     1250          1260        1270        1280        1290
           AAA TAC GAC TCA GCA GGC ACC AAT CTA GAA GGC AAA GCA GTC GAA ATT
           TTT ATG CTG AGT CGT CCG TGG TTA GAT CTT CCG TTT CGT CAG CTT TAA
            K   Y   D   S   A   G   T   N   L   E   G   K   A   V   E   I>

     1300          1310        1320        1330
           ACA ACA CTT AAA GAA CTT AAA AAC GCT TTA AAA TAA
           TGT TGT GAA TTT CTT GAA TTT TTG CGA AAT TTT ATT
            T   T   L   K   E   L   K   N   A   L   K   *>

                              FIG. 40C
```

```
              10             20             30             40
ATG GCT TGT AAT AAT TCA GGT GGG GAT TCT GCA TCT ACT AAT CCT GAT
TAC CGA ACA TTA TTA AGT CCA CCC CTA AGA CGT AGA TGA TTA GGA CTA
M   A   C   N   N   S   G   G   D   S   A   S   T   N   P   D>

50             60             70             80             90
GAG TCT GCA AAA GGA CCT AAT CTT ACC GTA ATA AGC AAA AAA ATT ACA
CTC AGA CGT TTT CCT GGA TTA GAA TGG CAT TAT TCG TTT TTT TAA TGT
E   S   A   K   G   P   N   L   T   V   I   S   K   K   I   T>

 100            110            120            130            140
GAT TCT AAT GCA TTT TTA CTG GCT GTG AAA GAA GTT GAG GCT TTG CTT
CTA AGA TTA CGT AAA AAT GAC CGA CAC TTT CTT CAA CTC CGA AAC GAA
D   S   N   A   F   L   L   A   V   K   E   V   E   A   L   L>

   150            160            170            180            190
TCA TCT ATA GAT GAA CTT TCT AAA GCT ATT GGT AAA AAA ATA AAA AAT
AGT AGA TAT CTA CTT GAA AGA TTT CGA TAA CCA TTT TTT TAT TTT TTA
S   S   I   D   E   L   S   K   A   I   G   K   K   I   K   N>

      200            210            220            230            240
GAT GGT ACT TTA GAT AAC GAA GCA AAT CGA AAC GAA TCA TTG ATA GCA
CTA CCA TGA AAT CTA TTG CTT CGT TTA GCT TTG CTT AGT AAC TAT CGT
D   G   T   L   D   N   E   A   N   R   N   E   S   L   I   A>

         250            260            270            280
GGA GCT TAT GAA ATA TCA AAA CTA ATA ACA CAA AAA TTA AGT GTA TTG
CCT CGA ATA CTT TAT AGT TTT GAT TAT TGT GTT TTT AAT TCA CAT AAC
G   A   Y   E   I   S   K   L   I   T   Q   K   L   S   V   L>

290            300            310            320            330
AAT TCA GAA GAA TTA AAG GAA AAA ATT AAA GAG GCT AAG GAT TGT TCC
TTA AGT CTT CTT AAT TTC CTT TTT TAA TTT CTC CGA TTC CTA ACA AGG
N   S   E   E   L   K   E   K   I   K   E   A   K   D   C   S>

 340            350            360            370            380
GAA AAA TTT ACT ACT AAG CTA AAA GAT AGT CAT GCA GAG CTT GGT ATA
CTT TTT AAA TGA TGA TTC GAT TTT CTA TCA GTA CGT CTC GAA CCA TAT
E   K   F   T   T   K   L   K   D   S   H   A   E   L   G   I>

   390            400            410            420            430
CAA AGC GTT CAG GAT GAT AAT GCA AAA AAA GCT ATT TTA AAA ACA CAT
GTT TCG CAA GTC CTA CTA TTA CGT TTT TTT CGA TAA AAT TTT TGT GTA
Q   S   V   Q   D   D   N   A   K   K   A   I   L   K   T   H>

      440            450            460            470            480
GGA ACT AAA GAC AAG GGT GCT AAA GAA CTT GAA GAG TTA TTT AAA TCA
CCT TGA TTT CTG TTC CCA CGA TTT CTT GAA CTT CTC AAT AAA TTT AGT
G   T   K   D   K   G   A   K   E   L   E   E   L   F   K   S>

         490            500            510            520
CTA GAA AGC TTG TCA AAA GCA GCG CAA GCA GCA TTA ACT AAT TCA GTT
GAT CTT TCG AAC AGT TTT CGT CGC GTT CGT CGT AAT TGA TTA AGT CAA
L   E   S   L   S   K   A   A   Q   A   A   L   T   N   S   V>
```

FIG. 41A

```
530        540         550         560         570
 AAA GAG CTT ACA AAT CCT GTT GTG GCA GAA AGT CCA AAA AAA CCT TCC
 TTT CTC GAA TGT TTA GGA CAA CAC CGT CTT TCA GGT TTT TTT GGA AGG
 K   E   L   T   N   P   V   V   A   E   S   P   K   K   P   S>

  580        590         600         610         620
 ATG GCC GTT TCA GTA GAT TTG CCT GGT GAA ATG AAA GTT CTT GTA AGC
 TAC CGG CAA AGT CAT CTA AAC GGA CCA CTT TAC TTT CAA GAA CAT TCG
 M   A   V   S   V   D   L   P   G   E   M   K   V   L   V   S>

    630        640         650         660         670
 AAA GAA AAA AAC AAA GAC GGC AAG TAC GAT CTA ATT GCA ACA GTA GAC
 TTT CTT TTT TTG TTT CTG CCG TTC ATG CTA GAT TAA CGT TGT CAT CTG
 K   E   K   N   K   D   G   K   Y   D   L   I   A   T   V   D>

      680        690         700         710         720
 AAG CTT GAG CTT AAA GGA ACT TCT GAT AAA AAC AAT GGA TCT GGA GTA
 TTC GAA CTC GAA TTT CCT TGA AGA CTA TTT TTG TTA CCT AGA CCT CAT
 K   L   E   L   K   G   T   S   D   K   N   N   G   S   G   V>

        730        740         750         760
 CTT GAA GGC GTA AAA GCT GAC AAA AGT AAA GTA AAA TTA ACA ATT TCT
 GAA CTT CCG CAT TTT CGA CTG TTT TCA TTT CAT TTT AAT TGT TAA AGA
 L   E   G   V   K   A   D   K   S   K   V   K   L   T   I   S>

770        780         790         800         810
 GAC GAT CTA GGT CAA ACC ACA CTT GAA GTT TTC AAA GAA GAT GGC AAA
 CTG CTA GAT CCA GTT TGG TGT GAA CTT CAA AAG TTT CTT CTA CCG TTT
 D   D   L   G   Q   T   T   L   E   V   F   K   E   D   G   K>

  820        830         840         850         860
 ACA CTA GTA TCA AAA AAA GTA ACT TCC AAA GAC AAG TCA TCA ACA GAA
 TGT GAT CAT AGT TTT TTT CAT TGA AGG TTT CTG TTC AGT AGT TGT CTT
 T   L   V   S   K   K   V   T   S   K   D   K   S   S   T   E>

    870        880         890         900         910
 GAA AAA TTC AAT GAA AAA GGT GAA GTA TCT GAA AAA ATA ATA ACA AGA
 CTT TTT AAG TTA CTT TTT CCA CTT CAT AGA CTT TTT TAT TAT TGT TCT
 E   K   F   N   E   K   G   E   V   S   E   K   I   I   T   R>

      920        930         940         950         960
 GCA GAC GGA ACC AGA CTT GAA TAC ACA GGA ATT AAA AGC GAT GGA TCT
 CGT CTG CCT TGG TCT GAA CTT ATG TGT CCT TAA TTT TCG CTA CCT AGA
 A   D   G   T   R   L   E   Y   T   G   I   K   S   D   G   S>

        970        980         990         1000
 GGA AAA GCT AAA GAG GTT TTA AAA AAA TTT ACT CTT GAA GGA AAA GTA
 CCT TTT CGA TTT CTC CAA AAT TTT TTT AAA TGA GAA CTT CCT TTT CAT
 G   K   A   K   E   V   L   K   K   F   T   L   E   G   K   V>

1010       1020        1030        1040        1050
 GCT AAT GAT AAA GTA ACA TTG GAA GTA AAA GAA GGA ACC GTT ACT TTA
 CGA TTA CTA TTT CAT TGT AAC CTT CAT TTT CTT CCT TGG CAA TGA AAT
 A   N   D   K   V   T   L   E   V   K   E   G   T   V   T   L>

  1060       1070        1080        1090        1100
 AGT AAG AAC ATT TCA AAA TCT GGG GAA GTT TCA GTT GAA CTT AAT GAC
```

FIG. 41B

```
   TCA TTC TTG TAA AGT TTT AGA CCC CTT CAA AGT CAA CTT GAA TTA CTG
   S   K   N   I   S   K   S   G   E   V   S   V   E   L   N   D>

     1110          1120          1130          1140          1150
   ACT GAC AGT AGT GCT GCT ACT AAA AAA ACT GCA GCT TGG AAT TCA AAA
   TGA CTG TCA TCA CGA CGA TGA TTT TTT TGA CGT CGA ACC TTA AGT TTT
   T   D   S   S   A   A   T   K   K   T   A   A   W   N   S   K>

         1160          1170          1180          1190          1200
   ACT TCT ACT TTA ACA ATT AGT GTT AAC AGC AAA AAA ACT ACA CAA CTT
   TGA AGA TGA AAT TGT TAA TCA CAA TTG TCG TTT TTT TGA TGT GTT GAA
   T   S   T   L   T   I   S   V   N   S   K   K   T   T   Q   L>

             1210          1220          1230          1240
   GTG TTT ACT AAA CAA GAC ACA ATA ACT GTA CAA AAA TAC GAC TCC GCA
   CAC AAA TGA TTT GTT CTG TGT TAT TGA CAT GTT TTT ATG CTG AGG CGT
   V   F   T   K   Q   D   T   I   T   V   Q   K   Y   D   S   A>

1250          1260          1270          1280          1290
   GGT ACC AAT TTA GAA GGC ACA GCA GTC GAA ATT AAA ACA CTT GAT GAA
   CCA TGG TTA AAT CTT CCG TGT CGT CAG CTT TAA TTT TGT GAA CTA CTT
   G   T   N   L   E   G   T   A   V   E   I   K   T   L   D   E>

   1300          1310
   CTT AAA AAC GCT TTA AAA TAA
   GAA TTT TTG CGA AAT TTT ATT
   L   K   N   A   L   K   *>
```

FIG. 41C

```
                10              20              30              40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50              60              70              80              90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100             110             120             130             140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150             160             170             180             190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

       200             210             220             230             240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

          250             260             270             280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290             300             310             320             330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340             350             360             370             380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390             400             410             420             430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

       440             450             460             470             480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

          490             500             510             520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 42A

```
530             540            550            560            570
 AAT TCA GTT AAA GAG CTT ACA AGC CCT GTT GTG GCA GAA AGT CCA AAA
 TTA AGT CAA TTT CTC GAA TGT TCG GGA CAA CAC CGT CTT TCA GGT TTT
 N   S   V   K   E   L   T   S   P   V   V   A   E   S   P   K>

   580            590            600            610            620
 AAA CCT TCC ATG GCC AAG CAA AAT GTT TCT GAA AAA ATA ATA ACA AGA
 TTT GGA AGG TAC CGG TTC GTT TTA CAA AGA CTT TTT TAT TAT TGT TCT
 K   P   S   M   A   K   Q   N   V   S   E   K   I   I   T   R>

     630            640            650            660            670
 GCA GAC GGA ACC AGA CTT GAA TAC ACA GGA ATT AAA AGC GAT GGA TCT
 CGT CTG CCT TGG TCT GAA CTT ATG TGT CCT TAA TTT TCG CTA CCT AGA
 A   D   G   T   R   L   E   Y   T   G   I   K   S   D   G   S>

        680            690            700            710            720
 GGA AAA GCT AAA GAG GTT TTA AAA GGC TAT GTT CTT GAA GGA ACT CTA
 CCT TTT CGA TTT CTC CAA AAT TTT CCG ATA CAA GAA CTT CCT TGA GAT
 G   K   A   K   E   V   L   K   G   Y   V   L   E   G   T   L>

            730            740            750            760
 ACT GCT GAA AAA ACA ACA TTG GTG GTT AAA GAA GGA ACT GTT ACT TTA
 TGA CGA CTT TTT TGT TGT AAC CAC CAA TTT CTT CCT TGA CAA TGA AAT
 T   A   E   K   T   T   L   V   V   K   E   G   T   V   T   L>

770            780            790            800            810
 AGC AAA AAT ATT TCA AAA TCT GGG GAA GTT TCA GTT GAA CTT AAT GAC
 TCG TTT TTA TAA AGT TTT AGA CCC CTT CAA AGT CAA CTT GAA TTA CTG
 S   K   N   I   S   K   S   G   E   V   S   V   E   L   N   D>

  820            830            840            850            860
 ACT GAC AGT AGT GCT GCT ACT AAA AAA ACT GCA GCT TGG AAT TCA GGC
 TGA CTG TCA TCA CGA CGA TGA TTT TTT TGA CGT CGA ACC TTA AGT CCG
 T   D   S   S   A   A   T   K   K   T   A   A   W   N   S   G>

     870            880            890            900            910
 ACT TCA ACT TTA ACA ATT ACT GTA AAC AGT AAA AAA ACT AAA GAC CTT
 TGA AGT TGA AAT TGT TAA TGA CAT TTG TCA TTT TTT TGA TTT CTG GAA
 T   S   T   L   T   I   T   V   N   S   K   K   T   K   D   L>

        920            930            940            950            960
 GTG TTT ACA AAA GAA AAC ACA ATT ACA GTA CAA CAA TAC GAC TCA AAT
 CAC AAA TGT TTT CTT TTG TGT TAA TGT CAT GTT GTT ATG CTG AGT TTA
 V   F   T   K   E   N   T   I   T   V   Q   Q   Y   D   S   N>

            970            980            990            1000
 GGC ACC AAA TTA GAG GGG TCA GCA GTT GAA ATT ACA AAA CTT GAT GAA
 CCG TGG TTT AAT CTC CCC AGT CGT CAA CTT TAA TGT TTT GAA CTA CTT
 G   T   K   L   E   G   S   A   V   E   I   T   K   L   D   E>

1010           1020
 ATT AAA AAC GCT TTA AAA TAA
 TAA TTT TTG CGA AAT TTT ATT
 I   K   N   A   L   K   *>
```

FIG. 42B

```
             10               20               30               40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50               60               70               80               90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100              110              120              130              140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150              160              170              180              190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

       200              210              220              230              240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

          250              260              270              280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290              300              310              320              330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340              350              360              370              380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390              400              410              420              430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

       440              450              460              470              480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

          490              500              510              520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 43A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTA TCT GAA AAA ATA ATA ACA AGA
TTT GGA AGG TAC CGG TTC GTT TTA CAT AGA CTT TTT TAT TAT TGT TCT
K P S M A K Q N V S E K I I T R>

630 640 650 660 670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
A D G T R L E Y T G I K S D G S>

680 690 700 710 720
GGA AAA GCT AAA GAG GTT TTA AAA GGC TAT GTT CTT GAA GGA ACT CTA
CCT TTT CGA TTT CTC CAA AAT TTT CCG ATA CAA GAA CTT CCT TGA GAT
G K A K E V L K G Y V L E G T L>

730 740 750 760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
T A E K T T L V V K E G T V T L>

770 780 790 800 810
AGC AAA AAT ATT TCA AAA TCT GGG GAA GTT TCA GTT GAA CTT AAT GAC
TCG TTT TTA TAA AGT TTT AGA CCC CTT CAA AGT CAA CTT GAA TTA CTG
S K N I S K S G E V S V E L N D>

820 830 840 850 860
ACT GAC AGT AGT GCT GCT ACT AAA AAA ACT GCA GCT TGG AAT TCA AAA
TGA CTG TCA TCA CGA CGA TGA TTT TTT TGA CGT CGA ACC TTA AGT TTT
T D S S A A T K K T A A W N S K>

870 880 890 900 910
ACT TCC ACT TTA ACA ATT AGT GTG AAT AGC CAA AAA ACC AAA AAC CTT
TGA AGG TGA AAT TGT TAA TCA CAC TTA TCG GTT TTT TGG TTT TTG GAA
T S T L T I S V N S Q K T K N L>

920 930 940 950 960
GTA TTC ACA AAA GAA GAC ACA ATA ACA GTA CAA AAA TAC GAC TCA GCA
CAT AAG TGT TTT CTT CTG TGT TAT TGT CAT GTT TTT ATG CTG AGT CGT
V F T K E D T I T V Q K Y D S A>

970 980 990 1000
GGC ACC AAT CTA GAA GGC AAA GCA GTC GAA ATT ACA ACA CTT AAA GAA
CCG TGG TTA GAT CTT CCG TTT CGT CAG CTT TAA TGT TGT GAA TTT CTT
G T N L E G K A V E I T T L K E>

1010 1020
CTT AAA AAC GCT TTA AAA TAA
GAA TTT TTG CGA AAT TTT ATT
L K N A L K *>

FIG. 43B

```
        10          20          30          40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50          60          70          80          90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100         110         120         130         140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150         160         170         180         190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

      200         210         220         230         240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

         250         260         270         280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290         300         310         320         330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340         350         360         370         380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

   390         400         410         420         430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

      440         450         460         470         480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

         490         500         510         520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 44A

```
530         540         550         560         570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

 580         590         600         610         620
AAA CCT TCC ATG GCC AAG CAA AAT GTA TCT GAA AAA ATA ATA ACA AGA
TTT GGA AGG TAC CGG TTC GTT TTA CAT AGA CTT TTT TAT TAT TGT TCT
K   P   S   M   A   K   Q   N   V   S   E   K   I   I   T   R>

   630         640         650         660         670
GCA GAC GGA ACC AGA CTT GAA TAC ACA GGA ATT AAA AGC GAT GGA TCT
CGT CTG CCT TGG TCT GAA CTT ATG TGT CCT TAA TTT TCG CTA CCT AGA
A   D   G   T   R   L   E   Y   T   G   I   K   S   D   G   S>

      680         690         700         710         720
GGA AAA GCT AAA GAG GTT TTA AAA GGC TAT GTT CTT GAA GGA ACT CTA
CCT TTT CGA TTT CTC CAA AAT TTT CCG ATA CAA GAA CTT CCT TGA GAT
G   K   A   K   E   V   L   K   G   Y   V   L   E   G   T   L>

         730         740         750         760
ACT GCT GAA AAA ACA ACA TTG GTG GTT AAA GAA GGA ACT GTT ACT TTA
TGA CGA CTT TTT TGT TGT AAC CAC CAA TTT CTT CCT TGA CAA TGA AAT
T   A   E   K   T   T   L   V   V   K   E   G   T   V   T   L>

770         780         790         800         810
AGC AAA AAT ATT TCA AAA TCT GGG GAA GTT TCA GTT GAA CTT AAT GAC
TCG TTT TTA TAA AGT TTT AGA CCC CTT CAA AGT CAA CTT GAA TTA CTG
S   K   N   I   S   K   S   G   E   V   S   V   E   L   N   D>

 820         830         840         850         860
ACT GAC AGT AGT GCT GCT ACT AAA AAA ACT GCA GCT TGG AAT TCA AAA
TGA CTG TCA TCA CGA CGA TGA TTT TTT TGA CGT CGA ACC TTA AGT TTT
T   D   S   S   A   A   T   K   K   T   A   A   W   N   S   K>

   870         880         890         900         910
ACT TCT ACT TTA ACA ATT AGT GTT AAC AGC AAA AAA ACT ACA CAA CTT
TGA AGA TGA AAT TGT TAA TCA CAA TTG TCG TTT TTT TGA TGT GTT GAA
T   S   T   L   T   I   S   V   N   S   K   K   T   T   Q   L>

      920         930         940         950         960
GTG TTT ACT AAA CAA GAC ACA ATA ACT GTA CAA AAA TAC GAC TCC GCA
CAC AAA TGA TTT GTT CTG TGT TAT TGA CAT GTT TTT ATG CTG AGG CGT
V   F   T   K   Q   D   T   I   T   V   Q   K   Y   D   S   A>

         970         980         990        1000
GGT ACC AAT TTA GAA GGC ACA GCA GTC GAA ATT AAA ACA CTT GAT GAA
CCA TGG TTA AAT CTT CCG TGT CGT CAG CTT TAA TTT TGT GAA CTA CTT
G   T   N   L   E   G   T   A   V   E   I   K   T   L   D   E>

1010        1020
CTT AAA AAC GCT TTA AAA TAA
GAA TTT TTG CGA AAT TTT ATT
L   K   N   A   L   K   *>
```

FIG. 44B

```
         10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

   150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

       200                 210                 220                 230                 240
ATA CAC CAA AAT AAT GGT TTG GAT ACC GAA TAT AAT CAC AAT GGA TCA
TAT GTG GTT TTA TTA CCA AAC CTA TGG CTT ATA TTA GTG TTA CCT AGT
I   H   Q   N   N   G   L   D   T   E   Y   N   H   N   G   S>

           250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290               300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

       440                 450                 460                 470                 480
AAA ACA AAT GGT ACT AAA ACT AAA GGT GCT GAA GAA CTT GGA AAA TTA
TTT TGT TTA CCA TGA TTT TGA TTT CCA CGA CTT CTT GAA CCT TTT AAT
K   T   N   G   T   K   T   K   G   A   E   E   L   G   K   L>

           490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 45A 530 540 550 560 570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N S V K E L T S P V V A E S P K>

580 590 600 610 620
AAA CCT TCC ATG GCC AAG CAA AAT GTT ACA TCT GAA AAA ACA ATA GTA
TTT GGA AGG TAC CGG TTC GTT TTA CAA TGT AGA CTT TTT TGT TAT CAT
K P S M A K Q N V T S E K T I V>

630 640 650 660 670
AGA GCA AAT GGA ACC AGA CTT GAA TAC ACA GAC ATA AAA AGC GAT GGA
TCT CGT TTA CCT TGG TCT GAA CTT ATG TGT CTG TAT TTT TCG CTA CCT
R A N G T R L E Y T D I K S D G>

680 690 700 710 720
TCC GGA AAA GCT AAA GAA GTT TTA AAA GAC TTT ACT CTT GAA GGA ACT
AGG CCT TTT CGA TTT CTT CAA AAT TTT CTG AAA TGA GAA CTT CCT TGA
S G K A K E V L K D F T L E G T>

730 740 750 760
CTA GCT GCT GAC GGC AAA ACA ACA TTG AAA GTT ACA GAA GGC ACT GTT
GAT CGA CGA CTG CCG TTT TGT TGT AAC TTT CAA TGT CTT CCG TGA CAA
L A A D G K T T L K V T E G T V>

770 780 790 800 810
GTT TTA AGC AAG AAC ATT TTA AAA TCC GGA GAA ATA ACA GTT GCA CTT
CAA AAT TCG TTC TTG TAA AAT TTT AGG CCT CTT TAT TGT CAA CGT GAA
V L S K N I L K S G E I T V A L>

820 830 840 850 860
GAT GAC TCT GAC ACT ACT CAG GCT ACT AAA AAA ACT GGA AAA TGG GAT
CTA CTG AGA CTG TGA TGA GTC CGA TGA TTT TTT TGA CCT TTT ACC CTA
D D S D T T Q A T K K T G K W D>

870 880 890 900 910
TCA AAT ACT TCC ACT TTA ACA ATT AGT GTG AAT AGC AAA AAA ACT AAA
AGT TTA TGA AGG TGA AAT TGT TAA TCA CAC TTA TCG TTT TTT TGA TTT
S N T S T L T I S V N S K K T K>

920 930 940 950 960
AAC ATT GTA TTT ACA AAA GAA GAC ACA ATA ACA GTA CAA AAA TAC GAC
TTG TAA CAT AAA TGT TTT CTT CTG TGT TAT TGT CAT GTT TTT ATG CTG
N I V F T K E D T I T V Q K Y D>

970 980 990 1000
TCA GCA GGC ACC AAT CTA GAA GGC AAC GCA GTC GAA ATT AAA ACA CTT
AGT CGT CCG TGG TTA GAT CTT CCG TTG CGT CAG CTT TAA TTT TGT GAA
S A G T N L E G N A V E I K T L>

1010 1020 1030
GAT GAA CTT AAA AAC GCT TTA AAA TAG
CTA CTT GAA TTT TTG CGA AAT TTT ATC
D E L K N A L K *>

FIG. 45B

```
            10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AAT AAA AAA
CGA CTA CTC AGA CAA TTT CCC GGA TTA GAA TGT CTT TAT TTA TTT TTT
A   D   E   S   V   K   G   P   N   L   T   E   I   N   K   K>

 100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAA ATT GCT GCT AAA GCT ATT GGT AAA AAA
AAC GAC AGT AGA TAT CTA CTT TAA CGA CGA TTT CGA TAA CCA TTT TTT
L   L   S   S   I   D   E   I   A   A   K   A   I   G   K   K>

        200                 210                 220                 230                 240
ATA CAC CAA AAT AAT GGT TTG GAT ACC GAA AAT AAT CAC AAT GGA TCA
TAT GTG GTT TTA TTA CCA AAC CTA TGG CTT TTA TTA GTG TTA CCT AGT
I   H   Q   N   N   G   L   D   T   E   N   N   H   N   G   S>

            250                 260                 270                 280
TTG TTA GCG GGA GCT TAT GCA ATA TCA ACC CTA ATA AAA CAA AAA TTA
AAC AAT CGC CCT CGA ATA CGT TAT AGT TGG GAT TAT TTT GTT TTT AAT
L   L   A   G   A   Y   A   I   S   T   L   I   K   Q   K   L>

290             300                 310                 320                 330
GAT GGA TTG AAA AAT GAA GGA TTA AAG GAA AAA ATT GAT GCG GCT AAG
CTA CCT AAC TTT TTA CTT CCT AAT TTC CTT TTT TAA CTA CGC CGA TTC
D   G   L   K   N   E   G   L   K   E   K   I   D   A   A   K>

 340                 350                 360                 370                 380
AAA TGT TCT GAA ACA TTT ACT AAT AAA TTA AAA GAA AAA CAC ACA GAT
TTT ACA AGA CTT TGT AAA TGA TTA TTT AAT TTT CTT TTT GTG TGT CTA
K   C   S   E   T   F   T   N   K   L   K   E   K   H   T   D>

    390                 400                 410                 420                 430
CTT GGT AAA GAA GGT GTT ACT GAT GCT GAT GCA AAA GAA GCC ATT TTA
GAA CCA TTT CTT CCA CAA TGA CTA CGA CTA CGT TTT CTT CGG TAA AAT
L   G   K   E   G   V   T   D   A   D   A   K   E   A   I   L>

        440                 450                 460                 470                 480
AAA GCA AAT GGT ACT AAA ACT AAA GGT GCT GAA GAA CTT GGA AAA TTA
TTT CGT TTA CCA TGA TTT TGA TTT CCA CGA CTT CTT GAA CCT TTT AAT
K   A   N   G   T   K   T   K   G   A   E   E   L   G   K   L>

            490                 500                 510                 520
TTT GAA TCA GTA GAG GTC TTG TCA AAA GCA GCT AAA GAG ATG CTT GCT
AAA CTT AGT CAT CTC CAG AAC AGT TTT CGT CGA TTT CTC TAC GAA CGA
F   E   S   V   E   V   L   S   K   A   A   K   E   M   L   A>
```

FIG. 46A

```
530          540          550          560          570
AAT TCA GTT AAA GAG CTT ACA AGC CCT GTT GTG GCA GAA AGT CCA AAA
TTA AGT CAA TTT CTC GAA TGT TCG GGA CAA CAC CGT CTT TCA GGT TTT
N   S   V   K   E   L   T   S   P   V   V   A   E   S   P   K>

 580          590          600          610          620
AAA CCT TCC ATG GCC GTT TCA GTA GAT TTG CCT GGT GAA ATG AAA GTT
TTT GGA AGG TAC CGG CAA AGT CAT CTA AAC GGA CCA CTT TAC TTT CAA
K   P   S   M   A   V   S   V   D   L   P   G   E   M   K   V>

   630          640          650          660          670
CTT GTA AGC AAA GAA AAA AAC AAA GAC GGC AAG TAC GAT CTA ATT GCA
GAA CAT TCG TTT CTT TTT TTG TTT CTG CCG TTC ATG CTA GAT TAA CGT
L   V   S   K   E   K   N   K   D   G   K   Y   D   L   I   A>

       680          690          700          710          720
ACA GTA GAC AAG CTT GAG CTT AAA GGA ACT TCT GAT AAA AAC AAT GGA
TGT CAT CTG TTC GAA CTC GAA TTT CCT TGA AGA CTA TTT TTG TTA CCT
T   V   D   K   L   E   L   K   G   T   S   D   K   N   N   G>

           730          740          750          760
TCT GGA GTA CTT GAA GGC GTA AAA GCT GAC AAA AGT AAA GTA AAA TTA
AGA CCT CAT GAA CTT CCG CAT TTT CGA CTG TTT TCA TTT CAT TTT AAT
S   G   V   L   E   G   V   K   A   D   K   S   K   V   K   L>

770          780          790          800          810
ACA ATT TCT GAC GAT CTA GGT CAA ACC ACA CTT GAA GTT TTC AAA GAA
TGT TAA AGA CTG CTA GAT CCA GTT TGG TGT GAA CTT CAA AAG TTT CTT
T   I   S   D   D   L   G   Q   T   T   L   E   V   F   K   E>

 820          830          840          850          860
GAT GGC AAA ACA CTA GTA TCA AAA AAA GTA ACT TCC AAA GAC AAG TCA
CTA CCG TTT TGT GAT CAT AGT TTT TTT CAT TGA AGG TTT CTG TTC AGT
D   G   K   T   L   V   S   K   K   V   T   S   K   D   K   S>

   870          880          890          900          910
TCA ACA GAA GAA AAA TTC AAT GAA AAA GGT GAA GTA TCT GAA AAA ATA
AGT TGT CTT CTT TTT AAG TTA CTT TTT CCA CTT CAT AGA CTT TTT TAT
S   T   E   E   K   F   N   E   K   G   E   V   S   E   K   I>

       920          930          940          950          960
ATA ACA AGA GCA GAC GGA ACC AGA CTT GAA TAC ACA GGA ATT AAA AGC
TAT TGT TCT CGT CTG CCT TGG TCT GAA CTT ATG TGT CCT TAA TTT TCG
I   T   R   A   D   G   T   R   L   E   Y   T   G   I   K   S>

           970          980          990          1000
GAT GGA TCT GGA AAA GCT AAA GAG GTT TTA AAA GGC TTT ACT CTT GAA
CTA CCT AGA CCT TTT CGA TTT CTC CAA AAT TTT CCG AAA TGA GAA CTT
D   G   S   G   K   A   K   E   V   L   K   G   F   T   L   E>

1010         1020         1030         1040         1050
GGA AAA GTA GCT AAT GAT AAA GTA ACA TTG GAA GTA AAA GAA GGA ACC
CCT TTT CAT CGA TTA CTA TTT CAT TGT AAC CTT CAT TTT CTT CCT TGG
G   K   V   A   N   D   K   V   T   L   E   V   K   E   G   T>

1060         1070         1080         1090         1100
GTT ACT TTA AGT AAG ATT TCA AAA TCT GGG GAA GTT TCA GTT GAA CTT
```

FIG. 46B

```
 CAA TGA AAT TCA TTC TAA AGT TTT AGA CCC CTT CAA AGT CAA CTT GAA
 V   T   L   S   K   I   S   K   S   G   E   V   S   V   E   L>

  1110        1120        1130        1140        1150
 AAT GAC ACT GAC AGT AGT GCT GCT ACT AAA AAA ACT GCA GCT TGG AAT
 TTA CTG TGA CTG TCA TCA CGA CGA TGA TTT TTT TGA CGT CGA ACC TTA
 N   D   T   D   S   S   A   A   T   K   K   T   A   A   W   N>

     1160        1170        1180        1190        1200
 TCA AAA ACT TCT ACT TTA ACA ATT AGT GTT AAC AGC AAA AAA ACT ACA
 AGT TTT TGA AGA TGA AAT TGT TAA TCA CAA TTG TCG TTT TTT TGA TGT
 S   K   T   S   T   L   T   I   S   V   N   S   K   K   T   T>

        1210        1220        1230        1240
 CAA CTT GTG TTT ACT AAA CAA GAC ACA ATA ACT GTA CAA AAA TAC GAC
 GTT GAA CAC AAA TGA TTT GTT CTG TGT TAT TGA CAT GTT TTT ATG CTG
 Q   L   V   F   T   K   Q   D   T   I   T   V   Q   K   Y   D>

1250        1260        1270        1280        1290
 TCC GCA GGT ACC AAT TTA GAA GGC ACA GCA GTC GAA ATT AAA ACA CTT
 AGG CGT CCA TGG TTA AAT CTT CCG TGT CGT CAG CTT TAA TTT TGT GAA
 S   A   G   T   N   L   E   G   T   A   V   E   I   K   T   L>

 1300        1310        1320
 GAT GAA CTT AAA AAC GCT TTA AAA TAA
 CTA CTT GAA TTT TTG CGA AAT TTT ATT
 D   E   L   K   N   A   L   K   *>
```

FIG. 46C

```
                10                  20                  30                  40
ATG GCT TGT AAT AAT TCA GGG AAA GAT GGG AAT ACA TCT GCA AAT TCT
TAC CGA ACA TTA TTA AGT CCC TTT CTA CCC TTA TGT AGA CGT TTA AGA
M   A   C   N   N   S   G   K   D   G   N   T   S   A   N   S>

50                  60                  70                  80                  90
GCT GAT GAG TCT GTT AAA GGG CCT AAT CTT ACA GAA ATA AGT AAA AAA
CGA CTA CTC AGA CAA TTT CCC GGA TTA GAA TGT CTT TAT TCA TTT TTT
A   D   E   S   V   K   G   P   N   L   T   E   I   S   K   K>

100                 110                 120                 130                 140
ATT ACG GAT TCT AAT GCG GTT TTA CTT GCT GTG AAA GAG GTT GAA GCG
TAA TGC CTA AGA TTA CGC CAA AAT GAA CGA CAC TTT CTC CAA CTT CGC
I   T   D   S   N   A   V   L   L   A   V   K   E   V   E   A>

    150                 160                 170                 180                 190
TTG CTG TCA TCT ATA GAT GAG CTT GCT AAA GCT ATT GGT AAA AAA ATA
AAC GAC AGT AGA TAT CTA CTC GAA CGA TTT CGA TAA CCA TTT TTT TAT
L   L   S   S   I   D   E   L   A   K   A   I   G   K   K   I>

        200                 210                 220                 230                 240
AAA AAC GAT GGT AGT TTA GAT AAT GAA GCA AAT CGC AAC GAG TCA TTG
TTT TTG CTA CCA TCA AAT CTA TTA CTT CGT TTA GCG TTG CTC AGT AAC
K   N   D   G   S   L   D   N   E   A   N   R   N   E   S   L>

            250                 260                 270                 280
TTA GCA GGA GCT TAT ACA ATA TCA ACC TTA ATA ACA CAA AAA TTA AGT
AAT CGT CCT CGA ATA TGT TAT AGT TGG AAT TAT TGT GTT TTT AAT TCA
L   A   G   A   Y   T   I   S   T   L   I   T   Q   K   L   S>

290                 300                 310                 320                 330
AAA TTA AAC GGA TCA GAA GGT TTA AAG GAA AAG ATT GCC GCA GCT AAG
TTT AAT TTG CCT AGT CTT CCA AAT TTC CTT TTC TAA CGG CGT CGA TTC
K   L   N   G   S   E   G   L   K   E   K   I   A   A   A   K>

340                 350                 360                 370                 380
AAA TGC TCT GAA GAG TTT AGT ACT AAA CTA AAA GAT AAT CAT GCA CAG
TTT ACG AGA CTT CTC AAA TCA TGA TTT GAT TTT CTA TTA GTA CGT GTC
K   C   S   E   E   F   S   T   K   L   K   D   N   H   A   Q>

    390                 400                 410                 420                 430
CTT GGT ATA CAG GGC GTT ACT GAT GAA AAT GCA AAA AAA GCT ATT TTA
GAA CCA TAT GTC CCG CAA TGA CTA CTT TTA CGT TTT TTT CGA TAA AAT
L   G   I   Q   G   V   T   D   E   N   A   K   K   A   I   L>

        440                 450                 460                 470                 480
AAA GCA AAT GCA GCG GGT AAA GAT AAG GGC GTT GAA GAA CTT GAA AAG
TTT CGT TTA CGT CGC CCA TTT CTA TTC CCG CAA CTT CTT GAA CTT TTC
K   A   N   A   A   G   K   D   K   G   V   E   E   L   E   K>

            490                 500                 510                 520
TTG TCC GGA TCA TTA GAA AGC TTA TCA AAA GCA GCT AAA GAG ATG CTT
AAC AGG CCT AGT AAT CTT TCG AAT AGT TTT CGT CGA TTT CTC TAC GAA
L   S   G   S   L   E   S   L   S   K   A   A   K   E   M   L>
```

FIG. 47A

```
530          540          550          560          570
GCT AAT TCA GTT AAA GAG CTT ACA AGC CCT GTT GTC CAT GGC GTT TCA
CGA TTA AGT CAA TTT CTC GAA TGT TCG GGA CAA CAG GTA CCG CAA AGT
 A   N   S   V   K   E   L   T   S   P   V   V   H   G   V   S>

 580          590          600          610          620
GTA GAT TTG CCT GGT GAA ATG AAA GTT CTT GTA AGC AAA GAA AAA AAC
CAT CTA AAC GGA CCA CTT TAC TTT CAA GAA CAT TCG TTT CTT TTT TTG
 V   D   L   P   G   E   M   K   V   L   V   S   K   E   K   N>

   630          640          650          660          670
AAA GAC GGC AAG TAC GAT CTA ATT GCA ACA GTA GAC AAG CTT GAG CTT
TTT CTG CCG TTC ATG CTA GAT TAA CGT TGT CAT CTG TTC GAA CTC GAA
 K   D   G   K   Y   D   L   I   A   T   V   D   K   L   E   L>

      680          690          700          710          720
AAA GGA ACT TCT GAT AAA AAC AAT GGA TCT GGA GTA CTT GAA GGC GTA
TTT CCT TGA AGA CTA TTT TTG TTA CCT AGA CCT CAT GAA CTT CCG CAT
 K   G   T   S   D   K   N   N   G   S   G   V   L   E   G   V>

         730          740          750          760
AAA GCT GAC AAA AGT AAA GTA AAA TTA ACA ATT TCT GAC GAT CTA GGT
TTT CGA CTG TTT TCA TTT CAT TTT AAT TGT TAA AGA CTG CTA GAT CCA
 K   A   D   K   S   K   V   K   L   T   I   S   D   D   L   G>

770          780          790          800          810
CAA ACC ACA CTT GAA GTT TTC AAA GAA GAT GGC AAA ACA CTA GTA TCA
GTT TGG TGT GAA CTT CAA AAG TTT CTT CTA CCG TTT TGT GAT CAT AGT
 Q   T   T   L   E   V   F   K   E   D   G   K   T   L   V   S>

 820          830          840          850          860
AAA AAA GTA ACT TCC AAA GAC AAG TCA TCA ACA GAA GAA AAA TTC AAT
TTT TTT CAT TGA AGG TTT CTG TTC AGT AGT TGT CTT CTT TTT AAG TTA
 K   K   V   T   S   K   D   K   S   S   T   E   E   K   F   N>

   870          880          890          900          910
GAA AAA GGT GAA GTA TCT GAA AAA ATA ATA ACA AGA GCA GAC GGA ACC
CTT TTT CCA CTT CAT AGA CTT TTT TAT TAT TGT TCT CGT CTG CCT TGG
 E   K   G   E   V   S   E   K   I   I   T   R   A   D   G   T>

      920          930          940          950          960
AGA CTT GAA TAC ACA GGA ATT AAA AGC GAT GGA TCT GGA AAA GCT AAA
TCT GAA CTT ATG TGT CCT TAA TTT TCG CTA CCT AGA CCT TTT CGA TTT
 R   L   E   Y   T   G   I   K   S   D   G   S   G   K   A   K>

         970          980          990          1000
GAG GTT TTA AAA GGC TTT ACT CTT GAA GGA AAA GTA GCT AAT GAT AAA
CTC CAA AAT TTT CCG AAA TGA GAA CTT CCT TTT CAT CGA TTA CTA TTT
 E   V   L   K   G   F   T   L   E   G   K   V   A   N   D   K>

1010         1020         1030         1040         1050
GTA ACA TTG GAA GTA AAA GAA GGA ACC GTT ACT TTA AGT AAG ATT TCA
CAT TGT AAC CTT CAT TTT CTT CCT TGG CAA TGA AAT TCA TTC TAA AGT
 V   T   L   E   V   K   E   G   T   V   T   L   S   K   I   S>

1060         1070         1080         1090         1100
AAA TCT GGG GAA GTT TCA GTT GAA CTT AAT GAC ACT GAC AGT AGT GCT
```

FIG. 47B

```
TTT AGA CCC CTT CAA AGT CAA CTT GAA TTA CTG TGA CTG TCA TCA CGA
K   S   G   E   V   S   V   E   L   N   D   T   D   S   S   A>

  1110            1120            1130            1140            1150
GCT ACT AAA AAA ACT GCA GCT TGG AAT TCA AAA ACT TCT ACT TTA ACA
CGA TGA TTT TTT TGA CGT CGA ACC TTA AGT TTT TGA AGA TGA AAT TGT
A   T   K   K   T   A   A   W   N   S   K   T   S   T   L   T>

     1160            1170            1180            1190            1200
ATT AGT GTT AAC AGC AAA AAA ACT ACA CAA CTT GTG TTT ACT AAA CAA
TAA TCA CAA TTG TCG TTT TTT TGA TGT GTT GAA CAC AAA TGA TTT GTT
I   S   V   N   S   K   K   T   T   Q   L   V   F   T   K   Q>

        1210            1220            1230            1240
GAC ACA ATA ACT GTA CAA AAA TAC GAC TCC GCA GGT ACC AAT TTA GAA
CTG TGT TAT TGA CAT GTT TTT ATG CTG AGG CGT CCA TGG TTA AAT CTT
D   T   I   T   V   Q   K   Y   D   S   A   G   T   N   L   E>

1250            1260            1270            1280            1290
GGC ACA GCA GTC GAA ATT AAA ACA CTT GAT GAA CTT AAA AAC GCT TTA
CCG TGT CGT CAG CTT TAA TTT TGT GAA CTA CTT GAA TTT TTG CGA AAT
G   T   A   V   E   I   K   T   L   D   E   L   K   N   A   L>

1300
AAA TAA
TTT ATT
K   *>
```

FIG. 47C

```
            10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

 50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 48A

```
390 400 410 420 430
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

440 450 460 470 480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

490 500 510 520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530 540 550 560 570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

580 590 600 610 620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

630 640 650 660 670
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

680 690 700 710 720
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

730 740 750 760
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770 780 790 800 810
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

820
AAA TAA
TTT ATT
Lys ***>
```

FIG. 48B

```
              10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 49A

```
     390         400         410         420         430
 *    *     *     *     *     *     *     *     *     *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
 *       *     *     *     *     *     *     *     *     *
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr>

           490         500         510         520
       *     *     *     *     *     *     *     *     *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
 *     *     *     *     *     *     *     *     *     *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
   *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630         640         650         660         670
 *    *     *     *     *     *     *     *     *     *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

        680         690         700         710         720
 *       *     *     *     *     *     *     *     *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

           730         740         750         760
       *     *     *     *     *     *     *     *     *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
 *     *     *     *     *     *     *     *     *     *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

  820
   *
AAA TAA
TTT ATT
Lys ***>
```

FIG. 49B

```
           10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

   100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

     150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

         250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

   340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 50A

```
     390         400         410         420         430
 *     *     *     *     *     *     *     *     *     *
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

          440         450         460         470         480
  *     *     *     *     *     *     *     *     *     *
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr>

           490         500         510         520
     *     *     *     *     *     *     *     *     *
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
 *     *     *     *     *     *     *     *     *     *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580         590         600         610         620
     *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
 *     *     *     *     *     *     *     *     *     *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

       680         690         700         710         720
  *     *     *     *     *     *     *     *     *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

          730         740         750         760
     *     *     *     *     *     *     *     *     *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
 *     *     *     *     *     *     *     *     *     *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
     *
AAA TAA
TTT ATT
Lys ***>
```

FIG. 59B

```
          10         20         30         40
     *     *     *     *     *     *     *     *     *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
 *     *     *     *     *     *     *     *     *     *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100        110        120        130        140
   *     *     *     *     *     *     *     *     *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150        160        170        180        190
 *     *     *     *     *     *     *     *     *     *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200        210        220        230        240
   *     *     *     *     *     *     *     *     *     *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

        250        260        270        280
     *     *     *     *     *     *     *     *     *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290        300        310        320        330
 *     *     *     *     *     *     *     *     *     *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340        350        360        370        380
     *     *     *     *     *     *     *     *     *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 51A

```
    390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

        440         450         460         470         480
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr

            490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

    580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

        680         690         700         710         720
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

            730         740         750         760
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

    820
AAA TAA
TTT ATT
Lys ***>
```

FIG. 51B

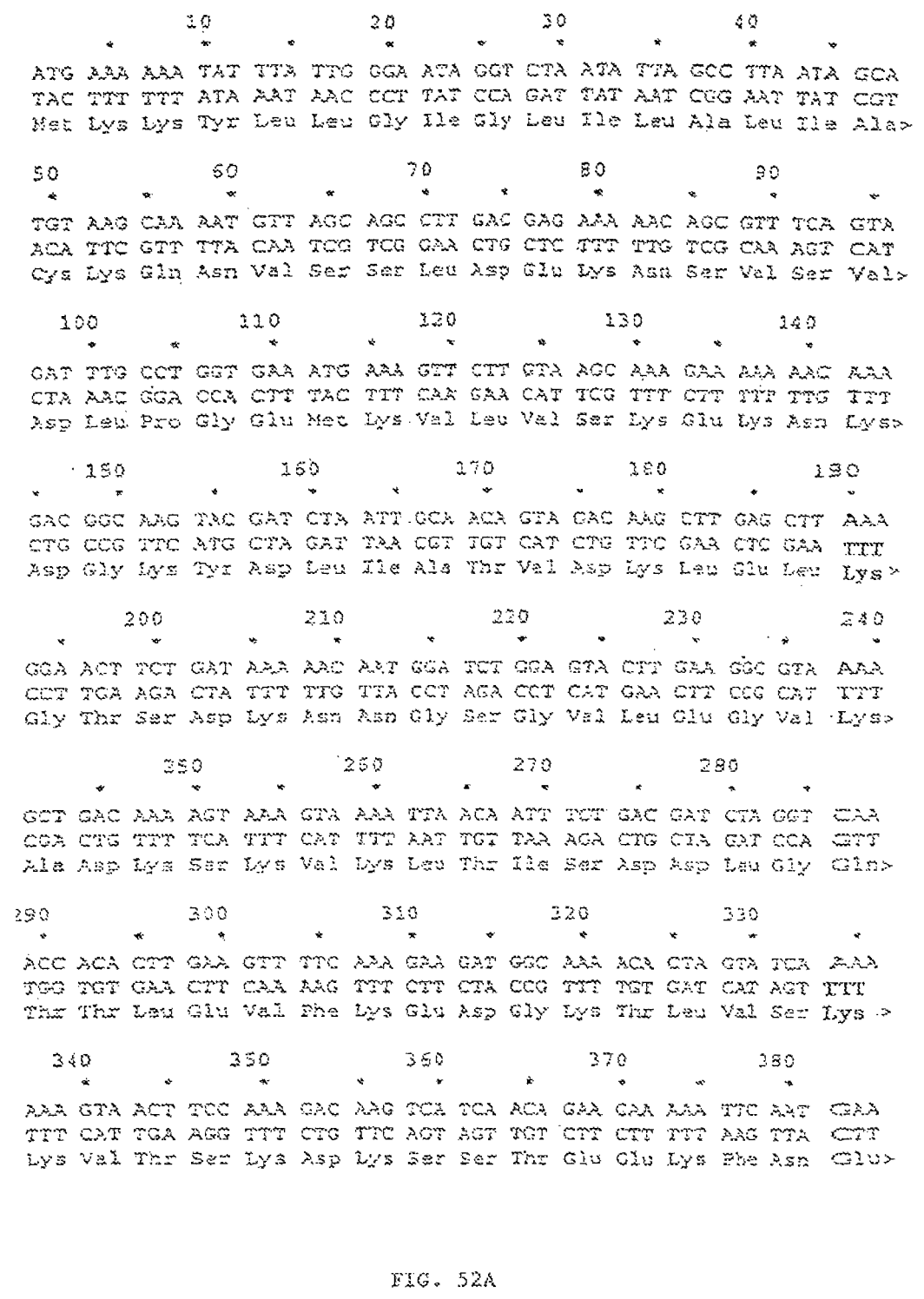

```
         10          20          30          40
    *    *      *    *      *    *      *    *
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

    50          60          70          80          90
    *    *      *    *      *    *      *    *      *    *
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

    100         110         120         130         140
    *    *      *    *      *    *      *    *      *    *
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
    *    *      *    *      *    *      *    *      *    *
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

    200         210         220         230         240
    *    *      *    *      *    *      *    *      *    *
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

    250         260         270         280
    *    *      *    *      *    *      *    *
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

    290         300         310         320         330
    *    *      *    *      *    *      *    *      *    *
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

    340         350         360         370         380
    *    *      *    *      *    *      *    *      *    *
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>

                       FIG. 52A
```

```
    390         400         410         420         430
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

      440         450         460         470         480
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr

        490         500         510         520
GTT TTA AAA GGC TAT GTT CTT GAA GGA ACT CTA ACT GCT GAA AAA ACA
CAA AAT TTT CCG ATA CAA GAA CTT CCT TGA GAT TGA CGA CTT TTT TGT
Val Leu Lys Gly Tyr Val Leu Glu Gly Thr Leu Thr Ala Glu Lys Thr>

530         540         550         560         570
ACA TTG GTG GTT AAA GAA GGA ACT GTT ACT TTA AGC ATG AAT ATT TCA
TGT AAC CAC CAA TTT CTT CCT TGA CAA TGA AAT TCG TAC TTA TAA AGT
Thr Leu Val Val Lys Glu Gly Thr Val Thr Leu Ser Met Asn Ile Ser>

  580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

      680         690         700         710         720
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

        730         740         750         760
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

  820
AAA TAA
TTT ATT
Lys ***>
```

FIG. 52B

```
         10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 53A

```
    390         400         410         420         430
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

      440         450         460         470         480
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

        490         500         510         520
GTT TTA AAA GGC TTT GTT CTT GAA GGA ACT CTA ACT GCT GAA AAA ACA
CAA AAT TTT CCG AAA CAA GAA CTT CCT TGA GAT TGA CGA CTT TTT TGT
Val Leu Lys Gly Phe Val Leu Glu Gly Thr Leu Thr Ala Glu Lys Thr>

530         540         550         560         570
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

    630         640         650         660         670
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

      680         690         700         710         720
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

        730         740         750         760
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

  820
AAA TAA
TTT ATT
Lys ***>
```

FIG. 53B

```
                10                  20                  30                  40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50                  60                  70                  80                  90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100                 110                 120                 130                 140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150                 160                 170                 180                 190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200                 210                 220                 230                 240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250                 260                 270                 280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290                 300                 310                 320                 330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340                 350                 360                 370                 380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 54A

```
      390             400            410            420            430
 *     *       *       *      *       *      *      *       *      *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

           440           450            460            470            480
  *         *       *       *      *       *      *      *        *     *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

            490            500            510            520
      *       *       *       *      *       *      *       *      *
GTT TTA AAA GGC TTT ACT CTT GAA GGA ACT CTA ACT GCT GAA AAA ACA
CAA AAT TTT CCG AAA TGA GAA CTT CCT TGA GAT TGA CGA CTT TTT TGT
Val Leu Lys Gly Phe Thr Leu Glu Gly Thr Leu Thr Ala Glu Lys Thr>

530            540            550            560            570
 *       *      *       *      *       *      *       *      *       *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580            590            600            610            620
     *       *      *       *      *       *      *       *      *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

      630            640            650            660            670
 *     *       *       *      *       *      *       *      *       *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

         680            690            700            710            720
  *       *      *       *      *       *      *       *      *       *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

            730            740            750            760
      *       *      *       *      *       *      *       *      *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770            780            790            800            810
 *       *      *       *      *       *      *       *      *       *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
     *
AAA TAA
TTT ATT
Lys ***>
```

FIG. 54B

```
        10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

 100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

       200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

          250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 55A

```
      390         400         410         420         430
 *     *     *     *     *     *     *     *     *     *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

          440         450         460         470         480
  *     *     *     *     *     *     *     *     *     *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490         500         510         520
     *     *     *     *     *     *     *     *     *
GTT TTA AAA GGC TAT ACT CTT GAA GGA ACT CTA ACT GCT GAA AAA ACA
CAA AAT TTT CCG ATA TGA GAA CTT CCT TGA GAT TGA CGA CTT TTT TGT
Val Leu Lys Gly Tyr Thr Leu Glu Gly Thr Leu Thr Ala Glu Lys Thr>

530         540         550         560         570
 *     *     *     *     *     *     *     *     *     *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580         590         600         610         620
    *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

      630         640         650         660         670
 *     *     *     *     *     *     *     *     *     *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

         680         690         700         710         720
  *     *     *     *     *     *     *     *     *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

          730         740         750         760
     *     *     *     *     *     *     *     *     *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770         780         790         800         810
 *     *     *     *     *     *     *     *     *     *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
    *
AAA TAA
TTT ATT
Lys ***>
```

FIG. 55B

```
        10          20          30          40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50          60          70          80          90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

  100         110         120         130         140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

    150         160         170         180         190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

        200         210         220         230         240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

            250         260         270         280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290         300         310         320         330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340         350         360         370         380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 56A

```
     390         400         410         420         430
 *    *     *     *     *     *     *     *     *     *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

         440         450         460         470         480
  *       *     *     *     *     *     *     *     *     *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

          490         500         510         520
     *     *     *     *     *     *     *     *     *
GTT TTA AAA GGC TAT ACT CTT GAA GGA AAG CTA ACT GCT GAA AAA ACA
CAA AAT TTT CCG ATA TGA GAA CTT CCT TTC GAT TGA CGA CTT TTT TGT
Val Leu Lys Gly Tyr Thr Leu Glu Gly Lys Leu Thr Ala Glu Lys Thr>

530          540         550         560         570
 *     *     *     *     *     *     *     *     *     *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

  580         590         600         610         620
   *     *     *     *     *     *     *     *     *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630         640         650         660         670
 *    *     *     *     *     *     *     *     *     *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

        680         690         700         710         720
  *      *     *     *     *     *     *     *     *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

          730         740         750         760
     *     *     *     *     *     *     *     *     *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770          780         790         800         810
 *     *     *     *     *     *     *     *     *     *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
     *
AAA TAA
TTT ATT
```

FIG. 56B

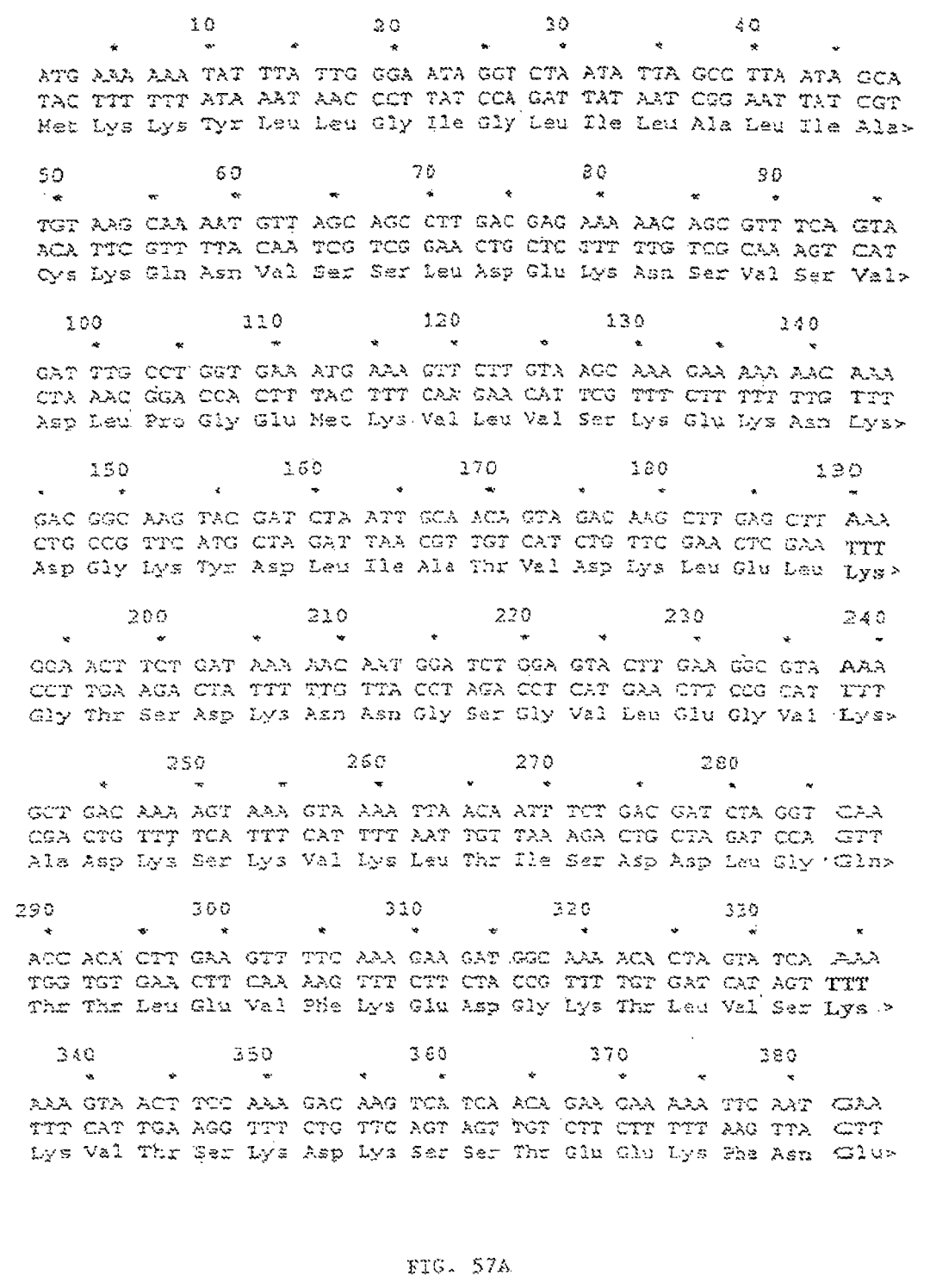

```
              10                  20                  30                  40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50                  60                  70                  80                  90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

   100                 110                 120                 130                 140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

      150                 160                 170                 180                 190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

         200                 210                 220                 230                 240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

            250                 260                 270                 280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290                 300                 310                 320                 330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

   340                 350                 360                 370                 380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 57A

```
     390            400            410            420            430
 *       *       *       *       *       *       *       *       *       *
AAA GGT GAA GTA TCT GAA AAA ATA ATA ACA AGA GCA GAC GGA ACC AGA
TTT CCA CTT CAT AGA CTT TTT TAT TAT TGT TCT CGT CTG CCT TGG TCT
Lys Gly Glu Val Ser Glu Lys Ile Ile Thr Arg Ala Asp Gly Thr Arg>

          440            450            460            470            480
  *       *       *       *       *       *       *       *       *       *
CTT GAA TAC ACA GGA ATT AAA AGC GAT GGA TCT GGA AAA GCT AAA GAG
GAA CTT ATG TGT CCT TAA TTT TCG CTA CCT AGA CCT TTT CGA TTT CTC
Leu Glu Tyr Thr Gly Ile Lys Ser Asp Gly Ser Gly Lys Ala Lys Glu>

           490            500            510            520
      *       *       *       *       *       *       *       *       *
GTT TTA AAA GGC TTT ACT CTT GAA GGA AAG CTA ACT GCT GAA AAA ACA
CAA AAT TTT CCG AAA TGA GAA CTT CCT TTC GAT TGA CGA CTT TTT TGT
Val Leu Lys Gly Phe Thr Leu Glu Gly Lys Leu Thr Ala Glu Lys Thr>

530            540            550            560            570
  *       *       *       *       *       *       *       *       *       *
ACA TTG GTG GTT AAA GAA GGA ACT GTT ACT TTA AGC AAA AAT ATT TCA
TGT AAC CAC CAA TTT CTT CCT TGA CAA TGA AAT TCG TTT TTA TAA AGT
Thr Leu Val Val Lys Glu Gly Thr Val Thr Leu Ser Lys Asn Ile Ser>

   580            590            600            610            620
      *       *       *       *       *       *       *       *       *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630            640            650            660            670
 *       *       *       *       *       *       *       *       *       *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

        680            690            700            710            720
  *       *       *       *       *       *       *       *       *       *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

           730            740            750            760
      *       *       *       *       *       *       *       *       *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770            780            790            800            810
  *       *       *       *       *       *       *       *       *       *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

    820
      *
AAA TAA
TTT ATT
Lys ***>
```

FIG. 57B

```
         10         20         30         40
ATG AAA AAA TAT TTA TTG GGA ATA GGT CTA ATA TTA GCC TTA ATA GCA
TAC TTT TTT ATA AAT AAC CCT TAT CCA GAT TAT AAT CGG AAT TAT CGT
Met Lys Lys Tyr Leu Leu Gly Ile Gly Leu Ile Leu Ala Leu Ile Ala>

50         60         70         80         90
TGT AAG CAA AAT GTT AGC AGC CTT GAC GAG AAA AAC AGC GTT TCA GTA
ACA TTC GTT TTA CAA TCG TCG GAA CTG CTC TTT TTG TCG CAA AGT CAT
Cys Lys Gln Asn Val Ser Ser Leu Asp Glu Lys Asn Ser Val Ser Val>

 100        110        120        130        140
GAT TTG CCT GGT GAA ATG AAA GTT CTT GTA AGC AAA GAA AAA AAC AAA
CTA AAC GGA CCA CTT TAC TTT CAA GAA CAT TCG TTT CTT TTT TTG TTT
Asp Leu Pro Gly Glu Met Lys Val Leu Val Ser Lys Glu Lys Asn Lys>

   150        160        170        180        190
GAC GGC AAG TAC GAT CTA ATT GCA ACA GTA GAC AAG CTT GAG CTT AAA
CTG CCG TTC ATG CTA GAT TAA CGT TGT CAT CTG TTC GAA CTC GAA TTT
Asp Gly Lys Tyr Asp Leu Ile Ala Thr Val Asp Lys Leu Glu Leu Lys>

      200        210        220        230        240
GGA ACT TCT GAT AAA AAC AAT GGA TCT GGA GTA CTT GAA GGC GTA AAA
CCT TGA AGA CTA TTT TTG TTA CCT AGA CCT CAT GAA CTT CCG CAT TTT
Gly Thr Ser Asp Lys Asn Asn Gly Ser Gly Val Leu Glu Gly Val Lys>

        250        260        270        280
GCT GAC AAA AGT AAA GTA AAA TTA ACA ATT TCT GAC GAT CTA GGT CAA
CGA CTG TTT TCA TTT CAT TTT AAT TGT TAA AGA CTG CTA GAT CCA GTT
Ala Asp Lys Ser Lys Val Lys Leu Thr Ile Ser Asp Asp Leu Gly Gln>

290        300        310        320        330
ACC ACA CTT GAA GTT TTC AAA GAA GAT GGC AAA ACA CTA GTA TCA AAA
TGG TGT GAA CTT CAA AAG TTT CTT CTA CCG TTT TGT GAT CAT AGT TTT
Thr Thr Leu Glu Val Phe Lys Glu Asp Gly Lys Thr Leu Val Ser Lys>

  340        350        360        370        380
AAA GTA ACT TCC AAA GAC AAG TCA TCA ACA GAA GAA AAA TTC AAT GAA
TTT CAT TGA AGG TTT CTG TTC AGT AGT TGT CTT CTT TTT AAG TTA CTT
Lys Val Thr Ser Lys Asp Lys Ser Ser Thr Glu Glu Lys Phe Asn Glu>
```

FIG. 58A

```
      390          400          410          420          430
 *     *       *       *     *     *     *     *     *     *
AAA GGT GAA GTA TCT GAA AAA ATA ATA ACA ATG GCA GAC GGA ACC AGA
TTT CCA CTT CAT AGA CTT TTT TAT TAT TGT TAC CGT CTG CCT TGG TCT
Lys Gly Glu Val Ser Glu Lys Ile Ile Thr Met Ala Asp Gly Thr Arg>

          440         450          460          470          480
  *        *       *      *     *      *     *     *      *    *
CTT GAA TAC ACA GGA ATT AAA AGC GAT GGA TCT GGA AAA GCT AAA TAT
GAA CTT ATG TGT CCT TAA TTT TCG CTA CCT AGA CCT TTT CGA TTT ATA
Leu Glu Tyr Thr Gly Ile Lys Ser Asp Gly Ser Gly Lys Ala Lys Tyr>

           490          500          510          520
      *      *      *      *      *      *      *      *      *
GTT TTA AAA GGC TTT ACT CTT GAA GGA AAG CTA ACT GCT GAA AAA ACA
CAA AAT TTT CCG AAA TGA GAA CTT CCT TTC GAT TGA CGA CTT TTT TGT
Val Leu Lys Gly Phe Thr Leu Glu Gly Lys Leu Thr Ala Glu Lys Thr>

530          540          550          560          570
 *      *      *      *      *      *      *      *      *      *
ACA TTG GTG GTT AAA GAA GGA ACT GTT ACT TTA AGC ATG AAT ATT TCA
TGT AAC CAC CAA TTT CTT CCT TGA CAA TGA AAT TCG TAC TTA TAA AGT
Thr Leu Val Val Lys Glu Gly Thr Val Thr Leu Ser Met Asn Ile Ser>

   580          590          600          610          620
    *      *      *      *      *      *      *      *      *
AAA TCT GGG GAA GTT TCA GTT GAA CTT AAT GAC ACT GAC AGT AGT GCT
TTT AGA CCC CTT CAA AGT CAA CTT GAA TTA CTG TGA CTG TCA TCA CGA
Lys Ser Gly Glu Val Ser Val Glu Leu Asn Asp Thr Asp Ser Ser Ala>

     630          640          650          660          670
 *     *       *       *      *      *      *      *      *
GCT ACT AAA AAA ACT GCA GCT TGG AAT TCA GGC ACT TCA ACT TTA ACA
CGA TGA TTT TTT TGA CGT CGA ACC TTA AGT CCG TGA AGT TGA AAT TGT
Ala Thr Lys Lys Thr Ala Ala Trp Asn Ser Gly Thr Ser Thr Leu Thr>

        680          690          700          710          720
  *      *      *      *      *      *      *      *      *     *
ATT ACT GTA AAC AGT AAA AAA ACT AAA GAC CTT GTG TTT ACA AAA GAA
TAA TGA CAT TTG TCA TTT TTT TGA TTT CTG GAA CAC AAA TGT TTT CTT
Ile Thr Val Asn Ser Lys Lys Thr Lys Asp Leu Val Phe Thr Lys Glu>

           730          740          750          760
      *      *      *      *      *      *      *      *      *
AAC ACA ATT ACA GTA CAA CAA TAC GAC TCA AAT GGC ACC AAA TTA GAG
TTG TGT TAA TGT CAT GTT GTT ATG CTG AGT TTA CCG TGG TTT AAT CTC
Asn Thr Ile Thr Val Gln Gln Tyr Asp Ser Asn Gly Thr Lys Leu Glu>

770          780          790          800          810
 *      *      *      *      *      *      *      *      *      *
GGG TCA GCA GTT GAA ATT ACA AAA CTT GAT GAA ATT AAA AAC GCT TTA
CCC AGT CGT CAA CTT TAA TGT TTT GAA CTA CTT TAA TTT TTG CGA AAT
Gly Ser Ala Val Glu Ile Thr Lys Leu Asp Glu Ile Lys Asn Ala Leu>

   820
    *
AAA TAA
TTT ATT
Lys ***>
```

FIG. 58B

SEQUENCE LISTING

```
<160> NUMBER OF SEQ ID NOS: 173

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1

cttaatgact ctgacactag tgc                                              23


<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2

gctactaaaa aaaccgggaa atggaattca                                       30


<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3

gcagcttggg attcaaaaac atccacttta aca                                   33


<210> SEQ ID NO 4
<211> LENGTH: 18
<212> TYPE: DNA
<213> ORGANISM: Artificial Sequence
<220> FEATURE:
<223> OTHER INFORMATION: Synthetic Construct

<400> SEQUENCE: 4

ggagaatata ttatgaaa                                                    18


<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5

ctccttattt taaagcg                                                     17


<210> SEQ ID NO 6
```

-continued

```
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 6

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys
```

<210> SEQ ID NO 7
<211> LENGTH: 273
<212> TYPE: PRT
<213> ORGANISM: Borrelia burgdorferi

<400> SEQUENCE: 7

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

<210> SEQ ID NO 8
<211> LENGTH: 825
<212> TYPE: DNA
<213> ORGANISM: Borrelia burgdorferi
<220> FEATURE:
<221> NAME/KEY: CDS
<222> LOCATION: (1)...(825)

<400> SEQUENCE: 8

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gat gaa aaa aat agc gtt tca gta       96
Cys Lys Gln Asn Val Ser Ser Leu Asp Glu Lys Asn Ser Val Ser Val
```

-continued

```
             20                  25                  30

gat tta cct ggt gga atg aca gtt ctt gta agt aaa gaa aaa gac aaa      144
Asp Leu Pro Gly Gly Met Thr Val Leu Val Ser Lys Glu Lys Asp Lys
         35                  40                  45

gac ggt aaa tac agt cta gag gca aca gta gac aag ctt gag ctt aaa      192
Asp Gly Lys Tyr Ser Leu Glu Ala Thr Val Asp Lys Leu Glu Leu Lys
     50                  55                  60

gga act tct gat aaa aac aac ggt tct gga aca ctt gaa ggt gaa aaa      240
Gly Thr Ser Asp Lys Asn Asn Gly Ser Gly Thr Leu Glu Gly Glu Lys
 65                  70                  75                  80

act gac aaa agt aaa gta aaa tta aca att gct gat gac cta agt caa      288
Thr Asp Lys Ser Lys Val Lys Leu Thr Ile Ala Asp Asp Leu Ser Gln
                 85                  90                  95

act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110

aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125

aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140

ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160

gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175

aca aca ttg aaa gtt aca gaa ggc act gtt gtt tta agc aag aac att      576
Thr Thr Leu Lys Val Thr Glu Gly Thr Val Val Leu Ser Lys Asn Ile
            180                 185                 190

tta aaa tcc gga gaa ata aca gtt gca ctt gat gac tct gac act act      624
Leu Lys Ser Gly Glu Ile Thr Val Ala Leu Asp Asp Ser Asp Thr Thr
        195                 200                 205

cag gct act aaa aaa act gga aaa tgg gat tca aaa act tcc act tta      672
Gln Ala Thr Lys Lys Thr Gly Lys Trp Asp Ser Lys Thr Ser Thr Leu
    210                 215                 220

aca att agt gtg aat agc caa aaa acc aaa aac ctt gta ttc aca aaa      720
Thr Ile Ser Val Asn Ser Gln Lys Thr Lys Asn Leu Val Phe Thr Lys
225                 230                 235                 240

gaa gac aca ata aca gta caa aaa tac gac tca gca ggc acc aat cta      768
Glu Asp Thr Ile Thr Val Gln Lys Tyr Asp Ser Ala Gly Thr Asn Leu
                245                 250                 255

gaa ggc aaa gca gtc gaa att aca aca ctt aaa gaa ctt aaa aac gct      816
Glu Gly Lys Ala Val Glu Ile Thr Thr Leu Lys Glu Leu Lys Asn Ala
            260                 265                 270

tta aaa taa                                                          825
Leu Lys


<210> SEQ ID NO 9
<211> LENGTH: 274
<212> TYPE: PRT
<213> ORGANISM: Borrelia burgdorferi

<400> SEQUENCE: 9

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30
```

```
Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Lys Tyr Asp Ser Ala Gly Thr Asn Leu
                245                 250                 255

Glu Gly Lys Ala Val Glu Ile Thr Thr Leu Lys Glu Leu Lys Asn Ala
            260                 265                 270

Leu Lys


<210> SEQ ID NO 10
<211> LENGTH: 822
<212> TYPE: DNA
<213> ORGANISM: Borrelia burgdorferi
<220> FEATURE:
<221> NAME/KEY: CDS
<222> LOCATION: (1)...(822)

<400> SEQUENCE: 10

atg aaa aaa tat tta ttg gga ata ggt cta ata tta gcc tta ata gca        48
Met Lys Lys Tyr Leu Leu Gly Ile Gly Leu Ile Leu Ala Leu Ile Ala
 1               5                  10                  15

tgc aag caa aat gtt agc agc ctt gat gaa aaa aac agc gct tca gta        96
Cys Lys Gln Asn Val Ser Ser Leu Asp Glu Lys Asn Ser Ala Ser Val
                20                  25                  30

gat ttg cct ggt gag atg aaa gtt ctt gta agt aaa gaa aaa gac aaa       144
Asp Leu Pro Gly Glu Met Lys Val Leu Val Ser Lys Glu Lys Asp Lys
         35                  40                  45

gac ggt aag tac agt cta aag gca aca gta gac aag att gag cta aaa       192
Asp Gly Lys Tyr Ser Leu Lys Ala Thr Val Asp Lys Ile Glu Leu Lys
     50                  55                  60

gga act tct gat aaa gac aat ggt tct gga gtg ctt gaa ggt aca aaa       240
Gly Thr Ser Asp Lys Asp Asn Gly Ser Gly Val Leu Glu Gly Thr Lys
 65                  70                  75                  80

gat gac aaa agt aaa gca aaa tta aca att gct gac gat cta agt aaa       288
```

-continued

```
Asp Asp Lys Ser Lys Ala Lys Leu Thr Ile Ala Asp Asp Leu Ser Lys
                 85                  90                  95

acc aca ttc gaa ctt tta aaa gaa gat ggc aaa aca tta gtg tca aga      336
Thr Thr Phe Glu Leu Leu Lys Glu Asp Gly Lys Thr Leu Val Ser Arg
            100                 105                 110

aaa gta agt tct aga gac aaa aca tca aca gat gaa atg ttc aat gaa      384
Lys Val Ser Ser Arg Asp Lys Thr Ser Thr Asp Glu Met Phe Asn Glu
        115                 120                 125

aaa ggt gaa ttg tct gca aaa acc atg aca aga gaa aat gga acc aaa      432
Lys Gly Glu Leu Ser Ala Lys Thr Met Thr Arg Glu Asn Gly Thr Lys
    130                 135                 140

ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160

gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175

aca ttg gaa gta aaa gaa gga acc gtt act tta agt aag gaa att gca      576
Thr Leu Glu Val Lys Glu Gly Thr Val Thr Leu Ser Lys Glu Ile Ala
            180                 185                 190

aaa tct gga gaa gta aca gtt gct ctt aat gac act aac act act cag      624
Lys Ser Gly Glu Val Thr Val Ala Leu Asn Asp Thr Asn Thr Thr Gln
        195                 200                 205

gct act aaa aaa act ggc gca tgg gat tca aaa act tct act tta aca      672
Ala Thr Lys Lys Thr Gly Ala Trp Asp Ser Lys Thr Ser Thr Leu Thr
    210                 215                 220

att agt gtt aac agc aaa aaa act aca caa ctt gtg ttt act aaa caa      720
Ile Ser Val Asn Ser Lys Lys Thr Thr Gln Leu Val Phe Thr Lys Gln
225                 230                 235                 240

tac aca ata act gta aaa caa tac gac tcc gca ggt acc aat tta gaa      768
Tyr Thr Ile Thr Val Lys Gln Tyr Asp Ser Ala Gly Thr Asn Leu Glu
                245                 250                 255

ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270

aaa taa                                                              822
Lys

<210> SEQ ID NO 11
<211> LENGTH: 273
<212> TYPE: PRT
<213> ORGANISM: Borrelia burgdorferi

<400> SEQUENCE: 11

Met Lys Lys Tyr Leu Leu Gly Ile Gly Leu Ile Leu Ala Leu Ile Ala
 1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                 85                  90                  95

Thr Thr Phe Glu Leu Leu Lys Glu Asp Gly Lys Thr Leu Val Ser Arg
            100                 105                 110
```

```
Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys


<210> SEQ ID NO 12
<211> LENGTH: 819
<212> TYPE: DNA
<213> ORGANISM: Borrelia burgdorferi
<220> FEATURE:
<221> NAME/KEY: CDS
<222> LOCATION: (1)...(819)

<400> SEQUENCE: 12

atg aaa aaa tat tta ttg gga ata ggt cta ata tta gct tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa gac aaa      144
Asp Leu Pro Gly Glu Met Lys Val Leu Val Ser Lys Glu Lys Asp Lys
        35                  40                  45

gac ggc aag tac agt cta atg gca aca gta gac aag ctt gag ctt aaa      192
Asp Gly Lys Tyr Ser Leu Met Ala Thr Val Asp Lys Leu Glu Leu Lys
     50                  55                  60

gga aca tct gat aaa aac aat gga tct ggg gtg ctt gaa ggc gta aaa      240
Gly Thr Ser Asp Lys Asn Asn Gly Ser Gly Val Leu Glu Gly Val Lys
 65                  70                  75                  80

gct gac aaa agc aaa gta aaa tta aca gtt tct gac gat cta agc aca      288
Ala Asp Lys Ser Lys Val Lys Leu Thr Val Ser Asp Asp Leu Ser Thr
                85                  90                  95

acc aca ctt gaa gtt tta aaa gaa gat ggc aaa aca tta gtg tca aaa      336
Thr Thr Leu Glu Val Leu Lys Glu Asp Gly Lys Thr Leu Val Ser Lys
            100                 105                 110

aaa aga act tct aaa gat aag tca tca aca gaa gaa aag ttc aat gaa      384
Lys Arg Thr Ser Lys Asp Lys Ser Ser Thr Glu Glu Lys Phe Asn Glu
        115                 120                 125

aaa ggc gaa tta gtt gaa aaa ata atg gca aga gca aac gga acc ata      432
Lys Gly Glu Leu Val Glu Lys Ile Met Ala Arg Ala Asn Gly Thr Ile
    130                 135                 140
```

-continued

```
ctt gaa tac aca gga att aaa agc gat gga tcc gga aaa gct aaa gaa      480
Leu Glu Tyr Thr Gly Ile Lys Ser Asp Gly Ser Gly Lys Ala Lys Glu
145                 150                 155                 160

act tta aaa gaa tat gtt ctt gaa gga act cta act gct gaa aaa gca      528
Thr Leu Lys Glu Tyr Val Leu Glu Gly Thr Leu Thr Ala Glu Lys Ala
                165                 170                 175

aca ttg gtg gtt aaa gaa gga act gtt act tta agt aag cac att tca      576
Thr Leu Val Val Lys Glu Gly Thr Val Thr Leu Ser Lys His Ile Ser
            180                 185                 190

aaa tct gga gaa gta aca gct gaa ctt aat gac act gac agt act caa      624
Lys Ser Gly Glu Val Thr Ala Glu Leu Asn Asp Thr Asp Ser Thr Gln
        195                 200                 205

gct act aaa aaa act ggg aaa tgg gat gca ggc act tca act tta aca      672
Ala Thr Lys Lys Thr Gly Lys Trp Asp Ala Gly Thr Ser Thr Leu Thr
    210                 215                 220

att act gta aac aac aaa aaa act aaa gcc ctt gta ttt aca aaa caa      720
Ile Thr Val Asn Asn Lys Lys Thr Lys Ala Leu Val Phe Thr Lys Gln
225                 230                 235                 240

gac aca att aca tca caa aaa tac gac tca gca gga acc aac ttg gaa      768
Asp Thr Ile Thr Ser Gln Lys Tyr Asp Ser Ala Gly Thr Asn Leu Glu
                245                 250                 255

ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270

aga                                                                  819
Arg


<210> SEQ ID NO 13
<211> LENGTH: 273
<212> TYPE: PRT
<213> ORGANISM: Borrelia burgdorferi

<400> SEQUENCE: 13

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Met Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Val Ser Asp Asp Leu Ser Thr
                85                  90                  95

Thr Thr Leu Glu Val Leu Lys Glu Asp Gly Lys Thr Leu Val Ser Lys
            100                 105                 110

Lys Arg Thr Ser Lys Asp Lys Ser Ser Thr Glu Glu Lys Phe Asn Glu
        115                 120                 125

Lys Gly Glu Leu Val Glu Lys Ile Met Ala Arg Ala Asn Gly Thr Ile
    130                 135                 140

Leu Glu Tyr Thr Gly Ile Lys Ser Asp Gly Ser Gly Lys Ala Lys Glu
145                 150                 155                 160

Thr Leu Lys Glu Tyr Val Leu Glu Gly Thr Leu Thr Ala Glu Lys Ala
                165                 170                 175

Thr Leu Val Val Lys Glu Gly Thr Val Thr Leu Ser Lys His Ile Ser
            180                 185                 190
```

```
Lys Ser Gly Glu Val Thr Ala Glu Leu Asn Asp Thr Asp Ser Thr Gln
        195                 200                 205

Ala Thr Lys Lys Thr Gly Lys Trp Asp Ala Gly Thr Ser Thr Leu Thr
    210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg
```

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct

<400> SEQUENCE: 14
gtctgcaaaa accatgacaa g 21

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
gtcatcaaca gaagaaaaat tc 22

<210> SEQ ID NO 16
<211> LENGTH: 30
<212> TYPE: DNA
<213> ORGANISM: Artificial Sequence
<220> FEATURE:
<223> OTHER INFORMATION: Synthetic Construct

<400> SEQUENCE: 16
ccggatccat atgaaaaaat atttattggg 30

<210> SEQ ID NO 17
<211> LENGTH: 32
<212> TYPE: DNA
<213> ORGANISM: Artificial Sequence
<220> FEATURE:
<223> OTHER INFORMATION: Synthetic Construct

<400> SEQUENCE: 17
ccgggatcca tatggctaag caaaatgtta gc 32

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
gcgttcaagt actccaga 18

<210> SEQ ID NO 19

<211> LENGTH: 27
<212> TYPE: DNA
<213> ORGANISM: Artificial Sequence
<220> FEATURE:
<223> OTHER INFORMATION: Synthetic Construct

<400> SEQUENCE: 19
gatatctaga tcttatttta aagcgtt 27

<210> SEQ ID NO 20
<211> LENGTH: 31
<212> TYPE: DNA
<213> ORGANISM: Artificial Sequence
<220> FEATURE:
<223> OTHER INFORMATION: Synthetic Construct

<400> SEQUENCE: 20
ggatccggtg accttttaaa gcgtttttaa t 31

<210> SEQ ID NO 21
<211> LENGTH: 825
<212> TYPE: DNA
<213> ORGANISM: Borrelia burgdorferi

<400> SEQUENCE: 21
atgaaaaaat atttattggg aataggtcta atattagcct taatagcatg taagcaaaat 60
gttagcagcc ttgatgaaaa aaatagcgtt tcagtagatt tacctggtgg aatgacagtt 120
cttgtaagta aagaaaaaga caaagacggt aaatacagtc tagaggcaac agtagacaag 180
cttgagctta aggaacttc tgataaaaac aacggttctg gaacacttga aggtgaaaaa 240
actgacaaaa gtaaagtaaa atcaacaatt gctgatgacc taagtcaaac taaatttgaa 300
attttcaaag aagatggcaa aacattagta tcaaaaaaag taacccttaa agacaagtca 360
tcaacagaag aaaaattcaa cggaaagggt gaaacatctg aaaaaacaat agtaagagca 420
aatggaacca gacttgaata cacagacata aaaagcgatg gatccggaaa agctaaagaa 480
gttttaaaag actttactct tgaaggaact ctagctgctg acggcaaaac aacattgaaa 540
gttacagaag gcactgttgt tttaagcaag aacattttaa aatccggaga aataacagct 600
gcacttgatg actctgacac tactcgggct actaaaaaaa ctggaaaatg ggattcaaag 660
acttccactt taacaattag tgtgaatagc caaaaaacca aaaaccttgt attcacaaaa 720
gaagacacaa taacagtaca aagatacgac tcagcaggca ccaatctaga aggcaaagca 780
gtcgaaatta caacacttaa agaacttaaa aacgctttaa aataa 825

<210> SEQ ID NO 22
<211> LENGTH: 824
<212> TYPE: DNA
<213> ORGANISM: Borrelia burgdorferi

<400> SEQUENCE: 22
atgaaaaaat atttattggg aataggtcta atattagcat taatagcatg taagcaaaat 60
gttagcagcc ttgatgaaaa aaatagcgtt tcagtagatt tacctggtgg aatgcaagtt 120
cttgtaagta aagaaaaaga caaagatggt aaatacagtc taatggcaac agtagacaag 180
cttgagctta aggaacttc tgataaaaac aacggttctg gaacacttga aggtgaaaaa 240
actgacaaaa gtaaagcaaa attaacaatt gctgaggatc taagtaaaac cacatttgaa 300
atcttcaaag aagatggcaa aacattagta tcaaaaaaag taacccttaa agacaagtca 360
tcaacagaag aaaaattcaa cgcaaagggt gaagcatctg aaaaaacaat agtaagagca 420
aatggaacca gacttgaata cacagacata aaaagcgata aaaccggaaa agctaaagaa 480
gttttaaaag actttgctct tgaaggaact ctagctgctg acggcaaaac aacattaaaa 540
gttacagaag gcactgttgt tttaagcaaa cacatttcaa actctggaga aataacagtt 600
gagcttaatg actctgacac tactcaggct actaaaaaaa ctggaacatg ggattcaaag 660
acttccactt taacaattag tgtgaatagc cgaaaaacca aaaaccttgt attcacaaaa 720
gaagacacaa taacagtaca aaaatacgac tcagcaggca ccaatctaga aggcaaagca 780
gtcgaaatta caacgcttaa agaacttaaa gatgctttaa aata 824

<210> SEQ ID NO 23
<211> LENGTH: 821
<212> TYPE: DNA
<213> ORGANISM: Borrelia burgdorferi

<400> SEQUENCE: 23
atgaaaaaat atttattggg aataggtcta atattagcct taatagcatg caagcaaaat 60
gttagcagcc ttgatgaaaa aaacagcgct tcagtagatt tgcctggtga gatgaaagtt 120
cttgtaagta aagaaaaaga caaagacggt aagtacagtc taaaggcaac agtagacaag 180
attgagctaa aaggaacttc tgataaagac aatggttctg ggtgcttgga aggtacaaaa 240
gatgacaaaa gtaaagcaaa attaacaatt gctgacgatc taggtaaaac cacattcgaa 300
cttttcaaag aagatggcaa aacattagtg tcaagaaaag taagttctaa agacaaaaca 360
tcaacagatg aaatgttcaa tgaaaaaggt gaattgtctg caaaaaccat gacaagagaa 420
aatggaacca aacttgaata tacagaaatg aaaagcgatg gaaccggaaa agctaaagaa 480
gttttaaaaa actttactct tgaaggaaaa gtagctaatg ataaagtaac attggaagta 540
aaagaaggaa ccgttacttt aagtaaggaa attgcaaaat ctggagaagt aacagttgct 600
cttaatgaca ctaacactac tcaggctact aaaaaaactg gcgcatggga ttcaaaaact 660
tctactttaa caattagtgt taacagcaaa aaaactacac aacttgtgtt tactaaacaa 720
gacacaataa ctgtacaaaa atacgactcc gcaggtacca atttagaagg cacagcagtc 780
gaaattaaaa cacttgatga acttaaaaac gctttaaaat a 821

<210> SEQ ID NO 24
<211> LENGTH: 821
<212> TYPE: DNA
<213> ORGANISM: Borrelia burgdorferi

<400> SEQUENCE: 24
atgaaaaaat atttattggg aataggtcta atattagcct taatagcatg caagcaaaat 60
gttagcagcc ttgatgaaaa aaacagcgct tcagtagatt tgcctggtga gattaaagtt 120
cttgtaagta aagaaaaaga caaagacggt aagtacagtc taaaggcaac agtagacaag 180
attgagctaa aaggaacttc tgataaagac aatggttctg gagtgcttga aggtacaaaa 240
gatgacaaaa gtaaagcaaa attaacaatt gctgacgatc taagtaaaac cacattcgaa 300
cttttcaaag aagatggcaa aacattagtg tcaagaaaag taagttctaa agacaaaaca 360
tcaacagatg aaatgttcaa tgaaaaaggt gaattgtctg caaaaaccat gacaagagaa 420
aatggaacca aacttgaata tacagaaatg aaaagcgatg gaaccggaaa agctaaagaa 480
gttttaaaaa actttactct tgaaggaaaa gtagctaatg ataaagtaac attggaagta 540
aaagaaggaa ccgttacttt aagtaaggaa attgcaaaat ctggagaagt aacagttgct 600

```
cttaatgaca ctaacactac tcaggctact aaaaaaactg gcgcatggga ttcaaaaact    660

tctactttaa caattagtgt taacagtaaa aaaactacac aacttgtgtt tactaaacaa    720

gacacaataa ctgtacaaaa atacgactcc gcaggtacca atttagaagg cacagcagtc    780

gaaattaaaa cacttgatga acttaaaaac gctttaaaat a                        821


<210> SEQ ID NO 25
<211> LENGTH: 821
<212> TYPE: DNA
<213> ORGANISM: Borrelia burgdorferi

<400> SEQUENCE: 25

atgaaaaaat atttattggg aataggtcta atattagcct taatagcatg caagcaaaat     60

gttagcagcc ttgatgaaaa aaacagcgct tcagtagatt tgcctggtga gatgaaagtt    120

cttgtaagta aagaaaaaga caaagacggt aagtacagtc taaaggcaac agtagacaag    180

attgagctaa aaggaacttc tgataaagac aatggttctg ggtgcttga aggtacaaaa     240

gatgacaaaa gtaaagcaaa attaacaatt gctgacgatc taggtaaaac cacattcgaa    300

cttttcaaag aagatggcaa aacattagtg tcaagaaaag taagttctaa agacaaaaca    360

tcaacagatg aaatgttcaa tgaaaaaggt gaattgtctg caaaaaccat gacaagagaa    420

aatggaacca aacttgaata tacagaaatg aaaagcgatg gaaccggaaa agctaaagaa    480

gttttaaaaa actttactct tgaaggaaaa gtagctaatg ataaagtaac attggaagta    540

aaagaaggaa ccgttacttt aagtaaggaa attgcaaaat ctggagaagt aacagttgct    600

cttaatgaca ctaacactac tcaggctact aaaaaaactg gcgcatggga ttcaaaaact    660

tctactttaa caattagtgt taacagcaaa aaaactacac aacttgtgtt tactaaacaa    720

gacacaataa ctgtacaaaa atacgactcc gcaggtacca atttagaagg cacagcagtc    780

gaaattaaaa cacttgatga acttaaaaac gctttaaaat a                        821


<210> SEQ ID NO 26
<211> LENGTH: 822
<212> TYPE: DNA
<213> ORGANISM: Borrelia burgdorferi

<400> SEQUENCE: 26

atgaaaaaat atttattggg aataggtcta atattagcct taatagcatg caagcaaaat     60

gttagcagcc ttgatgaaaa aaacagcgct tcagtagatt tgcctggtga gatgaaagtt    120

cttgtaagta aagaaaaaga caaagacggt aagtacagtc taaaggcaac agtagacaag    180

attgagctaa aaggaacttc tgataaagac aatggttctg gagtgcttga aggtacaaaa    240

gatgacaaaa gtaaagcaaa attaacaatt gctgacgatc taagtaaaac cacattcgaa    300

cttttcaaag aagatggcaa aacattagtg tcaagaaaag taagttctaa agacaaaaca    360

tcaacagatg aaatgttcaa tgaaaaaggt gaattgtctg caaaaaccat gacaagagaa    420

aatggaacca aacttgaata tacagaaatg aaaagcgatg gaaccggaaa agctaaagaa    480

gttttaaaaa actttactct tgaaggaaaa gtagctaatg ataaagtaac attggaagta    540

aaagaaggaa ccgttacttt aagtaaggaa attgcaaaat ctggagaagt aacagttgct    600

cttaatgaca ctaacactac tcaggctact aaaaaaactg gcgcatggga ttcaaaaact    660

tctactttaa caattagtgt taacagcaaa aaaactacac aacttgtgtt tactaaacaa    720

gacacaataa ctgtacaaaa atacgactcc gcaggtacca atttagaagg cacagcagtc    780

gaaattaaaa cacttgatga acttaaaaac gctttgaaat aa                       822
```

<210> SEQ ID NO 27
<211> LENGTH: 38
<212> TYPE: DNA
<213> ORGANISM: Artificial Sequence
<220> FEATURE:
<223> OTHER INFORMATION: Synthetic Construct

<400> SEQUENCE: 27
aaagtagaag tttttgaatc ccattttcca gttttttt 38

<210> SEQ ID NO 28
<211> LENGTH: 825
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(825)

<400> SEQUENCE: 28

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gat gaa aaa aat agc gtt tca gta       96
Cys Lys Gln Asn Val Ser Ser Leu Asp Glu Lys Asn Ser Val Ser Val
            20                  25                  30

gat tta cct ggt gga atg aca gtt ctt gta agt aaa gaa aaa gac aaa      144
Asp Leu Pro Gly Gly Met Thr Val Leu Val Ser Lys Glu Lys Asp Lys
        35                  40                  45

gac ggt aaa tac agt cta gag gca aca gta gac aag ctt gag ctt aaa      192
Asp Gly Lys Tyr Ser Leu Glu Ala Thr Val Asp Lys Leu Glu Leu Lys
    50                  55                  60

gga act tct gat aaa aac aac ggt tct gga aca ctt gaa ggt gaa aaa      240
Gly Thr Ser Asp Lys Asn Asn Gly Ser Gly Thr Leu Glu Gly Glu Lys
 65                  70                  75                  80

act gac aaa agt aaa gta aaa tta aca att gct gat gac cta agt caa      288
Thr Asp Lys Ser Lys Val Lys Leu Thr Ile Ala Asp Asp Leu Ser Gln
                85                  90                  95

act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110

aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125

aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140

ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160

gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175

aca aca ttg aaa gtt aca gaa ggc act gtt gtt tta agc aag aac att      576
Thr Thr Leu Lys Val Thr Glu Gly Thr Val Val Leu Ser Lys Asn Ile
            180                 185                 190

tta aaa tcc gga gaa ata aca gtt gca ctt gat gac tct gac act act      624
Leu Lys Ser Gly Glu Ile Thr Val Ala Leu Asp Asp Ser Asp Thr Thr
        195                 200                 205

cag gct act aaa aaa act gga aaa tgg gat tca aaa act tct act tta      672
Gln Ala Thr Lys Lys Thr Gly Lys Trp Asp Ser Lys Thr Ser Thr Leu
```

-continued

```
    210                 215                 220

aca att agt gtt aac agc aaa aaa act aca caa ctt gtg ttt act aaa      720
Thr Ile Ser Val Asn Ser Lys Lys Thr Thr Gln Leu Val Phe Thr Lys
225                 230                 235                 240

caa tac aca ata act gta aaa caa tac gac tcc gca ggt acc aat tta      768
Gln Tyr Thr Ile Thr Val Lys Gln Tyr Asp Ser Ala Gly Thr Asn Leu
                245                 250                 255

gaa ggc aca gca gtc gaa att aaa aca ctt gat gaa ctt aaa aac gct      816
Glu Gly Thr Ala Val Glu Ile Lys Thr Leu Asp Glu Leu Lys Asn Ala
            260                 265                 270

tta aaa taa                                                          825
Leu Lys


<210> SEQ ID NO 29
<211> LENGTH: 274
<212> TYPE: PRT
<213> ORGANISM: Artificial Sequence
<220> FEATURE:
<223> OTHER INFORMATION: Chimeric protein

<400> SEQUENCE: 29

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Lys Thr Ser Thr Leu
    210                 215                 220

Thr Ile Ser Val Asn Ser Lys Lys Thr Thr Gln Leu Val Phe Thr Lys
225                 230                 235                 240

Gln Tyr Thr Ile Thr Val Lys Gln Tyr Asp Ser Ala Gly Thr Asn Leu
                245                 250                 255

Glu Gly Thr Ala Val Glu Ile Lys Thr Leu Asp Glu Leu Lys Asn Ala
            260                 265                 270

Leu Lys
```

<210> SEQ ID NO 30
<211> LENGTH: 822
<212> TYPE: DNA
<213> ORGANISM: Artificial Sequence
<220> FEATURE:
<221> NAME/KEY: CDS
<222> LOCATION: (1)...(822)
<223> OTHER INFORMATION: Chimeric nucleic acid

<400> SEQUENCE: 30

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgc aag caa aat gtt agc agc ctt gat gaa aaa aac agc gct tca gta       96
Cys Lys Gln Asn Val Ser Ser Leu Asp Glu Lys Asn Ser Ala Ser Val
            20                  25                  30

gat ttg cct ggt gag atg aaa gtt ctt gta agt aaa gaa aaa gac aaa      144
Asp Leu Pro Gly Glu Met Lys Val Leu Val Ser Lys Glu Lys Asp Lys
        35                  40                  45

gac ggt aag tac agt cta aag gca aca gta gac aag att gag cta aaa      192
Asp Gly Lys Tyr Ser Leu Lys Ala Thr Val Asp Lys Ile Glu Leu Lys
    50                  55                  60

gga act tct gat aaa gac aat ggt tct gga gtg ctt gaa ggt aca aaa      240
Gly Thr Ser Asp Lys Asp Asn Gly Ser Gly Val Leu Glu Gly Thr Lys
65                  70                  75                  80

gat gac aaa agt aaa gca aaa tta aca att gct gac gat cta agt aaa      288
Asp Asp Lys Ser Lys Ala Lys Leu Thr Ile Ala Asp Asp Leu Ser Lys
                85                  90                  95

acc aca ttc gaa ctt tta aaa gaa gat ggc aaa aca tta gtg tca aga      336
Thr Thr Phe Glu Leu Leu Lys Glu Asp Gly Lys Thr Leu Val Ser Arg
            100                 105                 110

aaa gta agt tct aga gac aaa aca tca aca gat gaa atg ttc aat gaa      384
Lys Val Ser Ser Arg Asp Lys Thr Ser Thr Asp Glu Met Phe Asn Glu
        115                 120                 125

aaa ggt gaa ttg tct gca aaa acc atg aca aga gaa aat gga acc aaa      432
Lys Gly Glu Leu Ser Ala Lys Thr Met Thr Arg Glu Asn Gly Thr Lys
    130                 135                 140

ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160

gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175

aca ttg gaa gta aaa gaa gga acc gtt act tta agt aag gaa att gca      576
Thr Leu Glu Val Lys Glu Gly Thr Val Thr Leu Ser Lys Glu Ile Ala
            180                 185                 190

aaa tct gga gaa gta aca gtt gct ctt aat gac act aac act act cag      624
Lys Ser Gly Glu Val Thr Val Ala Leu Asn Asp Thr Asn Thr Thr Gln
        195                 200                 205

gct act aaa aaa act ggc gca tgg gat tca aaa act tct act tta aca      672
Ala Thr Lys Lys Thr Gly Ala Trp Asp Ser Lys Thr Ser Thr Leu Thr
    210                 215                 220

att agt gtt aac agc aaa aaa act aca caa ctt gtg ttt act aaa caa      720
Ile Ser Val Asn Ser Lys Lys Thr Thr Gln Leu Val Phe Thr Lys Gln
225                 230                 235                 240

tac aca ata act gta aaa caa tac gac tcc gca ggt acc aat tta gaa      768
Tyr Thr Ile Thr Val Lys Gln Tyr Asp Ser Ala Gly Thr Asn Leu Glu
                245                 250                 255

ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
```

```
            260                 265                 270

aaa taa                                                                    822
Lys


<210> SEQ ID NO 31
<211> LENGTH: 273
<212> TYPE: PRT
<213> ORGANISM: Artificial Sequence
<220> FEATURE:
<223> OTHER INFORMATION: Chimeric protein

<400> SEQUENCE: 31

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Tyr Thr Ile Thr Val Lys Gln Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys


<210> SEQ ID NO 32
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 32
```

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                 70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220

att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240

gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255

ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270

aaa taa                                                               822
Lys
```

<210> SEQ ID NO 33
<211> LENGTH: 273
<212> TYPE: PRT
<213> ORGANISM: Artificial Sequence
<220> FEATURE:
<223> OTHER INFORMATION: Chimeric protein

<400> SEQUENCE: 33

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

<210> SEQ ID NO 34
<211> LENGTH: 819
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(819)

<400> SEQUENCE: 34

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45
```

```
gac ggc aag tac gat cta att gca aca gta gac aag ctt gag ctt aaa      192
Asp Gly Lys Tyr Asp Leu Ile Ala Thr Val Asp Lys Leu Glu Leu Lys
     50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat gca ggc act tca act tta aca      672
Ala Thr Lys Lys Thr Ala Ala Trp Asn Ala Gly Thr Ser Thr Leu Thr
    210                 215                 220

att act gta aac aac aaa aaa act aaa gcc ctt gta ttt aca aaa caa      720
Ile Thr Val Asn Asn Lys Lys Thr Lys Ala Leu Val Phe Thr Lys Gln
225                 230                 235                 240

gac aca att aca tca caa aaa tac gac tca gca gga acc aac ttg gaa      768
Asp Thr Ile Thr Ser Gln Lys Tyr Asp Ser Ala Gly Thr Asn Leu Glu
                245                 250                 255

ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270

aga                                                                  819
Arg
```

<210> SEQ ID NO 35
<211> LENGTH: 273
<212> TYPE: PRT
<213> ORGANISM: Artificial Sequence
<220> FEATURE:
<223> OTHER INFORMATION: Chimeric protein

<400> SEQUENCE: 35

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45
```

-continued

```
Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ala Gly Thr Ser Thr Leu Thr
    210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg


<210> SEQ ID NO 36
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 36

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gat gaa aaa aat agc gtt tca gta       96
Cys Lys Gln Asn Val Ser Ser Leu Asp Glu Lys Asn Ser Val Ser Val
            20                  25                  30

gat tta cct ggt gga atg aca gtt ctt gta agt aaa gaa aaa gac aaa      144
Asp Leu Pro Gly Gly Met Thr Val Leu Val Ser Lys Glu Lys Asp Lys
        35                  40                  45

gac ggt aaa tac agt cta gag gca aca gta gac aag ctt gag ctt aaa      192
Asp Gly Lys Tyr Ser Leu Glu Ala Thr Val Asp Lys Leu Glu Leu Lys
    50                  55                  60

gga act tct gat aaa aac aac ggt tct gga aca ctt gaa ggt gaa aaa      240
Gly Thr Ser Asp Lys Asn Asn Gly Ser Gly Thr Leu Glu Gly Glu Lys
65                  70                  75                  80

act gac aaa agt aaa gta aaa tta aca att gct gat gac cta agt caa      288
Thr Asp Lys Ser Lys Val Lys Leu Thr Ile Ala Asp Asp Leu Ser Gln
                85                  90                  95
```

```
act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110

aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125

aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140

ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160

gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175

aca aca ttg aaa gtt aca gaa ggc act gtt gtt tta agc aag att tca      576
Thr Thr Leu Lys Val Thr Glu Gly Thr Val Val Leu Ser Lys Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220

att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240

gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255

ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270

aaa taa                                                              822
Lys


<210> SEQ ID NO 37
<211> LENGTH: 273
<212> TYPE: PRT
<213> ORGANISM: Artificial Sequence
<220> FEATURE:
<223> OTHER INFORMATION: Chimeric protein

<400> SEQUENCE: 37

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110
```

```
Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys


<210> SEQ ID NO 38
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 38

atg aaa aaa tat tta ttg gga ata ggt cta ata tta gcc tta ata gca      48
Met Lys Lys Tyr Leu Leu Gly Ile Gly Leu Ile Leu Ala Leu Ile Ala
 1               5                  10                  15

tgt aag caa aat gtt agc agc ctt gat gaa aaa aat agc gtt tca gta      96
Cys Lys Gln Asn Val Ser Ser Leu Asp Glu Lys Asn Ser Val Ser Val
            20                  25                  30

gat tta cct ggt gga atg aca gtt ctt gta agt aaa gaa aaa gac aaa     144
Asp Leu Pro Gly Gly Met Thr Val Leu Val Ser Lys Glu Lys Asp Lys
        35                  40                  45

gac ggt aaa tac agt cta gag gca aca gta gac aag ctt gag ctt aaa     192
Asp Gly Lys Tyr Ser Leu Glu Ala Thr Val Asp Lys Leu Glu Leu Lys
    50                  55                  60

gga act tct gat aaa aac aac ggt tct gga aca ctt gaa ggt gaa aaa     240
Gly Thr Ser Asp Lys Asn Asn Gly Ser Gly Thr Leu Glu Gly Glu Lys
 65                  70                  75                  80

act gac aaa agt aaa gta aaa tta aca att gct gat gac cta agt caa     288
Thr Asp Lys Ser Lys Val Lys Leu Thr Ile Ala Asp Asp Leu Ser Gln
                85                  90                  95

act aaa ttt gaa att ttc aaa gaa gat gcc aaa aca tta gta tca aaa     336
Thr Lys Phe Glu Ile Phe Lys Glu Asp Ala Lys Thr Leu Val Ser Lys
            100                 105                 110

aaa gta acc ctt aaa gac aag tca tca aca gaa gaa aaa ttc aac gaa     384
Lys Val Thr Leu Lys Asp Lys Ser Ser Thr Glu Glu Lys Phe Asn Glu
        115                 120                 125

aag ggt gaa aca tct gaa aaa aca ata gta aga gca aat gga acc aga     432
Lys Gly Glu Thr Ser Glu Lys Thr Ile Val Arg Ala Asn Gly Thr Arg
    130                 135                 140
```

```
ctt gaa tac aca gac ata aaa agc gat gga tcc gga aaa gct aaa gaa      480
Leu Glu Tyr Thr Asp Ile Lys Ser Asp Gly Ser Gly Lys Ala Lys Glu
145                 150                 155                 160

gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175

aca aca ttg aaa gtt aca gaa ggc act gtt gtt tta agc aag att tca      576
Thr Thr Leu Lys Val Thr Glu Gly Thr Val Val Leu Ser Lys Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220

att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240

gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255

ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270

aaa taa                                                              822
Lys


<210> SEQ ID NO 39
<211> LENGTH: 273
<212> TYPE: PRT
<213> ORGANISM: Artificial Sequence
<220> FEATURE:
<223> OTHER INFORMATION: Chimeric protein

<400> SEQUENCE: 39

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175
```

```
Thr Thr Leu Lys Val Thr Glu Gly Thr Val Val Leu Ser Lys Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys


<210> SEQ ID NO 40
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 40

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190
```

```
aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat gac agt act agc act tta aca      672
Ala Thr Lys Lys Thr Ala Ala Trp Asn Asp Ser Thr Ser Thr Leu Thr
    210                 215                 220

att agt gct gac agc aaa aaa act aaa gat ttg gtg ttc tta aca gat      720
Ile Ser Ala Asp Ser Lys Lys Thr Lys Asp Leu Val Phe Leu Thr Asp
225                 230                 235                 240

ggt aca att aca gta caa caa tac aac aca gct gga acc agc cta gaa      768
Gly Thr Ile Thr Val Gln Gln Tyr Asn Thr Ala Gly Thr Ser Leu Glu
                245                 250                 255

gga tca gca agt gaa att aaa aat ctt tca gag ctt aaa aac gct tta      816
Gly Ser Ala Ser Glu Ile Lys Asn Leu Ser Glu Leu Lys Asn Ala Leu
            260                 265                 270

aaa taa                                                              822
Lys


<210> SEQ ID NO 41
<211> LENGTH: 273
<212> TYPE: PRT
<213> ORGANISM: Artificial Sequence
<220> FEATURE:
<223> OTHER INFORMATION: Chimeric protein

<400> SEQUENCE: 41

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Asp Ser Thr Ser Thr Leu Thr
    210                 215                 220

Ile Ser Ala Asp Ser Lys Lys Thr Lys Asp Leu Val Phe Leu Thr Asp
225                 230                 235                 240
```

Gly Thr Ile Thr Val Gln Gln Tyr Asn Thr Ala Gly Thr Ser Leu Glu
245 250 255

Gly Ser Ala Ser Glu Ile Lys Asn Leu Ser Glu Leu Lys Asn Ala Leu
260 265 270

Lys

<210> SEQ ID NO 42
<211> LENGTH: 822
<212> TYPE: DNA
<213> ORGANISM: Borrelia burgdorferi

<400> SEQUENCE: 42
atgaaaaaat atttattggg aataggtcta atattagcct taatagcatg taagcaaaat 60
gttagcagcc ttgacgagaa aaacagcgtt tcagtagatt tgcctggtga aatgaaagtt 120
cttgtaagca aagaaaaaaa caaagacggc aagtacgatc taattgcaac agtagacaag 180
cttgagctta aaggaacttc tgataaaaac aatggatctg gagtacttga aggcgtaaaa 240
gctgacaaaa gtaaagtaaa attaacaatt tctgacgatc taggtcaaac cacacttgaa 300
gttttcaaag aagatggcaa aacactagta tcaaaaaaag taacttccaa agacaagtca 360
tcaacagaag aaaaattcaa tgaaaaaggt gaagtatctg aaaaaataat aacaagagca 420
gacggaacca gacttgaata cacaggaatt aaaagcgatg gatctggaaa agctaaagag 480
gttttaaaag gctatgttct tgaaggaact ctaactgctg aaaaaacaac attggtggtt 540
aaagaaggaa ctgttacttt aagcaaaaat atttcaaaat ctggggaagt ttcagttgaa 600
cttaatgaca ctgacagtag tgctgctact aaaaaaactg cagcttggaa ttcaggcact 660
tcaactttaa caattactgt aaacagtaaa aaaactaaag accttgtgtt tacaaaagaa 720
aacacaatta cagtacaaca atacgactca aatggcacca aattagaggg gtcagcagtt 780
gaaattacaa aacttgatga aattaaaaac gctttaaaat aa 822

<210> SEQ ID NO 43
<211> LENGTH: 822
<212> TYPE: DNA
<213> ORGANISM: Borrelia burgdorferi

<400> SEQUENCE: 43
atgaaaaaat atttattggg aataggtcta atattagcct taatagcatg taagcaaaat 60
gttagcagcc ttgacgagaa aaacagcgtt tcagtagatt tgcctggtga aatgaacgtt 120
cttgtaagca aagaaaaaaa caaagacggc aagtacgatc taattgcaac agtagacaag 180
cttgagctta aaggaacttc tgataaaaac aatggatctg gagtacttga aggcgtaaaa 240
gctgacaaaa gtaaagtaaa attaacaatt tctgacgatc taggtcaaac cacacttgaa 300
gttttcaaag aagatggcaa aacactagta tcaaaaaaag taacttccaa agacaagtca 360
tcaacagaag aaaaattcaa tgaaaaaggt gaagtatctg aaaaaataat aacaagagca 420
gacggaacca gacttgaata cacagaaatt aaaagcgatg gatctggaaa agctaaagag 480
gttttaaaag gctatgttct tgaaggaact ctaactgctg aaaaaacaac attggtggtt 540
aaagaaggaa ctgttacttt aagcaaaaat atttcaaaat ctggggaagt ttcagttgaa 600
cttaatgaca ctgacagtag tgctgctact aaaaaaactg cagcttggaa ttcaggcact 660
tcaactttaa caattactgt aaacagtaaa aaaactaaag accttgtgtt tacaaaagaa 720
aacacaatta cagtacaaca atacgactca aatggcacca aattagaggg gtcagcagtt 780
gaaattacaa aacttgatga aattaaaaac gctttaaaat aa 822

<210> SEQ ID NO 44
<211> LENGTH: 822
<212> TYPE: DNA
<213> ORGANISM: Borrelia burgdorferi

<400> SEQUENCE: 44
atgaaaaaat atttattggg aataggtcta atattagcct taatagcatg taagcaaaat 60
gttagcagcc ttgacgagaa aaacagcgtt tcagtagatt tgcctggtga aatgaacgtt 120
cttgtaagca aagaaaaaaa caaagacggc aagtacgatc taattgcaac agtagacaag 180
cttgagctta aaggaacttc tgataaaaac aatggatctg gagtacttga aggcgtaaaa 240
gctgacaaaa gtaaagtaaa attaacaatt tctgacgatc taggtcaaac cacacttgaa 300
gttttcaaag aagatggcaa aacactagta tcaaaaaaag taacttccaa agacaagtca 360
tcaacagaag aaaaattcaa tgaaaaaggt gaagtatctg aaaaaataat aacaagagca 420
gacggaacca gacttgaata cacagaaatt aaaagcgatg gatctggaaa agctaaagag 480
gttttaaaaa gctatgttct tgaaggaact ttaactgctg aaaaaacaac attggtggtt 540
aaagaaggaa ctgttacttt aagcaaaaat atttcaaaat ctggggaagt ttcagttgaa 600
cttaatgaca ctgacagtag tgctgctact aaaaaaactg cagcttggaa ttcaggcact 660
tcaactttaa caattactgt aaacagtaaa aaaactaaag accttgtgtt tacaaaagaa 720
aacacaatta cagtacaaca atacgactca aatggcacca aattagaggg gtcagcagtt 780
gaaattacaa aacttgatga aattaaaaac gctttaaaat aa 822

<210> SEQ ID NO 45
<211> LENGTH: 821
<212> TYPE: DNA
<213> ORGANISM: Borrelia burgdorferi

<400> SEQUENCE: 45
atgaaaaaat atttattggg aataggtcta atattagcct taatagcatg taagcaaaat 60
gttagcagcc ttgatgagaa aaacagcgtt tcagtagatt tacctggtga aatgaaagtt 120
cttgtaagca aagaaaaaga caaagatggt aaatacagtc taatggcaac agtagacaag 180
ctagagctta aaggaacttc tgataaaagc aacggttctg gaacacttga aggtgaaaaa 240
tctgacaaaa gtaaagcaaa attaacaatt tctgaagatc taagtaaaac cacatttgaa 300
attttcaaag aagatggcaa aacattagta tcaaaaaaag taaattctaa agataagtca 360
tcaatagaag aaaaattcaa cgcaaaaggt gaattatctg aaaaaacaat actaagagca 420
aacggaacca ggcttgaata cacagaaata aaaagcgatg gaaccggaaa agctaaagaa 480
gctttaaaag actttgctct tgaaggaact ctagctgccg acaaaacaac attgaaagtt 540
acagaaggca ctgttgtttt aagcaaacac attccaaact ctggagaaat aacagttgag 600
cttaatgact ctaactctac tcaggctact aaaaaaactg gaaaatggga ttcaaatact 660
tccactttaa caattagtgt gaatagcaaa aaaactaaaa acattgtatt tacaaaagaa 720
gacacaataa cagtacaaaa atacgactca gcaggcacca atctagaagg caacgcagtc 780
gaaattaaaa cacttgatga acttaaaaac gctttaaaat a 821

<210> SEQ ID NO 46
<211> LENGTH: 821
<212> TYPE: DNA
<213> ORGANISM: Borrelia burgdorferi

<400> SEQUENCE: 46

```
atgaaaaaat atttattggg aataggtcta atattagcct taatagcatg taagcaaaat     60
gttagcagcc ttgatgaaaa aaatagcgtt tcagtagatt tacctggtgg aatgaaagtt    120
cttgtaagta aagaaaaaga caaagatggt aaatacagtc taatggcaac agtagaaaag    180
cttgagctta aaggaacttc tgataaaaac aacggttctg gaacacttga aggtgaaaaa    240
actgacaaaa gtaaagtaaa attaacaatt gctgaggatc taagtaaaac cacatttgaa    300
atcttcaaag aagatggcaa aacattagta tcgaaaaaag taacccttaa agacaagtca    360
tcaacagaag aaaaattcaa cgaaaagggt gaaatatctg aaaaaacaat agtaagagca    420
aatggaacca gacttgaata cacagacata aaaagcgata aaaccggaaa agctaaagaa    480
gttttaaaag actttactct tgaaggaact ctagctgctg acggcaaaac aacattgaaa    540
gttacagagg gcactgttac tttaagcaag aacatttcaa aatccggaga aataacagtt    600
gcacttgatg acactgactc tagcggcaat aaaaaatccg gaacatggga ttcaggtact    660
tctactttaa caattagtaa aaacagacaa aaaactaaac aacttgtatt cacaaaagaa    720
gacacaataa cagtacaaaa ctacgactca gcaggcacca atctagaagg caaagcagtc    780
gaaattacaa cacttaaaga acttaaaaac gctttaaaat a                        821
```

<210> SEQ ID NO 47
<211> LENGTH: 825
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(825)

<400> SEQUENCE: 47

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gat gaa aaa aat agc gtt tca gta       96
Cys Lys Gln Asn Val Ser Ser Leu Asp Glu Lys Asn Ser Val Ser Val
            20                  25                  30

gat tta cct ggt gga atg aca gtt ctt gta agt aaa gaa aaa gac aaa      144
Asp Leu Pro Gly Gly Met Thr Val Leu Val Ser Lys Glu Lys Asp Lys
        35                  40                  45

gac ggt aaa tac agt cta gag gca aca gta gac aag ctt gag ctt aaa      192
Asp Gly Lys Tyr Ser Leu Glu Ala Thr Val Asp Lys Leu Glu Leu Lys
    50                  55                  60

gga act tct gat aaa aac aac ggt tct gga aca ctt gaa ggt gaa aaa      240
Gly Thr Ser Asp Lys Asn Asn Gly Ser Gly Thr Leu Glu Gly Glu Lys
 65                  70                  75                  80

act gac aaa agt aaa gta aaa tta aca att gct gat gac cta agt caa      288
Thr Asp Lys Ser Lys Val Lys Leu Thr Ile Ala Asp Asp Leu Ser Gln
                85                  90                  95

act aaa ttt gaa att ttc aaa gaa gat gcc aaa aca tta gta tca aaa      336
Thr Lys Phe Glu Ile Phe Lys Glu Asp Ala Lys Thr Leu Val Ser Lys
            100                 105                 110

aaa gta acc ctt aaa gac aag tca tca aca gaa gaa aaa ttc aac gaa      384
Lys Val Thr Leu Lys Asp Lys Ser Ser Thr Glu Glu Lys Phe Asn Glu
        115                 120                 125

aag ggt gaa aca tct gaa aaa aca ata gta aga gca aat gga acc aga      432
Lys Gly Glu Thr Ser Glu Lys Thr Ile Val Arg Ala Asn Gly Thr Arg
    130                 135                 140

ctt gaa tac aca gac ata aaa agc gat gga tcc gga aaa gct aaa gaa      480
```

-continued

```
Leu Glu Tyr Thr Asp Ile Lys Ser Asp Gly Ser Gly Lys Ala Lys Glu
145                 150                 155                 160

gtt tta aaa gac ttt act ctt gaa gga act cta gct gct gac ggc aaa      528
Val Leu Lys Asp Phe Thr Leu Glu Gly Thr Leu Ala Ala Asp Gly Lys
                165                 170                 175

aca aca ttg aaa gtt aca gaa ggc act gtt gtt tta agc aag aac att      576
Thr Thr Leu Lys Val Thr Glu Gly Thr Val Val Leu Ser Lys Asn Ile
            180                 185                 190

tta aaa tcc gga gaa ata aca gtt gca ctt gat gac tct gac act act      624
Leu Lys Ser Gly Glu Ile Thr Val Ala Leu Asp Asp Ser Asp Thr Thr
        195                 200                 205

cag gct act aaa aaa act gga aaa tgg gat tca aat act tcc act tta      672
Gln Ala Thr Lys Lys Thr Gly Lys Trp Asp Ser Asn Thr Ser Thr Leu
    210                 215                 220

aca att agt gtg aat agc aaa aaa act aaa aac att gta ttt aca aaa      720
Thr Ile Ser Val Asn Ser Lys Lys Thr Lys Asn Ile Val Phe Thr Lys
225                 230                 235                 240

gaa gac aca ata aca gta caa aaa tac gac tca gca ggc acc aat cta      768
Glu Asp Thr Ile Thr Val Gln Lys Tyr Asp Ser Ala Gly Thr Asn Leu
                245                 250                 255

gaa ggc aac gca gtc gaa att aaa aca ctt gat gaa ctt aaa aac gct      816
Glu Gly Asn Ala Val Glu Ile Lys Thr Leu Asp Glu Leu Lys Asn Ala
            260                 265                 270

tta aaa tag                                                          825
Leu Lys


<210> SEQ ID NO 48
<211> LENGTH: 274
<212> TYPE: PRT
<213> ORGANISM: Artificial Sequence
<220> FEATURE:
<223> OTHER INFORMATION: Chimeric protein

<400> SEQUENCE: 48

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190
```

```
Leu Lys Ser Gly Glu Ile Thr Val Ala Leu Asp Asp Ser Asp Thr Thr
        195                 200                 205

Gln Ala Thr Lys Lys Thr Gly Lys Trp Asp Ser Asn Thr Ser Thr Leu
    210                 215                 220

Thr Ile Ser Val Asn Ser Lys Lys Thr Lys Asn Ile Val Phe Thr Lys
225                 230                 235                 240

Glu Asp Thr Ile Thr Val Gln Lys Tyr Asp Ser Ala Gly Thr Asn Leu
                245                 250                 255

Glu Gly Asn Ala Val Glu Ile Lys Thr Leu Asp Glu Leu Lys Asn Ala
            260                 265                 270

Leu Lys
```

```
<210> SEQ ID NO 49
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 49

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgc aag caa aat gtt agc agc ctt gat gaa aaa aac agc gct tca gta       96
Cys Lys Gln Asn Val Ser Ser Leu Asp Glu Lys Asn Ser Ala Ser Val
            20                  25                  30

gat ttg cct ggt gag atg aaa gtt ctt gta agt aaa gaa aaa gac aaa      144
Asp Leu Pro Gly Glu Met Lys Val Leu Val Ser Lys Glu Lys Asp Lys
        35                  40                  45

gac ggt aag tac agt cta aag gca aca gta gac aag att gag cta aaa      192
Asp Gly Lys Tyr Ser Leu Lys Ala Thr Val Asp Lys Ile Glu Leu Lys
    50                  55                  60

gga act tct gat aaa gac aat ggt tct gga gtg ctt gaa ggt aca aaa      240
Gly Thr Ser Asp Lys Asp Asn Gly Ser Gly Val Leu Glu Gly Thr Lys
 65                  70                  75                  80

gat gac aaa agt aaa gca aaa tta aca att gct gac gat cta agt aaa      288
Asp Asp Lys Ser Lys Ala Lys Leu Thr Ile Ala Asp Asp Leu Ser Lys
                85                  90                  95

acc aca ttc gaa ctt tta aaa gaa gat ggc aaa aca tta gtg tca aga      336
Thr Thr Phe Glu Leu Leu Lys Glu Asp Gly Lys Thr Leu Val Ser Arg
            100                 105                 110

aaa gta agt tct aga gac aaa aca tca aca gat gaa atg ttc aat gaa      384
Lys Val Ser Ser Arg Asp Lys Thr Ser Thr Asp Glu Met Phe Asn Glu
        115                 120                 125

aaa ggt gaa ttg tct gca aaa acc atg aca aga gaa aat gga acc aaa      432
Lys Gly Glu Leu Ser Ala Lys Thr Met Thr Arg Glu Asn Gly Thr Lys
    130                 135                 140

ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160

gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175

aca ttg gaa gta aaa gaa gga acc gtt act tta agt aag gaa att gca      576
Thr Leu Glu Val Lys Glu Gly Thr Val Thr Leu Ser Lys Glu Ile Ala
            180                 185                 190

aaa tct gga gaa gta aca gtt gct ctt aat gac act aac act act cag      624
```

```
Lys Ser Gly Glu Val Thr Val Ala Leu Asn Asp Thr Asn Thr Thr Gln
        195                 200                 205

gct act aaa aaa act ggc gca tgg gat tca aaa act tct act tta aca      672
Ala Thr Lys Lys Thr Gly Ala Trp Asp Ser Lys Thr Ser Thr Leu Thr
    210                 215                 220

att agt gtt aac agc aaa aaa act aca caa ctt gtg ttt act aaa caa      720
Ile Ser Val Asn Ser Lys Lys Thr Thr Gln Leu Val Phe Thr Lys Gln
225                 230                 235                 240

gac aca ata act gta caa aaa tac gac tcc gca ggt acc aat tta gaa      768
Asp Thr Ile Thr Val Gln Lys Tyr Asp Ser Ala Gly Thr Asn Leu Glu
                245                 250                 255

ggt aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270

aaa tag                                                              822
Lys


<210> SEQ ID NO 50
<211> LENGTH: 273
<212> TYPE: PRT
<213> ORGANISM: Artificial Sequence
<220> FEATURE:
<223> OTHER INFORMATION: Chimeric protein

<400> SEQUENCE: 50

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190

Lys Ser Gly Glu Val Thr Val Ala Leu Asn Asp Thr Asn Thr Thr Gln
        195                 200                 205

Ala Thr Lys Lys Thr Gly Ala Trp Asp Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255
```

```
Gly Thr Ala Val Glu Ile Lys Thr Leu Asp Glu Leu Lys Asn Ala Leu
            260                 265                 270

Lys


<210> SEQ ID NO 51
<211> LENGTH: 822
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(822)

<400> SEQUENCE: 51

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgc aag caa aat gtt agc agc ctt gat gaa aaa aac agc gct tca gta       96
Cys Lys Gln Asn Val Ser Ser Leu Asp Glu Lys Asn Ser Ala Ser Val
            20                  25                  30

gat ttg cct ggt gag atg aaa gtt ctt gta agt aaa gaa aaa gac aaa      144
Asp Leu Pro Gly Glu Met Lys Val Leu Val Ser Lys Glu Lys Asp Lys
        35                  40                  45

gac ggt aag tac agt cta aag gca aca gta gac aag att gag cta aaa      192
Asp Gly Lys Tyr Ser Leu Lys Ala Thr Val Asp Lys Ile Glu Leu Lys
    50                  55                  60

gga act tct gat aaa gac aat ggt tct gga gtg ctt gaa ggt aca aaa      240
Gly Thr Ser Asp Lys Asp Asn Gly Ser Gly Val Leu Glu Gly Thr Lys
 65                  70                  75                  80

gat gac aaa agt aaa gca aaa tta aca att gct gac gat cta agt aaa      288
Asp Asp Lys Ser Lys Ala Lys Leu Thr Ile Ala Asp Asp Leu Ser Lys
                85                  90                  95

acc aca ttc gaa ctt tta aaa gaa gat ggc aaa aca tta gtg tca aga      336
Thr Thr Phe Glu Leu Leu Lys Glu Asp Gly Lys Thr Leu Val Ser Arg
            100                 105                 110

aaa gta agt tct aga gac aaa aca tca aca gat gaa atg ttc aat gaa      384
Lys Val Ser Ser Arg Asp Lys Thr Ser Thr Asp Glu Met Phe Asn Glu
        115                 120                 125

aaa ggt gaa ttg tct gca aaa acc atg aca aga gaa aat gga acc aaa      432
Lys Gly Glu Leu Ser Ala Lys Thr Met Thr Arg Glu Asn Gly Thr Lys
    130                 135                 140

ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160

gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175

aca ttg gaa gta aaa gaa gga acc gtt act tta agt aag gaa att tca      576
Thr Leu Glu Val Lys Glu Gly Thr Val Thr Leu Ser Lys Glu Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220

att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240

gac aca ata aca gta caa aaa tac gac tca gca ggc acc aat cta gaa      768
```

```
Asp Thr Ile Thr Val Gln Lys Tyr Asp Ser Ala Gly Thr Asn Leu Glu
                245                 250                 255

ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270

aaa taa                                                              822
Lys
```

<210> SEQ ID NO 52
<211> LENGTH: 273
<212> TYPE: PRT
<213> ORGANISM: Artificial Sequence
<220> FEATURE:
<223> OTHER INFORMATION: Chimeric protein

<400> SEQUENCE: 52

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Leu Lys Glu Asp Gly Lys Thr Leu Val Ser Arg
            100                 105                 110

Lys Val Ser Ser Arg Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys
```

<210> SEQ ID NO 53
<211> LENGTH: 822
<212> TYPE: DNA
<213> ORGANISM: Artificial Sequence
<220> FEATURE:

```
<223> OTHER INFORMATION: Chimeric nucleic acid
<221> NAME/KEY: CDS
<222> LOCATION: (1)...(822)

<400> SEQUENCE: 53

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
     50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca aat gga acc aaa      432
Lys Gly Glu Val Ser Glu Lys Ile Ile Thr Arg Ala Asn Gly Thr Lys
    130                 135                 140

ctt gaa tat aca gaa atg aaa agc gat gga acc gga aaa gct aaa gaa      480
Leu Glu Tyr Thr Glu Met Lys Ser Asp Gly Thr Gly Lys Ala Lys Glu
145                 150                 155                 160

gtt tta aaa aag ttt act ctt gaa gga aaa gta gct aat gat aaa gta      528
Val Leu Lys Lys Phe Thr Leu Glu Gly Lys Val Ala Asn Asp Lys Val
                165                 170                 175

aca ttg gaa gta aaa gaa gga acc gtt act tta agt aag gaa att tca      576
Thr Leu Glu Val Lys Glu Gly Thr Val Thr Leu Ser Lys Glu Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca aaa act tcc act tta aca      672
Ala Thr Lys Lys Thr Ala Ala Trp Asn Ser Lys Thr Ser Thr Leu Thr
    210                 215                 220

att agt gtg aat agc caa aaa acc aaa aac ctt gta ttc aca aaa gaa      720
Ile Ser Val Asn Ser Gln Lys Thr Lys Asn Leu Val Phe Thr Lys Glu
225                 230                 235                 240

gac aca ata aca gta caa aaa tac gac tca gca ggc acc aat cta gaa      768
Asp Thr Ile Thr Val Gln Lys Tyr Asp Ser Ala Gly Thr Asn Leu Glu
                245                 250                 255

ggc aaa gca gtc gaa att aca aca ctt aaa gaa ctt aaa aac gct tta      816
Gly Lys Ala Val Glu Ile Thr Thr Leu Lys Glu Leu Lys Asn Ala Leu
            260                 265                 270

aaa taa                                                              822
Lys

<210> SEQ ID NO 54
```

```
<211> LENGTH: 273
<212> TYPE: PRT
<213> ORGANISM: Artificial Sequence
<220> FEATURE:
<223> OTHER INFORMATION: Chimeric protein

<400> SEQUENCE: 54

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Lys Phe Thr Leu Glu Gly Lys Val Ala Asn Asp Lys Val
                165                 170                 175

Thr Leu Glu Val Lys Glu Gly Thr Val Thr Leu Ser Lys Glu Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Gln Lys Thr Lys Asn Leu Val Phe Thr Lys Glu
225                 230                 235                 240

Asp Thr Ile Thr Val Gln Lys Tyr Asp Ser Ala Gly Thr Asn Leu Glu
                245                 250                 255

Gly Lys Ala Val Glu Ile Thr Thr Leu Lys Glu Leu Lys Asn Ala Leu
            260                 265                 270

Lys


<210> SEQ ID NO 55
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 55

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
```

```
             20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
    50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt agc agc ctt gac gag aaa aac      624
Lys Pro Ser Met Ala Lys Gln Asn Val Ser Ser Leu Asp Glu Lys Asn
        195                 200                 205

agc gtt tca gta gat ttg cct ggt gaa atg aaa gtt ctt gta agc aaa      672
Ser Val Ser Val Asp Leu Pro Gly Glu Met Lys Val Leu Val Ser Lys
    210                 215                 220

gaa aaa aac aaa gac ggc aag tac gat cta att gca aca gta gac aag      720
Glu Lys Asn Lys Asp Gly Lys Tyr Asp Leu Ile Ala Thr Val Asp Lys
225                 230                 235                 240

ctt gag ctt aaa gga act tct gat aaa aac aat gga tct gga gta ctt      768
Leu Glu Leu Lys Gly Thr Ser Asp Lys Asn Asn Gly Ser Gly Val Leu
                245                 250                 255

gaa ggc gta aaa gct gac aaa agt aaa gta aaa tta aca att tct gac      816
Glu Gly Val Lys Ala Asp Lys Ser Lys Val Lys Leu Thr Ile Ser Asp
            260                 265                 270

gat cta ggt caa acc aca ctt gaa gtt ttc aaa gaa gat ggc aaa aca      864
Asp Leu Gly Gln Thr Thr Leu Glu Val Phe Lys Glu Asp Gly Lys Thr
        275                 280                 285

cta gta tca aaa aaa gta act tcc aaa gac aag tca tca aca gaa gaa      912
Leu Val Ser Lys Lys Val Thr Ser Lys Asp Lys Ser Ser Thr Glu Glu
    290                 295                 300

aaa ttc aat gaa aaa ggt gaa gta tct gaa aaa ata ata aca aga gca      960
Lys Phe Asn Glu Lys Gly Glu Val Ser Glu Lys Ile Ile Thr Arg Ala
305                 310                 315                 320

gac gga acc aga ctt gaa tac aca gga att aaa agc gat gga tct gga     1008
Asp Gly Thr Arg Leu Glu Tyr Thr Gly Ile Lys Ser Asp Gly Ser Gly
                325                 330                 335

aaa gct aaa gag gtt tta aaa ggc tat gtt ctt gaa gga act cta act     1056
```

```
Lys Ala Lys Glu Val Leu Lys Gly Tyr Val Leu Glu Gly Thr Leu Thr
            340                 345                 350

gct gaa aaa aca aca ttg gtg gtt aaa gaa gga act gtt act tta agc      1104
Ala Glu Lys Thr Thr Leu Val Val Lys Glu Gly Thr Val Thr Leu Ser
        355                 360                 365

aaa aat att tca aaa tct ggg gaa gtt tca gtt gaa ctt aat gac act      1152
Lys Asn Ile Ser Lys Ser Gly Glu Val Ser Val Glu Leu Asn Asp Thr
    370                 375                 380

gac agt agt gct gct act aaa aaa act gca gct tgg aat tca ggc act      1200
Asp Ser Ser Ala Ala Thr Lys Lys Thr Ala Ala Trp Asn Ser Gly Thr
385                 390                 395                 400

tca act tta aca att act gta aac agt aaa aaa act aaa gac ctt gtg      1248
Ser Thr Leu Thr Ile Thr Val Asn Ser Lys Lys Thr Lys Asp Leu Val
                405                 410                 415

ttt aca aaa gaa aac aca att aca gta caa caa tac gac tca aat ggc      1296
Phe Thr Lys Glu Asn Thr Ile Thr Val Gln Gln Tyr Asp Ser Asn Gly
            420                 425                 430

acc aaa tta gag ggg tca gca gtt gaa att aca aaa ctt gat gaa att      1344
Thr Lys Leu Glu Gly Ser Ala Val Glu Ile Thr Lys Leu Asp Glu Ile
        435                 440                 445

aaa aac gct tta aaa taa                                              1362
Lys Asn Ala Leu Lys
    450


<210> SEQ ID NO 56
<211> LENGTH: 453
<212> TYPE: PRT
<213> ORGANISM: Artificial Sequence
<220> FEATURE:
<223> OTHER INFORMATION: Chimeric protein

<400> SEQUENCE: 56

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205
```

```
Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365

Lys Asn Ile Ser Lys Ser Gly Glu Val Ser Val Glu Leu Asn Asp Thr
    370                 375                 380

Asp Ser Ser Ala Ala Thr Lys Lys Thr Ala Ala Trp Asn Ser Gly Thr
385                 390                 395                 400

Ser Thr Leu Thr Ile Thr Val Asn Ser Lys Lys Thr Lys Asp Leu Val
                405                 410                 415

Phe Thr Lys Glu Asn Thr Ile Thr Val Gln Gln Tyr Asp Ser Asn Gly
            420                 425                 430

Thr Lys Leu Glu Gly Ser Ala Val Glu Ile Thr Lys Leu Asp Glu Ile
        435                 440                 445

Lys Asn Ala Leu Lys
    450


<210> SEQ ID NO 57
<211> LENGTH: 1353
<212> TYPE: DNA
<213> ORGANISM: Artificial Sequence
<220> FEATURE:
<223> OTHER INFORMATION: Chimeric  nucleic acid
<221> NAME/KEY: CDS
<222> LOCATION: (1)...(1353)

<400> SEQUENCE: 57

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
```

```
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca gcc      576
Asn Ser Val Lys Glu Leu Thr Ser Pro Val Val Ala Glu Ser Pro Ala
            180                 185                 190

atg gcc aag caa aat gtt agc agc ctt gac gag aaa aac agc gtt tca      624
Met Ala Lys Gln Asn Val Ser Ser Leu Asp Glu Lys Asn Ser Val Ser
        195                 200                 205

gta gat ttg cct ggt gaa atg aaa gtt ctt gta agc aaa gaa aaa aac      672
Val Asp Leu Pro Gly Glu Met Lys Val Leu Val Ser Lys Glu Lys Asn
    210                 215                 220

aaa gac ggc aag tac gat cta att gca aca gta gac aag ctt gag ctt      720
Lys Asp Gly Lys Tyr Asp Leu Ile Ala Thr Val Asp Lys Leu Glu Leu
225                 230                 235                 240

aaa gga act tct gat aaa aac aat gga tct gga gta ctt gaa ggc gta      768
Lys Gly Thr Ser Asp Lys Asn Asn Gly Ser Gly Val Leu Glu Gly Val
                245                 250                 255

aaa gct gac aaa agt aaa gta aaa tta aca att tct gac gat cta ggt      816
Lys Ala Asp Lys Ser Lys Val Lys Leu Thr Ile Ser Asp Asp Leu Gly
            260                 265                 270

caa acc aca ctt gaa gtt ttc aaa gaa gat ggc aaa aca cta gta tca      864
Gln Thr Thr Leu Glu Val Phe Lys Glu Asp Gly Lys Thr Leu Val Ser
        275                 280                 285

aaa aaa gta act tcc aaa gac aag tca tca aca gaa gaa aaa ttc aat      912
Lys Lys Val Thr Ser Lys Asp Lys Ser Ser Thr Glu Glu Lys Phe Asn
    290                 295                 300

gaa aaa ggt gaa gta tct gaa aaa ata ata aca aga gca gac gga acc      960
Glu Lys Gly Glu Val Ser Glu Lys Ile Ile Thr Arg Ala Asp Gly Thr
305                 310                 315                 320

aga ctt gaa tac aca gga att aaa agc gat gga tct gga aaa gct aaa     1008
Arg Leu Glu Tyr Thr Gly Ile Lys Ser Asp Gly Ser Gly Lys Ala Lys
                325                 330                 335

gag gtt tta aaa ggc tat gtt ctt gaa gga act cta act gct gaa aaa     1056
Glu Val Leu Lys Gly Tyr Val Leu Glu Gly Thr Leu Thr Ala Glu Lys
            340                 345                 350

aca aca ttg gtg gtt aaa gaa gga act gtt act tta agc aaa aat att     1104
Thr Thr Leu Val Val Lys Glu Gly Thr Val Thr Leu Ser Lys Asn Ile
        355                 360                 365

tca aaa tct ggg gaa gtt tca gtt gaa ctt aat gac act gac agt agt     1152
Ser Lys Ser Gly Glu Val Ser Val Glu Leu Asn Asp Thr Asp Ser Ser
    370                 375                 380

gct gct act aaa aaa act gca gct tgg aat tca ggc act tca act tta     1200
```

```
Ala Ala Thr Lys Lys Thr Ala Ala Trp Asn Ser Gly Thr Ser Thr Leu
385                 390                 395                 400

aca att act gta aac agt aaa aaa act aaa gac ctt gtg ttt aca aaa      1248
Thr Ile Thr Val Asn Ser Lys Lys Thr Lys Asp Leu Val Phe Thr Lys
                405                 410                 415

gaa aac aca att aca gta caa caa tac gac tca aat ggc acc aaa tta      1296
Glu Asn Thr Ile Thr Val Gln Gln Tyr Asp Ser Asn Gly Thr Lys Leu
            420                 425                 430

gag ggg tca gca gtt gaa att aca aaa ctt gat gaa att aaa aac gct      1344
Glu Gly Ser Ala Val Glu Ile Thr Lys Leu Asp Glu Ile Lys Asn Ala
        435                 440                 445

tta aaa taa                                                          1353
Leu Lys
    450


<210> SEQ ID NO 58
<211> LENGTH: 450
<212> TYPE: PRT
<213> ORGANISM: Artificial Sequence
<220> FEATURE:
<223> OTHER INFORMATION: Chimeric protein

<400> SEQUENCE: 58

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ala
            180                 185                 190

Met Ala Lys Gln Asn Val Ser Ser Leu Asp Glu Lys Asn Ser Val Ser
        195                 200                 205

Val Asp Leu Pro Gly Glu Met Lys Val Leu Val Ser Lys Glu Lys Asn
    210                 215                 220

Lys Asp Gly Lys Tyr Asp Leu Ile Ala Thr Val Asp Lys Leu Glu Leu
225                 230                 235                 240

Lys Gly Thr Ser Asp Lys Asn Asn Gly Ser Gly Val Leu Glu Gly Val
                245                 250                 255

Lys Ala Asp Lys Ser Lys Val Lys Leu Thr Ile Ser Asp Asp Leu Gly
            260                 265                 270
```

```
Gln Thr Thr Leu Glu Val Phe Lys Glu Asp Gly Lys Thr Leu Val Ser
        275                 280                 285

Lys Lys Val Thr Ser Lys Asp Lys Ser Ser Thr Glu Glu Lys Phe Asn
    290                 295                 300

Glu Lys Gly Glu Val Ser Glu Lys Ile Ile Thr Arg Ala Asp Gly Thr
305                 310                 315                 320

Arg Leu Glu Tyr Thr Gly Ile Lys Ser Asp Gly Ser Gly Lys Ala Lys
                325                 330                 335

Glu Val Leu Lys Gly Tyr Val Leu Glu Gly Thr Leu Thr Ala Glu Lys
            340                 345                 350

Thr Thr Leu Val Val Lys Glu Gly Thr Val Thr Leu Ser Lys Asn Ile
        355                 360                 365

Ser Lys Ser Gly Glu Val Ser Val Glu Leu Asn Asp Thr Asp Ser Ser
    370                 375                 380

Ala Ala Thr Lys Lys Thr Ala Ala Trp Asn Ser Gly Thr Ser Thr Leu
385                 390                 395                 400

Thr Ile Thr Val Asn Ser Lys Lys Thr Lys Asp Leu Val Phe Thr Lys
                405                 410                 415

Glu Asn Thr Ile Thr Val Gln Gln Tyr Asp Ser Asn Gly Thr Lys Leu
            420                 425                 430

Glu Gly Ser Ala Val Glu Ile Thr Lys Leu Asp Glu Ile Lys Asn Ala
        435                 440                 445

Leu Lys
    450


<210> SEQ ID NO 59
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 59

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
     50                  55                  60

aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80

tta gca gga gct tat aca ata tca acc tta ata aca caa aaa tta agt      288
Leu Ala Gly Ala Tyr Thr Ile Ser Thr Leu Ile Thr Gln Lys Leu Ser
                85                  90                  95

aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110

aaa tgc tct gaa gag ttt agt act aaa cta aaa gat aat cat gca cag      384
Lys Cys Ser Glu Glu Phe Ser Thr Lys Leu Lys Asp Asn His Ala Gln
```

-continued

```
        115                 120                 125

ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140

aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160

ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175

gct aat tca gtt aaa gag ctt aca agc cct gtt gtc cat ggc aag caa      576
Ala Asn Ser Val Lys Glu Leu Thr Ser Pro Val Val His Gly Lys Gln
            180                 185                 190

aat gtt agc agc ctt gac gag aaa aac agc gtt tca gta gat ttg cct      624
Asn Val Ser Ser Leu Asp Glu Lys Asn Ser Val Ser Val Asp Leu Pro
        195                 200                 205

ggt gaa atg aaa gtt ctt gta agc aaa gaa aaa aac aaa gac ggc aag      672
Gly Glu Met Lys Val Leu Val Ser Lys Glu Lys Asn Lys Asp Gly Lys
    210                 215                 220

tac gat cta att gca aca gta gac aag ctt gag ctt aaa gga act tct      720
Tyr Asp Leu Ile Ala Thr Val Asp Lys Leu Glu Leu Lys Gly Thr Ser
225                 230                 235                 240

gat aaa aac aat gga tct gga gta ctt gaa ggc gta aaa gct gac aaa      768
Asp Lys Asn Asn Gly Ser Gly Val Leu Glu Gly Val Lys Ala Asp Lys
                245                 250                 255

agt aaa gta aaa tta aca att tct gac gat cta ggt caa acc aca ctt      816
Ser Lys Val Lys Leu Thr Ile Ser Asp Asp Leu Gly Gln Thr Thr Leu
            260                 265                 270

gaa gtt ttc aaa gaa gat ggc aaa aca cta gta tca aaa aaa gta act      864
Glu Val Phe Lys Glu Asp Gly Lys Thr Leu Val Ser Lys Lys Val Thr
        275                 280                 285

tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
    290                 295                 300

gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320

aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335

ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
            340                 345                 350

gtt aaa gaa gga act gtt act tta agc aaa aat att tca aaa tct ggg     1104
Val Lys Glu Gly Thr Val Thr Leu Ser Lys Asn Ile Ser Lys Ser Gly
        355                 360                 365

gaa gtt tca gtt gaa ctt aat gac act gac agt agt gct gct act aaa     1152
Glu Val Ser Val Glu Leu Asn Asp Thr Asp Ser Ser Ala Ala Thr Lys
    370                 375                 380

aaa act gca gct tgg aat tca ggc act tca act tta aca att act gta     1200
Lys Thr Ala Ala Trp Asn Ser Gly Thr Ser Thr Leu Thr Ile Thr Val
385                 390                 395                 400

aac agt aaa aaa act aaa gac ctt gtg ttt aca aaa gaa aac aca att     1248
Asn Ser Lys Lys Thr Lys Asp Leu Val Phe Thr Lys Glu Asn Thr Ile
                405                 410                 415

aca gta caa caa tac gac tca aat ggc acc aaa tta gag ggg tca gca     1296
Thr Val Gln Gln Tyr Asp Ser Asn Gly Thr Lys Leu Glu Gly Ser Ala
            420                 425                 430

gtt gaa att aca aaa ctt gat gaa att aaa aac gct tta aaa taa         1341
```

```
Val Glu Ile Thr Lys Leu Asp Glu Ile Lys Asn Ala Leu Lys
        435                 440                 445


<210> SEQ ID NO 60
<211> LENGTH: 446
<212> TYPE: PRT
<213> ORGANISM: Artificial Sequence
<220> FEATURE:
<223> OTHER INFORMATION: Chimeric protein

<400> SEQUENCE: 60

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
    210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350
```

```
Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Gly Thr Ser Thr Leu Thr Ile Thr Val
385                 390                 395                 400

Asn Ser Lys Lys Thr Lys Asp Leu Val Phe Thr Lys Glu Asn Thr Ile
                405                 410                 415

Thr Val Gln Gln Tyr Asp Ser Asn Gly Thr Lys Leu Glu Gly Ser Ala
            420                 425                 430

Val Glu Ile Thr Lys Leu Asp Glu Ile Lys Asn Ala Leu Lys
        435                 440                 445


<210> SEQ ID NO 61
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 61

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
    50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt agc agc ctt gac gag aaa aac      624
```

-continued

```
Lys Pro Ser Met Ala Lys Gln Asn Val Ser Ser Leu Asp Glu Lys Asn
        195                 200                 205

agc gtt tca gta gat ttg cct ggt gaa atg aaa gtt ctt gta agc aaa      672
Ser Val Ser Val Asp Leu Pro Gly Glu Met Lys Val Leu Val Ser Lys
    210                 215                 220

gaa aaa aac aaa gac ggc aag tac gat cta att gca aca gta gac aag      720
Glu Lys Asn Lys Asp Gly Lys Tyr Asp Leu Ile Ala Thr Val Asp Lys
225                 230                 235                 240

ctt gag ctt aaa gga act tct gat aaa aac aat gga tct gga gta ctt      768
Leu Glu Leu Lys Gly Thr Ser Asp Lys Asn Asn Gly Ser Gly Val Leu
                245                 250                 255

gaa ggc gta aaa gct gac aaa agt aaa gta aaa tta aca att tct gac      816
Glu Gly Val Lys Ala Asp Lys Ser Lys Val Lys Leu Thr Ile Ser Asp
            260                 265                 270

gat cta ggt caa acc aca ctt gaa gtt ttc aaa gaa gat ggc aaa aca      864
Asp Leu Gly Gln Thr Thr Leu Glu Val Phe Lys Glu Asp Gly Lys Thr
        275                 280                 285

cta gta tca aaa aaa gta act tcc aaa gac aag tca tca aca gaa gaa      912
Leu Val Ser Lys Lys Val Thr Ser Lys Asp Lys Ser Ser Thr Glu Glu
    290                 295                 300

aaa ttc aat gaa aaa ggt gaa gta tct gaa aaa ata ata aca aga gca      960
Lys Phe Asn Glu Lys Gly Glu Val Ser Glu Lys Ile Ile Thr Arg Ala
305                 310                 315                 320

gac gga acc aga ctt gaa tac aca gga att aaa agc gat gga tct gga     1008
Asp Gly Thr Arg Leu Glu Tyr Thr Gly Ile Lys Ser Asp Gly Ser Gly
                325                 330                 335

aaa gct aaa gag gtt tta aaa ggc tat gtt ctt gaa gga act cta act     1056
Lys Ala Lys Glu Val Leu Lys Gly Tyr Val Leu Glu Gly Thr Leu Thr
            340                 345                 350

gct gaa aaa aca aca ttg gtg gtt aaa gaa gga act gtt act tta agc     1104
Ala Glu Lys Thr Thr Leu Val Val Lys Glu Gly Thr Val Thr Leu Ser
        355                 360                 365

aaa aat att tca aaa tct ggg gaa gtt tca gtt gaa ctt aat gac act     1152
Lys Asn Ile Ser Lys Ser Gly Glu Val Ser Val Glu Leu Asn Asp Thr
    370                 375                 380

gac agt agt gct gct act aaa aaa act gca gct tgg aat tca aaa act     1200
Asp Ser Ser Ala Ala Thr Lys Lys Thr Ala Ala Trp Asn Ser Lys Thr
385                 390                 395                 400

tcc act tta aca att agt gtg aat agc caa aaa acc aaa aac ctt gta     1248
Ser Thr Leu Thr Ile Ser Val Asn Ser Gln Lys Thr Lys Asn Leu Val
                405                 410                 415

ttc aca aaa gaa gac aca ata aca gta caa aaa tac gac tca gca ggc     1296
Phe Thr Lys Glu Asp Thr Ile Thr Val Gln Lys Tyr Asp Ser Ala Gly
            420                 425                 430

acc aat cta gaa ggc aaa gca gtc gaa att aca aca ctt aaa gaa ctt     1344
Thr Asn Leu Glu Gly Lys Ala Val Glu Ile Thr Thr Leu Lys Glu Leu
        435                 440                 445

aaa aac gct tta aaa taa                                             1362
Lys Asn Ala Leu Lys
    450


<210> SEQ ID NO 62
<211> LENGTH: 453
<212> TYPE: PRT
<213> ORGANISM: Artificial Sequence
<220> FEATURE:
<223> OTHER INFORMATION: Chimeric protein

<400> SEQUENCE: 62

Met Ala Cys Asn Asn Ser Gly Lys Asp Gly Asn Thr Ser Ala Asn Ser
 1               5                  10                  15
```

-continued

```
Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365

Lys Asn Ile Ser Lys Ser Gly Glu Val Ser Val Glu Leu Asn Asp Thr
    370                 375                 380

Asp Ser Ser Ala Ala Thr Lys Lys Thr Ala Ala Trp Asn Ser Lys Thr
385                 390                 395                 400

Ser Thr Leu Thr Ile Ser Val Asn Ser Gln Lys Thr Lys Asn Leu Val
                405                 410                 415

Phe Thr Lys Glu Asp Thr Ile Thr Val Gln Lys Tyr Asp Ser Ala Gly
            420                 425                 430
```

```
Thr Asn Leu Glu Gly Lys Ala Val Glu Ile Thr Thr Leu Lys Glu Leu
        435                 440                 445

Lys Asn Ala Leu Lys
    450


<210> SEQ ID NO 63
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 63

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
     50                  55                  60

aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80

tta gca gga gct tat aca ata tca acc tta ata aca caa aaa tta agt      288
Leu Ala Gly Ala Tyr Thr Ile Ser Thr Leu Ile Thr Gln Lys Leu Ser
                85                  90                  95

aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110

aaa tgc tct gaa gag ttt agt act aaa cta aaa gat aat cat gca cag      384
Lys Cys Ser Glu Glu Phe Ser Thr Lys Leu Lys Asp Asn His Ala Gln
        115                 120                 125

ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140

aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160

ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175

gct aat tca gtt aaa gag ctt aca agc cct gtt gtc cat ggc aag caa      576
Ala Asn Ser Val Lys Glu Leu Thr Ser Pro Val Val His Gly Lys Gln
            180                 185                 190

aat gtt agc agc ctt gac gag aaa aac agc gtt tca gta gat ttg cct      624
Asn Val Ser Ser Leu Asp Glu Lys Asn Ser Val Ser Val Asp Leu Pro
        195                 200                 205

ggt gaa atg aaa gtt ctt gta agc aaa gaa aaa aac aaa gac ggc aag      672
Gly Glu Met Lys Val Leu Val Ser Lys Glu Lys Asn Lys Asp Gly Lys
    210                 215                 220

tac gat cta att gca aca gta gac aag ctt gag ctt aaa gga act tct      720
Tyr Asp Leu Ile Ala Thr Val Asp Lys Leu Glu Leu Lys Gly Thr Ser
225                 230                 235                 240

gat aaa aac aat gga tct gga gta ctt gaa ggc gta aaa gct gac aaa      768
```

```
Asp Lys Asn Asn Gly Ser Gly Val Leu Glu Gly Val Lys Ala Asp Lys
                245                 250                 255

agt aaa gta aaa tta aca att tct gac gat cta ggt caa acc aca ctt      816
Ser Lys Val Lys Leu Thr Ile Ser Asp Asp Leu Gly Gln Thr Thr Leu
            260                 265                 270

gaa gtt ttc aaa gaa gat ggc aaa aca cta gta tca aaa aaa gta act      864
Glu Val Phe Lys Glu Asp Gly Lys Thr Leu Val Ser Lys Lys Val Thr
        275                 280                 285

tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
    290                 295                 300

gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320

aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335

ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
            340                 345                 350

gtt aaa gaa gga act gtt act tta agc aaa aat att tca aaa tct ggg     1104
Val Lys Glu Gly Thr Val Thr Leu Ser Lys Asn Ile Ser Lys Ser Gly
        355                 360                 365

gaa gtt tca gtt gaa ctt aat gac act gac agt agt gct gct act aaa     1152
Glu Val Ser Val Glu Leu Asn Asp Thr Asp Ser Ser Ala Ala Thr Lys
    370                 375                 380

aaa act gca gct tgg aat tca aaa act tcc act tta aca att agt gtg     1200
Lys Thr Ala Ala Trp Asn Ser Lys Thr Ser Thr Leu Thr Ile Ser Val
385                 390                 395                 400

aat agc caa aaa acc aaa aac ctt gta ttc aca aaa gaa gac aca ata     1248
Asn Ser Gln Lys Thr Lys Asn Leu Val Phe Thr Lys Glu Asp Thr Ile
                405                 410                 415

aca gta caa aaa tac gac tca gca ggc acc aat cta gaa ggc aaa gca     1296
Thr Val Gln Lys Tyr Asp Ser Ala Gly Thr Asn Leu Glu Gly Lys Ala
            420                 425                 430

gtc gaa att aca aca ctt aaa gaa ctt aaa aac gct tta aaa taa         1341
Val Glu Ile Thr Thr Leu Lys Glu Leu Lys Asn Ala Leu Lys
        435                 440                 445


<210> SEQ ID NO 64
<211> LENGTH: 446
<212> TYPE: PRT
<213> ORGANISM: Artificial Sequence
<220> FEATURE:
<223> OTHER INFORMATION: Chimeric protein

<400> SEQUENCE: 64

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95
```

```
Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
    210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Lys Thr Ser Thr Leu Thr Ile Ser Val
385                 390                 395                 400

Asn Ser Gln Lys Thr Lys Asn Leu Val Phe Thr Lys Glu Asp Thr Ile
                405                 410                 415

Thr Val Gln Lys Tyr Asp Ser Ala Gly Thr Asn Leu Glu Gly Lys Ala
            420                 425                 430

Val Glu Ile Thr Thr Leu Lys Glu Leu Lys Asn Ala Leu Lys
        435                 440                 445
```

<210> SEQ ID NO 65
<211> LENGTH: 1362
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1362)

<400> SEQUENCE: 65

```
atg gct tgt aat aat tca ggg aaa gat ggg aat aca tct gca aat tct       48
```

-continued

```
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
             20                  25                  30

att acg tca tct aat gcg gtt tta ctt gct gtg aaa gag gtt gaa gcg      144
Ile Thr Ser Ser Asn Ala Val Leu Leu Ala Val Lys Glu Val Glu Ala
         35                  40                  45

ttg ctg gat tct ata gat gaa att gct gct aaa gct att ggt aaa aaa      192
Leu Leu Asp Ser Ile Asp Glu Ile Ala Ala Lys Ala Ile Gly Lys Lys
     50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt agc agc ctt gac gag aaa aac      624
Lys Pro Ser Met Ala Lys Gln Asn Val Ser Ser Leu Asp Glu Lys Asn
        195                 200                 205

agc gtt tca gta gat ttg cct ggt gaa atg aaa gtt ctt gta agc aaa      672
Ser Val Ser Val Asp Leu Pro Gly Glu Met Lys Val Leu Val Ser Lys
    210                 215                 220

gaa aaa aac aaa gac ggc aag tac gat cta att gca aca gta gac aag      720
Glu Lys Asn Lys Asp Gly Lys Tyr Asp Leu Ile Ala Thr Val Asp Lys
225                 230                 235                 240

ctt gag ctt aaa gga act tct gat aaa aac aat gga tct gga gta ctt      768
Leu Glu Leu Lys Gly Thr Ser Asp Lys Asn Asn Gly Ser Gly Val Leu
                245                 250                 255

gaa ggc gta aaa gct gac aaa agt aaa gta aaa tta aca att tct gac      816
Glu Gly Val Lys Ala Asp Lys Ser Lys Val Lys Leu Thr Ile Ser Asp
            260                 265                 270

gat cta ggt caa acc aca ctt gaa gtt ttc aaa gaa gat ggc aaa aca      864
Asp Leu Gly Gln Thr Thr Leu Glu Val Phe Lys Glu Asp Gly Lys Thr
        275                 280                 285

cta gta tca aaa aaa gta act tcc aaa gac aag tca tca aca gaa gaa      912
Leu Val Ser Lys Lys Val Thr Ser Lys Asp Lys Ser Ser Thr Glu Glu
    290                 295                 300

aaa ttc aat gaa aaa ggt gaa gta tct gaa aaa ata ata aca aga gca      960
Lys Phe Asn Glu Lys Gly Glu Val Ser Glu Lys Ile Ile Thr Arg Ala
305                 310                 315                 320
```

```
gac gga acc aga ctt gaa tac aca gga att aaa agc gat gga tct gga      1008
Asp Gly Thr Arg Leu Glu Tyr Thr Gly Ile Lys Ser Asp Gly Ser Gly
                325                 330                 335

aaa gct aaa gag gtt tta aaa ggc tat gtt ctt gaa gga act cta act      1056
Lys Ala Lys Glu Val Leu Lys Gly Tyr Val Leu Glu Gly Thr Leu Thr
            340                 345                 350

gct gaa aaa aca aca ttg gtg gtt aaa gaa gga act gtt act tta agc      1104
Ala Glu Lys Thr Thr Leu Val Val Lys Glu Gly Thr Val Thr Leu Ser
        355                 360                 365

aaa aat att tca aaa tct ggg gaa gtt tca gtt gaa ctt aat gac act      1152
Lys Asn Ile Ser Lys Ser Gly Glu Val Ser Val Glu Leu Asn Asp Thr
    370                 375                 380

gac agt agt gct gct act aaa aaa act gca gct tgg aat tca aaa act      1200
Asp Ser Ser Ala Ala Thr Lys Lys Thr Ala Ala Trp Asn Ser Lys Thr
385                 390                 395                 400

tct act tta aca att agt gtt aac agc aaa aaa act aca caa ctt gtg      1248
Ser Thr Leu Thr Ile Ser Val Asn Ser Lys Lys Thr Thr Gln Leu Val
                405                 410                 415

ttt act aaa caa gac aca ata act gta caa aaa tac gac tcc gca ggt      1296
Phe Thr Lys Gln Asp Thr Ile Thr Val Gln Lys Tyr Asp Ser Ala Gly
            420                 425                 430

acc aat tta gaa ggc aca gca gtc gaa att aaa aca ctt gat gaa ctt      1344
Thr Asn Leu Glu Gly Thr Ala Val Glu Ile Lys Thr Leu Asp Glu Leu
        435                 440                 445

aaa aac gct tta aaa taa                                              1362
Lys Asn Ala Leu Lys
    450


<210> SEQ ID NO 66
<211> LENGTH: 453
<212> TYPE: PRT
<213> ORGANISM: Artificial Sequence
<220> FEATURE:
<223> OTHER INFORMATION: Chimeric protein

<400> SEQUENCE: 66

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Ser Ser Asn Ala Val Leu Leu Ala Val Lys Glu Val Glu Ala
        35                  40                  45

Leu Leu Asp Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175
```

```
Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Glu Met Lys Val Leu Val Ser Lys
    210                 215                 220

Glu Lys Asn Lys Asp Gly Lys Tyr Asp Leu Ile Ala Thr Val Asp Lys
225                 230                 235                 240

Leu Glu Leu Lys Gly Thr Ser Asp Lys Asn Asn Gly Ser Gly Val Leu
                245                 250                 255

Glu Gly Val Lys Ala Asp Lys Ser Lys Val Lys Leu Thr Ile Ser Asp
            260                 265                 270

Asp Leu Gly Gln Thr Thr Leu Glu Val Phe Lys Glu Asp Gly Lys Thr
        275                 280                 285

Leu Val Ser Lys Lys Val Thr Ser Lys Asp Lys Ser Ser Thr Glu Glu
    290                 295                 300

Lys Phe Asn Glu Lys Gly Glu Val Ser Glu Lys Ile Ile Thr Arg Ala
305                 310                 315                 320

Asp Gly Thr Arg Leu Glu Tyr Thr Gly Ile Lys Ser Asp Gly Ser Gly
                325                 330                 335

Lys Ala Lys Glu Val Leu Lys Gly Tyr Val Leu Glu Gly Thr Leu Thr
            340                 345                 350

Ala Glu Lys Thr Thr Leu Val Val Lys Glu Gly Thr Val Thr Leu Ser
        355                 360                 365

Lys Asn Ile Ser Lys Ser Gly Glu Val Ser Val Glu Leu Asn Asp Thr
    370                 375                 380

Asp Ser Ser Ala Ala Thr Lys Lys Thr Ala Ala Trp Asn Ser Lys Thr
385                 390                 395                 400

Ser Thr Leu Thr Ile Ser Val Asn Ser Lys Lys Thr Thr Gln Leu Val
                405                 410                 415

Phe Thr Lys Gln Asp Thr Ile Thr Val Gln Lys Tyr Asp Ser Ala Gly
            420                 425                 430

Thr Asn Leu Glu Gly Thr Ala Val Glu Ile Lys Thr Leu Asp Glu Leu
        435                 440                 445

Lys Asn Ala Leu Lys
    450


<210> SEQ ID NO 67
<211> LENGTH: 1341
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1341)

<400> SEQUENCE: 67

atg gct tgt aat aat tca ggg aaa gat ggg aat aca tct gca aat tct        48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa        96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg       144
Ile Thr Asp Ser Asn Ala Val Leu Leu Ala Val Lys Glu Val Glu Ala
        35                  40                  45

ttg ctg tca tct ata gat gag ctt gct aaa gct att ggt aaa aaa ata       192
```

-continued

```
Leu Leu Ser Ser Ile Asp Glu Leu Ala Lys Ala Ile Gly Lys Lys Ile
     50                  55                  60

aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80

tta gca gga gct tat aca ata tca acc tta ata aca caa aaa tta agt      288
Leu Ala Gly Ala Tyr Thr Ile Ser Thr Leu Ile Thr Gln Lys Leu Ser
                 85                  90                  95

aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110

aaa tgc tct gaa gag ttt agt act aaa cta aaa gat aat cat gca cag      384
Lys Cys Ser Glu Glu Phe Ser Thr Lys Leu Lys Asp Asn His Ala Gln
        115                 120                 125

ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140

aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160

ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175

gct aat tca gtt aaa gag ctt aca agc cct gtt gtc cat ggc aag caa      576
Ala Asn Ser Val Lys Glu Leu Thr Ser Pro Val Val His Gly Lys Gln
            180                 185                 190

aat gtt agc agc ctt gac gag aaa aac agc gtt tca gta gat ttg cct      624
Asn Val Ser Ser Leu Asp Glu Lys Asn Ser Val Ser Val Asp Leu Pro
        195                 200                 205

ggt gaa atg aaa gtt ctt gta agc aaa gaa aaa aac aaa gac ggc aag      672
Gly Glu Met Lys Val Leu Val Ser Lys Glu Lys Asn Lys Asp Gly Lys
    210                 215                 220

tac gat cta att gca aca gta gac aag ctt gag ctt aaa gga act tct      720
Tyr Asp Leu Ile Ala Thr Val Asp Lys Leu Glu Leu Lys Gly Thr Ser
225                 230                 235                 240

gat aaa aac aat gga tct gga gta ctt gaa ggc gta aaa gct gac aaa      768
Asp Lys Asn Asn Gly Ser Gly Val Leu Glu Gly Val Lys Ala Asp Lys
                245                 250                 255

agt aaa gta aaa tta aca att tct gac gat cta ggt caa acc aca ctt      816
Ser Lys Val Lys Leu Thr Ile Ser Asp Asp Leu Gly Gln Thr Thr Leu
            260                 265                 270

gaa gtt ttc aaa gaa gat ggc aaa aca cta gta tca aaa aaa gta act      864
Glu Val Phe Lys Glu Asp Gly Lys Thr Leu Val Ser Lys Lys Val Thr
        275                 280                 285

tcc aaa gac aag tca tca aca gaa gaa aaa ttc aat gaa aaa ggt gaa      912
Ser Lys Asp Lys Ser Ser Thr Glu Glu Lys Phe Asn Glu Lys Gly Glu
    290                 295                 300

gta tct gaa aaa ata ata aca aga gca gac gga acc aga ctt gaa tac      960
Val Ser Glu Lys Ile Ile Thr Arg Ala Asp Gly Thr Arg Leu Glu Tyr
305                 310                 315                 320

aca gga att aaa agc gat gga tct gga aaa gct aaa gag gtt tta aaa     1008
Thr Gly Ile Lys Ser Asp Gly Ser Gly Lys Ala Lys Glu Val Leu Lys
                325                 330                 335

ggc tat gtt ctt gaa gga act cta act gct gaa aaa aca aca ttg gtg     1056
Gly Tyr Val Leu Glu Gly Thr Leu Thr Ala Glu Lys Thr Thr Leu Val
            340                 345                 350

gtt aaa gaa gga act gtt act tta agc aaa aat att tca aaa tct ggg     1104
Val Lys Glu Gly Thr Val Thr Leu Ser Lys Asn Ile Ser Lys Ser Gly
        355                 360                 365
```

```
gaa gtt tca gtt gaa ctt aat gac act gac agt agt gct gct act aaa      1152
Glu Val Ser Val Glu Leu Asn Asp Thr Asp Ser Ser Ala Ala Thr Lys
    370                 375                 380

aaa act gca gct tgg aat tca aaa act tct act tta aca att agt gtt      1200
Lys Thr Ala Ala Trp Asn Ser Lys Thr Ser Thr Leu Thr Ile Ser Val
385                 390                 395                 400

aac agc aaa aaa act aca caa ctt gtg ttt act aaa caa tac aca ata      1248
Asn Ser Lys Lys Thr Thr Gln Leu Val Phe Thr Lys Gln Tyr Thr Ile
                405                 410                 415

act gta aaa caa tac gac tcc gca ggt acc aat tta gaa ggc aca gca      1296
Thr Val Lys Gln Tyr Asp Ser Ala Gly Thr Asn Leu Glu Gly Thr Ala
            420                 425                 430

gtc gaa att aaa aca ctt gat gaa ctt aaa aac gct tta aaa taa          1341
Val Glu Ile Lys Thr Leu Asp Glu Leu Lys Asn Ala Leu Lys
        435                 440                 445


<210> SEQ ID NO 68
<211> LENGTH: 446
<212> TYPE: PRT
<213> ORGANISM: Artificial Sequence
<220> FEATURE:
<223> OTHER INFORMATION: Chimeric protein

<400> SEQUENCE: 68

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Glu Met Lys Val Leu Val Ser Lys Glu Lys Asn Lys Asp Gly Lys
    210                 215                 220

Tyr Asp Leu Ile Ala Thr Val Asp Lys Leu Glu Leu Lys Gly Thr Ser
225                 230                 235                 240

Asp Lys Asn Asn Gly Ser Gly Val Leu Glu Gly Val Lys Ala Asp Lys
                245                 250                 255

Ser Lys Val Lys Leu Thr Ile Ser Asp Asp Leu Gly Gln Thr Thr Leu
```

```
            260                 265                 270

Glu Val Phe Lys Glu Asp Gly Lys Thr Leu Val Ser Lys Lys Val Thr
        275                 280                 285

Ser Lys Asp Lys Ser Ser Thr Glu Glu Lys Phe Asn Glu Lys Gly Glu
    290                 295                 300

Val Ser Glu Lys Ile Ile Thr Arg Ala Asp Gly Thr Arg Leu Glu Tyr
305                 310                 315                 320

Thr Gly Ile Lys Ser Asp Gly Ser Gly Lys Ala Lys Glu Val Leu Lys
                325                 330                 335

Gly Tyr Val Leu Glu Gly Thr Leu Thr Ala Glu Lys Thr Thr Leu Val
            340                 345                 350

Val Lys Glu Gly Thr Val Thr Leu Ser Lys Asn Ile Ser Lys Ser Gly
        355                 360                 365

Glu Val Ser Val Glu Leu Asn Asp Thr Asp Ser Ser Ala Ala Thr Lys
    370                 375                 380

Lys Thr Ala Ala Trp Asn Ser Lys Thr Ser Thr Leu Thr Ile Ser Val
385                 390                 395                 400

Asn Ser Lys Lys Thr Thr Gln Leu Val Phe Thr Lys Gln Tyr Thr Ile
                405                 410                 415

Thr Val Lys Gln Tyr Asp Ser Ala Gly Thr Asn Leu Glu Gly Thr Ala
            420                 425                 430

Val Glu Ile Lys Thr Leu Asp Glu Leu Lys Asn Ala Leu Lys
        435                 440                 445


<210> SEQ ID NO 69
<211> LENGTH: 1365
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1365)

<400> SEQUENCE: 69

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60

ata cac caa aat aat ggt ttg gat acc gaa tat aat cac aat gga tca      240
Ile His Gln Asn Asn Gly Leu Asp Thr Glu Tyr Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125
```

-continued

```
ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa aca aat ggt act aaa act aaa ggt gct gaa gaa ctt gga aaa tta      480
Lys Thr Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt agc agc ctt gat gaa aaa aat      624
Lys Pro Ser Met Ala Lys Gln Asn Val Ser Ser Leu Asp Glu Lys Asn
        195                 200                 205

agc gtt tca gta gat tta cct ggt gga atg aca gtt ctt gta agt aaa      672
Ser Val Ser Val Asp Leu Pro Gly Gly Met Thr Val Leu Val Ser Lys
    210                 215                 220

gaa aaa gac aaa gac ggt aaa tac agt cta gag gca aca gta gac aag      720
Glu Lys Asp Lys Asp Gly Lys Tyr Ser Leu Glu Ala Thr Val Asp Lys
225                 230                 235                 240

ctt gag ctt aaa gga act tct gat aaa aac aac ggt tct gga aca ctt      768
Leu Glu Leu Lys Gly Thr Ser Asp Lys Asn Asn Gly Ser Gly Thr Leu
                245                 250                 255

gaa ggt gaa aaa act gac aaa agt aaa gta aaa tta aca att gct gat      816
Glu Gly Glu Lys Thr Asp Lys Ser Lys Val Lys Leu Thr Ile Ala Asp
            260                 265                 270

gac cta agt caa act aaa ttt gaa att ttc aaa gaa gat gcc aaa aca      864
Asp Leu Ser Gln Thr Lys Phe Glu Ile Phe Lys Glu Asp Ala Lys Thr
        275                 280                 285

tta gta tca aaa aaa gta acc ctt aaa gac aag tca tca aca gaa gaa      912
Leu Val Ser Lys Lys Val Thr Leu Lys Asp Lys Ser Ser Thr Glu Glu
    290                 295                 300

aaa ttc aac gaa aag ggt gaa aca tct gaa aaa aca ata gta aga gca      960
Lys Phe Asn Glu Lys Gly Glu Thr Ser Glu Lys Thr Ile Val Arg Ala
305                 310                 315                 320

aat gga acc aga ctt gaa tac aca gac ata aaa agc gat gga tcc gga     1008
Asn Gly Thr Arg Leu Glu Tyr Thr Asp Ile Lys Ser Asp Gly Ser Gly
                325                 330                 335

aaa gct aaa gaa gtt tta aaa gac ttt act ctt gaa gga act cta gct     1056
Lys Ala Lys Glu Val Leu Lys Asp Phe Thr Leu Glu Gly Thr Leu Ala
            340                 345                 350

gct gac ggc aaa aca aca ttg aaa gtt aca gaa ggc act gtt gtt tta     1104
Ala Asp Gly Lys Thr Thr Leu Lys Val Thr Glu Gly Thr Val Val Leu
        355                 360                 365

agc aag aac att tta aaa tcc gga gaa ata aca gtt gca ctt gat gac     1152
Ser Lys Asn Ile Leu Lys Ser Gly Glu Ile Thr Val Ala Leu Asp Asp
    370                 375                 380

tct gac act act cag gct act aaa aaa act gga aaa tgg gat tca aat     1200
Ser Asp Thr Thr Gln Ala Thr Lys Lys Thr Gly Lys Trp Asp Ser Asn
385                 390                 395                 400

act tcc act tta aca att agt gtg aat agc aaa aaa act aaa aac att     1248
Thr Ser Thr Leu Thr Ile Ser Val Asn Ser Lys Lys Thr Lys Asn Ile
                405                 410                 415

gta ttt aca aaa gaa gac aca ata aca gta caa aaa tac gac tca gca     1296
Val Phe Thr Lys Glu Asp Thr Ile Thr Val Gln Lys Tyr Asp Ser Ala
            420                 425                 430

ggc acc aat cta gaa ggc aac gca gtc gaa att aaa aca ctt gat gaa     1344
Gly Thr Asn Leu Glu Gly Asn Ala Val Glu Ile Lys Thr Leu Asp Glu
        435                 440                 445
```

```
ctt aaa aac gct tta aaa tag                                     1365
Leu Lys Asn Ala Leu Lys
    450


<210> SEQ ID NO 70
<211> LENGTH: 454
<212> TYPE: PRT
<213> ORGANISM: Artificial Sequence
<220> FEATURE:
<223> OTHER INFORMATION: Chimeric protein

<400> SEQUENCE: 70

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Ser Leu Asp Glu Lys Asn
        195                 200                 205

Ser Val Ser Val Asp Leu Pro Gly Gly Met Thr Val Leu Val Ser Lys
    210                 215                 220

Glu Lys Asp Lys Asp Gly Lys Tyr Ser Leu Glu Ala Thr Val Asp Lys
225                 230                 235                 240

Leu Glu Leu Lys Gly Thr Ser Asp Lys Asn Asn Gly Ser Gly Thr Leu
                245                 250                 255

Glu Gly Glu Lys Thr Asp Lys Ser Lys Val Lys Leu Thr Ile Ala Asp
            260                 265                 270

Asp Leu Ser Gln Thr Lys Phe Glu Ile Phe Lys Glu Asp Ala Lys Thr
        275                 280                 285

Leu Val Ser Lys Lys Val Thr Leu Lys Asp Lys Ser Ser Thr Glu Glu
    290                 295                 300

Lys Phe Asn Glu Lys Gly Glu Thr Ser Glu Lys Thr Ile Val Arg Ala
305                 310                 315                 320

Asn Gly Thr Arg Leu Glu Tyr Thr Asp Ile Lys Ser Asp Gly Ser Gly
                325                 330                 335

Lys Ala Lys Glu Val Leu Lys Asp Phe Thr Leu Glu Gly Thr Leu Ala
```

```
            340                 345                 350

Ala Asp Gly Lys Thr Thr Leu Lys Val Thr Glu Gly Thr Val Val Leu
        355                 360                 365

Ser Lys Asn Ile Leu Lys Ser Gly Glu Ile Thr Val Ala Leu Asp Asp
    370                 375                 380

Ser Asp Thr Thr Gln Ala Thr Lys Lys Thr Gly Lys Trp Asp Ser Asn
385                 390                 395                 400

Thr Ser Thr Leu Thr Ile Ser Val Asn Ser Lys Lys Thr Lys Asn Ile
                405                 410                 415

Val Phe Thr Lys Glu Asp Thr Ile Thr Val Gln Lys Tyr Asp Ser Ala
            420                 425                 430

Gly Thr Asn Leu Glu Gly Asn Ala Val Glu Ile Lys Thr Leu Asp Glu
        435                 440                 445

Leu Lys Asn Ala Leu Lys
    450


<210> SEQ ID NO 71
<211> LENGTH: 1344
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1344)

<400> SEQUENCE: 71

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
             20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
         35                  40                  45

ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
     50                  55                  60

aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80

tta gca gga gct tat aca ata tca acc tta ata aca caa aaa tta agt      288
Leu Ala Gly Ala Tyr Thr Ile Ser Thr Leu Ile Thr Gln Lys Leu Ser
                 85                  90                  95

aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110

aaa tgc tct gaa gag ttt agt act aaa cta aaa gat aat cat gca cag      384
Lys Cys Ser Glu Glu Phe Ser Thr Lys Leu Lys Asp Asn His Ala Gln
        115                 120                 125

ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140

aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160

ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175
```

-continued

```
gct aat tca gtt aaa gag ctt aca agc cct gtt gtc cat ggc aag caa      576
Ala Asn Ser Val Lys Glu Leu Thr Ser Pro Val Val His Gly Lys Gln
            180                 185                 190

aat gtt agc agc ctt gat gaa aaa aat agc gtt tca gta gat tta cct      624
Asn Val Ser Ser Leu Asp Glu Lys Asn Ser Val Ser Val Asp Leu Pro
        195                 200                 205

ggt gga atg aca gtt ctt gta agt aaa gaa aaa gac aaa gac ggt aaa      672
Gly Gly Met Thr Val Leu Val Ser Lys Glu Lys Asp Lys Asp Gly Lys
    210                 215                 220

tac agt cta gag gca aca gta gac aag ctt gag ctt aaa gga act tct      720
Tyr Ser Leu Glu Ala Thr Val Asp Lys Leu Glu Leu Lys Gly Thr Ser
225                 230                 235                 240

gat aaa aac aac ggt tct gga aca ctt gaa ggt gaa aaa act gac aaa      768
Asp Lys Asn Asn Gly Ser Gly Thr Leu Glu Gly Glu Lys Thr Asp Lys
                245                 250                 255

agt aaa gta aaa tta aca att gct gat gac cta agt caa act aaa ttt      816
Ser Lys Val Lys Leu Thr Ile Ala Asp Asp Leu Ser Gln Thr Lys Phe
            260                 265                 270

gaa att ttc aaa gaa gat gcc aaa aca tta gta tca aaa aaa gta acc      864
Glu Ile Phe Lys Glu Asp Ala Lys Thr Leu Val Ser Lys Lys Val Thr
        275                 280                 285

ctt aaa gac aag tca tca aca gaa gaa aaa ttc aac gaa aag ggt gaa      912
Leu Lys Asp Lys Ser Ser Thr Glu Glu Lys Phe Asn Glu Lys Gly Glu
    290                 295                 300

aca tct gaa aaa aca ata gta aga gca aat gga acc aga ctt gaa tac      960
Thr Ser Glu Lys Thr Ile Val Arg Ala Asn Gly Thr Arg Leu Glu Tyr
305                 310                 315                 320

aca gac ata aaa agc gat gga tcc gga aaa gct aaa gaa gtt tta aaa     1008
Thr Asp Ile Lys Ser Asp Gly Ser Gly Lys Ala Lys Glu Val Leu Lys
                325                 330                 335

gac ttt act ctt gaa gga act cta gct gct gac ggc aaa aca aca ttg     1056
Asp Phe Thr Leu Glu Gly Thr Leu Ala Ala Asp Gly Lys Thr Thr Leu
            340                 345                 350

aaa gtt aca gaa ggc act gtt gtt tta agc aag aac att tta aaa tcc     1104
Lys Val Thr Glu Gly Thr Val Val Leu Ser Lys Asn Ile Leu Lys Ser
        355                 360                 365

gga gaa ata aca gtt gca ctt gat gac tct gac act act cag gct act     1152
Gly Glu Ile Thr Val Ala Leu Asp Asp Ser Asp Thr Thr Gln Ala Thr
    370                 375                 380

aaa aaa act gga aaa tgg gat tca aat act tcc act tta aca att agt     1200
Lys Lys Thr Gly Lys Trp Asp Ser Asn Thr Ser Thr Leu Thr Ile Ser
385                 390                 395                 400

gtg aat agc aaa aaa act aaa aac att gta ttt aca aaa gaa gac aca     1248
Val Asn Ser Lys Lys Thr Lys Asn Ile Val Phe Thr Lys Glu Asp Thr
                405                 410                 415

ata aca gta caa aaa tac gac tca gca ggc acc aat cta gaa ggc aac     1296
Ile Thr Val Gln Lys Tyr Asp Ser Ala Gly Thr Asn Leu Glu Gly Asn
            420                 425                 430

gca gtc gaa att aaa aca ctt gat gaa ctt aaa aac gct tta aaa tag     1344
Ala Val Glu Ile Lys Thr Leu Asp Glu Leu Lys Asn Ala Leu Lys
        435                 440                 445
```

<210> SEQ ID NO 72
<211> LENGTH: 447
<212> TYPE: PRT
<213> ORGANISM: Artificial Sequence
<220> FEATURE:
<223> OTHER INFORMATION: Chimeric protein

<400> SEQUENCE: 72

```
Met Ala Cys Asn Asn Ser Gly Lys Asp Gly Asn Thr Ser Ala Asn Ser
```

-continued

```
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Lys Gln
            180                 185                 190

Asn Val Ser Ser Leu Asp Glu Lys Asn Ser Val Ser Val Asp Leu Pro
        195                 200                 205

Gly Gly Met Thr Val Leu Val Ser Lys Glu Lys Asp Lys Asp Gly Lys
    210                 215                 220

Tyr Ser Leu Glu Ala Thr Val Asp Lys Leu Glu Leu Lys Gly Thr Ser
225                 230                 235                 240

Asp Lys Asn Asn Gly Ser Gly Thr Leu Glu Gly Glu Lys Thr Asp Lys
                245                 250                 255

Ser Lys Val Lys Leu Thr Ile Ala Asp Asp Leu Ser Gln Thr Lys Phe
            260                 265                 270

Glu Ile Phe Lys Glu Asp Ala Lys Thr Leu Val Ser Lys Lys Val Thr
        275                 280                 285

Leu Lys Asp Lys Ser Ser Thr Glu Glu Lys Phe Asn Glu Lys Gly Glu
    290                 295                 300

Thr Ser Glu Lys Thr Ile Val Arg Ala Asn Gly Thr Arg Leu Glu Tyr
305                 310                 315                 320

Thr Asp Ile Lys Ser Asp Gly Ser Gly Lys Ala Lys Glu Val Leu Lys
                325                 330                 335

Asp Phe Thr Leu Glu Gly Thr Leu Ala Ala Asp Gly Lys Thr Thr Leu
            340                 345                 350

Lys Val Thr Glu Gly Thr Val Val Leu Ser Lys Asn Ile Leu Lys Ser
        355                 360                 365

Gly Glu Ile Thr Val Ala Leu Asp Asp Ser Asp Thr Thr Gln Ala Thr
    370                 375                 380

Lys Lys Thr Gly Lys Trp Asp Ser Asn Thr Ser Thr Leu Thr Ile Ser
385                 390                 395                 400

Val Asn Ser Lys Lys Thr Lys Asn Ile Val Phe Thr Lys Glu Asp Thr
                405                 410                 415

Ile Thr Val Gln Lys Tyr Asp Ser Ala Gly Thr Asn Leu Glu Gly Asn
            420                 425                 430
```

```
Ala Val Glu Ile Lys Thr Leu Asp Glu Leu Lys Asn Ala Leu Lys
        435                 440                 445


<210> SEQ ID NO 73
<211> LENGTH: 1305
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1305)

<400> SEQUENCE: 73

atg gct tgt aat aat tca gga aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att aca gaa tct aac gca gtt gtt ctg gct gtg aaa gaa att gaa act      144
Ile Thr Glu Ser Asn Ala Val Val Leu Ala Val Lys Glu Ile Glu Thr
        35                  40                  45

ttg ctt gca tct ata gat gaa ctt gct act aaa gct att ggt aaa aaa      192
Leu Leu Ala Ser Ile Asp Glu Leu Ala Thr Lys Ala Ile Gly Lys Lys
    50                  55                  60

ata caa caa aat ggt ggt tta gct gtc gaa gcg ggg cat aat gga aca      240
Ile Gln Gln Asn Gly Gly Leu Ala Val Glu Ala Gly His Asn Gly Thr
 65                  70                  75                  80

ttg tta gca ggt gct tat aca ata tca aaa cta ata aca caa aaa tta      288
Leu Leu Ala Gly Ala Tyr Thr Ile Ser Lys Leu Ile Thr Gln Lys Leu
                85                  90                  95

gat gga ttg aaa aat tca gaa aaa tta aag gaa aaa att gaa aat gct      336
Asp Gly Leu Lys Asn Ser Glu Lys Leu Lys Glu Lys Ile Glu Asn Ala
            100                 105                 110

aag aaa tgt tct gaa gat ttt act aaa aaa cta gaa gga gaa cat gcg      384
Lys Lys Cys Ser Glu Asp Phe Thr Lys Lys Leu Glu Gly Glu His Ala
        115                 120                 125

caa ctt gga att gaa aat gtt act gat gag aat gca aaa aaa gct att      432
Gln Leu Gly Ile Glu Asn Val Thr Asp Glu Asn Ala Lys Lys Ala Ile
    130                 135                 140

tta ata aca gat gca gct aaa gat aag ggc gct gca gag ctt gaa aag      480
Leu Ile Thr Asp Ala Ala Lys Asp Lys Gly Ala Ala Glu Leu Glu Lys
145                 150                 155                 160

cta ttt aaa gca gta gaa aac ttg gca aaa gca gct aaa gag atg ctt      528
Leu Phe Lys Ala Val Glu Asn Leu Ala Lys Ala Ala Lys Glu Met Leu
                165                 170                 175

gct aat tca gtt aaa gag ctt aca agt cct att gtg cat ggc gtt tca      576
Ala Asn Ser Val Lys Glu Leu Thr Ser Pro Ile Val His Gly Val Ser
            180                 185                 190

gta gat ttg cct ggt gaa atg aaa gtt ctt gta agc aaa gaa aaa aac      624
Val Asp Leu Pro Gly Glu Met Lys Val Leu Val Ser Lys Glu Lys Asn
        195                 200                 205

aaa gac ggc aag tac gat cta att gca aca gta gac aag ctt gag ctt      672
Lys Asp Gly Lys Tyr Asp Leu Ile Ala Thr Val Asp Lys Leu Glu Leu
    210                 215                 220

aaa gga act tct gat aaa aac aat gga tct gga gta ctt gaa ggc gta      720
Lys Gly Thr Ser Asp Lys Asn Asn Gly Ser Gly Val Leu Glu Gly Val
225                 230                 235                 240

aaa gct gac aaa agt aaa gta aaa tta aca att tct gac gat cta ggt      768
Lys Ala Asp Lys Ser Lys Val Lys Leu Thr Ile Ser Asp Asp Leu Gly
                245                 250                 255
```

```
caa acc aca ctt gaa gtt ttc aaa gaa gat ggc aaa aca cta gta tca      816
Gln Thr Thr Leu Glu Val Phe Lys Glu Asp Gly Lys Thr Leu Val Ser
            260                 265                 270

aaa aaa gta act tcc aaa gac aag tca tca aca gaa gaa aaa ttc aat      864
Lys Lys Val Thr Ser Lys Asp Lys Ser Ser Thr Glu Glu Lys Phe Asn
        275                 280                 285

gaa aaa ggt gaa gta tct gaa aaa ata ata aca aga gca gac gga acc      912
Glu Lys Gly Glu Val Ser Glu Lys Ile Ile Thr Arg Ala Asp Gly Thr
    290                 295                 300

aga ctt gaa tac aca gga att aaa agc gat gga tct gga aaa gct aaa      960
Arg Leu Glu Tyr Thr Gly Ile Lys Ser Asp Gly Ser Gly Lys Ala Lys
305                 310                 315                 320

gag gtt tta aaa aaa ttt act ctt gaa gga aaa gta gct aat gat aaa     1008
Glu Val Leu Lys Lys Phe Thr Leu Glu Gly Lys Val Ala Asn Asp Lys
                325                 330                 335

gta aca ttg gaa gta aaa gaa gga acc gtt act tta agt aag aac att     1056
Val Thr Leu Glu Val Lys Glu Gly Thr Val Thr Leu Ser Lys Asn Ile
            340                 345                 350

tca aaa tct ggg gaa gtt tca gtt gaa ctt aat gac act gac agt agt     1104
Ser Lys Ser Gly Glu Val Ser Val Glu Leu Asn Asp Thr Asp Ser Ser
        355                 360                 365

gct gct act aaa aaa act gca gct tgg aat tca ggc act tca act tta     1152
Ala Ala Thr Lys Lys Thr Ala Ala Trp Asn Ser Gly Thr Ser Thr Leu
    370                 375                 380

aca att act gta aac agt aaa aaa act aaa gac ctt gtg ttt aca aaa     1200
Thr Ile Thr Val Asn Ser Lys Lys Thr Lys Asp Leu Val Phe Thr Lys
385                 390                 395                 400

gaa aac aca att aca gta caa caa tac gac tca aat ggc acc aaa tta     1248
Glu Asn Thr Ile Thr Val Gln Gln Tyr Asp Ser Asn Gly Thr Lys Leu
                405                 410                 415

gag ggg tca gca gtt gaa att aca aaa ctt gat gaa att aaa aac gct     1296
Glu Gly Ser Ala Val Glu Ile Thr Lys Leu Asp Glu Ile Lys Asn Ala
            420                 425                 430

tta aaa taa                                                         1305
Leu Lys
```

<210> SEQ ID NO 74
<211> LENGTH: 434
<212> TYPE: PRT
<213> ORGANISM: Artificial Sequence
<220> FEATURE:
<223> OTHER INFORMATION: Chimeric protein

<400> SEQUENCE: 74

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Glu Ser Asn Ala Val Val Leu Ala Val Lys Glu Ile Glu Thr
        35                  40                  45

Leu Leu Ala Ser Ile Asp Glu Leu Ala Thr Lys Ala Ile Gly Lys Lys
    50                  55                  60

Ile Gln Gln Asn Gly Gly Leu Ala Val Glu Ala Gly His Asn Gly Thr
65                  70                  75                  80

Leu Leu Ala Gly Ala Tyr Thr Ile Ser Lys Leu Ile Thr Gln Lys Leu
                85                  90                  95

Asp Gly Leu Lys Asn Ser Glu Lys Leu Lys Glu Lys Ile Glu Asn Ala
            100                 105                 110
```

```
Lys Lys Cys Ser Glu Asp Phe Thr Lys Lys Leu Glu Gly Glu His Ala
        115                 120                 125

Gln Leu Gly Ile Glu Asn Val Thr Asp Glu Asn Ala Lys Lys Ala Ile
    130                 135                 140

Leu Ile Thr Asp Ala Ala Lys Asp Lys Gly Ala Ala Glu Leu Glu Lys
145                 150                 155                 160

Leu Phe Lys Ala Val Glu Asn Leu Ala Lys Ala Ala Lys Glu Met Leu
                165                 170                 175

Ala Asn Ser Val Lys Glu Leu Thr Ser Pro Ile Val His Gly Val Ser
            180                 185                 190

Val Asp Leu Pro Gly Glu Met Lys Val Leu Val Ser Lys Glu Lys Asn
        195                 200                 205

Lys Asp Gly Lys Tyr Asp Leu Ile Ala Thr Val Asp Lys Leu Glu Leu
    210                 215                 220

Lys Gly Thr Ser Asp Lys Asn Asn Gly Ser Gly Val Leu Glu Gly Val
225                 230                 235                 240

Lys Ala Asp Lys Ser Lys Val Lys Leu Thr Ile Ser Asp Asp Leu Gly
                245                 250                 255

Gln Thr Thr Leu Glu Val Phe Lys Glu Asp Gly Lys Thr Leu Val Ser
            260                 265                 270

Lys Lys Val Thr Ser Lys Asp Lys Ser Ser Thr Glu Glu Lys Phe Asn
        275                 280                 285

Glu Lys Gly Glu Val Ser Glu Lys Ile Ile Thr Arg Ala Asp Gly Thr
    290                 295                 300

Arg Leu Glu Tyr Thr Gly Ile Lys Ser Asp Gly Ser Gly Lys Ala Lys
305                 310                 315                 320

Glu Val Leu Lys Lys Phe Thr Leu Glu Gly Lys Val Ala Asn Asp Lys
                325                 330                 335

Val Thr Leu Glu Val Lys Glu Gly Thr Val Thr Leu Ser Lys Asn Ile
            340                 345                 350

Ser Lys Ser Gly Glu Val Ser Val Glu Leu Asn Asp Thr Asp Ser Ser
        355                 360                 365

Ala Ala Thr Lys Lys Thr Ala Ala Trp Asn Ser Gly Thr Ser Thr Leu
    370                 375                 380

Thr Ile Thr Val Asn Ser Lys Lys Thr Lys Asp Leu Val Phe Thr Lys
385                 390                 395                 400

Glu Asn Thr Ile Thr Val Gln Gln Tyr Asp Ser Asn Gly Thr Lys Leu
                405                 410                 415

Glu Gly Ser Ala Val Glu Ile Thr Lys Leu Asp Glu Ile Lys Asn Ala
            420                 425                 430

Leu Lys


<210> SEQ ID NO 75
<211> LENGTH: 1332
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1332)

<400> SEQUENCE: 75

atg gct tgt agt aat tca ggg aaa ggt ggg gat tct gca tct act aat       48
Met Ala Cys Ser Asn Ser Gly Lys Gly Gly Asp Ser Ala Ser Thr Asn
 1               5                  10                  15

cct gct gac gag tct gcg aaa ggg cct aat ctt aca gaa ata agc aaa       96
```

-continued

```
Pro Ala Asp Glu Ser Ala Lys Gly Pro Asn Leu Thr Glu Ile Ser Lys
            20                  25                  30

aaa att aca gat tct aat gca ttt gta ctt gct gtt aaa gaa gtt gag      144
Lys Ile Thr Asp Ser Asn Ala Phe Val Leu Ala Val Lys Glu Val Glu
        35                  40                  45

act ttg gtt tta tct ata gat gaa ctt gct aag aaa gct att ggt caa      192
Thr Leu Val Leu Ser Ile Asp Glu Leu Ala Lys Lys Ala Ile Gly Gln
    50                  55                  60

aaa ata gac aat aat aat ggt tta gct gct tta aat aat cag aat gga      240
Lys Ile Asp Asn Asn Asn Gly Leu Ala Ala Leu Asn Asn Gln Asn Gly
65                  70                  75                  80

tcg ttg tta gca gga gcc tat gca ata tca acc cta ata aca gaa aaa      288
Ser Leu Leu Ala Gly Ala Tyr Ala Ile Ser Thr Leu Ile Thr Glu Lys
                85                  90                  95

ttg agt aaa ttg aaa aat tta gaa gaa tta aag aca gaa att gca aag      336
Leu Ser Lys Leu Lys Asn Leu Glu Glu Leu Lys Thr Glu Ile Ala Lys
            100                 105                 110

gct aag aaa tgt tcc gaa gaa ttt act aat aaa cta aaa agt ggt cat      384
Ala Lys Lys Cys Ser Glu Glu Phe Thr Asn Lys Leu Lys Ser Gly His
        115                 120                 125

gca gat ctt ggc aaa cag gat gct acc gat gat cat gca aaa gca gct      432
Ala Asp Leu Gly Lys Gln Asp Ala Thr Asp Asp His Ala Lys Ala Ala
    130                 135                 140

att tta aaa aca cat gca act acc gat aaa ggt gct aaa gaa ttt aaa      480
Ile Leu Lys Thr His Ala Thr Thr Asp Lys Gly Ala Lys Glu Phe Lys
145                 150                 155                 160

gat tta ttt gaa tca gta gaa ggt ttg tta aaa gca gct caa gta gca      528
Asp Leu Phe Glu Ser Val Glu Gly Leu Leu Lys Ala Ala Gln Val Ala
                165                 170                 175

cta act aat tca gtt aaa gaa ctt aca agt cct gtt gta gca gaa agt      576
Leu Thr Asn Ser Val Lys Glu Leu Thr Ser Pro Val Val Ala Glu Ser
            180                 185                 190

cca aaa aaa cct tcc atg gcc gtt tca gta gat ttg cct ggt gaa atg      624
Pro Lys Lys Pro Ser Met Ala Val Ser Val Asp Leu Pro Gly Glu Met
        195                 200                 205

aaa gtt ctt gta agc aaa gaa aaa aac aaa gac ggc aag tac gat cta      672
Lys Val Leu Val Ser Lys Glu Lys Asn Lys Asp Gly Lys Tyr Asp Leu
    210                 215                 220

att gca aca gta gac aag ctt gag ctt aaa gga act tct gat aaa aac      720
Ile Ala Thr Val Asp Lys Leu Glu Leu Lys Gly Thr Ser Asp Lys Asn
225                 230                 235                 240

aat gga tct gga gta ctt gaa ggc gta aaa gct gac aaa agt aaa gta      768
Asn Gly Ser Gly Val Leu Glu Gly Val Lys Ala Asp Lys Ser Lys Val
                245                 250                 255

aaa tta aca att tct gac gat cta ggt caa acc aca ctt gaa gtt ttc      816
Lys Leu Thr Ile Ser Asp Asp Leu Gly Gln Thr Thr Leu Glu Val Phe
            260                 265                 270

aaa gaa gat ggc aaa aca cta gta tca aaa aaa gta act tcc aaa gac      864
Lys Glu Asp Gly Lys Thr Leu Val Ser Lys Lys Val Thr Ser Lys Asp
        275                 280                 285

aag tca tca aca gaa gaa aaa ttc aat gaa aaa ggt gaa gta tct gaa      912
Lys Ser Ser Thr Glu Glu Lys Phe Asn Glu Lys Gly Glu Val Ser Glu
    290                 295                 300

aaa ata ata aca aga gca gac gga acc aga ctt gaa tac aca gga att      960
Lys Ile Ile Thr Arg Ala Asp Gly Thr Arg Leu Glu Tyr Thr Gly Ile
305                 310                 315                 320

aaa agc gat gga tct gga aaa gct aaa gag gtt tta aaa aaa ttt act     1008
Lys Ser Asp Gly Ser Gly Lys Ala Lys Glu Val Leu Lys Lys Phe Thr
                325                 330                 335
```

```
ctt gaa gga aaa gta gct aat gat aaa gta aca ttg gaa gta aaa gaa     1056
Leu Glu Gly Lys Val Ala Asn Asp Lys Val Thr Leu Glu Val Lys Glu
            340                 345                 350

gga acc gtt act tta agt aag aat att tca aaa tct ggg gaa gtt tca     1104
Gly Thr Val Thr Leu Ser Lys Asn Ile Ser Lys Ser Gly Glu Val Ser
        355                 360                 365

gtt gaa ctt aat gac act gac agt agt gct gct act aaa aaa act gca     1152
Val Glu Leu Asn Asp Thr Asp Ser Ser Ala Ala Thr Lys Lys Thr Ala
    370                 375                 380

gct tgg aat tca aaa act tcc act tta aca att agt gtg aat agc caa     1200
Ala Trp Asn Ser Lys Thr Ser Thr Leu Thr Ile Ser Val Asn Ser Gln
385                 390                 395                 400

aaa acc aaa aac ctt gta ttc aca aaa gaa gac aca ata aca gta caa     1248
Lys Thr Lys Asn Leu Val Phe Thr Lys Glu Asp Thr Ile Thr Val Gln
                405                 410                 415

aaa tac gac tca gca ggc acc aat cta gaa ggc aaa gca gtc gaa att     1296
Lys Tyr Asp Ser Ala Gly Thr Asn Leu Glu Gly Lys Ala Val Glu Ile
            420                 425                 430

aca aca ctt aaa gaa ctt aaa aac gct tta aaa taa                     1332
Thr Thr Leu Lys Glu Leu Lys Asn Ala Leu Lys
        435                 440


<210> SEQ ID NO 76
<211> LENGTH: 443
<212> TYPE: PRT
<213> ORGANISM: Artificial Sequence
<220> FEATURE:
<223> OTHER INFORMATION: Chimeric protein

<400> SEQUENCE: 76

Met Ala Cys Ser Asn Ser Gly Lys Gly Gly Asp Ser Ala Ser Thr Asn
 1               5                  10                  15

Pro Ala Asp Glu Ser Ala Lys Gly Pro Asn Leu Thr Glu Ile Ser Lys
            20                  25                  30

Lys Ile Thr Asp Ser Asn Ala Phe Val Leu Ala Val Lys Glu Val Glu
        35                  40                  45

Thr Leu Val Leu Ser Ile Asp Glu Leu Ala Lys Lys Ala Ile Gly Gln
    50                  55                  60

Lys Ile Asp Asn Asn Asn Gly Leu Ala Ala Leu Asn Asn Gln Asn Gly
65                  70                  75                  80

Ser Leu Leu Ala Gly Ala Tyr Ala Ile Ser Thr Leu Ile Thr Glu Lys
                85                  90                  95

Leu Ser Lys Leu Lys Asn Leu Glu Glu Leu Lys Thr Glu Ile Ala Lys
            100                 105                 110

Ala Lys Lys Cys Ser Glu Glu Phe Thr Asn Lys Leu Lys Ser Gly His
        115                 120                 125

Ala Asp Leu Gly Lys Gln Asp Ala Thr Asp Asp His Ala Lys Ala Ala
    130                 135                 140

Ile Leu Lys Thr His Ala Thr Thr Asp Lys Gly Ala Lys Glu Phe Lys
145                 150                 155                 160

Asp Leu Phe Glu Ser Val Glu Gly Leu Leu Lys Ala Ala Gln Val Ala
                165                 170                 175

Leu Thr Asn Ser Val Lys Glu Leu Thr Ser Pro Val Val Ala Glu Ser
            180                 185                 190

Pro Lys Lys Pro Ser Met Ala Val Ser Val Asp Leu Pro Gly Glu Met
        195                 200                 205

Lys Val Leu Val Ser Lys Glu Lys Asn Lys Asp Gly Lys Tyr Asp Leu
    210                 215                 220
```

```
Ile Ala Thr Val Asp Lys Leu Glu Leu Lys Gly Thr Ser Asp Lys Asn
225                 230                 235                 240

Asn Gly Ser Gly Val Leu Glu Gly Val Lys Ala Asp Lys Ser Lys Val
                245                 250                 255

Lys Leu Thr Ile Ser Asp Asp Leu Gly Gln Thr Thr Leu Glu Val Phe
            260                 265                 270

Lys Glu Asp Gly Lys Thr Leu Val Ser Lys Lys Val Thr Ser Lys Asp
        275                 280                 285

Lys Ser Ser Thr Glu Glu Lys Phe Asn Glu Lys Gly Glu Val Ser Glu
    290                 295                 300

Lys Ile Ile Thr Arg Ala Asp Gly Thr Arg Leu Glu Tyr Thr Gly Ile
305                 310                 315                 320

Lys Ser Asp Gly Ser Gly Lys Ala Lys Glu Val Leu Lys Lys Phe Thr
                325                 330                 335

Leu Glu Gly Lys Val Ala Asn Asp Lys Val Thr Leu Glu Val Lys Glu
            340                 345                 350

Gly Thr Val Thr Leu Ser Lys Asn Ile Ser Lys Ser Gly Glu Val Ser
        355                 360                 365

Val Glu Leu Asn Asp Thr Asp Ser Ser Ala Ala Thr Lys Lys Thr Ala
    370                 375                 380

Ala Trp Asn Ser Lys Thr Ser Thr Leu Thr Ile Ser Val Asn Ser Gln
385                 390                 395                 400

Lys Thr Lys Asn Leu Val Phe Thr Lys Glu Asp Thr Ile Thr Val Gln
                405                 410                 415

Lys Tyr Asp Ser Ala Gly Thr Asn Leu Glu Gly Lys Ala Val Glu Ile
            420                 425                 430

Thr Thr Leu Lys Glu Leu Lys Asn Ala Leu Lys
        435                 440


<210> SEQ ID NO 77
<211> LENGTH: 1317
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1317)

<400> SEQUENCE: 77

atg gct tgt aat aat tca ggt ggg gat tct gca tct act aat cct gat       48
Met Ala Cys Asn Asn Ser Gly Gly Asp Ser Ala Ser Thr Asn Pro Asp
 1               5                  10                  15

gag tct gca aaa gga cct aat ctt acc gta ata agc aaa aaa att aca       96
Glu Ser Ala Lys Gly Pro Asn Leu Thr Val Ile Ser Lys Lys Ile Thr
             20                  25                  30

gat tct aat gca ttt tta ctg gct gtg aaa gaa gtt gag gct ttg ctt      144
Asp Ser Asn Ala Phe Leu Leu Ala Val Lys Glu Val Glu Ala Leu Leu
         35                  40                  45

tca tct ata gat gaa ctt tct aaa gct att ggt aaa aaa ata aaa aat      192
Ser Ser Ile Asp Glu Leu Ser Lys Ala Ile Gly Lys Lys Ile Lys Asn
     50                  55                  60

gat ggt act tta gat aac gaa gca aat cga aac gaa tca ttg ata gca      240
Asp Gly Thr Leu Asp Asn Glu Ala Asn Arg Asn Glu Ser Leu Ile Ala
 65                  70                  75                  80

gga gct tat gaa ata tca aaa cta ata aca caa aaa tta agt gta ttg      288
Gly Ala Tyr Glu Ile Ser Lys Leu Ile Thr Gln Lys Leu Ser Val Leu
                 85                  90                  95
```

-continued

```
aat tca gaa gaa tta aag gaa aaa att aaa gag gct aag gat tgt tcc      336
Asn Ser Glu Glu Leu Lys Glu Lys Ile Lys Glu Ala Lys Asp Cys Ser
            100                 105                 110

gaa aaa ttt act act aag cta aaa gat agt cat gca gag ctt ggt ata      384
Glu Lys Phe Thr Thr Lys Leu Lys Asp Ser His Ala Glu Leu Gly Ile
        115                 120                 125

caa agc gtt cag gat gat aat gca aaa aaa gct att tta aaa aca cat      432
Gln Ser Val Gln Asp Asp Asn Ala Lys Lys Ala Ile Leu Lys Thr His
    130                 135                 140

gga act aaa gac aag ggt gct aaa gaa ctt gaa gag tta ttt aaa tca      480
Gly Thr Lys Asp Lys Gly Ala Lys Glu Leu Glu Glu Leu Phe Lys Ser
145                 150                 155                 160

cta gaa agc ttg tca aaa gca gcg caa gca gca tta act aat tca gtt      528
Leu Glu Ser Leu Ser Lys Ala Ala Gln Ala Ala Leu Thr Asn Ser Val
                165                 170                 175

aaa gag ctt aca aat cct gtt gtg gca gaa agt cca aaa aaa cct tcc      576
Lys Glu Leu Thr Asn Pro Val Val Ala Glu Ser Pro Lys Lys Pro Ser
            180                 185                 190

atg gcc gtt tca gta gat ttg cct ggt gaa atg aaa gtt ctt gta agc      624
Met Ala Val Ser Val Asp Leu Pro Gly Glu Met Lys Val Leu Val Ser
        195                 200                 205

aaa gaa aaa aac aaa gac ggc aag tac gat cta att gca aca gta gac      672
Lys Glu Lys Asn Lys Asp Gly Lys Tyr Asp Leu Ile Ala Thr Val Asp
    210                 215                 220

aag ctt gag ctt aaa gga act tct gat aaa aac aat gga tct gga gta      720
Lys Leu Glu Leu Lys Gly Thr Ser Asp Lys Asn Asn Gly Ser Gly Val
225                 230                 235                 240

ctt gaa ggc gta aaa gct gac aaa agt aaa gta aaa tta aca att tct      768
Leu Glu Gly Val Lys Ala Asp Lys Ser Lys Val Lys Leu Thr Ile Ser
                245                 250                 255

gac gat cta ggt caa acc aca ctt gaa gtt ttc aaa gaa gat ggc aaa      816
Asp Asp Leu Gly Gln Thr Thr Leu Glu Val Phe Lys Glu Asp Gly Lys
            260                 265                 270

aca cta gta tca aaa aaa gta act tcc aaa gac aag tca tca aca gaa      864
Thr Leu Val Ser Lys Lys Val Thr Ser Lys Asp Lys Ser Ser Thr Glu
        275                 280                 285

gaa aaa ttc aat gaa aaa ggt gaa gta tct gaa aaa ata ata aca aga      912
Glu Lys Phe Asn Glu Lys Gly Glu Val Ser Glu Lys Ile Ile Thr Arg
    290                 295                 300

gca gac gga acc aga ctt gaa tac aca gga att aaa agc gat gga tct      960
Ala Asp Gly Thr Arg Leu Glu Tyr Thr Gly Ile Lys Ser Asp Gly Ser
305                 310                 315                 320

gga aaa gct aaa gag gtt tta aaa aaa ttt act ctt gaa gga aaa gta     1008
Gly Lys Ala Lys Glu Val Leu Lys Lys Phe Thr Leu Glu Gly Lys Val
                325                 330                 335

gct aat gat aaa gta aca ttg gaa gta aaa gaa gga acc gtt act tta     1056
Ala Asn Asp Lys Val Thr Leu Glu Val Lys Glu Gly Thr Val Thr Leu
            340                 345                 350

agt aag aac att tca aaa tct ggg gaa gtt tca gtt gaa ctt aat gac     1104
Ser Lys Asn Ile Ser Lys Ser Gly Glu Val Ser Val Glu Leu Asn Asp
        355                 360                 365

act gac agt agt gct gct act aaa aaa act gca gct tgg aat tca aaa     1152
Thr Asp Ser Ser Ala Ala Thr Lys Lys Thr Ala Ala Trp Asn Ser Lys
    370                 375                 380

act tct act tta aca att agt gtt aac agc aaa aaa act aca caa ctt     1200
Thr Ser Thr Leu Thr Ile Ser Val Asn Ser Lys Lys Thr Thr Gln Leu
385                 390                 395                 400

gtg ttt act aaa caa gac aca ata act gta caa aaa tac gac tcc gca     1248
Val Phe Thr Lys Gln Asp Thr Ile Thr Val Gln Lys Tyr Asp Ser Ala
                405                 410                 415
```

```
ggt acc aat tta gaa ggc aca gca gtc gaa att aaa aca ctt gat gaa      1296
Gly Thr Asn Leu Glu Gly Thr Ala Val Glu Ile Lys Thr Leu Asp Glu
            420                 425                 430

ctt aaa aac gct tta aaa taa                                          1317
Leu Lys Asn Ala Leu Lys
        435


<210> SEQ ID NO 78
<211> LENGTH: 438
<212> TYPE: PRT
<213> ORGANISM: Artificial Sequence
<220> FEATURE:
<223> OTHER INFORMATION: Chimeric protein

<400> SEQUENCE: 78

Met Ala Cys Asn Asn Ser Gly Gly Asp Ser Ala Ser Thr Asn Pro Asp
 1               5                  10                  15

Glu Ser Ala Lys Gly Pro Asn Leu Thr Val Ile Ser Lys Lys Ile Thr
            20                  25                  30

Asp Ser Asn Ala Phe Leu Leu Ala Val Lys Glu Val Glu Ala Leu Leu
        35                  40                  45

Ser Ser Ile Asp Glu Leu Ser Lys Ala Ile Gly Lys Lys Ile Lys Asn
    50                  55                  60

Asp Gly Thr Leu Asp Asn Glu Ala Asn Arg Asn Glu Ser Leu Ile Ala
65                  70                  75                  80

Gly Ala Tyr Glu Ile Ser Lys Leu Ile Thr Gln Lys Leu Ser Val Leu
                85                  90                  95

Asn Ser Glu Glu Leu Lys Glu Lys Ile Lys Glu Ala Lys Asp Cys Ser
            100                 105                 110

Glu Lys Phe Thr Thr Lys Leu Lys Asp Ser His Ala Glu Leu Gly Ile
        115                 120                 125

Gln Ser Val Gln Asp Asp Asn Ala Lys Lys Ala Ile Leu Lys Thr His
    130                 135                 140

Gly Thr Lys Asp Lys Gly Ala Lys Glu Leu Glu Glu Leu Phe Lys Ser
145                 150                 155                 160

Leu Glu Ser Leu Ser Lys Ala Ala Gln Ala Ala Leu Thr Asn Ser Val
                165                 170                 175

Lys Glu Leu Thr Asn Pro Val Val Ala Glu Ser Pro Lys Lys Pro Ser
            180                 185                 190

Met Ala Val Ser Val Asp Leu Pro Gly Glu Met Lys Val Leu Val Ser
        195                 200                 205

Lys Glu Lys Asn Lys Asp Gly Lys Tyr Asp Leu Ile Ala Thr Val Asp
    210                 215                 220

Lys Leu Glu Leu Lys Gly Thr Ser Asp Lys Asn Asn Gly Ser Gly Val
225                 230                 235                 240

Leu Glu Gly Val Lys Ala Asp Lys Ser Lys Val Lys Leu Thr Ile Ser
                245                 250                 255

Asp Asp Leu Gly Gln Thr Thr Leu Glu Val Phe Lys Glu Asp Gly Lys
            260                 265                 270

Thr Leu Val Ser Lys Lys Val Thr Ser Lys Asp Lys Ser Ser Thr Glu
        275                 280                 285

Glu Lys Phe Asn Glu Lys Gly Glu Val Ser Glu Lys Ile Ile Thr Arg
    290                 295                 300

Ala Asp Gly Thr Arg Leu Glu Tyr Thr Gly Ile Lys Ser Asp Gly Ser
305                 310                 315                 320
```

```
Gly Lys Ala Lys Glu Val Leu Lys Lys Phe Thr Leu Glu Gly Lys Val
                325                 330                 335

Ala Asn Asp Lys Val Thr Leu Glu Val Lys Glu Gly Thr Val Thr Leu
            340                 345                 350

Ser Lys Asn Ile Ser Lys Ser Gly Glu Val Ser Val Glu Leu Asn Asp
        355                 360                 365

Thr Asp Ser Ser Ala Ala Thr Lys Lys Thr Ala Ala Trp Asn Ser Lys
    370                 375                 380

Thr Ser Thr Leu Thr Ile Ser Val Asn Ser Lys Lys Thr Thr Gln Leu
385                 390                 395                 400

Val Phe Thr Lys Gln Asp Thr Ile Thr Val Gln Lys Tyr Asp Ser Ala
                405                 410                 415

Gly Thr Asn Leu Glu Gly Thr Ala Val Glu Ile Lys Thr Leu Asp Glu
            420                 425                 430

Leu Lys Asn Ala Leu Lys
        435


<210> SEQ ID NO 79
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 79

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
    50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175
```

```
aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt tct gaa aaa ata ata aca aga      624
Lys Pro Ser Met Ala Lys Gln Asn Val Ser Glu Lys Ile Ile Thr Arg
        195                 200                 205

gca gac gga acc aga ctt gaa tac aca gga att aaa agc gat gga tct      672
Ala Asp Gly Thr Arg Leu Glu Tyr Thr Gly Ile Lys Ser Asp Gly Ser
    210                 215                 220

gga aaa gct aaa gag gtt tta aaa ggc tat gtt ctt gaa gga act cta      720
Gly Lys Ala Lys Glu Val Leu Lys Gly Tyr Val Leu Glu Gly Thr Leu
225                 230                 235                 240

act gct gaa aaa aca aca ttg gtg gtt aaa gaa gga act gtt act tta      768
Thr Ala Glu Lys Thr Thr Leu Val Val Lys Glu Gly Thr Val Thr Leu
                245                 250                 255

agc aaa aat att tca aaa tct ggg gaa gtt tca gtt gaa ctt aat gac      816
Ser Lys Asn Ile Ser Lys Ser Gly Glu Val Ser Val Glu Leu Asn Asp
            260                 265                 270

act gac agt agt gct gct act aaa aaa act gca gct tgg aat tca ggc      864
Thr Asp Ser Ser Ala Ala Thr Lys Lys Thr Ala Ala Trp Asn Ser Gly
        275                 280                 285

act tca act tta aca att act gta aac agt aaa aaa act aaa gac ctt      912
Thr Ser Thr Leu Thr Ile Thr Val Asn Ser Lys Lys Thr Lys Asp Leu
    290                 295                 300

gtg ttt aca aaa gaa aac aca att aca gta caa caa tac gac tca aat      960
Val Phe Thr Lys Glu Asn Thr Ile Thr Val Gln Gln Tyr Asp Ser Asn
305                 310                 315                 320

ggc acc aaa tta gag ggg tca gca gtt gaa att aca aaa ctt gat gaa     1008
Gly Thr Lys Leu Glu Gly Ser Ala Val Glu Ile Thr Lys Leu Asp Glu
                325                 330                 335

att aaa aac gct tta aaa taa                                         1029
Ile Lys Asn Ala Leu Lys
            340


<210> SEQ ID NO 80
<211> LENGTH: 342
<212> TYPE: PRT
<213> ORGANISM: Artificial Sequence
<220> FEATURE:
<223> OTHER INFORMATION: Chimeric protein

<400> SEQUENCE: 80

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125
```

```
Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
    210                 215                 220

Gly Lys Ala Lys Glu Val Leu Lys Gly Tyr Val Leu Glu Gly Thr Leu
225                 230                 235                 240

Thr Ala Glu Lys Thr Thr Leu Val Val Lys Glu Gly Thr Val Thr Leu
                245                 250                 255

Ser Lys Asn Ile Ser Lys Ser Gly Glu Val Ser Val Glu Leu Asn Asp
            260                 265                 270

Thr Asp Ser Ser Ala Ala Thr Lys Lys Thr Ala Ala Trp Asn Ser Gly
        275                 280                 285

Thr Ser Thr Leu Thr Ile Thr Val Asn Ser Lys Lys Thr Lys Asp Leu
    290                 295                 300

Val Phe Thr Lys Glu Asn Thr Ile Thr Val Gln Gln Tyr Asp Ser Asn
305                 310                 315                 320

Gly Thr Lys Leu Glu Gly Ser Ala Val Glu Ile Thr Lys Leu Asp Glu
                325                 330                 335

Ile Lys Asn Ala Leu Lys
            340


<210> SEQ ID NO 81
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 81

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95

gat gga ttg aaa aat gaa gga tta aag gaa aaa att gat gcg gct aag      336
```

-continued

```
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt tct gaa aaa ata ata aca aga      624
Lys Pro Ser Met Ala Lys Gln Asn Val Ser Glu Lys Ile Ile Thr Arg
        195                 200                 205

gca gac gga acc aga ctt gaa tac aca gga att aaa agc gat gga tct      672
Ala Asp Gly Thr Arg Leu Glu Tyr Thr Gly Ile Lys Ser Asp Gly Ser
    210                 215                 220

gga aaa gct aaa gag gtt tta aaa ggc tat gtt ctt gaa gga act cta      720
Gly Lys Ala Lys Glu Val Leu Lys Gly Tyr Val Leu Glu Gly Thr Leu
225                 230                 235                 240

act gct gaa aaa aca aca ttg gtg gtt aaa gaa gga act gtt act tta      768
Thr Ala Glu Lys Thr Thr Leu Val Val Lys Glu Gly Thr Val Thr Leu
                245                 250                 255

agc aaa aat att tca aaa tct ggg gaa gtt tca gtt gaa ctt aat gac      816
Ser Lys Asn Ile Ser Lys Ser Gly Glu Val Ser Val Glu Leu Asn Asp
            260                 265                 270

act gac agt agt gct gct act aaa aaa act gca gct tgg aat tca aaa      864
Thr Asp Ser Ser Ala Ala Thr Lys Lys Thr Ala Ala Trp Asn Ser Lys
        275                 280                 285

act tcc act tta aca att agt gtg aat agc caa aaa acc aaa aac ctt      912
Thr Ser Thr Leu Thr Ile Ser Val Asn Ser Gln Lys Thr Lys Asn Leu
    290                 295                 300

gta ttc aca aaa gaa gac aca ata aca gta caa aaa tac gac tca gca      960
Val Phe Thr Lys Glu Asp Thr Ile Thr Val Gln Lys Tyr Asp Ser Ala
305                 310                 315                 320

ggc acc aat cta gaa ggc aaa gca gtc gaa att aca aca ctt aaa gaa     1008
Gly Thr Asn Leu Glu Gly Lys Ala Val Glu Ile Thr Thr Leu Lys Glu
                325                 330                 335

ctt aaa aac gct tta aaa taa                                         1029
Leu Lys Asn Ala Leu Lys
            340
```

<210> SEQ ID NO 82
<211> LENGTH: 342
<212> TYPE: PRT
<213> ORGANISM: Artificial Sequence
<220> FEATURE:
<223> OTHER INFORMATION: Chimeric protein

<400> SEQUENCE: 82

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30
```

-continued

```
Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Ser Glu Lys Ile Ile Thr Arg
        195                 200                 205

Ala Asp Gly Thr Arg Leu Glu Tyr Thr Gly Ile Lys Ser Asp Gly Ser
    210                 215                 220

Gly Lys Ala Lys Glu Val Leu Lys Gly Tyr Val Leu Glu Gly Thr Leu
225                 230                 235                 240

Thr Ala Glu Lys Thr Thr Leu Val Val Lys Glu Gly Thr Val Thr Leu
                245                 250                 255

Ser Lys Asn Ile Ser Lys Ser Gly Glu Val Ser Val Glu Leu Asn Asp
            260                 265                 270

Thr Asp Ser Ser Ala Ala Thr Lys Lys Thr Ala Ala Trp Asn Ser Lys
        275                 280                 285

Thr Ser Thr Leu Thr Ile Ser Val Asn Ser Gln Lys Thr Lys Asn Leu
    290                 295                 300

Val Phe Thr Lys Glu Asp Thr Ile Thr Val Gln Lys Tyr Asp Ser Ala
305                 310                 315                 320

Gly Thr Asn Leu Glu Gly Lys Ala Val Glu Ile Thr Thr Leu Lys Glu
                325                 330                 335

Leu Lys Asn Ala Leu Lys
            340


<210> SEQ ID NO 83
<211> LENGTH: 1029
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1029)

<400> SEQUENCE: 83

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
             20                  25                  30
```

-continued

```
att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
    50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt tct gaa aaa ata ata aca aga      624
Lys Pro Ser Met Ala Lys Gln Asn Val Ser Glu Lys Ile Ile Thr Arg
        195                 200                 205

gca gac gga acc aga ctt gaa tac aca gga att aaa agc gat gga tct      672
Ala Asp Gly Thr Arg Leu Glu Tyr Thr Gly Ile Lys Ser Asp Gly Ser
    210                 215                 220

gga aaa gct aaa gag gtt tta aaa ggc tat gtt ctt gaa gga act cta      720
Gly Lys Ala Lys Glu Val Leu Lys Gly Tyr Val Leu Glu Gly Thr Leu
225                 230                 235                 240

act gct gaa aaa aca aca ttg gtg gtt aaa gaa gga act gtt act tta      768
Thr Ala Glu Lys Thr Thr Leu Val Val Lys Glu Gly Thr Val Thr Leu
                245                 250                 255

agc aaa aat att tca aaa tct ggg gaa gtt tca gtt gaa ctt aat gac      816
Ser Lys Asn Ile Ser Lys Ser Gly Glu Val Ser Val Glu Leu Asn Asp
            260                 265                 270

act gac agt agt gct gct act aaa aaa act gca gct tgg aat tca aaa      864
Thr Asp Ser Ser Ala Ala Thr Lys Lys Thr Ala Ala Trp Asn Ser Lys
        275                 280                 285

act tct act tta aca att agt gtt aac agc aaa aaa act aca caa ctt      912
Thr Ser Thr Leu Thr Ile Ser Val Asn Ser Lys Lys Thr Thr Gln Leu
    290                 295                 300

gtg ttt act aaa caa gac aca ata act gta caa aaa tac gac tcc gca      960
Val Phe Thr Lys Gln Asp Thr Ile Thr Val Gln Lys Tyr Asp Ser Ala
305                 310                 315                 320

ggt acc aat tta gaa ggc aca gca gtc gaa att aaa aca ctt gat gaa     1008
Gly Thr Asn Leu Glu Gly Thr Ala Val Glu Ile Lys Thr Leu Asp Glu
                325                 330                 335

ctt aaa aac gct tta aaa taa                                         1029
Leu Lys Asn Ala Leu Lys
```

340

<210> SEQ ID NO 84
<211> LENGTH: 342
<212> TYPE: PRT
<213> ORGANISM: Artificial Sequence
<220> FEATURE:
<223> OTHER INFORMATION: Chimeric protein

<400> SEQUENCE: 84

Met Ala Cys Asn Asn Ser Gly Lys Asp Gly Asn Thr Ser Ala Asn Ser
1 5 10 15

Ala Asp Glu Ser Val Lys Gly Pro Asn Leu Thr Glu Ile Asn Lys Lys
20 25 30

Ile Thr Asp Ser Asn Ala Val Leu Leu Ala Val Lys Glu Val Glu Ala
35 40 45

Leu Leu Ser Ser Ile Asp Glu Ile Ala Ala Lys Ala Ile Gly Lys Lys
50 55 60

Ile His Gln Asn Asn Gly Leu Asp Thr Glu Asn Asn His Asn Gly Ser
65 70 75 80

Leu Leu Ala Gly Ala Tyr Ala Ile Ser Thr Leu Ile Lys Gln Lys Leu
85 90 95

Asp Gly Leu Lys Asn Glu Gly Leu Lys Glu Lys Ile Asp Ala Ala Lys
100 105 110

Lys Cys Ser Glu Thr Phe Thr Asn Lys Leu Lys Glu Lys His Thr Asp
115 120 125

Leu Gly Lys Glu Gly Val Thr Asp Ala Asp Ala Lys Glu Ala Ile Leu
130 135 140

Lys Ala Asn Gly Thr Lys Thr Lys Gly Ala Glu Glu Leu Gly Lys Leu
145 150 155 160

Phe Glu Ser Val Glu Val Leu Ser Lys Ala Ala Lys Glu Met Leu Ala
165 170 175

Asn Ser Val Lys Glu Leu Thr Ser Pro Val Val Ala Glu Ser Pro Lys
180 185 190

Lys Pro Ser Met Ala Lys Gln Asn Val Ser Glu Lys Ile Ile Thr Arg
195 200 205

Ala Asp Gly Thr Arg Leu Glu Tyr Thr Gly Ile Lys Ser Asp Gly Ser
210 215 220

Gly Lys Ala Lys Glu Val Leu Lys Gly Tyr Val Leu Glu Gly Thr Leu
225 230 235 240

Thr Ala Glu Lys Thr Thr Leu Val Val Lys Glu Gly Thr Val Thr Leu
245 250 255

Ser Lys Asn Ile Ser Lys Ser Gly Glu Val Ser Val Glu Leu Asn Asp
260 265 270

Thr Asp Ser Ser Ala Ala Thr Lys Lys Thr Ala Ala Trp Asn Ser Lys
275 280 285

Thr Ser Thr Leu Thr Ile Ser Val Asn Ser Lys Lys Thr Thr Gln Leu
290 295 300

Val Phe Thr Lys Gln Asp Thr Ile Thr Val Gln Lys Tyr Asp Ser Ala
305 310 315 320

Gly Thr Asn Leu Glu Gly Thr Ala Val Glu Ile Lys Thr Leu Asp Glu
325 330 335

Leu Lys Asn Ala Leu Lys
340

```
<210> SEQ ID NO 85
<211> LENGTH: 1035
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1035)

<400> SEQUENCE: 85

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
    50                  55                  60

ata cac caa aat aat ggt ttg gat acc gaa tat aat cac aat gga tca      240
Ile His Gln Asn Asn Gly Leu Asp Thr Glu Tyr Asn His Asn Gly Ser
65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa aca aat ggt act aaa act aaa ggt gct gaa gaa ctt gga aaa tta      480
Lys Thr Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc aag caa aat gtt aca tct gaa aaa aca ata gta      624
Lys Pro Ser Met Ala Lys Gln Asn Val Thr Ser Glu Lys Thr Ile Val
        195                 200                 205

aga gca aat gga acc aga ctt gaa tac aca gac ata aaa agc gat gga      672
Arg Ala Asn Gly Thr Arg Leu Glu Tyr Thr Asp Ile Lys Ser Asp Gly
    210                 215                 220

tcc gga aaa gct aaa gaa gtt tta aaa gac ttt act ctt gaa gga act      720
Ser Gly Lys Ala Lys Glu Val Leu Lys Asp Phe Thr Leu Glu Gly Thr
225                 230                 235                 240

cta gct gct gac ggc aaa aca aca ttg aaa gtt aca gaa ggc act gtt      768
Leu Ala Ala Asp Gly Lys Thr Thr Leu Lys Val Thr Glu Gly Thr Val
                245                 250                 255

gtt tta agc aag aac att tta aaa tcc gga gaa ata aca gtt gca ctt      816
Val Leu Ser Lys Asn Ile Leu Lys Ser Gly Glu Ile Thr Val Ala Leu
            260                 265                 270
```

-continued

```
gat gac tct gac act act cag gct act aaa aaa act gga aaa tgg gat      864
Asp Asp Ser Asp Thr Thr Gln Ala Thr Lys Lys Thr Gly Lys Trp Asp
        275                 280                 285

tca aat act tcc act tta aca att agt gtg aat agc aaa aaa act aaa      912
Ser Asn Thr Ser Thr Leu Thr Ile Ser Val Asn Ser Lys Lys Thr Lys
    290                 295                 300

aac att gta ttt aca aaa gaa gac aca ata aca gta caa aaa tac gac      960
Asn Ile Val Phe Thr Lys Glu Asp Thr Ile Thr Val Gln Lys Tyr Asp
305                 310                 315                 320

tca gca ggc acc aat cta gaa ggc aac gca gtc gaa att aaa aca ctt     1008
Ser Ala Gly Thr Asn Leu Glu Gly Asn Ala Val Glu Ile Lys Thr Leu
                325                 330                 335

gat gaa ctt aaa aac gct tta aaa tag                                 1035
Asp Glu Leu Lys Asn Ala Leu Lys
            340


<210> SEQ ID NO 86
<211> LENGTH: 344
<212> TYPE: PRT
<213> ORGANISM: Artificial Sequence
<220> FEATURE:
<223> OTHER INFORMATION: Chimeric protein

<400> SEQUENCE: 86

Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Lys Gln Asn Val Thr Ser Glu Lys Thr Ile Val
        195                 200                 205

Arg Ala Asn Gly Thr Arg Leu Glu Tyr Thr Asp Ile Lys Ser Asp Gly
   210                 215                 220

Ser Gly Lys Ala Lys Glu Val Leu Lys Asp Phe Thr Leu Glu Gly Thr
225                 230                 235                 240

Leu Ala Ala Asp Gly Lys Thr Thr Leu Lys Val Thr Glu Gly Thr Val
                245                 250                 255

Val Leu Ser Lys Asn Ile Leu Lys Ser Gly Glu Ile Thr Val Ala Leu
```

```
            260                 265                 270

Asp Asp Ser Asp Thr Thr Gln Ala Thr Lys Lys Thr Gly Lys Trp Asp
        275                 280                 285

Ser Asn Thr Ser Thr Leu Thr Ile Ser Val Asn Ser Lys Lys Thr Lys
    290                 295                 300

Asn Ile Val Phe Thr Lys Glu Asp Thr Ile Thr Val Gln Lys Tyr Asp
305                 310                 315                 320

Ser Ala Gly Thr Asn Leu Glu Gly Asn Ala Val Glu Ile Lys Thr Leu
                325                 330                 335

Asp Glu Leu Lys Asn Ala Leu Lys
            340


<210> SEQ ID NO 87
<211> LENGTH: 1323
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1323)

<400> SEQUENCE: 87

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata aat aaa aaa       96
Ala Asp Glu Ser Val Lys Gly Pro Asn Leu Thr Glu Ile Asn Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60

ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80

ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                85                  90                  95

gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110

aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125

ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140

aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160

ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175

aat tca gtt aaa gag ctt aca agc cct gtt gtg gca gaa agt cca aaa      576
Asn Ser Val Lys Glu Leu Thr Ser Pro Val Val Ala Glu Ser Pro Lys
            180                 185                 190

aaa cct tcc atg gcc gtt tca gta gat ttg cct ggt gaa atg aaa gtt      624
Lys Pro Ser Met Ala Val Ser Val Asp Leu Pro Gly Glu Met Lys Val
```

```
        195                 200                 205

ctt gta agc aaa gaa aaa aac aaa gac ggc aag tac gat cta att gca      672
Leu Val Ser Lys Glu Lys Asn Lys Asp Gly Lys Tyr Asp Leu Ile Ala
    210                 215                 220

aca gta gac aag ctt gag ctt aaa gga act tct gat aaa aac aat gga      720
Thr Val Asp Lys Leu Glu Leu Lys Gly Thr Ser Asp Lys Asn Asn Gly
225                 230                 235                 240

tct gga gta ctt gaa ggc gta aaa gct gac aaa agt aaa gta aaa tta      768
Ser Gly Val Leu Glu Gly Val Lys Ala Asp Lys Ser Lys Val Lys Leu
                245                 250                 255

aca att tct gac gat cta ggt caa acc aca ctt gaa gtt ttc aaa gaa      816
Thr Ile Ser Asp Asp Leu Gly Gln Thr Thr Leu Glu Val Phe Lys Glu
            260                 265                 270

gat ggc aaa aca cta gta tca aaa aaa gta act tcc aaa gac aag tca      864
Asp Gly Lys Thr Leu Val Ser Lys Lys Val Thr Ser Lys Asp Lys Ser
        275                 280                 285

tca aca gaa gaa aaa ttc aat gaa aaa ggt gaa gta tct gaa aaa ata      912
Ser Thr Glu Glu Lys Phe Asn Glu Lys Gly Glu Val Ser Glu Lys Ile
    290                 295                 300

ata aca aga gca gac gga acc aga ctt gaa tac aca gga att aaa agc      960
Ile Thr Arg Ala Asp Gly Thr Arg Leu Glu Tyr Thr Gly Ile Lys Ser
305                 310                 315                 320

gat gga tct gga aaa gct aaa gag gtt tta aaa ggc ttt act ctt gaa     1008
Asp Gly Ser Gly Lys Ala Lys Glu Val Leu Lys Gly Phe Thr Leu Glu
                325                 330                 335

gga aaa gta gct aat gat aaa gta aca ttg gaa gta aaa gaa gga acc     1056
Gly Lys Val Ala Asn Asp Lys Val Thr Leu Glu Val Lys Glu Gly Thr
            340                 345                 350

gtt act tta agt aag att tca aaa tct ggg gaa gtt tca gtt gaa ctt     1104
Val Thr Leu Ser Lys Ile Ser Lys Ser Gly Glu Val Ser Val Glu Leu
        355                 360                 365

aat gac act gac agt agt gct gct act aaa aaa act gca gct tgg aat     1152
Asn Asp Thr Asp Ser Ser Ala Ala Thr Lys Lys Thr Ala Ala Trp Asn
    370                 375                 380

tca aaa act tct act tta aca att agt gtt aac agc aaa aaa act aca     1200
Ser Lys Thr Ser Thr Leu Thr Ile Ser Val Asn Ser Lys Lys Thr Thr
385                 390                 395                 400

caa ctt gtg ttt act aaa caa gac aca ata act gta caa aaa tac gac     1248
Gln Leu Val Phe Thr Lys Gln Asp Thr Ile Thr Val Gln Lys Tyr Asp
                405                 410                 415

tcc gca ggt acc aat tta gaa ggc aca gca gtc gaa att aaa aca ctt     1296
Ser Ala Gly Thr Asn Leu Glu Gly Thr Ala Val Glu Ile Lys Thr Leu
            420                 425                 430

gat gaa ctt aaa aac gct tta aaa taa                                 1323
Asp Glu Leu Lys Asn Ala Leu Lys
        435                 440
```

<210> SEQ ID NO 88
<211> LENGTH: 440
<212> TYPE: PRT
<213> ORGANISM: Artificial Sequence
<220> FEATURE:
<223> OTHER INFORMATION: Chimeric protein

<400> SEQUENCE: 88

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
```

```
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Ala Val Ser Val Asp Leu Pro Gly Glu Met Lys Val
        195                 200                 205

Leu Val Ser Lys Glu Lys Asn Lys Asp Gly Lys Tyr Asp Leu Ile Ala
    210                 215                 220

Thr Val Asp Lys Leu Glu Leu Lys Gly Thr Ser Asp Lys Asn Asn Gly
225                 230                 235                 240

Ser Gly Val Leu Glu Gly Val Lys Ala Asp Lys Ser Lys Val Lys Leu
                245                 250                 255

Thr Ile Ser Asp Asp Leu Gly Gln Thr Thr Leu Glu Val Phe Lys Glu
            260                 265                 270

Asp Gly Lys Thr Leu Val Ser Lys Lys Val Thr Ser Lys Asp Lys Ser
        275                 280                 285

Ser Thr Glu Glu Lys Phe Asn Glu Lys Gly Glu Val Ser Glu Lys Ile
    290                 295                 300

Ile Thr Arg Ala Asp Gly Thr Arg Leu Glu Tyr Thr Gly Ile Lys Ser
305                 310                 315                 320

Asp Gly Ser Gly Lys Ala Lys Glu Val Leu Lys Gly Phe Thr Leu Glu
                325                 330                 335

Gly Lys Val Ala Asn Asp Lys Val Thr Leu Glu Val Lys Glu Gly Thr
            340                 345                 350

Val Thr Leu Ser Lys Ile Ser Lys Ser Gly Glu Val Ser Val Glu Leu
        355                 360                 365

Asn Asp Thr Asp Ser Ser Ala Ala Thr Lys Lys Thr Ala Ala Trp Asn
    370                 375                 380

Ser Lys Thr Ser Thr Leu Thr Ile Ser Val Asn Ser Lys Lys Thr Thr
385                 390                 395                 400

Gln Leu Val Phe Thr Lys Gln Asp Thr Ile Thr Val Gln Lys Tyr Asp
                405                 410                 415

Ser Ala Gly Thr Asn Leu Glu Gly Thr Ala Val Glu Ile Lys Thr Leu
            420                 425                 430

Asp Glu Leu Lys Asn Ala Leu Lys
        435                 440
```

<210> SEQ ID NO 89

```
<211> LENGTH: 1302
<212> TYPE: DNA
<213> ORGANISM: Artificial Sequence
<220> FEATURE:
<223> OTHER INFORMATION: Chimeric nucleic acid
<221> NAME/KEY: CDS
<222> LOCATION: (1)...(1302)

<400> SEQUENCE: 89

atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15

gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30

att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45

ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
    50                  55                  60

aaa aac gat ggt agt tta gat aat gaa gca aat cgc aac gag tca ttg      240
Lys Asn Asp Gly Ser Leu Asp Asn Glu Ala Asn Arg Asn Glu Ser Leu
 65                  70                  75                  80

tta gca gga gct tat aca ata tca acc tta ata aca caa aaa tta agt      288
Leu Ala Gly Ala Tyr Thr Ile Ser Thr Leu Ile Thr Gln Lys Leu Ser
                85                  90                  95

aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110

aaa tgc tct gaa gag ttt agt act aaa cta aaa gat aat cat gca cag      384
Lys Cys Ser Glu Glu Phe Ser Thr Lys Leu Lys Asp Asn His Ala Gln
        115                 120                 125

ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140

aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160

ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175

gct aat tca gtt aaa gag ctt aca agc cct gtt gtc cat ggc gtt tca      576
Ala Asn Ser Val Lys Glu Leu Thr Ser Pro Val Val His Gly Val Ser
            180                 185                 190

gta gat ttg cct ggt gaa atg aaa gtt ctt gta agc aaa gaa aaa aac      624
Val Asp Leu Pro Gly Glu Met Lys Val Leu Val Ser Lys Glu Lys Asn
        195                 200                 205

aaa gac ggc aag tac gat cta att gca aca gta gac aag ctt gag ctt      672
Lys Asp Gly Lys Tyr Asp Leu Ile Ala Thr Val Asp Lys Leu Glu Leu
    210                 215                 220

aaa gga act tct gat aaa aac aat gga tct gga gta ctt gaa ggc gta      720
Lys Gly Thr Ser Asp Lys Asn Asn Gly Ser Gly Val Leu Glu Gly Val
225                 230                 235                 240

aaa gct gac aaa agt aaa gta aaa tta aca att tct gac gat cta ggt      768
Lys Ala Asp Lys Ser Lys Val Lys Leu Thr Ile Ser Asp Asp Leu Gly
                245                 250                 255

caa acc aca ctt gaa gtt ttc aaa gaa gat ggc aaa aca cta gta tca      816
Gln Thr Thr Leu Glu Val Phe Lys Glu Asp Gly Lys Thr Leu Val Ser
            260                 265                 270

aaa aaa gta act tcc aaa gac aag tca tca aca gaa gaa aaa ttc aat      864
```

```
Lys Lys Val Thr Ser Lys Asp Lys Ser Ser Thr Glu Glu Lys Phe Asn
        275                 280                 285

gaa aaa ggt gaa gta tct gaa aaa ata ata aca aga gca gac gga acc      912
Glu Lys Gly Glu Val Ser Glu Lys Ile Ile Thr Arg Ala Asp Gly Thr
    290                 295                 300

aga ctt gaa tac aca gga att aaa agc gat gga tct gga aaa gct aaa      960
Arg Leu Glu Tyr Thr Gly Ile Lys Ser Asp Gly Ser Gly Lys Ala Lys
305                 310                 315                 320

gag gtt tta aaa ggc ttt act ctt gaa gga aaa gta gct aat gat aaa     1008
Glu Val Leu Lys Gly Phe Thr Leu Glu Gly Lys Val Ala Asn Asp Lys
                325                 330                 335

gta aca ttg gaa gta aaa gaa gga acc gtt act tta agt aag att tca     1056
Val Thr Leu Glu Val Lys Glu Gly Thr Val Thr Leu Ser Lys Ile Ser
            340                 345                 350

aaa tct ggg gaa gtt tca gtt gaa ctt aat gac act gac agt agt gct     1104
Lys Ser Gly Glu Val Ser Val Glu Leu Asn Asp Thr Asp Ser Ser Ala
        355                 360                 365

gct act aaa aaa act gca gct tgg aat tca aaa act tct act tta aca     1152
Ala Thr Lys Lys Thr Ala Ala Trp Asn Ser Lys Thr Ser Thr Leu Thr
    370                 375                 380

att agt gtt aac agc aaa aaa act aca caa ctt gtg ttt act aaa caa     1200
Ile Ser Val Asn Ser Lys Lys Thr Thr Gln Leu Val Phe Thr Lys Gln
385                 390                 395                 400

gac aca ata act gta caa aaa tac gac tcc gca ggt acc aat tta gaa     1248
Asp Thr Ile Thr Val Gln Lys Tyr Asp Ser Ala Gly Thr Asn Leu Glu
                405                 410                 415

ggc aca gca gtc gaa att aaa aca ctt gat gaa ctt aaa aac gct tta     1296
Gly Thr Ala Val Glu Ile Lys Thr Leu Asp Glu Leu Lys Asn Ala Leu
            420                 425                 430

aaa taa                                                             1302
Lys
```

<210> SEQ ID NO 90
<211> LENGTH: 433
<212> TYPE: PRT
<213> ORGANISM: Artificial Sequence
<220> FEATURE:
<223> OTHER INFORMATION: Chimeric protein

<400> SEQUENCE: 90

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Thr Leu Ile Thr Gln Lys Leu Ser
                85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140
```

-continued

Lys Ala Asn Ala Ala Gly Lys Asp Lys Gly Val Glu Glu Leu Glu Lys
145 150 155 160

Leu Ser Gly Ser Leu Glu Ser Leu Ser Lys Ala Ala Lys Glu Met Leu
165 170 175

Ala Asn Ser Val Lys Glu Leu Thr Ser Pro Val Val His Gly Val Ser
180 185 190

Val Asp Leu Pro Gly Glu Met Lys Val Leu Val Ser Lys Glu Lys Asn
195 200 205

Lys Asp Gly Lys Tyr Asp Leu Ile Ala Thr Val Asp Lys Leu Glu Leu
210 215 220

Lys Gly Thr Ser Asp Lys Asn Asn Gly Ser Gly Val Leu Glu Gly Val
225 230 235 240

Lys Ala Asp Lys Ser Lys Val Lys Leu Thr Ile Ser Asp Asp Leu Gly
245 250 255

Gln Thr Thr Leu Glu Val Phe Lys Glu Asp Gly Lys Thr Leu Val Ser
260 265 270

Lys Lys Val Thr Ser Lys Asp Lys Ser Ser Thr Glu Glu Lys Phe Asn
275 280 285

Glu Lys Gly Glu Val Ser Glu Lys Ile Ile Thr Arg Ala Asp Gly Thr
290 295 300

Arg Leu Glu Tyr Thr Gly Ile Lys Ser Asp Gly Ser Gly Lys Ala Lys
305 310 315 320

Glu Val Leu Lys Gly Phe Thr Leu Glu Gly Lys Val Ala Asn Asp Lys
325 330 335

Val Thr Leu Glu Val Lys Glu Gly Thr Val Thr Leu Ser Lys Ile Ser
340 345 350

Lys Ser Gly Glu Val Ser Val Glu Leu Asn Asp Thr Asp Ser Ser Ala
355 360 365

Ala Thr Lys Lys Thr Ala Ala Trp Asn Ser Lys Thr Ser Thr Leu Thr
370 375 380

Ile Ser Val Asn Ser Lys Lys Thr Thr Gln Leu Val Phe Thr Lys Gln
385 390 395 400

Asp Thr Ile Thr Val Gln Lys Tyr Asp Ser Ala Gly Thr Asn Leu Glu
405 410 415

Gly Thr Ala Val Glu Ile Lys Thr Leu Asp Glu Leu Lys Asn Ala Leu
420 425 430

Lys

<210> SEQ ID NO 91
<211> LENGTH: 31
<212> TYPE: DNA
<213> ORGANISM: Artificial Sequence
<220> FEATURE:
<223> OTHER INFORMATION: Synthetic Construct

<400> SEQUENCE: 91
gtcatatggc ttgtaataat tcagggaaag a 31

<210> SEQ ID NO 92
<211> LENGTH: 30
<212> TYPE: DNA
<213> ORGANISM: Artificial Sequence
<220> FEATURE:
<223> OTHER INFORMATION: Synthetic Construct

<400> SEQUENCE: 92
tttccatgga aggttttttt ggactttctg 30

<210> SEQ ID NO 93
<211> LENGTH: 30
<212> TYPE: DNA
<213> ORGANISM: Artificial Sequence
<220> FEATURE:
<223> OTHER INFORMATION: Synthetic Construct

<400> SEQUENCE: 93
tttccatggc caagcaaaat gttagcagcc 30

<210> SEQ ID NO 94
<211> LENGTH: 27
<212> TYPE: DNA
<213> ORGANISM: Artificial Sequence
<220> FEATURE:
<223> OTHER INFORMATION: Synthetic Construct

<400> SEQUENCE: 94
taaggatcct tattttaaag cgttttt 27

<210> SEQ ID NO 95
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 95

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca atg gca gac gga acc aga      432
Lys Gly Glu Val Ser Glu Lys Ile Ile Thr Met Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
```

```
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys


<210> SEQ ID NO 96
<211> LENGTH: 273
<212> TYPE: PRT
<213> ORGANISM: Artificial Sequence
<220> FEATURE:
<223> OTHER INFORMATION: Altered OspA protein

<400> SEQUENCE: 96

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Met Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
```

```
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 97
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 97

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa tat      480
Leu Glu Tyr Thr Gly Ile Lys Ser Asp Gly Ser Gly Lys Ala Lys Tyr
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
```

```
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys


<210> SEQ ID NO 98
<211> LENGTH: 273
<212> TYPE: PRT
<213> ORGANISM: Artificial Sequence
<220> FEATURE:
<223> OTHER INFORMATION: Altered OspA protein

<400> SEQUENCE: 98

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Tyr
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

```
<210> SEQ ID NO 99
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 99

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                 70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca atg gca gac gga acc aga      432
Lys Gly Glu Val Ser Glu Lys Ile Ile Thr Met Ala Asp Gly Thr Arg
    130                 135                 140

ctt gaa tac aca gga att aaa agc gat gga tct gga aaa gct aaa tat      480
Leu Glu Tyr Thr Gly Ile Lys Ser Asp Gly Ser Gly Lys Ala Lys Tyr
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
```

```
            260                 265                 270

aaa taa                                                                822
Lys


<210> SEQ ID NO 100
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 100

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Met Ala Asp Gly Thr Arg
    130                 135                 140

Leu Glu Tyr Thr Gly Ile Lys Ser Asp Gly Ser Gly Lys Ala Lys Tyr
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 101
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 101
```

-continued atg aaa aaa tat tta ttg gga ata ggt cta ata tta gcc tta ata gca 48
Met Lys Lys Tyr Leu Leu Gly Ile Gly Leu Ile Leu Ala Leu Ile Ala
1 5 10 15 tgt aag caa aat gtt agc agc ctt gac gag aaa aac agc gtt tca gta 96
Cys Lys Gln Asn Val Ser Ser Leu Asp Glu Lys Asn Ser Val Ser Val
20 25 30 gat ttg cct ggt gaa atg aaa gtt ctt gta agc aaa gaa aaa aac aaa 144
Asp Leu Pro Gly Glu Met Lys Val Leu Val Ser Lys Glu Lys Asn Lys
35 40 45 gac ggc aag tac gat cta att gca aca gta gac aag ctt gag ctt aaa 192
Asp Gly Lys Tyr Asp Leu Ile Ala Thr Val Asp Lys Leu Glu Leu Lys
50 55 60 gga act tct gat aaa aac aat gga tct gga gta ctt gaa ggc gta aaa 240
Gly Thr Ser Asp Lys Asn Asn Gly Ser Gly Val Leu Glu Gly Val Lys
65 70 75 80 gct gac aaa agt aaa gta aaa tta aca att tct gac gat cta ggt caa 288
Ala Asp Lys Ser Lys Val Lys Leu Thr Ile Ser Asp Asp Leu Gly Gln
85 90 95 acc aca ctt gaa gtt ttc aaa gaa gat ggc aaa aca cta gta tca aaa 336
Thr Thr Leu Glu Val Phe Lys Glu Asp Gly Lys Thr Leu Val Ser Lys
100 105 110 aaa gta act tcc aaa gac aag tca tca aca gaa gaa aaa ttc aat gaa 384
Lys Val Thr Ser Lys Asp Lys Ser Ser Thr Glu Glu Lys Phe Asn Glu
115 120 125 aaa ggt gaa gta tct gaa aaa ata ata aca aga gca gac gga acc aga 432
Lys Gly Glu Val Ser Glu Lys Ile Ile Thr Arg Ala Asp Gly Thr Arg
130 135 140 ctt gaa tac aca gga att aaa agc gat gga tct gga aaa gct aaa tat 480
Leu Glu Tyr Thr Gly Ile Lys Ser Asp Gly Ser Gly Lys Ala Lys Tyr
145 150 155 160 gtt tta aaa ggc tat gtt ctt gaa gga act cta act gct gaa aaa aca 528
Val Leu Lys Gly Tyr Val Leu Glu Gly Thr Leu Thr Ala Glu Lys Thr
165 170 175 aca ttg gtg gtt aaa gaa gga act gtt act tta agc aaa aat att tca 576
Thr Leu Val Val Lys Glu Gly Thr Val Thr Leu Ser Lys Asn Ile Ser
180 185 190 aaa tct ggg gaa gtt tca gtt gaa ctt aat gac act gac agt agt gct 624
Lys Ser Gly Glu Val Ser Val Glu Leu Asn Asp Thr Asp Ser Ser Ala
195 200 205 gct act aaa aaa act gca gct tgg aat tca ggc act tca act tta aca 672
Ala Thr Lys Lys Thr Ala Ala Trp Asn Ser Gly Thr Ser Thr Leu Thr
210 215 220 att act gta aac agt aaa aaa act aaa gac ctt gtg ttt aca aaa gaa 720
Ile Thr Val Asn Ser Lys Lys Thr Lys Asp Leu Val Phe Thr Lys Glu
225 230 235 240 aac aca att aca gta caa caa tac gac tca aat ggc acc aaa tta gag 768
Asn Thr Ile Thr Val Gln Gln Tyr Asp Ser Asn Gly Thr Lys Leu Glu
245 250 255 ggg tca gca gtt gaa att aca aaa ctt gat gaa att aaa aac gct tta 816
Gly Ser Ala Val Glu Ile Thr Lys Leu Asp Glu Ile Lys Asn Ala Leu
260 265 270 aaa taa 822
Lys

<210> SEQ ID NO 102
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 102

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Tyr
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

<210> SEQ ID NO 103
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 103

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45
```

```
gac ggc aag tac gat cta att gca aca gta gac aag ctt gag ctt aaa      192
Asp Gly Lys Tyr Asp Leu Ile Ala Thr Val Asp Lys Leu Glu Leu Lys
     50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca atg gca gac gga acc aga      432
Lys Gly Glu Val Ser Glu Lys Ile Ile Thr Met Ala Asp Gly Thr Arg
    130                 135                 140

ctt gaa tac aca gga att aaa agc gat gga tct gga aaa gct aaa tat      480
Leu Glu Tyr Thr Gly Ile Lys Ser Asp Gly Ser Gly Lys Ala Lys Tyr
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aug aat att tca      576
Thr Leu Val Val Lys Glu Gly Thr Val Thr Leu Ser Met Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys
```

<210> SEQ ID NO 104
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 104

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45
```

```
Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Met Ala Asp Gly Thr Arg
    130                 135                 140

Leu Glu Tyr Thr Gly Ile Lys Ser Asp Gly Ser Gly Lys Ala Lys Tyr
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Met Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 105
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 105

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95
```

```
acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc ttt gtt ctt gaa gga act cta act gct gaa aaa aca      528
Val Leu Lys Gly Phe Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                               822
Lys
```

<210> SEQ ID NO 106
<211> LENGTH: 273
<212> TYPE: PRT
<213> ORGANISM: Artificial Sequence
<220> FEATURE:
<223> OTHER INFORMATION: Altered OspA protein

<400> SEQUENCE: 106

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110
```

```
Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Phe Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 107
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 107

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
     50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                 85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140
```

```
ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc ttt act ctt gaa gga act cta act gct gaa aaa aca      528
Val Leu Lys Gly Phe Thr Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys
```

<210> SEQ ID NO 108
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 108

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Phe Thr Leu Glu Gly Thr Leu Thr Ala Glu Lys Thr
                165                 170                 175
```

```
Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 109
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 109

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat act ctt gaa gga act cta act gct gaa aaa aca      528
Val Leu Lys Gly Tyr Thr Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190
```

```
aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys
```

<210> SEQ ID NO 110
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 110

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Thr Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240
```

```
Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 111
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 111

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat act ctt gaa gga aag cta act gct gaa aaa aca      528
Val Leu Lys Gly Tyr Thr Leu Glu Gly Lys Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240
```

```
aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys


<210> SEQ ID NO 112
<211> LENGTH: 273
<212> TYPE: PRT
<213> ORGANISM: Artificial Sequence
<220> FEATURE:
<223> OTHER INFORMATION: Altered OspA Protein

<400> SEQUENCE: 112

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Thr Leu Glu Gly Lys Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys


<210> SEQ ID NO 113
<211> LENGTH: 822
<212> TYPE: DNA
```

-continued

```
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 113

atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc ttt act ctt gaa gga aag cta act gct gaa aaa aca      528
Val Leu Lys Gly Phe Thr Leu Glu Gly Lys Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca      672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa      720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag      768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta      816
Gly Ser Ala Val Glu Ile Thr Lys Leu Asp Glu Ile Lys Asn Ala Leu
            260                 265                 270

aaa taa                                                              822
Lys
```

<210> SEQ ID NO 114
<211> LENGTH: 273
<212> TYPE: PRT
<213> ORGANISM: Artificial Sequence
<220> FEATURE:
<223> OTHER INFORMATION: Altered OspA protein

<400> SEQUENCE: 114

```
Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Phe Thr Leu Glu Gly Lys Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

<210> SEQ ID NO 115
<211> LENGTH: 822
<212> TYPE: DNA
<213> ORGANISM: Artificial Sequence
<220> FEATURE:
<223> OTHER INFORMATION: Altered OspA Nucleic Acid
<221> NAME/KEY: CDS
<222> LOCATION: (1)...(822)

<400> SEQUENCE: 115

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15
```

-continued

```
tgt aag caa aat gtt agc agc ctt gac gag aaa aac agc gtt tca gta        96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa       144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa       192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa       240
Gly Thr Ser Asp Lys Asn Asn Gly Ser Gly Val Leu Glu Gly Val Lys
65                  70                  75                  80

gct gac aaa agt aaa gta aaa tta aca att tct gac gat cta ggt caa       288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa       336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa       384
Lys Val Thr Ser Lys Asp Lys Ser Ser Thr Glu Glu Lys Phe Asn Glu
        115                 120                 125

aaa ggt gaa gta tct gaa aaa ata ata aca atg gca gac gga acc aga       432
Lys Gly Glu Val Ser Glu Lys Ile Ile Thr Met Ala Asp Gly Thr Arg
    130                 135                 140

ctt gaa tac aca gga att aaa agc gat gga tct gga aaa gct aaa tat       480
Leu Glu Tyr Thr Gly Ile Lys Ser Asp Gly Ser Gly Lys Ala Lys Tyr
145                 150                 155                 160

gtt tta aaa ggc ttt act ctt gaa gga aag cta act gct gaa aaa aca       528
Val Leu Lys Gly Phe Thr Leu Glu Gly Lys Leu Thr Ala Glu Lys Thr
                165                 170                 175

aca ttg gtg gtt aaa gaa gga act gtt act tta agc atg aat att tca       576
Thr Leu Val Val Lys Glu Gly Thr Val Thr Leu Ser Met Asn Ile Ser
            180                 185                 190

aaa tct ggg gaa gtt tca gtt gaa ctt aat gac act gac agt agt gct       624
Lys Ser Gly Glu Val Ser Val Glu Leu Asn Asp Thr Asp Ser Ser Ala
        195                 200                 205

gct act aaa aaa act gca gct tgg aat tca ggc act tca act tta aca       672
Ala Thr Lys Lys Thr Ala Ala Trp Asn Ser Gly Thr Ser Thr Leu Thr
    210                 215                 220

att act gta aac agt aaa aaa act aaa gac ctt gtg ttt aca aaa gaa       720
Ile Thr Val Asn Ser Lys Lys Thr Lys Asp Leu Val Phe Thr Lys Glu
225                 230                 235                 240

aac aca att aca gta caa caa tac gac tca aat ggc acc aaa tta gag       768
Asn Thr Ile Thr Val Gln Gln Tyr Asp Ser Asn Gly Thr Lys Leu Glu
                245                 250                 255

ggg tca gca gtt gaa att aca aaa ctt gat gaa att aaa aac gct tta       816
Gly Ser Ala Val Glu Ile Thr Lys Leu Asp Glu Ile Lys Asn Ala Leu
            260                 265                 270

aaa taa                                                               822
Lys
```

<210> SEQ ID NO 116
<211> LENGTH: 273
<212> TYPE: PRT
<213> ORGANISM: Artificial Sequence
<220> FEATURE:
<223> OTHER INFORMATION: Altered OspA protein

<400> SEQUENCE: 116

```
Met Lys Lys Tyr Leu Leu Gly Ile Gly Leu Ile Leu Ala Leu Ile Ala
1               5                   10                  15
```

```
Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Met Ala Asp Gly Thr Arg
    130                 135                 140

Leu Glu Tyr Thr Gly Ile Lys Ser Asp Gly Ser Gly Lys Ala Lys Tyr
145                 150                 155                 160

Val Leu Lys Gly Phe Thr Leu Glu Gly Lys Leu Thr Ala Glu Lys Thr
                165                 170                 175

Thr Leu Val Val Lys Glu Gly Thr Val Thr Leu Ser Met Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys
```

<210> SEQ ID NO 117
<211> LENGTH: 30
<212> TYPE: DNA
<213> ORGANISM: Artificial Sequence
<220> FEATURE:
<223> OTHER INFORMATION: Synthetic Construct

<400> SEQUENCE: 117
gaaaaaataa taacaatggc agacggaacc 30

<210> SEQ ID NO 118
<211> LENGTH: 30
<212> TYPE: DNA
<213> ORGANISM: Artificial Sequence
<220> FEATURE:
<223> OTHER INFORMATION: Synthetic Construct

<400> SEQUENCE: 118
ggttccgtct gccattgtta ttattttttc 30

<210> SEQ ID NO 119
<211> LENGTH: 27
<212> TYPE: DNA

<213> ORGANISM: Artificial Sequence
<220> FEATURE:
<223> OTHER INFORMATION: Synthetic Construct

<400> SEQUENCE: 119
ggaaaagcta aatatgtttt aaaaggc 27

<210> SEQ ID NO 120
<211> LENGTH: 27
<212> TYPE: DNA
<213> ORGANISM: Artificial Sequence
<220> FEATURE:
<223> OTHER INFORMATION: Synthetic Construct

<400> SEQUENCE: 120
gccttttaaa acatatttag cttttcc 27

<210> SEQ ID NO 121
<211> LENGTH: 29
<212> TYPE: DNA
<213> ORGANISM: Artificial Sequence
<220> FEATURE:
<223> OTHER INFORMATION: Synthetic Construct

<400> SEQUENCE: 121
gttactttaa gcatgaatat ttcaaaatc 29

<210> SEQ ID NO 122
<211> LENGTH: 29
<212> TYPE: DNA
<213> ORGANISM: Artificial Sequence
<220> FEATURE:
<223> OTHER INFORMATION: Synthetic Construct

<400> SEQUENCE: 122
gattttgaaa tattcatgct taaagtaac 29

<210> SEQ ID NO 123
<211> LENGTH: 34
<212> TYPE: DNA
<213> ORGANISM: Artificial Sequence
<220> FEATURE:
<223> OTHER INFORMATION: Synthetic Construct

<400> SEQUENCE: 123
gaggttttaa aaggctttac tcttgaagga actc 34

<210> SEQ ID NO 124
<211> LENGTH: 34
<212> TYPE: DNA
<213> ORGANISM: Artificial Sequence
<220> FEATURE:
<223> OTHER INFORMATION: Synthetic Construct

<400> SEQUENCE: 124
gagttccttc aagagtaaag ccttttaaaa cctg 34

<210> SEQ ID NO 125
<211> LENGTH: 23
<212> TYPE: DNA
<213> ORGANISM: Artificial Sequence
<220> FEATURE:
<223> OTHER INFORMATION: Synthetic Construct

<400> SEQUENCE: 125
tcttgaagga aagctaactg ctg 23

<210> SEQ ID NO 126
<211> LENGTH: 23
<212> TYPE: DNA
<213> ORGANISM: Artificial Sequence
<220> FEATURE:
<223> OTHER INFORMATION: Synthetic Construct

<400> SEQUENCE: 126

```
cagcagttag ctttccttca aga                                         23
```

<210> SEQ ID NO 127
<211> LENGTH: 819
<212> TYPE: DNA
<213> ORGANISM: Borrelia burgdorferi
<220> FEATURE:
<221> NAME/KEY: CDS
<222> LOCATION: (1)...(819)

<400> SEQUENCE: 127

```
atg aaa aaa tat tta ttg gga ata ggt cta ata tta gcc tta ata gca       48
Met Lys Lys Tyr Leu Leu Gly Ile Gly Leu Ile Leu Ala Leu Ile Ala
 1               5                  10                  15

tgt aag caa aat gtt agc agc ctt gac gag aaa aac agc gtt tca gta       96
Cys Lys Gln Asn Val Ser Ser Leu Asp Glu Lys Asn Ser Val Ser Val
            20                  25                  30

gat ttg cct ggt gaa atg aaa gtt ctt gta agc aaa gaa aaa aac aaa      144
Asp Leu Pro Gly Glu Met Lys Val Leu Val Ser Lys Glu Lys Asn Lys
        35                  40                  45

gac ggc aag tac gat cta att gca aca gta gac aag ctt gag ctt aaa      192
Asp Gly Lys Tyr Asp Leu Ile Ala Thr Val Asp Lys Leu Glu Leu Lys
    50                  55                  60

gga act tct gat aaa aac aat gga tct gga gta ctt gaa ggc gta aaa      240
Gly Thr Ser Asp Lys Asn Asn Gly Ser Gly Val Leu Glu Gly Val Lys
 65                  70                  75                  80

gct gac aaa agt aaa gta aaa tta aca att tct gac gat cta ggt caa      288
Ala Asp Lys Ser Lys Val Lys Leu Thr Ile Ser Asp Asp Leu Gly Gln
                85                  90                  95

acc aca ctt gaa gtt ttc aaa gaa gat ggc aaa aca cta gta tca aaa      336
Thr Thr Leu Glu Val Phe Lys Glu Asp Gly Lys Thr Leu Val Ser Lys
            100                 105                 110

aaa gta act tcc aaa gac aag tca tca aca gaa gaa aaa ttc aat gaa      384
Lys Val Thr Ser Lys Asp Lys Ser Ser Thr Glu Glu Lys Phe Asn Glu
        115                 120                 125

aaa ggt gaa gta tct gaa aaa ata ata aca aga gca gac gga acc aga      432
Lys Gly Glu Val Ser Glu Lys Ile Ile Thr Arg Ala Asp Gly Thr Arg
    130                 135                 140

ctt gaa tac aca gga att aaa agc gat gga tct gga aaa gct aaa gag      480
Leu Glu Tyr Thr Gly Ile Lys Ser Asp Gly Ser Gly Lys Ala Lys Glu
145                 150                 155                 160

gtt tta aaa ggc tat gtt ctt gaa gga act cta act gct gaa aaa aca      528
Val Leu Lys Gly Tyr Val Leu Glu Gly Thr Leu Thr Ala Glu Lys Thr
                165                 170                 175

aca ttg gtg gtt aaa gaa gga act gtt act tta agc aaa aat att tca      576
Thr Leu Val Val Lys Glu Gly Thr Val Thr Leu Ser Lys Asn Ile Ser
            180                 185                 190

aaa tct ggg gaa gtt tca gtt gaa ctt aat gac act gac agt agt gct      624
Lys Ser Gly Glu Val Ser Val Glu Leu Asn Asp Thr Asp Ser Ser Ala
        195                 200                 205

gct act aaa aaa act gca gct tgg aat gca ggc act tca act tta aca      672
Ala Thr Lys Lys Thr Ala Ala Trp Asn Ala Gly Thr Ser Thr Leu Thr
    210                 215                 220
```

```
att act gta aac aac aaa aaa act aaa gcc ctt gta ttt aca aaa caa      720
Ile Thr Val Asn Asn Lys Lys Thr Lys Ala Leu Val Phe Thr Lys Gln
225                 230                 235                 240

gac aca att aca tca caa aaa tac gac tca gca gga acc aac ttg gaa      768
Asp Thr Ile Thr Ser Gln Lys Tyr Asp Ser Ala Gly Thr Asn Leu Glu
                245                 250                 255

ggc aca gca gtc gaa att aaa aca ctt gat gaa ctt aaa aac gct tta      816
Gly Thr Ala Val Glu Ile Lys Thr Leu Asp Glu Leu Lys Asn Ala Leu
            260                 265                 270

aga                                                                  819
Arg


<210> SEQ ID NO 128
<211> LENGTH: 273
<212> TYPE: PRT
<213> ORGANISM: Borrelia burgdorferi

<400> SEQUENCE: 128

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Glu Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ala Gly Thr Ser Thr Leu Thr
    210                 215                 220

Ile Thr Val Asn Asn Lys Lys Thr Lys Ala Leu Val Phe Thr Lys Gln
225                 230                 235                 240

Asp Thr Ile Thr Ser Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Arg


<210> SEQ ID NO 129
```

<211> LENGTH: 9
<212> TYPE: PRT
<213> ORGANISM: Artificial Sequence
<220> FEATURE:
<223> OTHER INFORMATION: Residue 165-173 of B31 OspA

<400> SEQUENCE: 129

Tyr Val Leu Glu Gly Thr Leu Thr Ala
 1               5

<210> SEQ ID NO 130
<211> LENGTH: 9
<212> TYPE: PRT
<213> ORGANISM: Artificial Sequence
<220> FEATURE:
<223> OTHER INFORMATION: Residue 332-340 of hLFA-1

<400> SEQUENCE: 130

Tyr Val Ile Glu Gly Thr Ser Lys Gln
 1               5

<210> SEQ ID NO 131
<211> LENGTH: 8
<212> TYPE: PRT
<213> ORGANISM: Borrelia burgdorferi

<400> SEQUENCE: 131

Leu Pro Gly Glu Met Lys Val Leu
 1               5

<210> SEQ ID NO 132
<211> LENGTH: 8
<212> TYPE: PRT
<213> ORGANISM: Borrelia burgdorferi

<400> SEQUENCE: 132

Leu Pro Gly Glu Met Lys Val Leu
 1               5

<210> SEQ ID NO 133
<211> LENGTH: 8
<212> TYPE: PRT
<213> ORGANISM: Borrelia burgdorferi

<400> SEQUENCE: 133

Leu Pro Gly Gly Met Thr Val Leu
 1               5

<210> SEQ ID NO 134
<211> LENGTH: 8
<212> TYPE: PRT
<213> ORGANISM: Borrelia burgdorferi

<400> SEQUENCE: 134

Leu Pro Gly Gly Met Thr Val Leu
 1               5

<210> SEQ ID NO 135
<211> LENGTH: 8
<212> TYPE: PRT
<213> ORGANISM: Borrelia burgdorferi

<400> SEQUENCE: 135

Leu Pro Gly Glu Met Lys Val Leu
 1               5

<210> SEQ ID NO 136
<211> LENGTH: 8
<212> TYPE: PRT
<213> ORGANISM: Borrelia burgdorferi

<400> SEQUENCE: 136

Leu Pro Gly Glu Met Lys Val Leu
1 5

<210> SEQ ID NO 137
<211> LENGTH: 8
<212> TYPE: PRT
<213> ORGANISM: Borrelia burgdorferi

<400> SEQUENCE: 137

Leu Pro Gly Glu Ile Lys Val Leu
1 5

<210> SEQ ID NO 138
<211> LENGTH: 8
<212> TYPE: PRT
<213> ORGANISM: Borrelia burgdorferi

<400> SEQUENCE: 138

Leu Pro Gly Gly Met Gly Val Leu
1 5

<210> SEQ ID NO 139
<211> LENGTH: 8
<212> TYPE: PRT
<213> ORGANISM: Borrelia burgdorferi

<400> SEQUENCE: 139

Leu Pro Gly Glu Met Lys Val Leu
1 5

<210> SEQ ID NO 140
<211> LENGTH: 11
<212> TYPE: PRT
<213> ORGANISM: Borrelia burgdorferi

<400> SEQUENCE: 140

Gly Thr Ser Asp Lys Asn Asn Gly Ser Gly Val
1 5 10

<210> SEQ ID NO 141
<211> LENGTH: 11
<212> TYPE: PRT
<213> ORGANISM: Borrelia burgdorferi

<400> SEQUENCE: 141

Gly Thr Ser Asp Lys Ser Asn Gly Ser Gly Thr
1 5 10

<210> SEQ ID NO 142
<211> LENGTH: 11
<212> TYPE: PRT
<213> ORGANISM: Borrelia burgdorferi

<400> SEQUENCE: 142

Gly Thr Ser Asp Lys Asn Asn Gly Ser Gly Thr
1 5 10

<210> SEQ ID NO 143

<211> LENGTH: 11
<212> TYPE: PRT
<213> ORGANISM: Borrelia burgdorferi

<400> SEQUENCE: 143

Gly Thr Ser Asp Lys Asn Asn Gly Ser Gly Thr
1 5 10

<210> SEQ ID NO 144
<211> LENGTH: 11
<212> TYPE: PRT
<213> ORGANISM: Borrelia burgdorferi

<400> SEQUENCE: 144

Gly Thr Ser Asp Lys Asp Asn Gly Ser Gly Thr
1 5 10

<210> SEQ ID NO 145
<211> LENGTH: 11
<212> TYPE: PRT
<213> ORGANISM: Borrelia burgdorferi

<400> SEQUENCE: 145

Gly Thr Ser Asp Lys Asp Asn Gly Ser Gly Thr
1 5 10

<210> SEQ ID NO 146
<211> LENGTH: 11
<212> TYPE: PRT
<213> ORGANISM: Borrelia burgdorferi

<400> SEQUENCE: 146

Gly Thr Ser Asp Lys Asp Asn Gly Ser Gly Val
1 5 10

<210> SEQ ID NO 147
<211> LENGTH: 11
<212> TYPE: PRT
<213> ORGANISM: Borrelia burgdorferi

<400> SEQUENCE: 147

Gly Thr Ser Asp Lys Asn Asn Gly Ser Gly Thr
1 5 10

<210> SEQ ID NO 148
<211> LENGTH: 11
<212> TYPE: PRT
<213> ORGANISM: Borrelia burgdorferi

<400> SEQUENCE: 148

Gly Thr Ser Asp Lys Asn Asn Gly Ser Gly Val
1 5 10

<210> SEQ ID NO 149
<211> LENGTH: 31
<212> TYPE: PRT
<213> ORGANISM: Borrelia burgdorferi

<400> SEQUENCE: 149

Asn Ile Ser Lys Ser Gly Glu Val Ser Val Glu Leu Asn Asp Thr Asp
1 5 10 15

Ser Ser Ala Ala Thr Lys Lys Thr Ala Ala Trp Asn Ser Gly Thr
20 25 30

<210> SEQ ID NO 150
<211> LENGTH: 31
<212> TYPE: PRT
<213> ORGANISM: Borrelia burgdorferi

<400> SEQUENCE: 150

```
His Ile Pro Asn Ser Gly Glu Ile Thr Val Glu Leu Asn Asp Ser Asn
 1               5                  10                  15

Ser Thr Gln Ala Thr Lys Lys Thr Gly Lys Trp Asp Ser Asn Thr
            20                  25                  30
```

<210> SEQ ID NO 151
<211> LENGTH: 29
<212> TYPE: PRT
<213> ORGANISM: Borrelia burgdorferi

<400> SEQUENCE: 151

```
Asn Ile Leu Lys Ser Gly Glu Ile Thr Val Asp Asp Ser Asp Thr Thr
 1               5                  10                  15

Gln Ala Thr Lys Lys Thr Gly Lys Trp Asp Ser Lys Thr
            20                  25
```

<210> SEQ ID NO 152
<211> LENGTH: 31
<212> TYPE: PRT
<213> ORGANISM: Borrelia burgdorferi

<400> SEQUENCE: 152

```
Asn Ile Leu Lys Ser Gly Glu Ile Thr Ala Ala Leu Asp Asp Ser Asp
 1               5                  10                  15

Thr Thr Arg Ala Thr Lys Lys Thr Gly Lys Trp Asp Ser Lys Thr
            20                  25                  30
```

<210> SEQ ID NO 153
<211> LENGTH: 29
<212> TYPE: PRT
<213> ORGANISM: Borrelia burgdorferi

<400> SEQUENCE: 153

```
Glu Ile Ala Lys Ser Gly Glu Val Thr Val Asn Asp Thr Asn Thr Thr
 1               5                  10                  15

Gln Ala Thr Lys Lys Thr Gly Ala Trp Asp Ser Lys Thr
            20                  25
```

<210> SEQ ID NO 154
<211> LENGTH: 29
<212> TYPE: PRT
<213> ORGANISM: Borrelia burgdorferi

<400> SEQUENCE: 154

```
Glu Ile Ala Lys Ser Gly Glu Val Thr Val Asn Asp Thr Asn Thr Thr
 1               5                  10                  15

Gln Ala Thr Lys Lys Thr Gly Ala Trp Asp Ser Lys Thr
            20                  25
```

<210> SEQ ID NO 155
<211> LENGTH: 29
<212> TYPE: PRT
<213> ORGANISM: Borrelia burgdorferi

<400> SEQUENCE: 155

```
Glu Ile Ala Lys Ser Gly Glu Val Thr Val Asn Asp Thr Asn Thr Thr
 1               5                  10                  15
```

Gln Ala Thr Lys Lys Thr Gly Ala Trp Asp Ser Lys Thr
20 25

<210> SEQ ID NO 156
<211> LENGTH: 29
<212> TYPE: PRT
<213> ORGANISM: Borrelia burgdorferi

<400> SEQUENCE: 156

His Asn Ser Gly Glu Ile Thr Val Glu Leu Asn Asp Ser Asp Thr Thr
1 5 10 15

Gln Ala Thr Lys Lys Thr Gly Thr Trp Asp Ser Lys Thr
20 25

<210> SEQ ID NO 157
<211> LENGTH: 29
<212> TYPE: PRT
<213> ORGANISM: Borrelia burgdorferi

<400> SEQUENCE: 157

His Lys Ser Gly Glu Val Thr Ala Glu Leu Asn Asp Thr Asp Ser Thr
1 5 10 15

Gln Ala Thr Lys Lys Thr Gly Lys Trp Asp Ala Gly Thr
20 25

<210> SEQ ID NO 158
<211> LENGTH: 21
<212> TYPE: PRT
<213> ORGANISM: Borrelia burgdorferi

<400> SEQUENCE: 158

Ser Asn Gly Thr Lys Leu Glu Gly Ser Ala Val Glu Ile Thr Lys Leu
1 5 10 15

Asp Glu Ile Lys Asn
20

<210> SEQ ID NO 159
<211> LENGTH: 21
<212> TYPE: PRT
<213> ORGANISM: Borrelia burgdorferi

<400> SEQUENCE: 159

Ser Ala Gly Thr Asn Leu Glu Gly Asn Ala Val Glu Ile Lys Thr Leu
1 5 10 15

Asp Glu Leu Lys Asn
20

<210> SEQ ID NO 160
<211> LENGTH: 21
<212> TYPE: PRT
<213> ORGANISM: Borrelia burgdorferi

<400> SEQUENCE: 160

Ser Ala Gly Thr Asn Leu Glu Gly Lys Ala Val Glu Ile Thr Thr Leu
1 5 10 15

Lys Glu Leu Lys Asn
20

<210> SEQ ID NO 161
<211> LENGTH: 21
<212> TYPE: PRT
<213> ORGANISM: Borrelia burgdorferi

<400> SEQUENCE: 161

Ser Ala Gly Thr Asn Leu Glu Gly Lys Ala Val Glu Ile Thr Thr Leu
1 5 10 15

Lys Glu Leu Lys Asn
20

<210> SEQ ID NO 162
<211> LENGTH: 21
<212> TYPE: PRT
<213> ORGANISM: Borrelia burgdorferi

<400> SEQUENCE: 162

Ser Ala Gly Thr Asn Leu Glu Gly Thr Ala Val Glu Ile Lys Thr Leu
1 5 10 15

Asp Glu Leu Lys Asn
20

<210> SEQ ID NO 163
<211> LENGTH: 21
<212> TYPE: PRT
<213> ORGANISM: Borrelia burgdorferi

<400> SEQUENCE: 163

Ser Ala Gly Thr Asn Leu Glu Gly Thr Ala Val Glu Ile Lys Thr Leu
1 5 10 15

Asp Glu Leu Lys Asn
20

<210> SEQ ID NO 164
<211> LENGTH: 21
<212> TYPE: PRT
<213> ORGANISM: Borrelia burgdorferi

<400> SEQUENCE: 164

Ser Ala Gly Thr Asn Leu Glu Gly Thr Ala Val Glu Ile Lys Thr Leu
1 5 10 15

Asp Glu Leu Lys Asn
20

<210> SEQ ID NO 165
<211> LENGTH: 21
<212> TYPE: PRT
<213> ORGANISM: Borrelia burgdorferi

<400> SEQUENCE: 165

Ser Ala Gly Thr Asn Leu Glu Gly Lys Ala Val Glu Ile Thr Thr Leu
1 5 10 15

Lys Glu Leu Lys Asn
20

<210> SEQ ID NO 166
<211> LENGTH: 21
<212> TYPE: PRT
<213> ORGANISM: Borrelia burgdorferi

<400> SEQUENCE: 166

Ser Ala Gly Thr Asn Leu Glu Gly Thr Ala Val Glu Ile Lys Thr Leu
1 5 10 15

Asp Glu Ile Lys Asn
20

<210> SEQ ID NO 167
<211> LENGTH: 21
<212> TYPE: PRT
<213> ORGANISM: Borrelia burgdorferi

<400> SEQUENCE: 167

Glu Leu Asn Asp Thr Asp Ser Ser Ala Ala Thr Lys Lys Thr Ala Ala
1 5 10 15

Trp Asn Ser Gly Thr
20

<210> SEQ ID NO 168
<211> LENGTH: 21
<212> TYPE: PRT
<213> ORGANISM: Borrelia burgdorferi

<400> SEQUENCE: 168

Ala Leu Asp Asp Ser Asp Thr Thr Gln Ala Thr Lys Lys Thr Gly Lys
1 5 10 15

Trp Asp Ser Lys Thr
20

<210> SEQ ID NO 169
<211> LENGTH: 21
<212> TYPE: PRT
<213> ORGANISM: Borrelia burgdorferi

<400> SEQUENCE: 169

Glu Leu Asn Asp Ser Asp Thr Ser Ala Ala Thr Lys Lys Thr Ala Ala
1 5 10 15

Trp Asn Ser Gly Thr
20

<210> SEQ ID NO 170
<211> LENGTH: 21
<212> TYPE: PRT
<213> ORGANISM: Borrelia burgdorferi

<400> SEQUENCE: 170

Glu Leu Asn Asp Thr Asp Ser Ser Ala Ala Thr Lys Lys Thr Gly Lys
1 5 10 15

Trp Asn Ser Gly Thr
20

<210> SEQ ID NO 171
<211> LENGTH: 21
<212> TYPE: PRT
<213> ORGANISM: Borrelia burgdorferi

<400> SEQUENCE: 171

Glu Leu Asn Asp Thr Asp Ser Ser Ala Ala Thr Lys Lys Thr Ala Ala
1 5 10 15

Trp Asp Ser Lys Thr
20

<210> SEQ ID NO 172
<211> LENGTH: 21
<212> TYPE: PRT
<213> ORGANISM: Borrelia burgdorferi

<400> SEQUENCE: 172

Glu Leu Asn Asp Ser Asp Thr Ser Ala Ala Thr Lys Lys Thr Gly Lys

-continued

```
 1               5                   10                  15

Trp Asn Ser Gly Thr
            20


<210> SEQ ID NO 173
<211> LENGTH: 21
<212> TYPE: PRT
<213> ORGANISM: Borrelia burgdorferi

<400> SEQUENCE: 173

Glu Leu Asn Asp Ser Asp Thr Ser Ala Ala Thr Lys Lys Thr Ala Ala
 1               5                   10                  15

Trp Asp Ser Lys Thr
            20
```

ALTERED OSPA OF *BORRELIA BURGDORFERI*

RELATED APPLICATIONS

This application is a divisional of U.S. application Ser. No. 12/313,443, filed Nov. 19, 2008, now U.S. Pat. No. 8,680, 236, which is a continuation of U.S. application Ser. No. 10/369,339, filed Feb. 18, 2003, now abandoned, which is a continuation of International Application . No. PCT/US01/25852, which designated the United States, was published in English and was filed on Aug. 17, 2001, which claims the benefit of U.S. Provisional Application No. 60/226,484, filed on Aug 18, 2000. The entire teachings of these applications are incorporated herein by reference.

GOVERNMENT SUPPORT

The invention was supported, in whole or in part, by Grant 2R01AI37256-05A1 from the National Institute of Allergy and Infectious Diseases and Grant NIH GM057215 from the National Institutes of Health. The Government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

a) File name: 26312001023SubSequenceListing; created Oct. 1, 2013, 340 KB in size.

BACKGROUND OF THE INVENTION

Lyme disease (Lyme borreliosis) is the most common tick-borne infectious disease in North America and Europe, and has been found in Russia, Japan, China and Australia. Lyme disease begins at the site of a tick bite, producing a primary infection with spread of the organism to secondary sites occurring during the course of infection. The causative bacterial agent of this disease is the spirochete *Borrelia burgdorferi*, which was first isolated and cultivated in 1982 (Burgdorferi, W. A. et al., *Science* 216: 1317-1319 (1982); Steere, A. R. et al., *N. Engl. J. Med.,* 308:733-740 (1983)).

Three pathogenic genospecies of *Borrelia, B. burgdorferi* sensu stricto (*B. burgdorferi* or B.b.s.s.), *B. afzelii* and *B. garinii* have been described (Baranton, G., et al., *Int. J. Syst. Bacteriol.,* 42:378-383 (1992)). These are members of a species complex, *B. burgdorferi* sensu lato, which consists of at least 10 different genospecies (Piken, R. N. et al., *J. Invest. Dermatol.,* 110:211-214 (1998); Postic, D. et al., *Int. J. Syst. Bacteriol.,* 44:743-752 (1994); Valsangiacomo, C. T. et al., *Int. J. Syst. Bacteriol.,* 47:1-10 (1997)). The three genospecies, *B. burgdorferi* sensu stricto, *B. afzelii* and *B. garinii*, are all thought to be pathogenic and all are found in Europe.

*B. burgdorferi* has an outer membrane whose major protein constituents are the outer surface proteins A and B (OspA and OspB). OspA is a basic lipoprotein of approximately 31 kd, which is encoded on a large linear plasmid along with OspB, a basic lipoprotein of approximately 34 kd (Szczepanski, A., and J. L. Benach, *Microbiol. Rev.,* 55:21 (1991)). The immune response to these outer surface proteins tends to occur late in the disease, if at all (Craft, J. E. et al., *J. Clin Invest.* 78:934-939 (1986); Dattwyler, R. J. and B. J. Luft, *Rheum. Clin. North Am.,* 15:727-734 (1989)). Furthermore, patients acutely and chronically infected with *B. burgdorferi* respond variably to the different antigens, including OspA, OspB, OspC, OspD, p39, p41 and p93.

Currently, Lyme Disease is treated with a range of antibiotics, e.g., tetracyclines, penicillin and cephalosporins. However, such treatment is not always successful in clearing the infection. Treatment is often delayed due to improper diagnosis with the deleterious effect that the infection proceeds to a chronic condition, where treatment with antibiotics is often not useful. One of the factors contributing to delayed treatment is the lack of effective diagnostic tools.

Vaccines against Lyme borreliosis have been attempted. However, a vaccine that consists of recombinant OspA may require frequent booster immunizations. An additional concern of OspA-based vaccines is the recent identification of a putative autoreactive OspA domain with a high degree of similarity to a region of human leukocyte function-associated antigen-1 (hLFA-1) (Gross, D. M. et al., *Science,* 281: 703-706 (1998)).

Therefore, it should be advantageous to develop modified OspA proteins having decreased cross-reactivity to hLFA-1 in order to reduce potential side effects of an OspA vaccine. Development of OspA proteins with decreased hLFA-1 cross-reactivity that maintain or have increased immunoreactivity to more than one member of the *Borrelia* complex would also be desirable. To be useful as vaccines, the conformations of these modified proteins must be sufficiently stable to retain certain OspA structural features that are required to elicit a protective immune response. OspA proteins with these features would allow for improvements in diagnosis and/or vaccination against all, or most, of the *Borrelia* that cause Lyme Disease.

Analysis of the immune status of OspA immunized individuals revealed that the overall quantitative response is not predictive of protection, but rather the reactivity with a specific epitope of the OspA lipoprotein directly correlates to protective immunity. The anti-OspA monoclonal antibody, LA-2 (Kramer et al., 1990) defines an epitope of the lipoprotein that is apparently necessary for protective immunity after OspA vaccination. For instance, passive immunization of mice with this antibody leads to protection against infection with the spirochete (Schaible et al., 1993). In addition, immunization of mice and canines with OspA resulting in significant titers of LA-2 equivalent serum antibody accurately predicts protection from tick transmission of infection (Golde, 1997). Insufficient levels of LA-2 equivalent antibody result in a lack of protection in the face of high serum antibody titers to OspA (Johnson et al., 1995).

SUMMARY OF THE INVENTION

The present invention is drawn to altered forms of OspA from *Borrelia burgdorferi* that have increased conformational stability while maintaining at least some of the antigenicity of wild type OspA. In some embodiments, the altered OspA polypeptide has decreased cross-reactivity with hLFA-1, as compared to the corresponding unaltered OspA polypeptide. The altered OspA polypeptides can comprise almost all or only a portion of the native OspA polypeptide. In some embodiments, the altered OspA polypeptide can be part of a cocktail which includes one or more other proteins, such as, for example, other *Borrelia burgdorferi* polypeptides including OspA, OspB, OspC, OspD, p93 and p41. In other embodiments, the altered OspA polypeptide can be part of a chimeric protein, such as those described in U.S. Pat. No. 6,248,562, the entire teachings of which are incorporated herein by reference.

In one embodiment, the altered OspA polypeptides of the present invention comprise an amino acid sequence of OspA protein from *Borrelia burgdorferi* from about residue 139 to about residue 273, wherein the sequence includes at least one alteration selected from the group consisting of: residue 139 changed to methionine, residue 160 changed to tyrosine, residue 189 changed to methionine and combinations thereof. In other embodiments, the altered OspA polypeptides of the present invention comprise an amino acid sequence of OspA protein from *Borrelia burgdorferi* from about residue 131 to about residue 273 or from about residue 17 to about residue 273. The OspA polypeptides of the present invention can comprise longer or shorter fragments of OspA protein. The numbering of the residues corresponds to the numbering of SEQ ID NO:7 (OspA from B31).

In another embodiment, the OspA polypeptides of the present invention comprise an amino acid sequence of OspA protein from *Borrelia burgdorferi* from about residue 160 to about residue 170, wherein the sequence includes at least two alterations selected from the group consisting of: residue 165 changed to phenylalanine, residue 166 changed to threonine and residue 170 changed to lysine. In yet another embodiment, the OspA polypeptides of the present invention comprise an amino acid sequence of OspA protein from a sensu stricto strain of *Borrelia burgdorferi* from about residue 160 to about residue 170, wherein the sequence includes at least one alteration selected from the group consisting of: residue 165 changed to phenylalanine, residue 166 changed to threonine, residue 170 changed to lysine and combinations thereof. In other embodiments, the altered OspA polypeptides of the present invention comprise an amino acid sequence of OspA protein from *Borrelia burgdorferi* from about residue 150 to about residue 180 or from about residue 17 to about residue 273. The OspA polypeptides of the present invention can comprise longer or shorter fragments of OspA protein. The numbering of the residues corresponds to the numbering of SEQ ID NO:7.

The polypeptides of the present invention include polypeptides selected from the group consisting of: SEQ ID NO:96, 98, 100, 102, 104, 106, 108, 110, 112, 114 and 116.

The present invention is also drawn to polynucleotides encoding the amino acid sequences described herein, such as polynucleotides encoding OspA polypeptides from *Borrelia burgdorferi* from about residue 131 to about residue 273, wherein the sequence encodes at least one alteration selected from the group consisting of: codon 139 encoding methionine, codon 160 encoding tyrosine, codon 189 encoding methionine and combinations thereof. The polynucleotide encoding OspA polypeptides of the present invention can encode longer or shorter fragments of OspA protein. The numbering of the residues corresponds to the numbering of SEQ ID NO:7.

In another embodiment, the polynucleotide encodes an amino acid sequence of an OspA polypeptide from *Borrelia burgdorferi* from about residue 160 to about residue 170, wherein the sequence encodes at least one alteration selected from the group consisting of: codon 165 encoding phenylalanine, codon 166 encoding threonine, codon 170 encoding lysine and combinations thereof. The polynucleotides which encode OspA polypeptides of the present invention can encode longer or shorter fragments of OspA protein. The numbering of the residues corresponds to the numbering of SEQ ID NO:7.

The polynucleotides of the present invention include a polynucleotide selected from the group consisting of: SEQ ID NO:95, 97, 99, 101, 103, 105, 107, 109, 111, 113 and 115.

The present invention is also drawn to a method of generating an altered *Borrelia burgdorferi* OspA polypeptide with increased conformational stability, as compared to the corresponding unaltered *Borrelia burgdorferi* OspA polypeptide. The method comprises selecting a polynucleotide encoding a *Borrelia burgdorferi* OspA polypeptide that includes at least one of residues 139, 160 and 189, wherein the numbering corresponds to the numbering of SEQ ID NO:7. The polynucleotide is altered such that at least one of the following alterations is present: residue 139 is changed to methionine, residue 160 is changed to tyrosine and residue 189 is changed to methionine or a combination thereof. In one embodiment, both the alteration at residue 160 and the alteration at 189 is made. In another embodiment, the alterations at all three residues are made. The altered polynucleotide is expressed, thereby generating an altered *Borrelia burgdorferi* OspA polypeptide with increased conformational stability, as compared to the corresponding unaltered *Borrelia burgdorferi* OspA polypeptide.

In another embodiment, the present invention is drawn to a method of generating an altered *Borrelia burgdorferi* OspA polypeptide with reduced cross-reactivity with an hLFA-1 molecule, as compared to the corresponding unaltered *Borrelia burgdorferi* OspA polypeptide. The method comprises selecting a polynucleotide encoding an OspA polypeptide from *Borrelia burgdorferi* that includes at least one of residues 165, 166 and 170, wherein the numbering corresponds to the numbering of SEQ ID NO:7. The polynucleotide is altered such that at least one alteration from the following list is present: residue 165 is changed to phenylalanine, residue 166 is changed to threonine and residue 170 is changed to lysine or combination thereof. The altered polynucleotide is expressed, thereby generating an altered *Borrelia burgdorferi* OspA polypeptide with reduced cross-reactivity with the hLFA-1 molecule, as compared to the corresponding unaltered *Borrelia burgdorferi* OspA polypeptide.

The present invention is also drawn to an expression vector which comprises an isolated DNA encoding an altered *Borrelia* OspA protein. The present invention also encompasses a host cell which comprises a recombinant nucleic acid that encodes an altered OspA protein as described herein.

The present invention is also drawn to a method of delivering the altered *Borrelia* OspA polypeptides described herein. In one embodiment, the method comprises administering the altered OspA polypeptide in a physiologically-acceptable carrier to an individual. As a result of the administration of the altered OspA protein, the individual develops at least some immune response to the protein. As an example, the individual generates a humoral immune response, wherein antibodies that recognize at least a portion of said polypeptide are produced by the individual. In a preferred embodiment, the individual generates an immunoprotective response, for example, by generating antibodies that recognize the LA-2 epitope.

The present invention is also drawn to a method of delivering a nucleic acid which encodes an altered OspA polypeptide described herein. In one embodiment, the method comprises administering the nucleic acid in a physiologically-acceptable carrier to an individual. As a result of the administration of the nucleic acid, the altered OspA polypeptide is at least transiently expressed and the individual develops at least some immune response, preferably an immunoprotective response to the altered OspA protein encoded by the nucleic acid. As an example, the individual generates a humoral immune response, wherein antibodies that recognize at least a portion of the altered OspA polypeptide produced from the nucleic acid are produced by the individual. In a preferred embodiment, the individual generates an immunoprotective response, for example, by generating antibodies that recognize the LA-2 epitope.

The invention also encompasses methods of using the proteins described herein in diagnostic assays. In one embodiment, the method can be used to detect the presence of OspA specific antibodies in a host sample of interest. The method comprises contacting a host sample of interest with the altered protein, under conditions wherein antibodies, if present in the host sample, bind to the altered protein, forming antigen-antibody complexes. The antigen-antibody complexes are then detected using standard methods known in the art.

The present invention is also drawn to a diagnostic kit comprising the altered polypeptides described herein. The kit comprises an altered *Borrelia burgdorferi* OspA protein as described herein. The kit also includes reagents for detecting antibody-antigen complexes that are formed between the OspA altered protein and antibodies that are present in the user-supplied host sample.

As a result of the present invention, OspA proteins, or fragments thereof, having either increased conformational stability while maintaining at least some antigenicity, or having reduced cross-reactivity to hLFA-1, are available for use in research, vaccines and/or diagnostic assays. Furthermore, as a result of the present invention, nucleic acids encoding OspA polypeptides having reduced cross-reactivity with hLFA-1 are available for research and vaccines. The altered OspA polypeptides of the present invention are expected to allow for improved vaccines having fewer side effects.

For a better understanding of the present invention together with other and further objects, reference is made to the following description, taken together with the accompanying drawings.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2A-2D depict comparison of the antigenic domains depicted in FIG. 1, for OspA in nine strains of *B. burgdorferi*. FIG. 2A, Domain 1: B-31 (SEQ ID NO: 131); TRo (SEQ ID NO:132); K48 (SEQ ID NO:133); DK29 (SEQ ID NO:134); P-Gau (SEQ ID NO:135); PKo (SEQ ID NO:136); IP3 (SEQ ID NO:137); IP90 (SEQ ID NO:138); and 25015 (SEQ ID NO:139). FIG. 2B, Domain 2: B-31 (SEQ ID NO: 140); TRo (SEQ ID NO:141); K48 (SEQ ID NO:142); DK29 (SEQ ID NO:143); P-Gau (SEQ ID NO:144); PKo (SEQ ID NO:145); IP3 (SEQ ID NO:146); IP90 (SEQ ID NO:147); and 25015 (SEQ ID NO:148). FIG. 2C, Domain 3: B-31 (SEQ ID NO: 149); TRo (SEQ ID NO:150); K48 (SEQ ID NO:151); DK29 (SEQ ID NO:152); P-Gau (SEQ ID NO:153); PKo (SEQ ID NO:154); IP3 (SEQ ID NO:155); IP90 (SEQ ID NO:156); and 25015 (SEQ ID NO:157). FIG. 2D, Domain 4: B-31 (SEQ ID NO: 158); TRo (SEQ ID NO:159); K48 (SEQ ID NO:160); DK29 (SEQ ID NO:161); P-Gau (SEQ ID NO:162); PKo (SEQ ID NO:163); IP3 (SEQ ID NO:164); IP90 (SEQ ID NO:165); and 25015 (SEQ ID NO:166).

FIG. 4 depicts the amino acid alignment of residues 200 through 220 for OspAs from strains B31 (SEQ ID NO:167) and K48 (SEQ ID NO:168) as well as for the site-directed mutants 613 (SEQ ID NO:169), 625 (SEQ ID NO:170), 640 (SEQ ID NO:171), 613/625 (SEQ ID NO:172), and 613/640 (SEQ ID NO:173). Arrow indicates Trp216. Amino acid changes are underlined.

FIGS. 6A and 6B depict the nucleic acid sequence of OspA-B31 (SEQ ID NO:6), and the encoded protein sequence (SEQ ID NO:7).

FIGS. 7A, 7B and 7C depict the nucleic acid sequence of OspA-K48 (SEQ ID NO:8), and the encoded protein sequence (SEQ ID NO:9).

FIGS. 8A, 8B and 8C depict the nucleic acid sequence of OspA-PGau (SEQ ID NO:10), and the encoded protein sequence (SEQ ID NO:11).

FIGS. 9A and 9B depict the nucleic acid sequence of an OspA gene (SEQ ID NO:127 and its encoded protein sequence (SEQ ID NO:128).

FIGS. 10A, 10B and 10C depict the nucleic acid sequence of the OspA-K48/OspA-PGau chimer (SEQ ID NO:28) and the encoded chimeric protein sequence (SEQ ID NO:29).

FIGS. 11A, 11B and 11C depict the nucleic acid sequence of the OspA-B31/OspA-PGau chimer (SEQ ID NO:30) and the encoded chimeric protein sequence (SEQ ID NO:31).

FIGS. 12A and 12B depict the nucleic acid sequence of the OspA-B31/OspA-K48 chimer (SEQ ID NO:32) and the encoded chimeric protein sequence (SEQ ID NO:33).

FIGS. 13A, 13B and 13C depict the nucleic acid sequence of the OspA-B31/OspA-25015 chimer (SEQ ID NO:34) and the encoded chimeric protein sequence (SEQ ID NO:35).

FIGS. 14A, 14B and 14C depict the nucleic acid sequence of the OspA-K48/OspA-B31/OspA-K48 chimer (SEQ ID NO:36) and the encoded chimeric protein sequence (SEQ ID NO:37).

FIGS. 15A, 15B and 15C depict the nucleic acid sequence of the OspA-B31/OspA-K48/OspA-B31/OspA-K48 chimer (SEQ ID NO:38) and the encoded chimeric protein sequence (SEQ ID NO:39).

FIGS. 16A, 16B and 16C depict the nucleic acid sequence of the OspA-B31/OspB-B31 chimer (SEQ ID NO:40) and the encoded chimeric protein sequence (SEQ ID NO:41).

FIGS. 17A, 17B, 17C, 17D, 17E, 17F, 17G, 17H, 17I, 17J, 17K, 17L, 17M, 17N, 17O, and 17P, depict an alignment of the nucleic acid sequences for OspA-B31 (SEQ ID NO:6), OspA-pKa1 (SEQ ID NO:42), OspA-N40 (SEQ ID NO:43), OspA-ZS7 (SEQ ID NO:44), OspA-25015 (SEQ ID NO:12), OspA-pTrob (SEQ ID NO:45), OspA-K48 (SEQ ID NO:8), OspA-Hei (SEQ ID NO:46), OspA-DK29 (SEQ ID NO:21), OspA-Ip90 (SEQ ID NO:22), OspA-pBo (SEQ ID NO:23), OspA-Ip3 (SEQ ID NO:24), OspA-Pko (SEQ ID NO:25), OspA-ACAI (SEQ ID NO:26), and OspA-PGau (SEQ ID NO:10). Nucleic acids which are identical to those in the lead nucleic acid sequence (here, OspA-B31) are represented by a period (.); differing nucleic acids are shown in lower case letters.

FIGS. 18A and 18B depict the nucleic acid sequence of the OspA-Tro/OspA-Bo chimer (SEQ ID NO:47) and the encoded chimeric protein sequence (SEQ ID NO:48).

FIGS. 19A and 19B depict the nucleic acid sequence of the OspA-PGau/OspA-Bo chimer (SEQ ID NO:49) and the encoded chimeric protein sequence (SEQ ID NO:50).

FIGS. 20A and 20B depict the nucleic acid sequence of the OspA-B31/OspA-PGau/OspA-B31/OspA-K48 chimer (SEQ ID NO:53) and the encoded chimeric protein sequence (SEQ ID NO:54).

FIGS. 21A and 21B depict the nucleic acid sequence of the OspA-PGau/OspA-B31/OspA-K48 chimer (SEQ ID NO:51) and the encoded chimeric protein sequence (SEQ ID NO:52).

FIGS. 30A, 30B and 30C depict the nucleic acid sequence of the OspC-B31 (bp 55-633)/OspA-B31 (bp 52-822) chimer (SEQ ID NO:55) and the encoded chimeric protein sequence (SEQ ID NO:56).

FIGS. 31A, 31B and 31C depict the nucleic acid sequence of the OspC-B31 (bp 55-624)/OspA-B31 (bp 52-822) chimer (SEQ ID NO:57) and the encoded chimeric protein sequence (SEQ ID NO:58).

FIGS. 32A, 32B and 32C depict the nucleic acid sequence of the OspC-C2 (bp 55-612)/OspA-B31 (bp 52-822) chimer (SEQ ID NO:59) and the encoded chimeric protein sequence (SEQ ID NO:60).

FIGS. 33A, 33B, and 33C depict the nucleic acid sequence of the OspC-B31 (bp 55-633)/OspA-B31 (bp 52-651)/OspA-K48 (bp 652-820) chimer (SEQ ID NO:61) and the encoded chimeric protein sequence (SEQ ID NO:62).

FIGS. 34A, 34B and 34C depict the nucleic acid sequence of the OspC-C2 (bp 55-612)/OspA-B31 (bp 52-651)/OspA-K48 (bp 652-820) chimer (SEQ ID NO:63) and the encoded chimeric protein sequence (SEQ ID NO:64).

FIGS. 35A, 35B and 35C depict the nucleic acid sequence of the OspC-B31 (bp 55-633)/OspA-B31 (bp 52-651)/OspA-Pko (bp 652-820) chimer (SEQ ID NO:65) and the encoded chimeric protein sequence (SEQ ID NO:66).

FIGS. 36A, 36B and 36C depict the nucleic acid sequence of the OspC-C2 (bp 55-612)/OspA-B31 (bp 52-651)/OspA-Pko (bp 652-820) chimer (SEQ ID NO:67) and the encoded chimeric protein sequence (SEQ ID NO:68).

FIGS. 37A, 37B and 37C depict the nucleic acid sequence of the OspC-B31 (bp 55-633)/OspA-K48 (bp 52-654)/OspA-Tro (bp 655-819) chimer (SEQ ID NO:69) and the encoded chimeric protein sequence (SEQ ID NO:70).

FIGS. 38A, 38B and 38C depict the nucleic acid sequence of the OspC-C2 (bp 55-612)/OspA-K48 (bp 52-654)/OspA-Tro (bp 655-819) chimer (SEQ ID NO:71) and the encoded chimeric protein sequence (SEQ ID NO:72).

FIGS. 39A, 39B, 39C depict the nucleic acid sequence of the OspC-C12 (bp 55-612)/OspA-B31 (bp 88-450)/OspA-Pko (bp 451-537)/OspA-B31 (bp 538-822) chimer (SEQ ID NO:73) and the encoded chimeric protein sequence (SEQ ID NO:74).

FIGS. 40A, 40B and 40C depict the nucleic acid sequence of the OspC-Pko (bp 55-639)/OspA-B31 (bp 88-450)/OspA-Pko (bp 451-537)/OspA-B31 (bp 538-651)/OspA-K48 (bp 652-825) chimer (SEQ ID NO:75) and the encoded chimeric protein sequence (SEQ ID NO:76).

FIGS. 41A, 41B and 41C depict the nucleic acid sequence of the OspC-Tro (bp 55-624)/OspA-B31 (bp 88-450)/OspA-Pko (bp 451-537)/OspA-B31 (bp 538-651)/OspA-Pko (bp 652-822) chimer (SEQ ID NO:77) and the encoded chimeric protein sequence (SEQ ID NO:78).

FIGS. 42A and 42B depict the nucleic acid sequence of the OspC-B31 (bp 55-633)/OspA-B31 (bp 394-820) chimer (SEQ ID NO:79) and the encoded chimeric protein sequence (SEQ ID NO:80).

FIGS. 43A and 43B depict the nucleic acid sequence of the OspC-B31 (bp 55-631)/OspA-B31 (bp 394-651)/OspA-K48 (bp 652-820) chimer (SEQ ID NO:81) and the encoded chimeric protein sequence (SEQ ID NO:82).

FIGS. 44A and 44B depict the nucleic acid sequence of the OspC-B31 (bp 55-633)/OspA-B31 (bp 394-651)/OspA-Pko (bp 652-820) chimer (SEQ ID NO:83) and the encoded chimeric protein sequence (SEQ ID NO:84).

FIGS. 45A and 45B depict the nucleic acid sequence of the OspC-B31 (bp 55-633)/OspA-K48 (bp 394-654)/OspA-Tro (bp 655-819) chimer (SEQ ID NO:85) and the encoded chimeric protein sequence (SEQ ID NO:86).

FIGS. 46A, 46B and 46C depict the nucleic acid sequence of the OspC-B31 (bp 55-633)/OspA-B31 (bp 88-450)/OspA-Pko (bp 451-537)/OspA-B31 (bp 541-651)/OspA-Pko (bp 652-822) chimer (SEQ ID NO:87) and the encoded chimeric protein sequence (SEQ ID NO:88).

FIGS. 47A, 47B, and 47C depict the nucleic acid sequence of the OspC-C2 (bp 55-612)/OspA-B31 (bp 88-450)/OspA-Pko (bp 451-537)/OspA-B31 (bp 541-651)/OspA-Pko (bp 652-822) chimer (SEQ ID NO:89) and the encoded chimeric protein sequence (SEQ ID NO:90).

FIGS. 48A and 48B depict the nucleic acid and encoded protein sequence of an R139M altered OspA (SEQ ID NO:95 and 96).

FIGS. 49A and 49B depict the nucleic acid and encoded protein sequence of an E160Y altered OspA (SEQ ID NO:97 and 98).

FIGS. 50A and 50B depict the nucleic acid and encoded protein sequence of an R139M, E160Y altered OspA (SEQ ID NO:99 and 100).

FIGS. 51A and 51B depict the nucleic acid and encoded protein sequence of an E160Y altered OspA (SEQ ID NO:101 and 102).

FIGS. 52A and 52B depict the nucleic acid and encoded protein sequence of an R139M, E160Y, K189M altered OspA (SEQ ID NO:103 and 104).

FIGS. 53A and 53B depict the nucleic acid and encoded protein sequence of an Y165F altered OspA (SEQ ID NO:105 and 106).

FIGS. 54A and 54B depict the nucleic acid and encoded protein sequence of an Y165F, V166T altered OspA (SEQ ID NO:107 and 108).

FIGS. 55A and 55B depict the nucleic acid and encoded protein sequence of a V166T altered OspA (SEQ ID NO:109 and 110).

FIGS. 56A and 56B depict the nucleic acid and encoded protein sequence of a V166T, T170K altered OspA (SEQ ID NO:111 and 112).

FIGS. 57A and 57B depict the nucleic acid and encoded protein sequence of an Y165F, V166T, T170K altered OspA (SEQ ID NO:113 and 114).

FIGS. 58A and 58B depict the nucleic acid and encoded protein sequence of an R139M, E160Y, K189M, Y165F, V166T, T170K altered OspA (SEQ ID NO:115 and 116).

DETAILED DESCRIPTION OF THE INVENTION

Figure 1:
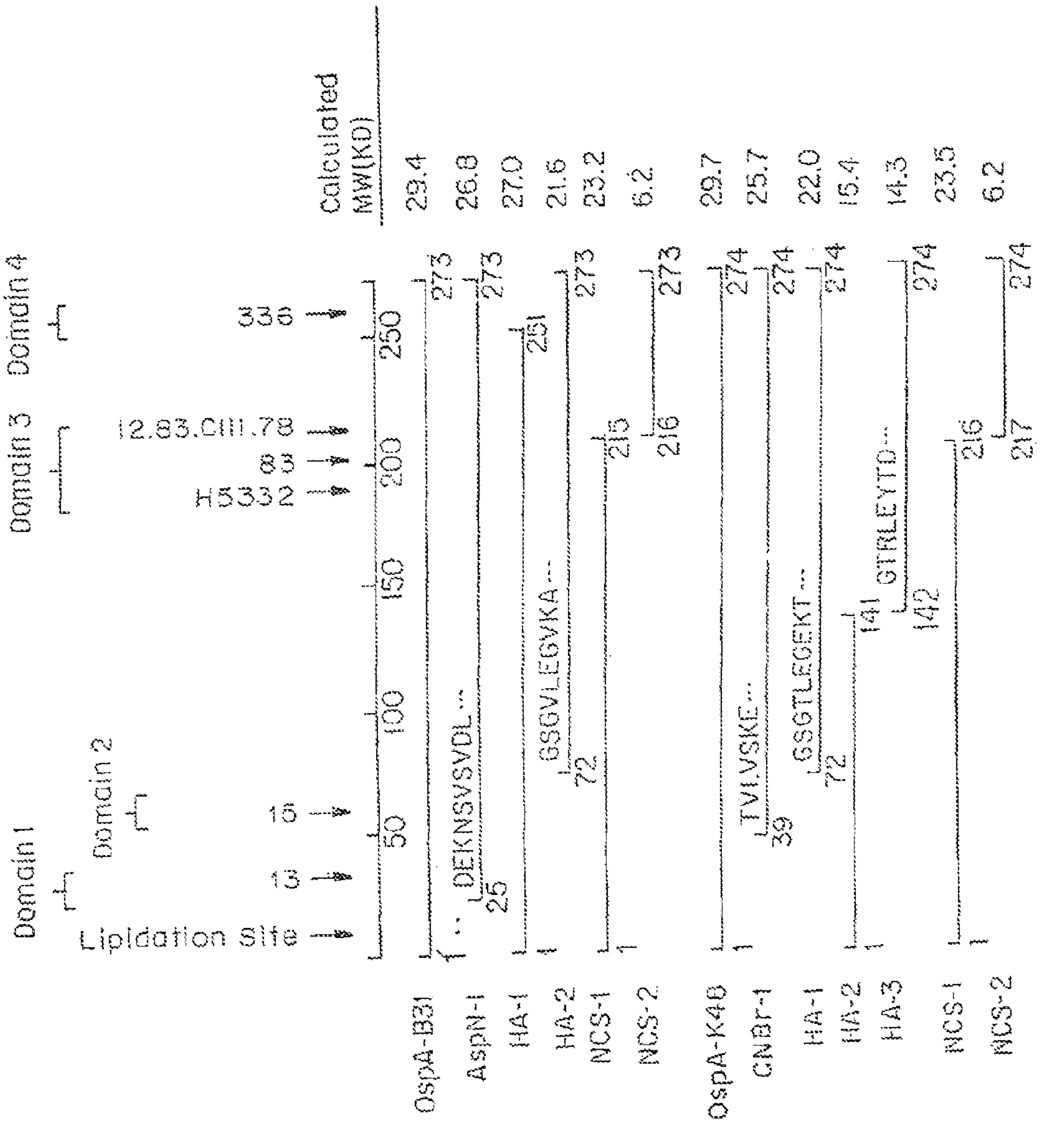
FIG. 1 summarizes peptides and antigenic domains localized by proteolytic and chemical fragmentation of OspA.
Figure 3:
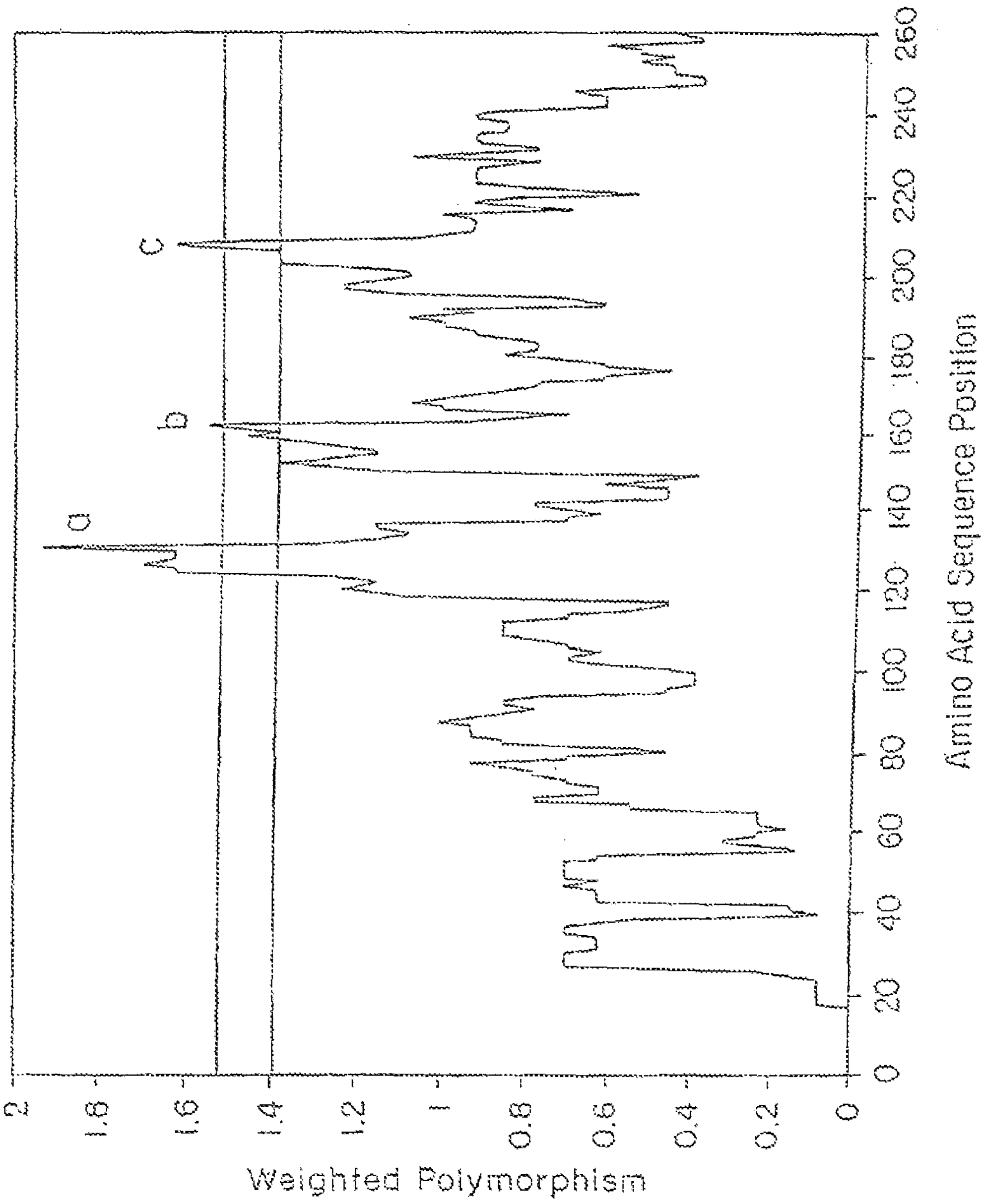
FIG. 3 is a graph depicting a plot of weighted polymorphism versus amino acid position among 14 OspA variants. The marked peaks are: a) amino acids 132-145; b) amino acids 163-177; c) amino acids 208-221. The lower dotted line at polymorphism value 1.395 demarcates statistically significant excesses of polymorphism at p=0.05. The upper dotted line at 1.520 is the same, except that the first 29 amino acids at the monomorphic—terminus have been removed from the original analysis.
Figure 5:
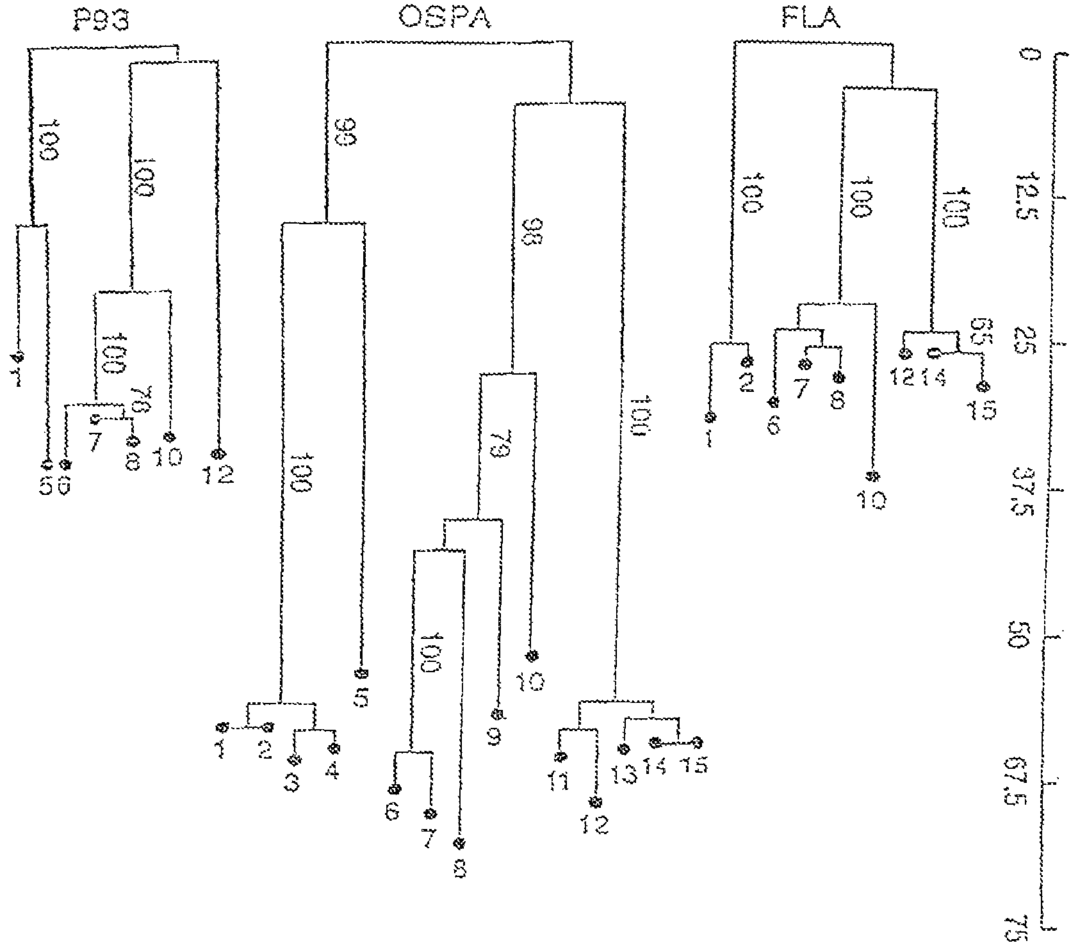
FIG. 5 depicts a phylogenetic tree for strains of *Borrelia* described in Table I. The strains are as follows: 1=B31; 2=Pka1; 3=ZS7; 4=N40; 5=25015; 6=K48; 7=DK29; 8=PHei; 9=Ip90; 10=PTrob; 11=ACAI; 12=PGau; 13=Ip3; 14=PBo; 15=Pko.

A description of preferred embodiments of the invention follows.

The present invention is drawn to altered forms of OspA from *Borrelia burgdorferi* that have increased conformational stability while maintaining antigenicity, as indicated, for example, by the ability to be bound by the LA-2 monoclonal antibody. In some embodiments, the altered OspA polypeptides also have decreased cross-reactivity with hLFA-1. The altered OspA polypeptides can comprise all (with the exception of the alterations described herein) or a portion, such as the C-terminal portion, of a wild type OspA polypeptide. Applicants have found that some forms of the OspA protein, such as truncated versions of OspA, do not elicit a strong immunoprotective response when administered to an animal even when the OspA polypeptide has the immunoprotective LA-2 epitope sequence.

The structure for recombinant OspA has been determined to 1.95□ resolution in a binary complex with the Fab fragment of the nonprotective mouse mAb184.1, which is reactive with the OspA-terminus (Li et al., *Proc. Natl. Acad. Sci. U.S.A.* 94:3584-3589 (1997)). The OspA polypeptide folds into 21 consecutive antiparallel β-strands followed by a C-terminal α-helix. The structure is conveniently described as two discrete folded domains, an N-terminal sandwich domain and a C-terminal barrel domain, connected by a long central β-sheet. One set of altered polypeptides described herein is designed to remove buried charges and/or salt bridges in the OspA C-terminal portion and replace them with residues that promote hydrophobic interactions.

Accordingly, in one embodiment, the altered OspA polypeptides of the present invention comprise altered OspA protein or polypeptides from *Borrelia burgdorferi* from about residue 139 to about residue 273, wherein the sequence includes at least one alteration selected from the group consisting of: residue 139 changed to methionine, residue 160 changed to tyrosine, residue 189 changed to methionine and combinations thereof. The numbering of the residues corresponds to the numbering of SEQ ID NO:7. In one embodiment, the altered OspA polypeptide has a tyrosine at residue position 160 and a methionine at residue position 189. These alterations have been found to stabilize the conformation of the immunoprotective LA-2 epitope in LA-2-containing OspA polypeptides. In another embodiment, the altered OspA polypeptide has a methionine at residue position 139, a tyrosine at residue position 160 and a methionine at residue position 189. In other embodiments, the altered OspA polypeptides have both increased conformational stability and reduced cross-reactivity to the hLFA-1 protein.

For the alterations at positions 139, 160 and 189, the altered OspA sequence can be from any Lyme borreliosis strain of *Borrelia burgdorferi*, such as strains from *Borrelia burgdorferi* sensu stricto, *Borrelia afzelii* and *Borrelia garinii*. Strains of *Borrelia burgdorferi* are well known to those of skill in the art. For example, strains of *Borrelia burgdorferi* sensu stricto include B31, strains of *Borrelia afzelii* include Pgau and Pko and strains of *Borrelia garinii* include K48.

In one embodiment, the OspA polypeptides of the present invention comprise an amino acid sequence of OspA protein from *Borrelia burgdorferi* from about residue 160 to about residue 170, wherein the sequence includes at least two alterations selected from the group consisting of: residue 165 changed to phenylalanine, residue 166 changed to threonine and residue 170 changed to lysine, wherein the numbering of the residues corresponds to the numbering of SEQ ID NO:7. In another embodiment, the OspA polypeptides of the present invention comprise an amino acid sequence of OspA protein from a sensu stricto strain of *Borrelia burgdorferi* from about residue 160 to about residue 170, wherein the sequence includes at least one alteration selected from the group consisting of: residue 165 changed to phenylalanine, residue 166 changed to threonine, residue 170 changed to lysine and combinations thereof. The numbering of the residues corresponds to the numbering of SEQ ID NO:7. In another embodiment, the altered OspA polypeptide has a phenylalanine at residue position 165 and a threonine at residue position 166. In still another embodiment, the altered OspA polypeptide has a phenylalanine at residue position 165, a threonine at residue position 166 and a lysine at residue position 170. In yet another embodiment, the altered OspA polypeptide includes all of the alterations described herein. In this embodiment, the altered OspA polypeptide has a methionine at residue position 139, a tyrosine at residue position 160, a methionine at residue position 189, a phenylalanine at residue position 165, a threonine at residue position 166 and a lysine at residue position 170.

This invention also pertains to polypeptides comprising SEQ ID NO:96, 98, 100, 102, 104, 106, 108, 110, 112, 114, or 116. The altered OspA polypeptides of the invention can be partially or substantially purified (e.g., purified to homogeneity), and/or substantially free of other proteins.

The present invention is also drawn to polynucleotides encoding the amino acid sequences described herein. As defined herein, the term "polynucleotide" refers to a nucleotide multimer or oligomer which is composed of deoxyribonucleotides or ribonucleotides, or a combination thereof, having from a few, e.g., 2-20, to many, e.g., 20 to several thousand or more, nucleotides. As such, polynucleotides include nucleic acids of any length and further encompass both naturally-occurring and synthetic oligonucleotides and polynucleotides.

The polynucleotides of the present invention include polynucleotides encoding OspA polypeptides from *Borrelia burgdorferi* from about residue 139 to about residue 189, wherein the sequence encodes at least one alteration selected from the group consisting of: codon 139 encoding methionine, codon 160 encoding tyrosine, codon 189 encoding methionine and combinations thereof. The numbering of the residues corresponds to the numbering of SEQ ID NO:7. As described above for the polypeptides, in the case of alterations at positions 139, 160 and 189, the polynucleotide encoding the altered OspA sequence can be from any Lyme borreliosis strain of *Borrelia burgdorferi.*

In another embodiment, the polynucleotide encodes an amino acid sequence of an OspA polypeptide from *Borrelia burgdorferi* from about residue 160 to about residue 170, wherein the sequence encodes at least one alteration selected from the group consisting of: codon 165 encoding phenylalanine, codon 166 encoding threonine, codon 170 encoding lysine and combinations thereof. The numbering of the residues corresponds to the numbering of SEQ ID NO:7.

The polynucleotides of the present invention include polynucleotides selected from the group consisting of: SEQ ID NO:95, 97, 99, 101, 103, 105, 107, 109, 111, 113 and 115.

The altered OspA polypeptides of the present invention can be derived from OspA molecules comprising fragments, derivatives, analogs, variants and mutants of the OspA protein (modified OspA) or can be fragmented, derivatized, or otherwise altered after having the alterations described herein inserted. These modified OspA molecules possess OspA antigenic activity.

The present invention is also drawn to a method of generating an altered *Borrelia burgdorferi* OspA polypeptide with increased conformational stability, as compared to the corresponding unaltered *Borrelia burgdorferi* OspA polypeptide. The method comprises selecting a polynucleotide encoding a *Borrelia burgdorferi* OspA polypeptide that includes residues 139, 160 and 189, wherein the numbering corresponds to the numbering of SEQ ID NO:7. The polynucleotide is altered such that residue 139 is methionine, residue 160 is tyrosine or residue 189 is methionine or combination thereof. The altered polynucleotide is expressed, thereby generating an altered *Borrelia burgdorferi* OspA polypeptide with increased conformational stability compared to the corresponding unaltered *Borrelia burgdorferi* OspA polypeptide. Methods of altering a polynucleotide are described below and in the Exemplification and are well known to those of skill in the art. Methods of expressing the altered polypeptides of the invention are also described below and in the Exemplification and are well known to those of skill in the art.

Residues 165-173 on β-strand 13 of OspA have been implicated in induction of Lyme-related arthritis (Gross D. M. et al., *Science* 281:703-706 (1998)). This region has homology to residues 332-340 of hLFA-1, suggesting that this protein has a cross-reactive T cell epitope (YVLEGTLTA-B31 (SEQ ID NO:129 and YVIEGTSKQ-hLFA-1 (SEQ ID NO:130), respectively). Although *B. burgdorferi* sensu stricto is generally believed to be more arthritogenic that other *Borrelia* strains, a recent study of ospA alleles in synovial fluid of patients with Lyme arthritis indicates that *B. garinii* and *B. afzelii* may also cause arthritis (Eiffert, L. F. et al., Scand. J. Infect. Dis. 30:265-268 (1998)).

One way to eliminate the cross-reactive sequence is to replace the β-13 region of OspA-B31 (YVLEGTLTA (SEQ ID NO:129)) with an analogous region from a strain that does not possess the same sequence, such as that from a *B. Afzelii* strain, e.g., Pgau or Pko (U.S. patent application entitled "Recombinant Constructs of *Borrelia burgdorferi*" by Luft et al., filed on Aug. 7, 2001, the entire teachings of which are incorporated herein by reference).

Accordingly, in another embodiment, the present invention is drawn to a method of generating an altered *Borrelia burgdorferi* OspA polypeptide with reduced cross-reactivity with the hLFA-1 molecule, as compared to the corresponding unaltered *Borrelia burgdorferi* OspA polypeptide. The method comprises selecting a polynucleotide encoding an OspA polypeptide from *Borrelia burgdorferi* that includes residues 165, 166 and 170, wherein the numbering corresponds to the numbering of SEQ ID NO:7. The polynucleotide is altered such that residue 165 is changed to phenylalanine, residue 166 is changed to threonine or residue 170 is changed to lysine or combination thereof. The altered polynucleotide is expressed, thereby generating an altered *Borrelia burgdorferi* OspA polypeptide with reduced cross-reactivity with the hLFA-1 molecule compared to the corresponding unaltered *Borrelia burgdorferi* OspA polypeptide. In another embodiment, an altered OspA polypeptide having reduced cross-reactivity to hLFA-1 while retaining the ability to be bound by LA-2 is generated. In that embodiment, for example, residue 130 is methionine, residue 160 is tyrosine, residue 165 is phenylalanine, residue 166 is threonine, residue 170 is lysine and residue 189 is methionine. Polynucleotides encoding *Borrelia burgdorferi* OspA polypeptides can be selected as described herein.

In one embodiment, the altered OspA polypeptide includes the minimal sequence that includes the positions of the alterations. For example, the altered polypeptide can comprise OspA from about residue 139 to about residue 189, wherein the numbering corresponds to SEQ ID NO:7. In another embodiment, the altered polypeptide can comprise OspA from about residue 165 to about residue 170, wherein the numbering corresponds to SEQ ID NO:7. The altered OspA polypeptides of the present invention also include larger fragments of OspA. For example, the altered OspA polypeptides include, but are not limited to, altered OspA polypeptides which comprise OspA from about residue 160 to about residue 170, OspA from about residue 150 to 180, OspA from about residue 131 to 273 or OspA from about residue 17 to 273. Methods of generating and expressing varying-sized fragments of OspA which incorporate one or more of the alterations described herein are described below and are well known to those of skill in the art.

As described herein, the OspA sequence used to generate the altered OspA polypeptide can itself be a chimeric OspA polypeptide, having two or more segments derived from OspA proteins from different genospecies or strains of *Borrelia*. The size of the altered OspA polypeptide can vary depending on the method used to generate the altered polypeptide and/or the purpose for which it is generated, and such altered OspA chimeric polypeptides can include fragments of OspA. The altered polypeptide can be part of a larger polypeptide, including additional OspA sequences on the N-terminus, the C-terminus or both termini. A fragment of OspA protein can encompass polypeptides that are only a part of the full-length OspA protein. Such OspA fragments typically include at least one of the altered residues described herein and possess at least some of the antigenicity of wild type OspA. OspA fragments can be produced by amino and/or carboxyl terminal deletions, as well as internal deletions. Fragments can also be produced by enzymatic digestion. Such modified OspA molecules can be tested for antigenic activity as described herein or using methods known in the art.

In some embodiments, the altered OspA polypeptide can be part of a cocktail with one or more other proteins, such as other *Borrelia burgdorferi* polypeptides, including but not limited to, OspA, OspB, OspC, OspD, p93 and p41. In other embodiments, the altered OspA polypeptide can be part of a larger molecule, such as a chimeric polypeptide, for example, as described in U.S. Pat. No. 6,248,562 and U.S. patent application entitled "Recombinant Constructs of *Borrelia burgdorferi*", by Luft et al., filed on Aug. 7, 2001. Such larger polypeptides can include amino acid sequences from other proteins including but not limited to, other *Borrelia burgdorferi* proteins and/or other proteins useful in generating fusion proteins for vaccine and/or immunodiagnostic methods. Additional components, for example, labels (a radioisotope, an epitope label (tag)(e.g., a hemagglutinin (HA) epitope, a hexahistidine tag), an affinity label (e.g., biotin, avidin), a spin label, an enzyme label, a fluorescent group, a chemiluminescent group) can be incorporated into the altered OspA polypeptides of the invention to assist in the isolation and/or purification of the polypeptide. For example, a hexahistidine tag would permit ready purification by nickel chromatography. These and other components can also be incorporated in the altered OspA polypeptides of the invention in order to extend the half life of the polypeptides. Methods of incorporating such components into the polypeptides of the invention are well known to those of skill in the art.

In one embodiment, the altered OspA polypeptide of the invention is a chimeric polypeptide. In a particular embodiment, the altered OspA polypeptide comprises the following: a) an amino acid sequence of a first OspA polypeptide from about residue 1 to about residue 164 from a first strain of *Borrelia burgdorferi*; b) an amino acid sequence of a second OspA polypeptide from about residue 165 to about residue 179 from a second strain of *Borrelia burgdorferi*, wherein said second strain is a different strain from said first strain; c) an amino acid sequence of a third OspA polypeptide from about residue 180 to about residue 216 from a third strain of *Borrelia burgdorferi*, wherein said third strain is a different strain from said second strain; d) an amino acid sequence of a fourth OspA polypeptide from about residue 217 to about residue 273 from a fourth strain of *Borrelia burgdorferi*, wherein said fourth strain is a different strain from said third strain; wherein the sequence includes at least one alteration selected from the group consisting of: residue 139 being methionine, residue 160 being tyrosine, residue 189 being methionine and combinations thereof, wherein the numbering corresponds to the numbering of SEQ ID NO:7.

Polypeptides described herein can be isolated from naturally-occurring sources, chemically synthesized or recombinantly produced. The altered OspA polypeptides of the present invention can be derived from naturally-occurring OspA molecules or from nucleic acids which encode such molecules. The OspA polypeptides of the present invention can comprise fragments, derivatives, analogs, variants and mutants of an OspA protein (modified OspA) and/or can be fragmented, derivatized or otherwise altered after having the alterations described herein inserted (also referred to as modified OspA). Such modified OspA molecules possess at least some OspA antigenic activity. According to the invention, the amino acid sequence of the altered OspA polypeptides of the invention can be that of a naturally-occurring protein or can comprise additional modifications. Such additional modifications include conservative and/or non-conservative amino acid substitutions, additions of one or more amino acids, and/or deletions of one or more amino acids. Such additional modifications should also preserve at least some activity of the encoded protein or polypeptide. For example, the further modified polypeptide or protein should have similar or improved conformational stability, similar or improved immunoprotective activity or reduced cross-reactivity to hLFA-1, as compared to the corresponding altered OspA polypeptide (i.e., the OspA polypeptide comprising one or more of the alterations described herein but not comprising the further modification(s)).

For example, the further modification(s) preferably preserve the three-dimensional configuration of an antibody binding site of the native protein such as the LA-2 binding site. The presence or absence of biological activity or activities can be determined by various functional assays as described herein or using methods that are known in the art, e.g., recognition using an ELISA assay, elicitation of an immune response (e.g., an immunoprotective response) in an animal. Appropriate amino acid alterations that fall within the scope of the invention can be made on the basis of several criteria, including hydrophobicity, basic or acidic character, charge, polarity, size, the presence or absence of a functional group (e.g., —SH or a glycosylation site), and aromatic character, provided that the resulting molecule has at least one of the alterations described herein and maintains increased conformational stability and/or reduced cross-reactivity to hLFA-1. Assignment of various amino acids to similar groups based on the properties above will be readily apparent to the skilled artisan; further appropriate amino acid changes can also be found in Bowie (*Science,* 247:1306-1310 (1990)).

"Variants" and "mutants" of OspA can be produced using in vitro and/or in vivo techniques well-known to those of skill in the art, for example, site-specific mutagenesis, and oligonucleotide mutagenesis. Manipulations of the OspA polypeptide sequence can be made at the protein level as well. Chemical modifications can be carried out using known techniques including but not limited to, specific chemical cleavage using cyanogen bromide, trypsin and/or papain. OspA can also be structurally modified and/or denatured, for example, using heat. In general, mutations can be conservative or non-conservative amino acid substitutions, amino acid insertions or amino acid deletions.

For example, a nucleic acid (e.g., DNA) encoding a modified OspA polypeptide can be prepared by site-directed mutagenesis of the nucleic acid (e.g., DNA) that encodes a wild type OspA. Site-directed (site-specific) mutagenesis allows the production of OspA variants through the use of specific oligonucleotide sequences that encode the DNA sequence of the desired mutation (e.g., alteration, deletion, insertion), as well as a sufficient number of adjacent nucleotides, to provide a primer sequence of sufficient size and sequence complexity to form a stable duplex on both sides of the desired mutation. Typically, a primer of about 20 to 25 nucleotides in length is preferred, with about 5 to 10 complementary residues on both sides of the mutation of the sequence being altered. In general, the techniques of site-specific mutagenesis are well known in the art, as exemplified by publications such as Edelman et al., DNA, 2:183, 1983. For example, a site-specific mutagenesis technique can employ a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam, 1981. This and other phage vectors are commercially available and their use is well known to those skilled in the art. A versatile and efficient procedure for the construction of oligonucleotide directed site-specific mutations in DNA fragments using M13-derived vectors was published by Zoller, M. J. and Smith, M., *Nucleic Acids Res.,* 10:6487-6500, 1982. In addition, plasmid vectors that contain a single-stranded phage origin of replication can be employed to obtain single-stranded DNA (see for example, Veira et al., *Meth Enzymol.,* 153:3, (1987)).

Alternatively, nucleotide substitutions can be introduced by synthesizing the appropriate DNA fragment in vitro, and amplifying it using PCR procedures known in the art.

In general, site-specific mutagenesis can be performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc Natl Acad Sci USA.,* 75:5765, 1978. This primer can then be annealed with the single-stranded protein sequence-containing vector, and subjected to DNA polymerizing enzymes, e.g., *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector can then be used to transform appropriate host cells such as JM 101 cells, and clones can be selected that include recombinant vectors bearing the mutated sequence arrangement. Thereafter, the mutated region can be removed and placed in an appropriate expression vector for protein production.

The PCR technique can be used in creating amino acid sequence variants of OspA. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers can be designed to overlap the position of the mutation and to contain the mutation; the sequence of the other primer is preferably identical to a stretch of sequence of the opposite strand of the plasmid, but this sequence can be located anywhere along the plasmid DNA. It is preferred, however, that the sequence of the second primer be located within 500 nucleotides from that of the first, such that in the end the entire amplified region of DNA bounded by the primers can be easily sequenced. PCR amplification using a primer pair like the one just described results in a population of DNA fragments that differ at the end position of the mutation specified by the primer.

The DNA fragments produced bearing the desired mutation can be used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

An additional method for preparing variants, cassette mutagenesis, is based on the technique described by Wells et al., *Gene,* 34:315, 1985. The starting material can be the plasmid (or vector) comprising the OspA DNA to be mutated. The codon(s) within the OspA to be mutated are identified. There must be unique restriction endonuclease sites on each side of the identified mutation site(s). If such restriction sites do not exist, they can be generated using the above-described oligonucleotide-mediated mutagenesis method to introduce them at appropriate locations in the OspA DNA or they can be generated using PCR and the desired primers as described in the Exemplification. After the restriction sites have been introduced into the plasmid, the plasmid is cut at these sites to linearize it. A double stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. The plasmid now contains the mutated OspA DNA sequence, and can be subcloned and/or expressed to produce the modified OspA polypeptide or protein.

The OspA encoding nucleic acid molecules (e.g., polynucleotides) of the present invention have at least one of the alterations described herein and generally hybridize under high stringency hybridization conditions to a polynucleotide-encoding OspA nucleic acid or fragment thereof from a sensu stricto strain of *Borrelia burgdorferi*, e.g., SEQ ID NO:7. In one embodiment, the OspA-encoding nucleic acid molecules (e.g., polynucleotides) of the present invention hybridize under high stringency hybridization conditions to a polynucleotide encoding OspA or fragment thereof from *Borrelia afzelii*, e.g., SEQ ID NO:10. In another embodiment, the OspA-encoding nucleic acid molecules (e.g., polynucleotides) of the present invention hybridize under high stringency hybridization conditions to a polynucleotide encoding OspA or fragment thereof from *Borrelia garinii*, e.g., SEQ ID NO:8. Thus, the polynucleotides and polypeptides of the present invention include modified versions of OspA as described herein.

Appropriate selective stringency conditions are known to those skilled in the art or can be found in standard texts such as *Current Protocols in Molecular Biology*, John Wiley & Sons, N.Y. (1989), 6.3.1-6.3.6. For example, stringent hybridization conditions include a sodium ion concentration of no more than 1 M and a temperature of at least 25° C. In one embodiment, conditions of 5×SSPE (750 mM NaCl, 50 mM NaPhosphate, 5 mM EDTA, pH 7.4) and a temperature of 25-30° C., or equivalent conditions, are suitable for specific hybridization. Equivalent conditions can be determined by varying one or more of the parameters, as is known in the art, while maintaining a similar degree of identity or similarity between the target nucleic acid molecule and the primer or probe used. Hybridizable nucleic acid molecules are useful as probes and primers for diagnostic applications.

Accordingly, the invention pertains to nucleic acid molecules which have a substantial identity with the nucleic acid molecules encoding the altered OspA polypeptides described herein wherein the nucleic acid encodes for one or more of the alterations described herein; particularly preferred are nucleic acid molecules which have at least about 90%, more preferably at least about 95% and most preferably at least about 98% identity with nucleic acid molecules described herein, wherein the nucleic acid encodes for at least one of the alterations described herein. Sequence identity can be determined using publically or commercially available sequence alignment algorithms, using, for example, default parameters.

Thus, DNA molecules which comprise a sequence which is different from the naturally-occurring nucleic acid molecule but which, due to the degeneracy of the genetic code, encode the same protein or polypeptide are encompassed by the present invention. The invention also encompasses variations of the nucleic acid molecules of the invention, such as those encoding portions, analogues or derivatives of the encoded protein or polypeptide. Such variations can be naturally-occurring, such as in the case of allelic variation, or non-naturally-occurring, such as those induced by various mutagens and mutagenic processes, so long as the nucleic acid molecule encodes at least one of the alterations described herein and the encoded protein has either increased conformational stability and/or decreased cross-reactivity to hLFA-1 (as compared to the corresponding unaltered protein) that is conferred by the alterations described herein. Intended variations include, but are not limited to, addition, deletion and/or substitution of one or more nucleotides which can result in conservative or non-conservative amino acid changes, including additions and deletions. Preferably, such nucleotide or amino acid variations are silent; that is, they do not alter one or more characteristics or activity of the encoded altered OspA protein or polypeptide. As used herein, activities of the encoded protein or polypeptide include, but are not limited to, binding function, antigenic function and conformational stability.

The invention also provides expression vectors containing a nucleic acid sequence described herein, operably linked to at least one regulatory sequence. Many such vectors are commercially available, and other suitable vectors can be readily prepared by the skilled artisan. “Operably linked” is intended to mean that the nucleic acid molecule is linked to a regulatory sequence in a manner which allows expression of the nucleic acid sequence. Regulatory sequences are art-recognized and are selected to produce the encoded polypeptide or protein. Accordingly, the term “regulatory sequence” includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual,* 2nd Ed., ed. Sambrook et al., (Cold Spring Harbor Laboratory Press, 1989) Chapters 16 and 17). Typically, expression constructs will contain one or more selectable markers, including but not limited to, the gene that encodes dihydrofolate reductase and the genes that confer resistance to neomycin, tetracycline, ampicillin, chloramphenicol, kanamycin or streptomycin.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12, BL21, DH5a strains), *Streptomyces, Pseudomonas, Serratia marcescens* and *Salmonella typhimurium*, insect cells (baculovirus) including *Drosophila*, fungal cells, such as yeast cells, plant cells and mammalian cells, such as thymocytes, Chinese hamster ovary cells (CHO) and COS cells.

Thus, a nucleic acid molecule comprising, for example SEQ ID NO:6 with at least one of the specific alterations described herein, or a nucleic acid molecule which encodes, for example SEQ ID NO:7 with at least one of the specific alterations described herein, can be used to produce a recombinant form of the protein via microbial or eukaryotic cellular processes. Ligating the nucleic acid molecule (e.g., polynucleotide) into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

The present invention also pertains to pharmaceutical compositions comprising polypeptides and other compounds described herein. For instance, a polypeptide or protein of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include gene therapy, rechargeable or biodegradable devices and slow release polymeric devices. The pharmaceutical compositions of this invention can also be administered as part of a combinatorial therapy with other agents.

The altered OspA proteins described herein can be produced so that they are highly soluble, hyper-produced in *E. coli*, and non-lipidated. In addition, the altered OspA proteins can be designed to begin or end in a suitable affinity tag (e.g., a His-tag) to facilitate purification. The recombinant proteins described herein have been constructed to maintain high levels of antigenicity and improved conformational stability.

The altered OspA proteins of the current invention are advantageous in that they retain at least some specific reactivity to monoclonal and/or polyclonal antibodies against wild-type *Borrelia* proteins, are immunogenic, and inhibit the growth or induce lysis of *Borrelia* in vitro. The proteins are particularly useful in immunodiagnostic assays. For example, proteins of the present invention can be used as reagents in assays to detect the presence of antibodies to native *Borrelia* in potentially infected individuals. These proteins can also be used as immunodiagnostic reagents, such as in dot blots, Western blots, enzyme-linked immunosorbent assays, or agglutination assays. The altered OspA proteins of the present invention can be produced by known techniques, such as by recombinant methodology, polymerase chain reaction, or mutagenesis.

Furthermore, the proteins of the current invention are useful as vaccine immunogens against *Borrelia* infection. One or more of the altered proteins can be combined with a physiologically acceptable carrier and administered to a vertebrate animal through standard methods (e.g., intravenously or intramuscularly, for example).

The altered forms of the OspA proteins described herein were bioengineered such that at least one immunoprotective domain of the protein was maintained. As described herein, antigenic refers to the ability of a compound to bind products of an immune response, such as antibodies, T-cell receptors or both. Such responses can be measured using standard antibody detection assays, such as ELISA or standard T-cell activation assays. In a preferred embodiment, the altered forms of OspA described herein elicit an immunoprotective response, for example, by eliciting antibodies that recognize the LA-2 epitope.

It is understood that the nucleic acids that encode the polypeptides that comprise the altered OspA protein can include extra nucleotides or fewer nucleotides in order to simplify the construction of the gene encoding the chimeric polypeptide, e.g., to allow for the use of convenient restriction endonuclease sites, or to allow the ligation of the gene fragments such that a contiguous coding region is created. Based on the guidance provided herein, one of ordinary skill in the art would readily be able to add or remove nucleotides from the termini of the gene fragments encoding the polypeptides of the OspA protein in order to generate the altered OspA proteins of the present invention with no experimentation or using only routine experimentation. The altered OspA polypeptides of the present invention can be lipidated or non-lipidated.

To test the antigenicity of the altered OspA polypeptides, mice can be immunized with OspA polypeptides or proteins containing the polypeptide sequences in aluminum hydroxide. Mice are then bled and tested for antibody responses against OspA derived from various strains of *Borrelia*. In additional experiments, these immunized mice can be challenged with ticks infected with *Borrelia burgdorferi* and transmission of infection can be assessed as described in the Exemplification which use OspA, OspC and OspC/OspA chimeric molecules. The results of such a tick challenge reveals whether the animal has developed a protective immune response. For example, an immunized animal that does not seroconvert in response to subsequent tick challenge has likely generated an immunoprotective response to the immunization.

The immunogenic compositions of the present invention can be used to immunize animals including humans. Immunization is understood to elicit specific immunogenic responses, preferably immunoprotective responses, as described above. As described herein, an immunogenic response includes responses that result in at least some level of immune response in the treated animal, where the animal was previously treated with a composition comprising at least one altered OspA polypeptide of the present invention.

Immunity, as described herein, is understood to mean the ability of the treated animal to resist infection, to resist systemic infection, or to overcome infection such as systemic infection more easily or more quickly when compared to non-immunized or non-treated individuals. Immunity can also include an improved ability of the treated individual to sustain an infection with reduced or no clinical symptoms of systemic infection. The individual may be treated with the altered OspA proteins of the present invention either proactively, e.g., once a year or, alternatively, after sustaining a tick bite.

In one embodiment, the altered OspA protein of the present invention, together with suitable excipients and/or adjuvants, is administered to an animal such that the animal develops an immune response to the OspA polypeptide of the composition. The pharmaceutical composition can also be administered with other components suitable for in vitro and/or in vivo use. These additional components include buffers, carrier proteins, adjuvants, preservatives and combinations thereof. In a preferred embodiment, the individual generates an immunoprotective response, for example, by generating antibodies that recognize the LA-2 epitope.

The present invention is also drawn to a physiological composition comprising an altered OspA protein. The composition is useful to administer to an animal in order to generate an immune response or in the diagnostic methods described herein.

For use as a vaccine, the composition of the present invention can include suitable adjuvants, well known in the art, to enhance immunogenicity, potency or half-life of the chimeric proteins in the treated animal. Adjuvants and their use are well known in the art (see for example PCT Publication WO 96/40290, the entire teachings of which are incorporated herein by reference). The composition can be prepared by known methods of preparing vaccines. For example, the altered OspA polypeptides described herein can be isolated and/or purified using known techniques, such as by size exclusion chromatography, ion exchange chromatography, affinity chromatography, preparative electrophoresis, selective precipitation or combinations thereof. The prepared proteins can be mixed with suitable other reagents as described above, wherein the protein is at a suitable concentration. The dosage of the protein will vary and depends upon the age, weight and/or physical condition of the animal to be treated. The optimal dosage can be determined by routine optimization techniques, using suitable animal models.

The composition to be used as a vaccine can be administered by any suitable technique. In one embodiment, administration is by injection, e.g., subcutaneous, intramuscular, intravenous, or intra peritoneal injection. In another embodiment, the composition is administered to mucosa, e.g., by exposing nasal mucosa to nose drops containing the proteins of chimeric proteins of the present invention. In another embodiment, the immunogenic composition is administered by oral administration. In another embodiment of the present invention the chimeric proteins are administered by DNA immunization using nucleic acids encoding an altered OspA polypeptide.

The present invention is also drawn to a diagnostic kit comprising the altered OspA polypeptides described herein. The kit also includes reagents for detecting antibody-antigen complexes that are formed between the OspA protein and antibodies that are present in an sample, e.g., a user-supplied host sample.

The present invention is also drawn to methods of detecting an immune response to Lyme Disease-causing *Borrelia* in a host sample. The method comprises contacting a host sample with an OspA altered protein, such that anti-OspA antibodies, if present in said sample, bind to said OspA protein. The quantity of antibodies that have bound said OspA protein are measured, thereby detecting an immune response to Lyme disease-causing *Borrelia*.

EXEMPLIFICATION

Example 1

Purification of *Borrelia burgdorferi* Outer Surface Protein A and Analysis of Antibody Binding Domains This example details a method for the purification of large amounts of native outer surface protein A (OspA) to homogeneity, and describes mapping of the antigenic specificities of several anti-OspA MAbs. OspA was purified to homogeneity by exploiting its resistance to trypsin digestion. Intrinsic labeling with $^{14}C$-palmitic acid confirmed that OspA was lipidated, and partial digestion established lipidation at the amino-terminal cysteine of the molecule.

The reactivity of seven anti-OspA murine monoclonal antibodies to nine different *Borrelia* isolates was ascertained by Western blot analysis. The reactivity of the altered OspA polypeptides described herein was tested using similar methods. Intact, lipidated or non-lipidated OspA and altered OspA can also be tested using similar methods. Purified OspA was fragmented by enzymatic or chemical cleavage, and the monoclonal antibodies were able to define four distinct immunogenic domains (see FIG. 1). Domain 3, which included residues 190-220 of OspA, was reactive with protective antibodies known to agglutinate the organism in vitro, and included distinct specificities, some of which were not restricted to a genotype of *B. burgdorferi.*

A. Purification of Native OspA

Detergent solubilization of *B. burgdorferi* strips the outer surface proteins and yields partially-purified preparations containing both OspA and outer surface protein B (OspB) (Barbour, A. G. et al., *Infect. Immun.,* 52(5):549-554 (1986); Coleman, J. L. et al., *J Infect. Dis.,* 155 (4):756-765 (1987); Cunningham, T. M. et al., *Ann. NY Acad. Sci.,* 539:376-378 (1988); Brandt, M. E. et al., *Infect. Immun.,* 58: 983-991 (1990); Sambri, V. and R. Cevenini, *Microbiol.,* 14:307-314 (1991)). Although both OspA and OspB are sensitive to proteinase K digestion, in contrast to OspB, OspA is resistant to cleavage by trypsin (Dunn, J. et al., *Prot. Exp. Purif.,* 1:159-168 (1990); Barbour, A. G. et al., *Infect. Immun.,* 45:94-100 (1984)). The relative insensitivity to trypsin is surprising in view of the fact that OspA has a high (16% for B31) lysine content, and may relate to the relative configuration of OspA and B in the outer membrane.

Intrinsic Radiolabeling of *Borrelia*

Labeling for lipoproteins was performed as described by Brandt et al. (Brandt et al., *Infect. Immun.,* 58:983-991 (1990)). $^{14}C$-palmitic acid (ICN, Irvine, Calif.) was added to the BSK II media to a final concentration of 0.5 μCi per milliliter (ml). Organisms were cultured at 34° C. in this medium until a density of $10^8$ cells per ml was achieved.

Purification of OspA Protein from *Borrelia* Strain B31

*Borrelia burgdorferi*, either $^{14}C$-palmitic acid-labeled or unlabeled, were harvested and washed as described (Brandt, M. E. et al., *Infect. Immun.,* 58:983-991 (1990)). Whole organisms were trypsinized according to the protocol of Barbour et al., (*Infect. Immun.,* 45:94-100 (1984)) with some modifications. The pellet was suspended in phosphate buffered saline (PBS, 10 mM, pH 7.2), containing 0.8% tosyl-L-phenylalanine chloromethyl ketone (TPCK)-treated trypsin (Sigma, St. Louis, Mo.), the latter at a ratio of 1 μg per $10^8$ cells. Reaction was carried out at 25° C. for 1 hour, following which the cells were centrifuged. The pellet was washed in PBS with 100 μg/mlphenylmethylsulfonyl fluoride (PMSF). Triton X-114 partitioning of the pellet was carried out as described by Brandt et al., (Brandt et al., *Infect. Immun.,* 58:983-991 (1990)). Following trypsin treatment, cells were resuspended in ice-cold 2% (v/v) Triton X-114 in PBS at $10^9$ cells per ml. The suspension was rotated overnight at 4° C., and the insoluble fraction removed as a pellet after centrifugation at 10,000×g for 15 minutes at 4° C. The supernatant (soluble fraction) was incubated at 37° C. for 15 minutes and centrifuged at room temperature at 1000×g for 15 minutes to separate the aqueous and detergent phases. The aqueous phase was decanted, and ice cold PBS added to the lower Triton phase, mixed, warmed to 37° C., and again centrifuged at 1000×g for 15 minutes. Washing was repeated twice more. Finally, detergent was removed from the preparation using a spin column of Bio-beads SM2 (BioRad, Melville, N.Y.) as described (Holloway, P. W., *Anal. Biochem.,* 53:304-308 (1973)).

Ion exchange chromatography was carried out as described by Dunn et al., (Dunn et al., *Prot. Exp. Purif.,* 1:159-168 (1990)) with minor modifications. Crude OspA was dissolved in buffer A (1% Triton X-100, 10 mM phosphate buffer (pH 5.0)) and loaded onto a SP Sepharose resin (Pharmacia, Piscataway, N.J.), pre-equilibrated with buffer A at 25° C. After washing the column with 10 bed-volumes of buffer A, the bound OspA was eluted with buffer B (1% Triton X-100, 10 mM phosphate buffer (pH 8.0)). OspA fractions were detected by protein assay using the BCA method (Pierce, Rockford, Ill.), or as radioactivity when intrinsically labeled material was fractionated. Triton X-100 was removed using a spin column of Bio-beads SM2.

This method purifies OspA from an outer surface membrane preparation. In the absence of trypsin-treatment, OspA and B were the major components of the soluble fraction obtained after Triton partitioning of strain B31. In contrast, when Triton extraction was carried out after trypsin-treatment, the OspB band is not seen. Further purification of OspA-B31 on a SP Sepharose column resulted in a single band by SDS-PAGE. The yield following removal of detergent was approximately 2 mg per liter of culture. This method of purification of OspA, as described herein for strain B31, can be used for other isolates of *Borrelia* as well. For strains such as strain K48, which lack OspB, trypsin treatment can be omitted.

Lipidation Site of OspA-B31

$^{14}C$-palmitic acid labeled OspA from strain B31 was purified as described above and partially digested with endoproteinase Asp-N. Following digestion, a new band of lower molecular weight was apparent by SDS-PAGE, found by direct amino-terminal sequencing to begin at $Asp_{25}$. This band had no trace of radioactivity by autoradiography. OspA and B contain a signal sequence (L-X-Y-C) similar to the consensus described for lipoproteins of *E. coli*, and it has been predicted that the lipidation site of OspA and B should be the amino-terminal cysteine (Brandt, M. E. et al., *Infect. Immun,* 58:983-991 (1990)). The results presented herein support this prediction.

B. Comparison of OspA Antibody Binding Regions in Nine Strains of *Borrelia burgdorferi*

The availability of the amino acid sequenced for OspA from a number of different isolates, combined with peptide mapping and Western blot analysis, permitted the identification of the antigenic domains recognized by monoclonal antibodies (MAbs) and allowed inference of the key amino acid residues responsible for specific antibody reactivity.

Strains of *Borrelia burgdorferi*

Nine strains of *Borrelia*, including seven European strains and two North American strains, were used in this study of antibody binding domains of several proteins. Information concerning the strains is summarized in Table I, below.

TABLE I

| Representative *Borrelia* Strains | | |
|---|---|---|
| Strain | Location and Source | Reference for Strain |
| K48 | Czechoslovakia, *Ixodes ricinus* | none |
| PGau | Germany, human ACA | Wilske, B. et al., *J. Clin. Microbiol.* 32: 340-350 (1993) |
| DK29 | Denmark, human EM | Wilske, B. et al. |
| Pko | Germany, human EM | Wilske, B. et al. |
| PTrob | Germany, human skin | Wilske, B. et al. |
| Ip3 | Khabarovsk, Russia, *I. persulcatus* | Asbrink, E. et al., *Acta Derm. Venereol.*, 64: 506-512 (1984) |
| Ip90 | Khabarovsk, Russia, *I. persulcatus* | Asbrink, E. et al. |
| 25015 | Millbrook, NY, *I. persulcatus* | Barbour, A. G. et al., *Curr. Microbiol.*, 8: 123-126 (1983) |
| B31 | Shelter Island, NY, *I. scapularis* | Luft, B. J. et al., *Infect. Immun*, 60: 4309-4321 (1992); ATCC 35210 |
| PKa1 | Germany, human CSF | Wilske, B. et al. |
| ZS7 | Freiburg, Germany, *I. ricinus* | Wallich, R. et al., *Nucl. Acids Res*, 17: 8864 (1989) |
| N40 | Westchester Co., NY | Fikrig, E. et al., *Science*, 250: 553-556 (1990) |
| PHei | Germany, human CSF | Wilske, B. et al. |
| ACAI | Sweden, human ACA | Luft, B. J. et al., FEMS *Microbiol. Lett.* 93: 73-68 (1992) |
| PBo | Germany, human CSF | Wilske, B. et al. |

ACA = patient with acrodermatitis chronica atrophicans;
EM = patient with erythema migrans;
CSF = cerebrospinal fluid of patient with Lyme disease.

Strains K48, PGau and DK29 were supplied by R. Johnson, University of Minnesota; Pko and pTrob were provided by B. Wilske and V. Preac-Mursic of the Pettenkhofer Institute, Munich, Germany; and Ip3 and Ip90 were supplied by L. Mayer of the Center for Disease Control, Atlanta, Ga. The North American strains included strain 25015, provided by J. Anderson of the Connecticut Department of Agriculture; and strain B31 (ATCC 35210).

Monoclonal Antibodies

Seven monoclonal antibodies (MAbs) were utilized in this study. Five of the MAbs (12, 13, 15, 83 and 336) were produced from hybridomas cloned and subcloned as previously described (Schubach, W. H., et al., *Infect. Immun.*, 59(6): 1911-1915 (1991)). MAb H5332 (Barbour, A. G. et al., *Infect. Immun.*, 41: 795-804 (1983)) was a gift from Drs. Alan Barbour, University of Texas, and MAb CIII.78 (Sears, J. E. et al., *J. Immunol.*, 147(6):1995-2000 (1991)) was a gift from Richard A. Flavell, Yale University. MAbs 12 and 15 were raised against whole sonicated B3; MAb 336 was produced against whole PGau; and MAbs 13 and 83 were raised to a truncated form of OspA cloned from the K48 strain and expressed in *E. coli* using the T7 RNA polymerase system (McGrath, B. C. et al., *Vaccines*, Cold Spring Harbor Laboratory Press, Plainview, N.Y., pp. 365-370 (1993)). All MAbs were typed as being Immunoglobulin G (IgG).

Methods of Protein Cleavage, Western Blotting and Amino-Terminal Sequencing

Prediction of the various cleavage sites was achieved by knowledge of the primary amino acid sequence derived from the full nucleotide sequences of OspA, many of which are currently available (see Table II, below). Cleavage sites can also be predicted based on the peptide sequence of OspA, which can be determined by standard techniques after isolation and purification of OspA by the method described above. Cleavage of several OspA isolates was conducted to determine the localization of monoclonal antibody binding of the proteins.

Hydroxylamine-HCl (HA), N-chlorosuccinimide (NCS), and cyanogen bromide cleavage of OspA followed the methods described by Bornstein (*Biochem.* 9 (12):2408-2421 (1970)), Shechter et al., (*Biochem.*, 15 (23):5071-5075 (1976)), and Gross (in Hirs, C. H. W. (ed): *Methods in Enzymology*, (N.Y. Acad. Press), 11:238-255 (1967)) respectively. Protease cleavage by endoproteinase, Asp-N (Boehringer Mannheim, Indianapolis, Ind.), was performed as described by Cleveland D. W. et al., (*J. Biol. Chem.*, 252:1102-1106 (1977)). Ten micrograms of OspA were used for each reaction. The ratio of enzyme to OspA was approximately 1 to 10 (w/w).

Proteins and peptides generated by cleavage were separated by SDS-polyacrylamide gel electrophoresis (SDS-PAGE) (Laemmli, U. K., *Nature* (*London*) 227:680-685 (1970)), and electroblotted onto immobilon Polyvinylidine Difluoride (PVDF) membranes (Ploskal, M. G. et al., *Biotechniques*, 4:272-283 (1986)). They were detected by amido black staining or by immunostaining with murine MAbs, followed by alkaline phosphatase-conjugated goat anti-mouse IgG. Specific binding was detected using a 5-bromo-4-chloro-3-indolylphosphate (BCIP)/nitroblue tetrazolium (NBT) developer system (KPL Inc., Gathersburg, Md.).

In addition, amino-terminal amino acid sequence analysis was carried out on several cleavage products, as described by Luft et al., (*Infect. Immun.*, 57:3637-3645 (1989)). Amido black stained bands were excised from PVDF blots and sequenced by Edman degradation using a Biosystems model 475A sequenator with model 120A PTH analyzer and model 900A control/data analyzer.

Cleavage Products of Outer Surface Protein A Isolates

Purified OspA-B31, labeled with $^{14}C$-palmitic acid, was fragmented with hydroxylamine-HCl (HA) into two peptides, designated HA1 and HA2 (data not shown). The HA1 band migrated at 27 kd and retained its radioactivity, indicating that the peptide included the lipidation site at the N-terminus of the molecule (data not shown). From the predicted cleavage point, HA1 should correspond to residues 1 to 251 of OspA-B31. HA2 had a MW of 21.6 kd by SDS-PAGE, with amino-terminal sequence analysis showing it to begin at Gly72, i.e. residues 72 to 273 of OspA-B31. By contrast, HA cleaved OspA-K48 into three peptides, designated HA1, HA2, and HA3 with apparent MWs of 22 kd, 16 kd and 12 kd, respectively. Amino-terminal sequencing showed HA1 to start at Gly72, and HA3 at Gly142. HA2 was found to have a blocked amino-terminus, as was observed for the full-length OspA protein. HA1, 2 and 3 of OspA-K48 were predicted to be residues 72-274, 1 to 141 and 142 to 274, respectively.

N-Chlorosuccinimide (NCS) cleaves tryptophan (W), which is at residue 216 of OspA-B31 or residue 217 of OspA-K48 (data not shown). NCS cleaved OspA-B31 into 2 fragments, NCS1, with MW of 23 kd, residues 1-216 of the protein, and NCS2 with a MW of 6.2 kd, residues 217 to 273 (data not shown). Similarly, K48 OspA was divided into 2 pieces, NCS1 residues 1-217, and NCS2 residues 218 to 274 (data not shown).

Cleavage of OspA by cyanogen bromide (CNBr) occurs at the carboxy side of methionine, residue 39. The major fragment, CNBr1, has a MW of 25.7 kd, residues 39-274 by amino-terminal amino acid sequence analysis (data not shown). CNBr2 (about 4 kd) could not be visualized by amido black staining; instead, lightly stained bands of about 20 kd MW were seen. These bands reacted with anti-OspA MAbs, and most likely were degradation products due to cleavage by formic acid.

Determination of Antibody Binding Domains for Anti-OspA Monoclonal Antibodies

The cleavage products of OspA-B31 and OspA-K48 were analyzed by Western blot to assess their ability to bind to the six different MAbs. Preliminary Western blot analysis of the cleavage products demonstrated that strains K48 and DK29 have similar patterns of reactivity, as do IP3, PGau and Pko. The OspA of strain PTrob was immunologically distinct from the others, being recognized only by MAb 336. MAb 12 recognized only the two North American strains, B31 and 25015. When the isolates were separated into genogroups, it was remarkable that all the MAbs, except MAb 12, crossed over to react with multiple genogroups.

MAb12, specific for OspA-B31, bound to both HA1 and HA2 of OspA-B31. However, cleavage of OspA-B31 by NCS at residue Trp216 created fragments which did not react with MAb 12, suggesting that the relevant domain is near or is structurally dependent upon the integrity of this residue (data not shown). MAb 13 bound only to OspA-K48, and to peptides containing the amino-terminus of that molecule (e.g. HA2; NCS1). It did not bind to CNBr1 residues 39 to 274. Thus the domain recognized by MAb13 is in the amino-terminal end of OspA-K48, near Met38.

MAb15 reacts with the OspA of both the B31 and K48 strains, and to peptides containing the N-terminus of OspA, such as HA1 of OspA-B31 and NCS1, but not to peptides HA2 of OspA-B31 and HA1 of OspA-K48 (data not shown). Both peptides include residue 72 to the C-terminus of the molecules. MAb15 bound to CNBr1 of OspA-K48, indicating the domain for this antibody to be residues 39 to 72, specifically near Gly72 (data not shown).

MAb83 binds to OspA-K48, and to peptides containing the C-terminal portion of the molecule, such as HA1. They do not bind to HA2 of OspA-K48, most likely because the C-terminus of HA2 of OspA-K48 ends at 141. Similar to MAb12 and OspA-B31, binding of MAbs 83 and CIII.78 is eliminated by cleavage of OspA at the tryptophan residue. Thus binding of MAbs 12, 83 and CIII.78 to OspA depends on the structural integrity of the $Trp_{216}$ residue, which appears to be critical for antigenicity. Also apparent is that, although these MAbs bind to a common antigenic domain, the precise epitopes which they recognize are distinct from one another given the varying degrees of cross-reactivity to these MAbs among strains.

Although there is similar loss of binding activity of MAb336 with cleavage at $Trp_{216}$, this MAb does not bind to HA1 of OspA-B31, suggesting the domain for this antibody includes the carboxy-terminal end of the molecule, inclusive of residues 251 to 273. Low MW peptides, such as HA3 (10 kd) and NCS2 (6 kd), of OspA-K48 do not bind this MAb on Western blots. In order to confirm this observation, we tested binding of the 6 MAbs with a recombinant fusion construct p3A/EC that contains a trpE leader protein fused with residues 217 to 273 of OspA-B31 (Schubach, W. H. et al., *Infect. Immun.,* 59(6):1911-1915 (1991)). Only MAb336 reacted with this construct (data not shown). Peptides and antigenic domains localized by fragmentation of OspA are summarized in FIG. 1.

Example 2

Site-Directed Mutagenesis within Hypervariable Domains A., (Residues 120-140), B., (Residues 150-180) and C., (Residues 200-216 or 217)

Site-directed mutagenesis was performed to convert residues within the 204-219 domain of the recombinant B31 OspA to the analogous residues of a European OspA variant, K48. In the region of OspA between residues 204 and 219, there are seven amino acid differences between OspA-B31 and OspA-K48. Three oligonucleotides were generated, each containing nucleotide changes which would incorporate K48 amino acids at their analogous positions in the B31 OspA protein. The oligonucleotides used to create the site-directed mutants were:

5'-CTTAATGACTCTGACACTAGTGC-3' (#613, which converts threonine at position 204 to serine, and serine at 206 to threonine (Thr204-Ser, Thr206-Ser)) (SEQ ID NO:1);

5'-GCTACTAAAAAAACCGGGAAATGGAATTCA-3' (#625, which converts alanine at 214 to glycine, and alanine at 215 to lysine (Ala214-Gly, Ala215-Lys)) (SEQ ID NO:2); and 5'-GCAGCTTGGGATTCAAAAACATCCACTTTAACA-3' (#640, which converts asparagine at 217 to aspartate, and glycine at 219 to lysine (Asn217-Asp, Gly219-Lys)) (SEQ ID NO:3).

Site-directed mutagenesis was carried out by performing mutagenesis with pairs of the above oligonucleotides. Three site-directed mutants were created, each with two changes: OspA 613 (Thr204-Ser, Thr206-Ser), OspA 625 (Ala214-Gly, Ala215-Lys), and 640 (Asn217-Asp, Gly219-Lys). There were also two proteins with four changes: OspA 613/625 (Thr204-Ser, Thr206-Ser, Ala214-Gly, Ala215-Lys) and OspA 613/640 (Thr204-Ser, Thr206-Ser, Asn217-Asp, Gly219-Lys).

Specificity of Antibody Binding to Epitopes of the Non-Mutated Hypervariable Region Monoclonal antibodies that agglutinate spirochetes, including several which are neutralizing in vitro, recognize epitopes that map to the hypervariable region around Trp216 (Barbour, A. G. et al., *Infect. and Immun.,* 41:759 (1983); Schubach, W. H. et al., *Infect. and Immun.,* 59:1911 (1991)). Western Blot analysis demonstrated that chemical cleavage of OspA from the B31 strain at Trp 216 abolishes reactivity of the protein with the agglutinating MAB 105, a monoclonal raised against B31 spirochetes. The reagent, n-chlorosuccinimide (NCS), cleaves OspA at the Trp 216, forming a 23.2 kd fragment and a 6.2 kd peptide which is not retained on the Imobilon-P membrane after transfer. The uncleaved material binds MAb 105; however, the 23.2 kd fragment is unreactive. Similar Western blots with a TrpE-OspA fusion protein containing the carboxy-terminal portion of the OspA protein demonstrated that the small 6.2 kd piece also fails to bind MAb 105 (Schubach, W. H. et al., *Infect. and Immun.,* 59:1911 (1991)).

Monoclonal antibodies H5332 and H3TS (Barbour, A. G. et al., *Infect. and Immun.,* 41:759 (1983)) have been shown by immunofluorescence to decorate the surface of fixed spirochetes (Wilske, B. et al., *World J. Microbiol.,* 7:130 (1991)). These monoclonal antibodies also inhibit the growth of the organism in culture. Epitope mapping with fusion proteins has confirmed that the epitopes which bind these MAbs are conformationally determined and reside in the carboxy half of the protein. MAb H5332 is cross-reactive among all of the known phylogenetic groups, whereas MAb H3TS and MAb 105 seem to be specific to the B31 strain to which they were raised. Like MAb 105, the reactivities of H5332 and H3TS to OspA are abrogated by fragmentation of the protein at Trp216. MAb 336 was raised to whole spirochetes of the strain PGau. It cross-reacts to OspA from group 1 (the group to which B31 belongs) but not to group 2 (of which K48 is a member). Previous studies using fusion proteins and chemical cleavage have indicated that this antibody recognizes a domain of OspA in the region between residues 217 and 273. All of these MAbs agglutinate the B31 spirochete.

Western Blot Analysis of Antibody Binding to Mutated Hypervariable Regions

MAbs were used for Western Blot analysis of the site-directed OspA mutants induced in *E. coli* using the T7 expression system (Dunn, J. J. et al., *Protein Expression and Purification,* 1:159 (1990)). *E. coli* cells carrying pET9c plasmids having a site-directed OspA mutant insert were induced at mid-log phase growth with IPTG for four hours at 37° C. Cell lysates were made by boiling an aliquot of the induced cultures in SDS gel loading dye, and this material was then loaded onto a 12% SDS gel (BioRad mini-Protean II), and subjected to electrophoresis. The proteins were then transferred to Imobilon-P membranes (Millipore) 70V, 2 hour at 4° C. using the BioRad mini transfer system. Western analysis was carried out as described by Schubach et al., (*Infect. Immun.,* 59:1911 (1991)).

Western Blot analysis indicated that only the 625 mutant (Ala214-Gly and Ala215-Lys) retained binding to the agglutinating monoclonal H3TS. However, the 613/625 mutant which has additional alterations to the amino terminus of Trp216 (Ser204-Thr and Thr206-Ser) did not bind this monoclonal. Both 640 and 613/640 OspAs which have the Asn217-Asp and Gly219-Lys changes on the carboxy-terminal side of Trp216 also failed to bind MAb H3TS. This indicated that the epitope of the B31 OspA which binds H3TS is comprised of amino acid side-chains on both sides of Trp216.

The 613/625 mutant failed to bind MAbs 105 and H5332, while the other mutants retained their ability to bind these MAbs. This is important in light of the data using fusion proteins that indicate that MAb 105 behaves more like MAb H3TS in terms of its serotype specificity and binding to OspA (Wilske, B. et al., *Med. Microbiol. Immunol.,* 181:191 (1992)). The 613/625 protein has, in addition to the differences at residues Thr204 and Ser206, changes immediately amino-terminal to Trp216 (Ala214-Gly and Ala215-Lys). The abrogation of reactivity of MAbs 105 and H5332 to this protein indicated that the epitopes of OspA which bind these monoclonal antibodies are comprised of residues on the amino-terminal side of Trp216.

The two proteins carrying the Asn217-Asp and Gly219-Lys replacements on the carboxy-terminal side of Trp216 (OspAs 640 and 613/640) retained binding to MAbs 105 and H5332; however, they failed to react with MAb 336, a monoclonal which has been mapped with TrpE-OspA fusion proteins and by chemical cleavage to a more carboxy-terminal domain. This result may explain why MAb 336 failed to recognize the K48-type of OspA (Group 2).

It is clear that amino acids Ser204 and Thr206 play an important part in the agglutinating epitopes in the region of the B31 OspA flanking Trp216. Replacement of these two residues altered the epitopes of OspA that bind MAbs 105, H3TS and H5332. The ability of the 640 changes alone to abolish reactivity of MAb 336 indicated that Thr204 and Ser206 are not involved in direct interaction with MAb 336.

The results indicated that the epitopes of OspA which are available to MAbs that agglutinate spirochetes are comprised at least in part by amino acids in the immediate vicinity of Trp216. Since circular dichroism analysis indicated that the structures of B31 and K48 OspA differ very little within this domain, it is unlikely that the changes made by mutation have radically altered the overall structure of the OspA protein (France, L. L. et al., *Biochem. Biophys. Acta,* 1120:59 (1992); and France et al., *Biochem. Biophys Acta*, submitted (1993)). This hypothesis is supported by the finding that the recombinant, mutant OspAs exhibit the same high solubility and purification properties as the parent B31 protein (data not shown).

In summary, amino acid side-chains at Ser204 and Thr206 are important for many of the agglutinating epitopes. However, a limited set of conservative changes at these sites were not sufficient to abolish binding of all of the agglutinating MAbs. These results suggested that the agglutinating epitopes of OspA are distinct, yet may have some overlap. The results also supported the hypothesis that the surface-exposed epitope around Trp216 which is thought to be important for immune recognition and neutralization is a conformationally-determined and complex domain of OspA.

Example 3

*Borrelia* Strains and Proteins

A. Genes Encoding *Borrelia* Proteins

The altered OspA polypeptides of the current invention can be part of a cocktail with other proteins or can be joined to other proteins to form a chimeric protein. The other polypeptides of the cocktail or chimeric can be derived from any *Borrelia*. Representative proteins include OspA, OspB, OspC, OspD, p12, p39, p41 (fla), p66, and p93. Nucleic acid sequences encoding several *Borrelia* proteins are available (see Table II for examples); alternatively, nucleic acid sequences encoding *Borrelia* proteins can be isolated and characterized using methods such as those described below.

TABLE II

References for Nucleic Acid Sequences for Several Proteins of Various *Borrelia* Strains

| Strain | OspA |
|---|---|
| K48 | X62624 (SID 8) |
| PGau | X62387 (SID 10) |
| DK29 | X63412 (SID 21) |
| Pko | X65599 (SID 25) |
| PTrob | X65598 (SID 45) |
| Ip3 | X70365 (SID 24) |
| Ip90 | Kryuchechnikov, V. N. et al., *J.Microbiol. Epid. Immunobiol.* 12: 41-44 (1988) (SID 22) |
| 25015 | Fikrig, E. S. et al., *J. Immunol.* 7: 2256-2260 (1992) (SID 12) |
| B31 | Bergstrom, S. et al., *Mol. Microbiol.* 3: 479-486 (1989) (SID 6) |
| PKa1 | X69606 (SID 42) |
| ZS7 | Jonsson, M. et al., *Infect. Immun.* 60: 1845-1853 (1992) (SID 44) |
| N40 | Kryuchechnikov, V. N. et al. (SID 43) |
| PHei | X65600 (SID 46) |
| ACAI | Kryuchechnikov, V. N. et al. (SID 26) |
| PBo | X65605 (SID 23) |

Numbers with an "X" prefix are GenBank data base accession numbers.
SID = SEQ ID NO.

B. Isolation of *Borrelia* Genes

Nucleic acid sequences encoding full length, lipidated proteins from known *Borrelia* strains were isolated using the polymerase chain reaction (PCR) as described below. In addition, nucleic acid sequences were generated which encoded truncated proteins (proteins in which the lipidation signal has been removed, such as by eliminating the nucleic acid sequence encoding the first 18 amino acids, resulting in non-lipidated proteins). Other proteins were generated which encoded polypeptides of a particular gene (i.e., encoding a segment of the protein which has a different number of amino acids than the protein does in nature). Using similar methods as those described below, primers can be generated from known nucleic acid sequences encoding *Borrelia* proteins and used to isolate other genes encoding *Borrelia* proteins. Primers can be designed to amplify all of a gene, as well as to amplify a nucleic acid sequence encoding truncated protein sequences, such as described below for OspC, or nucleic acid sequences encoding a polypeptide derived from a *Borrelia* protein. Primers can also be designed to incorporate unique restriction enzyme cleavage sites into the amplified nucleic acid sequences. Sequence analysis of the amplified nucleic acid sequences can then be performed using standard techniques.

Cloning and Sequencing of OspA Genes and Relevant Nucleic Acid Sequences

*Borrelia* OspA sequences were isolated in the following manner: 100 μl reaction mixtures containing 50 mM KCl, 10 mM TRIS-HCl (pH 8.3), 1.5 mM $MgCl_2$, 200 μM each NTP, 2.5 units of TaqI DNA polymerase (Amplitaq, Perkin-Elmer/Cetus) and 100 pmol each of the 5' and 3' primers (described below) were used. Amplification was performed in a Perkin-Elmer/Cetus thermal cycler as described (Schubach, W. H. et al., *Infect. Immun.,* 59:1811-1915 (1991)). The amplicon was visualized on an agarose gel by ethidium bromide staining Twenty nanograms of the chloroform-extracted PCR product were cloned directly into the PC-TA vector (Invitrogen) by following the manufacturer's instructions. Recombinant colonies containing the amplified fragment were selected, the plasmids were prepared, and the nucleic acid sequence of each OspA was determined by the dideoxy chain-termination technique using the Sequenase kit (United States Biochemical). Directed sequencing was performed with M13 primers followed by OspA-specific primers derived from sequences, previously obtained with M13 primers.

Because the 5' and 3' ends of the OspA gene are highly conserved (Fikrig, E. S. et al., *J. Immunol.,* 7:2256-2260 (1992); Bergstrom, S. et al., *Mol. Microbiol.* 3:479-486 (1989); Zumstein, G. et al., *Med. Microbiol. Immunol.,* 181: 57-70 (1992)), the 5' and 3' primers for cloning can be based upon any known OspA sequences. For example, the following primers based upon the OspA nucleic acid sequence from strain B31 were used:

```
                                    (SEQ ID NO: 4)
5'-GGAGAATATATTATGAAA-3' (-12 to +6);
and

                                    (SEQ ID NO: 5)
5'-CTCCTTATTTTAAAGCG-3' (+826 to +809).
```

(Schubach, W. H. *et al., Infect. Immun,* 59:1811-1915 (1991)).

OspA genes isolated in this manner include those for strains B31, K48, PGau, and 25015; the nucleic acid sequences are depicted in the sequence listing as SEQ ID NO:6 (OspA-B31), SEQ ID NO:8 (OspA-K48), SEQ ID NO:10 (OspA-PGau), and SEQ ID NO:12 (OspA-25015). An alignment of these and other OspA nucleic acid sequences is shown in FIG. 17. The amino acid sequences of the proteins encoded by these nucleic acid sequences are represented as SEQ ID NO:7 (OspA-B31), SEQ ID NO:9 (OspA-K48), SEQ ID NO:11 (OspA-PGau), and SEQ ID NO:13 (OspA-25015).

The following primers were used to generate specific nucleic acid sequences of the OspA gene:

```
                                    (SEQ ID NO: 14)
5'-GTCTGCAAAAACCATGACAAG-3'
(plus strand primer #369);

                                    (SEQ ID NO: 15)
5'-GTCATCAACAGAAGAAAAATTC-3'
(plus strand primer #357);

                                    (SEQ ID NO: 16)
5'-CCGGATCCATATGAAAAAATATTTATTGGG-3'
(plus strand primer #607);

                                    (SEQ ID NO: 17)
5'-CCGGGATCCATATGGCTAAGCAAAATGTTAGC-3'
(plus strand primer #584);

                                    (SEQ ID NO: 18)
5'-GCGTTCAAGTACTCCAGA-3'
(minus strand primer #200);

                                    (SEQ ID NO: 19)
5'-GATATCTAGATCTTATTTTAAAGCGTT-3'
(minus strand primer #586);
and

                                    (SEQ ID NO: 20)
5'-GGATCCGGTGACCTTTTAAAGCGTTTTTAAT-3'
(minus strand primer #1169).
```

C. Expression of Proteins from *Borrelia* Genes

The nucleic acid sequences described above can be incorporated into expression plasmids, using standard techniques, and transfected into compatible host cells in order to express the proteins encoded by the nucleic acid sequences. As an example, the expression of the p12 gene and the isolation of p12 protein is set forth.

Amplification of the p12 nucleic acid sequence was conducted with primers that included a NdeI restriction site into the nucleic acid sequence. The PCR product was extracted with phenol/chloroform and precipitated with ethanol. The precipitated product was digested and ligated into an expression plasmid as follows: 15 μl (approximately 1 μg) of PCR DNA was combined with 2 μl 10× restriction buffer for NdeI (Gibco/BRL), 1 μl NdeI (Gibco/BRL), and 2 μl distilled water, and incubated overnight at 37° C. This mixture was subsequently combined with 3 μl 10× buffer (buffer 3, New England BioLabs), 1 μl BamHI (NEB), and 6 μl distilled water, and incubated at 37° for two hours. The resultant material was purified by preparative gel electrophoresis using low melting point agarose, and the band was visualized under long wave ultraviolet light and excised from the gel. The gel slice was treated with Gelase using conditions recommended by the manufacturer (Epicentre Technologies). The resulting DNA pellet was resuspended in 25-50 μl of 10 mM TRIS-CL (pH 8.0) and 1 mM EDTA (TE). An aliquot of this material was ligated into the pET9c expression vector (Dunn, J. J. et al., *Protein Expression and Purification,* 1:159 (1990)).

To ligate the material into the pET9c expression vector, 20-50 ng of p12 nucleic acid sequences cut and purified as described above was combined with 5 μl 10 One-Phor-All (OPA) buffer (Pharmacia), 30-60 ng pET9c cut with NdeI and BamHI, 2.5 μl 20 mM ATP, 2 μl T4 DNA ligase (Pharmacia) diluted 1:5 in 1×OPA buffer, and sufficient distilled water to bring the final volume to 50 μl. The mixture was incubated at 12° C. overnight.

The resultant ligations were transformed into competent DH5-alpha cells and plated on nutrient agar plates containing 50 μg/ml kanamycin and incubated overnight at 37° C. DH5-alpha is used as a "storage strain" for T7 expression clones, because it is RecA deficient, so that recombination and concatenation are not problematic, and because it lacks the T7 RNA polymerase gene necessary to express the cloned gene. The use of this strain allows for cloning of potentially toxic gene products while minimizing the chance of deletion and/or rearrangement of the desired genes. Other cell lines having similar properties may also be used.

Kanamycin resistant colonies were single-colony purified on nutrient agar plates supplemented with kanamycin at 50 μg/ml. A colony from each isolate was inoculated into 3-5 ml of liquid medium containing 50 μg/ml kanamycin, and incubated at 37° C. without agitation. Plasmid DNA was obtained from 1 ml of each isolate using a hot alkaline lysis procedure (Maniatis, T. et al., *Molecular Cloning: A Laboratory Manual*, Cold Spring Harbor Laboratory, Cold Spring Harbor, N.Y. (1982)).

Plasmid DNA was digested with EcoRI and BglII in the following manner: 15 μl plasmid DNA was combined with 2 μl 10× buffer 3 (NEB), 1 μl EcoRI (NEB), 1 μl BglII (NEB) and 1 μl distilled water, and incubated for two hours at 37° C. The entire reaction mixture was subjected to electrophoresis on an analytical agarose gel. Plasmids carrying the p12 insert were identified by the presence of a band corresponding to 925 base-pairs (full length p12) or 875 base-pairs (nonlipidated p12). One or two plasmid DNAs from the full length and nonlipidated p12 clones in pET9c were used to transform BL21 DE3 pLysS to kanamycin resistance as described by Studier et al., (*Methods in Enzymology*, Goeddel, D. (Ed.), Academic Press, 185: 60-89 (1990)). One or two transformants of the full length and nonlipidated clones were single-colony purified on nutrient plates containing 25 μg/ml chloramphenicol (to maintain pLysS) and 50 μg/ml kanamycin at 37° C. One colony of each isolate was inoculated into liquid medium supplemented with chloramphenicol and kanamycin and incubated overnight at 37° C. The overnight culture was subcultured the following morning into 500 ml of liquid broth with chloramphenicol (25 μg/ml) and kanamycin (50 μg/ml) and grown with aeration at 37° C. in an orbital air-shaker until the absorbance at 600 nm reached 0.4-0.7. Isopropyl-thio-galactoside (IPTG) was added to a final concentration of 0.5 mM, for induction, and the culture was incubated for 3-4 hours at 37° C. as before. The induced cells were pelleted by centrifugation and resuspended in 25 ml of 20 mM $NaPO_4$ (pH 7.7). A small aliquot was removed for analysis by gel electrophoresis. Expressing clones produced proteins which migrated at the 12 kd position.

A crude cell lysate was prepared from the culture as described for recombinant OspA by Dunn, J. J. et al., (*Protein Expression and Purification,* 1:159 (1990)). The crude lysate was first passed over a Q-sepharose column (Pharmacia) which had been pre-equilibrated in Buffer A: 10 mM $NaPO_4$ (pH 7.7), 10 mM NaCl, 0.5 mM PMSF. The column was washed with 10 mM $NaPO_4$, 50 mM NaCl and 0.5 mM PMSF and then p12 was eluted in 10 mM $NaPO_4$, 0.5 mM PMSF with a NaCl gradient from 50-400 mM. p12 eluted approximately halfway through the gradient between 100 and 200 mM NaCl. The peak fractions were pooled and dialyzed against 10 mM NaPO4 (pH 7.7), 10 mM NaCl, 0.5 mM PMSF. The protein was then concentrated and applied to a Sephadex G50 gel filtration column of approximately 50 ml bed volume (Pharmacia), in 10 mM $NaPO_4$, 200 mM NaCl, 0.5 mM PMSF. p12 would typically elute shortly after the excluded volume marker. Peak fractions were determined by running small aliquots of all fractions on a gel. The p12 peak was pooled and stored in small aliquots at −20° C.

Example 4

Generation of Chimeric Nucleic Acid Sequences and Chimeric Proteins

A. General Protocol for Creation of Chimeric Nucleic Acid Sequences

The megaprimer method of site directed mutagenesis and a modification were used to generate chimeric nucleic acid sequences (Sarkar and Sommer, *Biotechniques,* 8(4): 404-407 (1990); Aiyar, A. and J. Leis, *Biotechniques,* 14(3): 366-369 (1993)). A 5' primer for the first genomic template and a 3' fusion oligo are used to amplify the desired region. The fusion primer consists of a 3' end of the first template (DNA that encodes the amino-proximal polypeptide of the fusion protein), coupled to a 5' end of the second template (DNA that encodes the carboxy-proximal polypeptide of the fusion protein).

The PCR amplifications are performed using Taq DNA polymerase, 10×PCR buffer, and $MgCl_2$ (Promega Corp., Madison, Wis.), and Ultrapure dNTPs (Pharmacia, Piscataway, N.J.). One μg of genomic template 1, 5 μl of 10 μM 5' oligo and 5 μl of 10 μM fusion oligo are combined with the following reagents at indicated final concentrations: 10× Buffer-Mg FREE (1×), $MgCl_2$ (2 mM), dNTP mix (200 μM each dNTP), Taq DNA polymerase (2.5 units), water to bring final volume to 100 μl. A Thermal Cycler (Perkin Elmer Cetus, Norwalk, Conn.) is used to amplify under the following conditions: 35 cycles at 95° C. for one minute, 55° C. for two minutes, and 72° for three minutes. This procedure results in a “megaprimer”.

The resulting megaprimer is run on a 1×TAE, 4% low-melt agarose gel. The megaprimer band is cut from the gel and purified using the Promega Magic PCR Preps DNA purification system. Purified megaprimer is then used in a second PCR step. One μg of genomic template 2, approximately 0.5 μg of the megaprimer, and 5 μl of 10 μM 3' oligo are added to a cocktail of 10× buffer, $MgCl_2$, dNTPs and Taq at the same final concentrations as noted above, and brought to 100 μl with water. PCR conditions are the same as above. The fusion product resulting from this amplification is also purified using the Promega Magic PCR Preps DNA purification system.

The fusion product is then ligated into TA vector and transformed into *E. coli* using the Invitrogen (San Diego, Calif.) TA Cloning Kit. Approximately 50 ng of PCR fusion product is ligated to 50 ng of pCRII vector with 1× Ligation Buffer, 4 units of T4 ligase, and brought to 10 μl with water. This ligated product mixture is incubated at 12° C. overnight (approximately 14 hours). Two μl of the ligation product mixture is added to 50 μl competent INC F' cells and 2 μl beta mercaptoethanol. The cells are then incubated for 30 minutes, followed by heat shock treatment at 42° C. for 60 seconds, and an ice quenching for two minutes. 450 μl of warmed SOC media is then added to the cells, resulting in a transformed cell culture which is incubated at 37° C. for one hour with slight shaking 50 μl of the transformed cell culture is plated on LB+50 μg/μl ampicillin plates and incubated overnight at 37° C. Single white colonies are picked and added to individual overnight cultures containing 3 ml LB with ampicillin (50 μg/μl).

The individual overnight cultures are prepared using Promega's Magic Miniprep DNA purification system. A small amount of the resulting DNA is cut using a restriction digest as a check. DNA sequencing is then performed to check the sequence of the fusion nucleic acid sequence, using the United States Biochemical (Cleveland, Ohio) Sequenase Version 2.0 DNA sequencing kit. Three to five µg of plasmid DNA is used per reaction. 2 µl 2M NaOH/2 mM EDTA are added to the DNA, and the volume is brought to 20 µl with water. The mixture is then incubated at room temperature for five minutes. 7 µl water, 3 µl 3M NaAc, 75 µl ethanol are added. The resultant mixture is mixed by vortex and incubated for ten minutes at −70° C., and then subjected to microcentrifugation. After microcentrifugating for ten minutes, the supernatant is aspirated off, and the pellet is dried in the speed vac for 30 second. 6 µl water, 2 µl annealing buffer, and 2 µl of 10 µM of the appropriate oligo is then added. This mixture is incubated for 10 minutes at 37° C. and then allowed to stand at room temperature for 10 minutes. Subsequently, 5.5 µl of label cocktail (described above) is added to each sample of the mixture, which are incubated at room temperature for an additional five minutes. 3.5 µl labeled DNA is then added to each sample which is then incubated for five minutes at 37° C. 4 µl stop solution is added to each well. The DNA is denatured at 95° for two minutes, and then placed on ice.

Clones with the desired fusion nucleic acid sequences are then recloned in frame in the pET expression system in the lipidated (full length) and non-lipidated (truncated, i.e., without first 17 amino acids) forms. The product is amplified using restriction sites contained in the PCR primers. The vector and product are cut with the same enzymes and ligated together with T4 ligase. The resultant plasmid is transformed into competent *E. coli* using standard transformation techniques. Colonies are screened as described earlier and positive clones are transformed into expression cells, such as *E. coli* BL21, for protein expression with IPTG for induction. The expressed protein in its bacterial culture lysate form and/or purified form is then injected in mice for antibody production. The mice are bled, and the sera collected for agglutination, in vitro growth inhibition, and complement-dependent and -independent lysis tests.

A specific example of chimeric OspA is as follows. Other OspA chimeras can be made using the same method with suitable primers.

OspA-K48/OspA-PGau

A chimer of OspA from strain K48 (OspA-K48) and OspA from strain PGau (OspA-PGau) was generated using the method described above. This chimeric nucleic acid sequence included by 1-654 from OspA-K48, followed by by 655-820 from OspA-PGau. Primers used included: the amino-terminal sequence of OspA primer #607 (SEQ ID NO:16); the fusion primer, 5'-AAAGTAGAAGTTTTTGAATC-CCATTTTCCAGTTTTTTT-3' (minus strand primer #668-654) (SEQ ID NO:27); the carboxy-terminal sequence of OspA primer #586 (SEQ ID NO:19); and the sequence primers #369 (SEQ ID NO:14) and #357 (SEQ ID NO:15). The chimeric nucleic acid sequence is presented as SEQ ID NO:28; the chimeric protein encoded by this chimeric nucleic acid sequence is presented as SEQ ID NO:29.

C. Purification of Proteins Generated by Chimeric Nucleic Acid Sequences

The chimeric nucleic acid sequences described above, as well as chimeric nucleic acid sequences produced by the methods described above, are used to produce chimeric proteins encoded by the nucleic acid sequences. Standard methods, such as those described above in Example 3, concerning the expression of proteins from *Borrelia* genes, can be used to express the proteins in a compatible host organism. The chimeric proteins can then be isolated and purified using standard techniques.

Nucleic acid encoding altered versions of OspA can be used to generate OspA chimeras. In addition, nucleic acid encoding OspA chimeras can be used to generate the altered OspA polypeptides of the present invention.

If the chimeric protein is soluble, it can be purified on a Sepharose column. Insoluble proteins can be solubilized in guanidine and purified on a $Ni^{2+}$ column; alternatively, they can be solubilized in 10 mM $NaPO_4$ with 0.1-1% TRIXON X 114, and subsequently purified over an S column (Pharmacia). Lipidated proteins were generally purified by the latter method. Solubility was determined by separating both soluble and insoluble fractions of cell lysate on a 12% PAGE gel, and checking for the localization of the protein by Coomassie staining, or by Western blotting with monoclonal antibodies directed to an antigenic polypeptide of the chimeric protein.

Example 5

Generation of OspC/OspA Chimeric Nucleic Acids and Chimeric Proteins

A. General Protocol for Creation of Chimeric Nucleic Acid Sequences

A large number of chimeric nucleic acid sequences encoding proteins comprising at least a first and a second polypeptide from *Borrelia burgdorferi* were generated. These chimeric nucleic acid sequences were produced such that the encoded chimeric protein comprised a *Borrelia burgdorferi* OspC polypeptide upstream of (or N-terminal to) a *Borrelia burgdorferi* OspA polypeptide. The chimeric nucleic acid sequences were also produced such that the nucleic acid encoding one polypeptide was in the same reading frame as the nucleic acid sequence encoding the next polypeptide in the chimeric protein.

The general cloning strategy used to construct the chimeric nucleic acid sequences was as follows. The desired fragment of OspC was amplified using a 5' primer containing a restriction site suitable for cloning the resultant product into a vector of interest and a 3' primer containing a restriction site suitable for ligating the OspC fragment to the OspA fragment. The OspC product was cloned into a suitable vector. For the OspA portion of the chimeric nucleic acid, the desired OspA fragment was amplified using a 5' primer containing a restriction site for ligating the resultant OspA fragment to the OspC fragment and a 3' primer containing a restriction site suitable for cloning the resultant OspA product into the vector with the OspC product. The use of a restriction site to allow ligation of the OspC and OspA fragments results in the insertion of 0 to about 3 amino acids between the OspC and OspA fragments.

A specific example of such a construction follows. It is understood that other suitable restriction sites could be used with no or only routine experimentation. The resultant OspC/OspA Chimer could have, therefore, the addition of 0 to about 3 amino acids or more between the OspC and OspA fragments, depending on the restriction site used.

For the OspC portions of the chimeric nucleic acids, desired fragments of OspC genes from various strains or genospecies were PCR amplified using a 5' primer containing an NdeI site and a 3' primer containing a NcoI site and a BamHI site. The amplified OspC product was then cloned into the NdeI and BamHI sites of the T7 promoter driven expression vector, pET9c. For the OspA portion of the chimeric nucleic acid, desired fragments of OspA genes from a strain of interest or genospecies of interest were PCR amplified using a 5' primer containing an NcoI site and a 3' primer containing a BamHI site. This OspA portion could then be directly cloned into the NcoI and BamHI sites of the pET9c vector containing the desired OspC sequence, thereby producing the desired OspC-OspA construct. By including the sequence for the NcoI restriction site in the primers, a nine nucleotide linker sequence encoding the amino acids Ser-Met-Ala was produced at the junction between the N-terminal OspC sequence and the C-terminal OspA sequence. The use of the NcoI restriction enzyme (CCATGG) in this cloning strategy was a suitable choice as *Borrelia* is an AT-rich organism which possesses only a few NcoI sites in its genome. One of ordinary skill in the art would know that different restriction sites wold be utilized and would know how to generate the chimeric OspC/A constructs for use in subsequent alterations described herein with no or only routine experimentation.

As an example, OspC-OspA chimeric nucleic acids which contain nonlipidated OspC B31 were generated using the following primers:

```
(5'OspC-NdeI):
                                        (SEQ ID NO: 91)
5'-GT CAT ATG GCT TGT AAT AAT TCA GGG AAA GA-3';
and

(3'OspC-NcoI):
                                        (SEQ ID NO: 92)
5'-T TTC CAT GGA AGG TTT TTT TGG ACT TTC TG-3'.
```

For OspC-OspA chimeric nucleic acids which contain nonlipidated OspA B31, the following primers were used:

```
(5'OspA-NcoI:)
                                        (SEQ ID NO: 93)
5'-TT TCC ATG GCC AAG CAA AAT GTT AGC AGC C-3';
and

(3'OspA-BamHI):
                                        (SEQ ID NO: 94)
5'-TAA GGA TCC TTA TTT TAA AGC GTT TTT-3'.
```

Lipidated versions of the OspC/OspA chimeras can be constructed by designing primers to amplify the a portion of the template that includes the lipidation signal sequence or by generating a nucleic acid construct with a suitable lipidation signal sequence. The leader sequence comprising a lipidation signal can be, for example, from a gene encoding the OspA, OspB or OspC polypeptides.

B. Protein Expression

As described in the previous examples, it is possible to express and purify *Borrelia* proteins or polypeptides, for example, OspA polypeptides, OspC polypeptides, chimeric OspC/OspA polypeptides and polypeptides comprising the OspA alterations described herein. This is accomplished by incorporating the desired nucleic acid sequence, which encodes the protein of choice, into an expression plasmid, for example, using standard techniques. This expression plasmid can then be transfected into a compatible host cell in order to express the desired protein.

For example, the purified OspA, OspC or OspC/OspA chimeric proteins that were used to immunize mice and in the ELISA tests described below, were generated and purified by cloning either OspA, OspC or OspC/OspA chimeric nucleic acid sequences, in frame, into the pET expression plasmid. The expression plasmid was then transfected into the compatible expression cell line *Escherichia coli* strain BL21 (pLysS) or strain B834 (DE3). The BL21 or B834 cells were grown in 10 mL LB media (5 g/L NaCl, 10 g/L tryptone, 5 g/L yeast extract, 25 mg/L chloramphenicol and 50 mg/L ampicillin) at 37° C., with shaking. When the optical density at 600λ reached 0.3-0.4 units, recombinant protein expression was induced by adding IPTG (isopropyl B-D-thiogalactopyranoside) to a final concentration of 0.5 mM and the cells were grown for an additional three hours. The cultures were harvested by centrifugation at 3800×g for five minutes. The cells were resuspended in 20 mM $NaPO_4$, pH 7.7, and stored at −20° C. overnight. Once thawed, the crude extracts were incubated with DNase (2 μg/mL) in the presence of 2.5 mM $MgCl_2$ at room temperature for thirty minutes and then spun at 14,000 rpm (Eppendorf 5417C) for five minutes.

To purify the OspC proteins described below, the crude extracts from the OspC-expressing cells were loaded onto an anion exchange column (Q Sepharose Fast Flow, 2.2×10 cm, Pharmacia) which had been pre-equilibrated with 20 mM Tris-Cl, pH 9.3. The column was washed in the same buffer (20 mM Tris-Cl, pH 9.3) which eluted the OspC protein. The wash fractions that contained OspC were concentrated using Amicon 10K and then were dialyzed with a solution containing 20 mM $NaPO_4$, pH 8.0, and 250 mM NaCl. The partially purified OspC was then passed over a $Ni^{2+}$ metal affinity column (Chelating Sepharose Fast Flow 2.2×10 cm, Pharmacia) equilibrated with 20 mM $NaPO_4$, pH 8.0, and 250 mM NaCl. The column was washed using a decreasing pH gradient of 20 mM sodium acetic acid and 250 mM NaCl and the bound OspC eluted around pH 5.7. The OspC fractions were then concentrated by ultrafiltration and stored at −70° C.

For purification of OspA proteins, the same procedure was followed, except that the dialysis step, after the Amicon 10K cutoff, was done in 20 mM $NaPO_4$, pH 6.0. The partially purified OspA was then applied to a cation exchange column (S Sepharose Fast Flow 2.2×10 cm, Pharmacia) equilibrated with 20 nM $NaPO_4$, pH 6.0. The column was washed using an increasing NaCl gradient from 0 to 100 mM. The OspA-containing fractions were concentrated by ultrafiltration and stored at −70° C.

As previously indicated, both lipidated and non-lipidated (e.g., truncated, lacking the first 17 amino acids) forms of OspC, OspA and OspC/OspA chimeric proteins were generated.

The above-described techniques were also used to express proteins comprising the altered OspA polypeptides of the present invention.

C. Immunization of Mice and Serologic Characterization Using ELISA (Enzyme-Linked Immunosorbent Assay)

Immunization of Mice

Mice, either C3H-J or ICR, were immunized with 3 mg of lipidated OspC/OspA chimeric protein or 6 mg of non-lipidated OspC/OspA chimer in 100 mL of aluminum hydroxide adjuvant (concentration of 1.8 mg/mL) by (SC) subcutaneous injection. As a negative control, mice were immunized with 100 mL of aluminum hydroxide adjuvant only. All mice received a total of three injections which were given at two week intervals. One week after the final immunization, blood was drawn from each mouse (including negative control mice) and the serum was tested for IgG reactivity using the ELISA method described below, for the presence of anti-OspA antibodies to three different purified OspA proteins (*Borrelia burgdorferi* sensu stricto (B31), *Borrelia garinii* (K48) and *Borrelia afzelii* (PGau). The sera was tested at a dilution of 1:1000.

Mice were immunized with the chimeric proteins described in Table III.

TABLE III

Chimeric Proteins Used to Immunize Mice

| Name | Description (amino acid) | SEQ ID NO: (nucleic acid) | SEQ ID NO: (polypeptide) | FIG. NO: |
|---|---|---|---|---|
| OspA | OspA-B31(18-273) | 6 | 7 | 22, 23 |
| OspC | OspC-B31(19-211) | * | * | 22, 23 |
| OspC2-OspA | OspC-C2(19-204)/ OspA-B31(18-273) | 59 | 60 | 22, 23 |
| [1]lipOspAP/Bo | OspA-PGau(1-217)/ OspA-Bo(218-273) | 49 | 50 | 24, 25 |
| [1]lipOspAB/P | OspA-B31(1-216)/ OspA-Pko(217-273) | * | * | 24, 25 |
| OspC-OspAB/P | OspC-B31(19-211)/ OspA-B31 (18-216)/ OspA-Pko(217-273) | 65 | 66 | 24, 25, 27, 28, 29 |
| OspCB31-OspAB31 | OspC-B31(19-211)/ OspA-B31(18-273) | 55 | 56 | 26, 27, 28, 29 |
| OspC2-OspAB31 | OspC-C2(19-204)/ OspA-B31(18-273) | 59 | 60 | 26, 27 |
| [1]lip OspA K/T | OspA-K48(1-217)/ OspA-Tro(218-273) | * | * | 27 |
| [1]lip OspC-B31 | OspC-B31(1-211) | * | * | 26 |
| OspCB31-OspABPBP | OspC-B31(19-211)/ OspA-B31(30-150)/ OspA-Pko(151-179)/ OspA-B31(180-216) (190 N deletion)/ OspA-Pko(217-273) B31/B31/Pko | 87 | 88 | 28, 29 |

[1]"lip" means the chimeric protein contains its native N-terminal lipidation signal Serologic Characterization Using ELISA (Enzyme-Linked Immunosorbent Assay)

Immobilization of Antigen onto ELISA Plates

A solution of purified recombinant OspC or OspA protein from each of the *Borrelia burgdorferi* strains B31 (*Borrelia burgdorferi* sensu stricto), K48 (*Borrelia garinii*) and PGau (*Borrelia afzelii*) was added to sodium phosphate buffer, pH 9.0, and was used to coat a commercial microwell plate (MaxiSorp®, Nunc). The coating procedure was as follows: 100 μl of a solution containing the appropriate OspA or OspC protein (made up at a concentration of 250 ng/ml in the following coating buffer: 100 mM Bis-Tris propane, pH 9.7) was added to each well of a microtiter plate which was incubated for one hour at 37° C. The antigen solution was removed from the wells, the plate was washed three times with phosphate buffered saline (PBS) pH 9.0, and 300 μl of blocking buffer solution was added (3% dry milk, 0.1% polyoxyethylenesorbitan (referred to herein as Tween 20™), 0.02% $NaN_3$ in 100 nM Bis-Tris propane, pH 9.7). Following a one hour incubation at 37° C., the plates were washed four times with TBS-Tween 20™ wash buffer (20 mM Tris-Cl, pH 7.5, 136 mM NaCl, 0.1% Tween 20™ and 0.02% $NaN_3$) and then were allowed to dry. The plates were then wrapped in plastic and stored at 4° C. until they were used.

ELISA (Enzyme-Linked Immunosorbent Assay) Tests

The standard procedure for the ELISA tests was as follows: mouse serum was diluted 1:1000 in sample dilution buffer (1% dry milk, 136 mM NaCl, 0.1% Tween 20™, 0.02% $NaN_3$ in 20 mM Tris-Cl, pH7.5) and 100 μl of the diluted serum was added to the ELISA microtiter plate wells that had been coated with antigen as described above. Following incubation for 1 hour at 37° C., the samples were removed and the plates were washed four times in TBS-Tween™ (20 mM Tris-Cl, pH 7.5; 136 mM NaCl; 0.1% Tween 20™ and 0.02% $NaN_3$). For the secondary antibody, goat anti-mouse antisera conjugated to alkaline phosphatase-specific for either IgM (Fc) or IgG (Fab), (Jackson Immuno Research Laboratories) was diluted 1:750 in sample dilution buffer (1% dry milk, 136 mM NaCl, 0.1% Tween 20™, 0.02% $NaN_3$ in 20 mM Tris-Cl, pH7.5) and 100 μl of the diluted secondary antibody was added to each well. Following incubation for thirty minutes at 37° C., the plates were washed three times with TBS-Tween™ and 100 μl of Phosphatase Substrate solution (5 mg of p-nitrophenylphosphate tablets dissolved in 1× diethanolamine substrate buffer to yield a 2 mg/ml solution—Kirkegaard Perry Laboratory) was added to each well. The plates were incubated for thirty minutes at 37° C. and 100 μl of stop solution (5% EDTA) was added to each well. The absorbance at 405 nm was read on a microplate reader (Dynatech). A sample was considered positive if it produced an average absorbance greater than the mean of the negative controls plus three standard deviations.

Previous work has demonstrated that it is the carboxy-terminal region of OspA that contains the antigenic sites that provide the immunoprotective response. Thus, in addition to the ELISA test described above, a modified ELISA was performed (herein referred to as the Protective ELISA Test), wherein the purified N-terminal region of B31 OspA (amino acids 18-139) was used in excess to block any antibodies present in the mouse serum that had specificity to this N-terminal OspA region. These protective ELISA tests were performed as above, except that 80 μg/ml of a purified B31 OspA fragment (amino acids 18-139) was added to the diluted mouse serum prior to adding the sera to the antigen-coated ELISA microtiter plate wells.

Results of ELISA Tests

Figure 22:
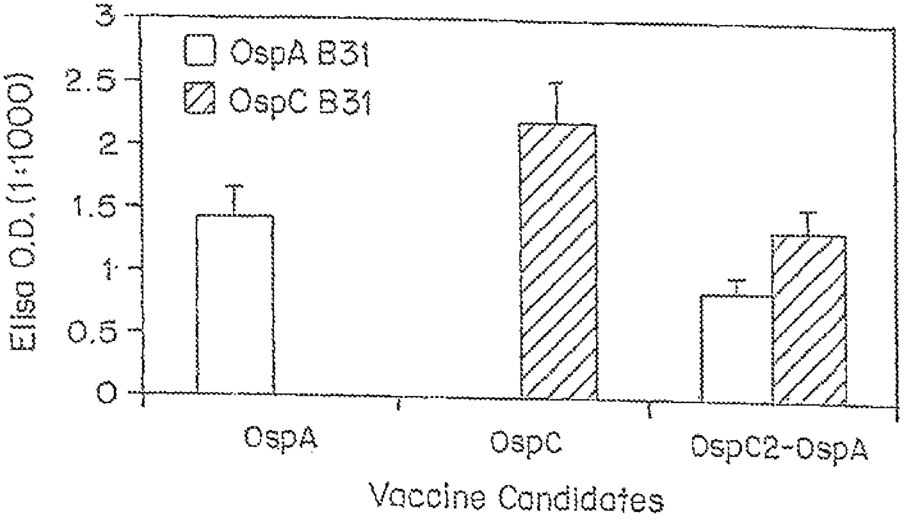
FIG. 22 is a bar graph showing the reactivity (as measured by ELISA) of sera from mice immunized with the indicated *Borrelia* protein (OspA or OspC) or recombinant chimeric protein (OspC2-OspA)(X-axis) against the indicated OspA or OspC antigens (legend) from the strain B31 (*Borrelia burgdorferi* sensu stricto).

Using the above-described ELISA tests, it was demonstrated that mice immunized with a non-lipidated OspC/OspA chimeric protein (OspC2-OspA—composed of OspC (a.a. 19-204 from strain C2)/OspA (a.a. 18-273 from strain B31) (SEQ ID NO:60) produced an immune response both to OspA and OspC that was comparable to the immune response generated to non-lipidated OspA (OspA—a.a. 18-273 from strain B31) and non-lipidated OspC (OspC—a.a. 19-211 from strain B31) control proteins (FIG. 22). As indicated in FIG. 22 and described above, mice were immunized with OspA, OspC or OspC2-OspA proteins and immune responses of the sera were measured against B31 OspA antigen (stippled bars) and B31 OspC antigen (solid bars).

Figure 23:
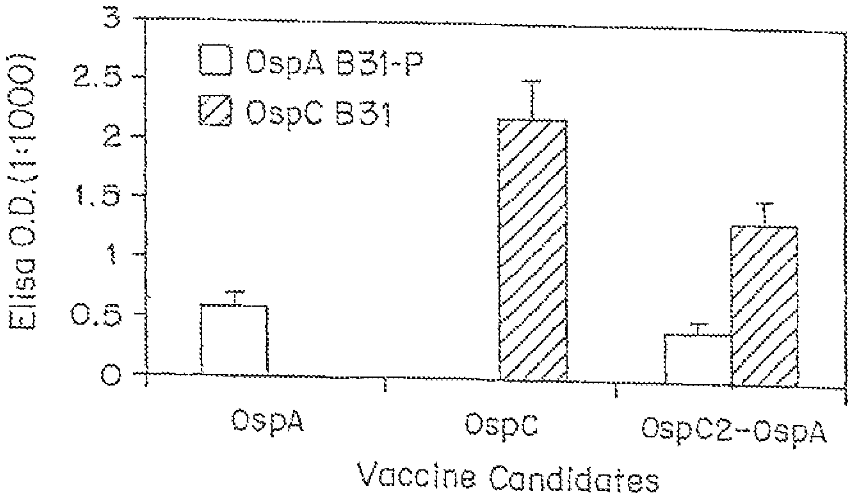
FIG. 23 is a bar graph showing the reactivity (as measured by ELISA) of sera from mice immunized with the indicated *Borrelia* protein (OspA or OspC) or recombinant chimeric protein (OspC2-OspA)(X-axis) against the indicated OspA or OspC antigens (legend) from the strain B31 (*Borrelia burgdorferi* sensu stricto). For the ELISA results to the B31 OspA antigen, a purified fragment of B31 OspA (amino acids 18-139) was added in excess to the sera so that the detected immune response was specific for the C-terminal region of OspA.

Using the above-described Protective ELISA Test, it was also shown that mice immunized with the same non-lipidated OspC/OspA chimeric protein (OspC2-OspA—composed of OspC (a.a. 19-204 from strain C2)/OspA (a.a. 18-273 from strain B31) (SEQ ID NO:60) produced an immune response to the C-terminal portion of OspA that was comparable to the immune response generated to the C-terminal portion of a non-lipidated OspA (OspA—a.a. 18-273 from strain B31) control protein (FIG. 23). As indicated in FIG. 23, mice were immunized with OspA, OspC or OspC2-OspA proteins and immune responses of the sera were measured against B31 OspA antigen. The protective antibody response to B31 OspA antigen is indicated in the stippled bars.

Thus, these results clearly demonstrate that non-lipidated chimeric OspC/OspA proteins are able to induce immune responses in mice that are comparable to the immune response generated against non-lipidated OspC and OspA control proteins.

It had been previously thought that the lipidation signals that are present on *Borrelia burgdorferi* outer surface proteins were required for immunogenicity and that OspC and OspA proteins that lacked this lipidation signal would be less or non-immunogenic. To test this idea, mice were immunized with a non-lipidated OspC/OspA chimeric protein (OspC-OspAB/P—composed of OspC (a.a. 19-211 from strain B31)/OspA (a.a. 18-216 from strain B31)/OspA (a.a. 217-

Figure 24:
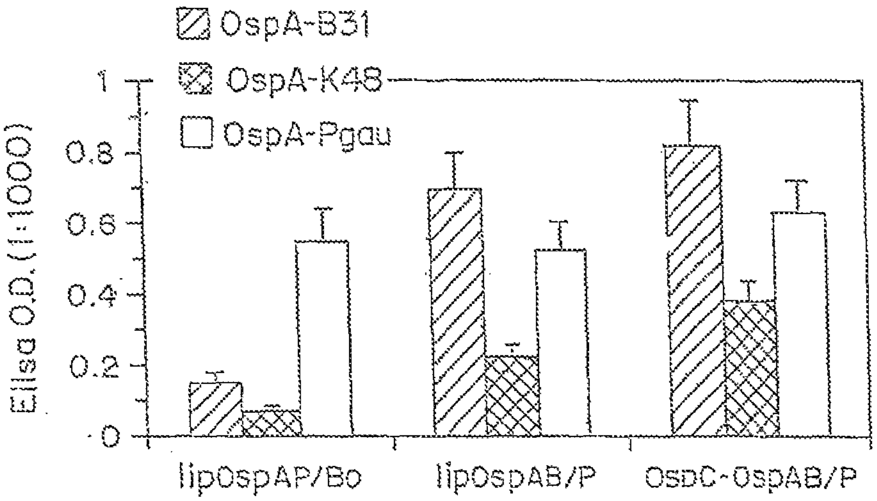
FIG. 24 is a bar graph showing the reactivity of sera from mice immunized with the indicated *Borrelia* chimeric protein (lipOspA/Bo, lipOspAB/P or OspC-OspAB/P)(X-axis) against the indicated OspA antigens (legend) from strains B31 (*Borrelia burgdorferi* sensu stricto), K48 (*Borrelia garinii*) and Pgau (*Borrelia afzelii*).

273 from strain Pko) (SEQ ID NO:66) as well as two lipidated OspA proteins, lipOspAP/Bo (composed of OspA (a.a. 1-217 from strain PGau)/OspA (a.a. 218-273 from strain Bo)) and lipOspAB/P (composed of OspA (a.a. 1-216 from strain B31)/OspA (a.a. 217-273 from strain Pko)) and were subjected ELISA tests. Mice immunized with the non-lipidated OspC/OspA chimeric protein (OspC-OspAB/P) produced an immune response to OspA from each of the *Borrelia burgdorferi* strains B31 (*Borrelia burgdorferi* sensu stricto), K48 (*Borrelia garinii*) and PGau (*Borrelia afzelii*), that was equivalent or greater than the immune response generated to the two lipidated OspA control proteins (lipOspAP/Bo and lipOspAb/P) (FIG. 24).

Figure 25:
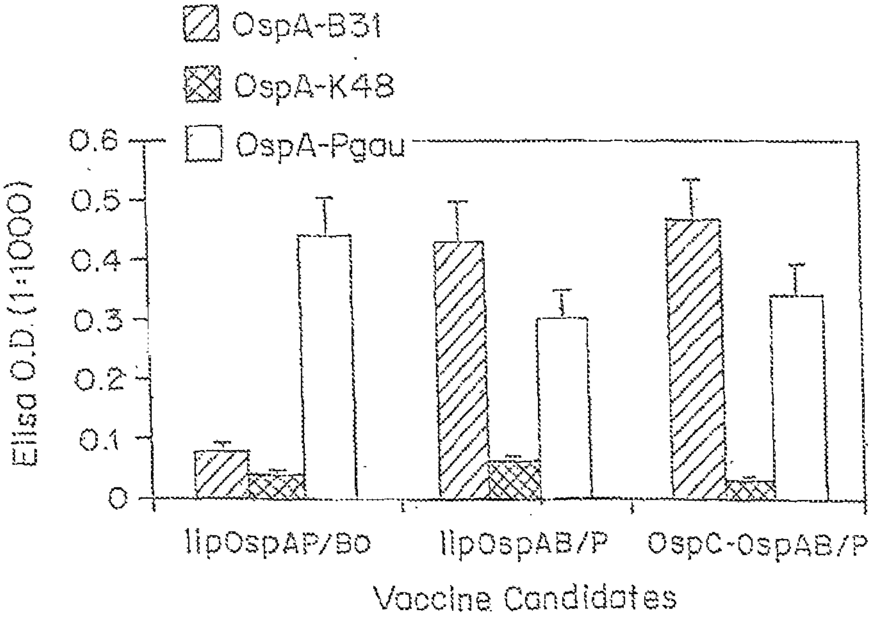
FIG. 25 is a bar graph showing the reactivity of sera from mice immunized with the indicated *Borrelia* chimeric protein (lipOspAP/Bo, lipOspAB/P or OspC-OspAB/P)(X-axis) against the indicated OspA (legend) from strains B31 (*Borrelia burgdorferi* sensu stricto), K48 (*Borrelia garinii*) and Pgau (*Borrelia afzelii*). In all cases, a purified fragment of B31 OspA (amino acids 18-139) was added in excess to the sera so that the detected immune response is specific for the C-terminal region of OspA.

Similar results to these were obtained using the Protective ELISA Test described above. Mice immunized with the non-lipidated OspC/OspA chimeric protein (OspC-OspAB/P) produced an immune response to the C-terminal region of OspA from each of the *Borrelia burgdorferi* strains B31 (*Borrelia burgdorferi* sensu stricto), K48 (*Borrelia garinii*) and PGau (*Borrelia afzelii*), that was equivalent or greater than the immune response generated to the C-terminal region of OspA from the two lipidated OspA control proteins (lipOspAP/Bo and lipOspAb/P) (FIG. 25).

Figure 26:
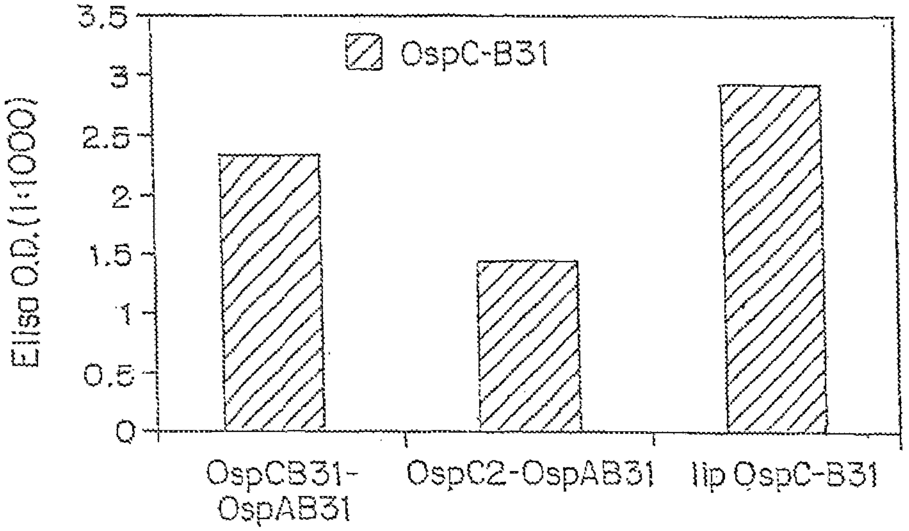
FIG. 26 is a bar graph showing the reactivity of sera from mice immunized with the indicated *Borrelia* chimeric protein (OspCB31-OspAB31, OspC2-OspAB31 or lip OspC-B31) (X-axis) against the indicated OspC antigen (legend) from the strain B31 (*Borrelia burgdorferi* sensu stricto).

In addition to the comparisons between non-lipidated OspC/OspA chimeric proteins and lipidated OspA control proteins, experiments were also performed to compare non-lipidated OspC/OspA chimeric proteins with a lipidated OspC control protein (FIG. 26). Mice that were immunized with either the non-lipidated OspC/OspA chimeric protein OspCB31-OspAB31 (composed of OspC (a.a. 19-211 from strain B31)/OspA (a.a. 18-273 from strain B31) (SEQ ID NO:56) or the non-lipidated OspC/OspA chimeric protein OspC2-OspAB31 (composed of OspC (a.a. 19-204 from strain C2)/OspA (a.a. 18-273 from strain B31) (SEQ ID NO:60) produced an immune response to OspC derived from the *Borrelia burgdorferi* strain B31 that was comparable to the immune response produced by a lipidated OspC control protein (lip OspC-B31-composed of OspC (a.a. 1-211 from strain B31)) (FIG. 26).

Thus, these results clearly demonstrate that non-lipidated chimeric OspC/OspA proteins are able to induce immune responses against OspA and OspC that are comparable to the immune response generated against OspA and OspC using lipidated OspA or OspC control proteins. The use of unlipidated forms of these proteins as vaccine immunogens or diagnostic antigens is highly desirable because the product yield is much greater and the proteins are much easier to purify. For these reasons, the production of these proteins is less expensive.

Figure 27:
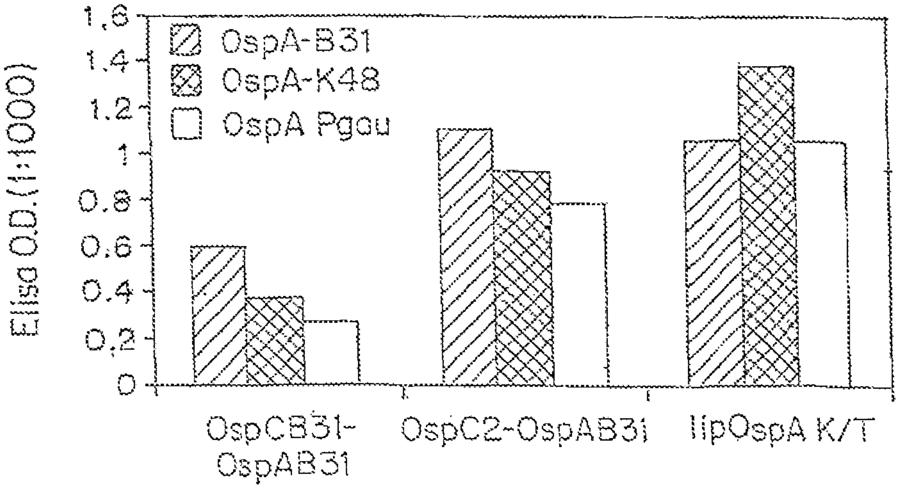
FIG. 27 is a bar graph showing the reactivity of sera from mice immunized with the indicated *Borrelia* chimeric protein (OspCB31-OspAB31, OspC2-OspAB31 or Lip OspA K/T) (X-axis) against the indicated OspA antigens (legend) from strains B31 (*Borrelia burgdorferi* sensu stricto), K48 (*Borrelia garinii*) and Pgau (*Borrelia afzelii*).

The OspC/OspA chimeric proteins of the present invention are also able to generate immune responses against OspA proteins that are derived from strains that are not represented in the chimeric protein. Mice immunized with the OspC/OspA chimeric proteins, OspCB31-OspAB31 (SEQ ID NO:56) and OspC2-OspAB31 (SEQ ID NO:60), are not only able to generate immune responses that recognize OspA derived from strain B31 (*Borrelia burgdorferi* sensu stricto), but also recognize OspA derived from strain K48 (*Borrelia garinii*) and strain PGau (*Borrelia afzelii*) (FIG. 27). For comparison, mice were also immunized with the lipidated OspA chimeric protein, Lip OspA K/T (composed of OspA (a.a. 1-217 from strain K48)/OspA (a.a. 218-273 from strain Tro)) (FIG. 27).

Figure 28:
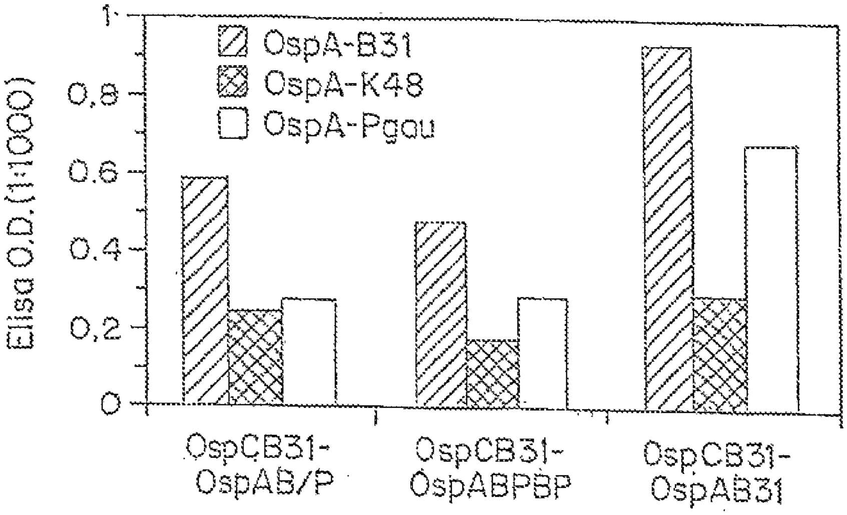
FIG. 28 is a bar graph showing the reactivity of sera from mice immunized with the indicated *Borrelia* chimeric protein (OspCB31-OspAB/P, OspCB31-OspABPBP or OspCB31-OspAB31)(X-axis) against the indicated OspA antigens (legend) from strains B31 (*Borrelia burgdorferi* sensu stricto), K48 (*Borrelia garinii*) and Pgau (*Borrelia afzelii*).
Figure 29:
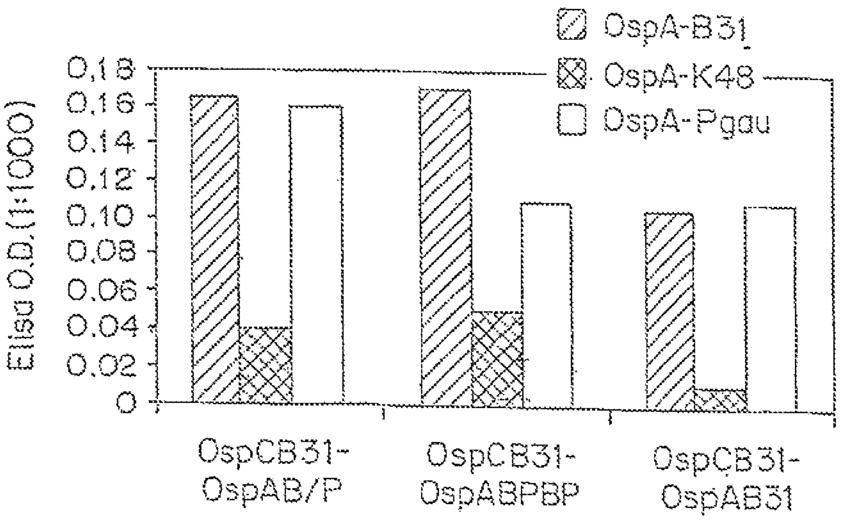
FIG. 29 is a bar graph showing the reactivity of sera from mice immunized with the indicated *Borrelia* chimeric protein (OspCB31-OspAB/P, OspCB31-OspABPBP or OspCB31-OspAB31)(X-axis) against the indicated OspA (legend) from strains B31 (*Borrelia burgdorferi* sensu stricto), K48 (*Borrelia garinii*) and Pgau (*Borrelia afzelii*). In all cases, a purified fragment of B31 OspA (amino acids 18-139) was added in excess to the sera so that the detected immune response is specific for the C-terminal region of OspA.

Additional antibody responses to OspA derived from strain B31 (*Borrelia burgdorferi* sensu stricto), strain K48 (*Borrelia garinii*) and strain PGau (*Borrelia afzelii*) are also presented for sera from mice immunized with other OspC/OspA chimeric proteins. Thus, FIG. 28 presents the ELISA results from mice immunized with either OspCB31-OspAB/P (SEQ ID NO:66), OspCB31-OspABPBP (SEQ ID NO:88) or OspCB31-OspAB31 (SEQ ID NO:56). In each case, sera from the immunized mice was tested against OspA derived from each of strain B31 (*Borrelia burgdorferi* sensu stricto), K48 (*Borrelia garinii*) and PGau (*Borrelia afzelii*). In all cases, a strong immune response was generated (FIG. 28). As with the previously described OspC/OspA chimeric proteins, the three OspC/OspA chimeric proteins used to immunize the mice in FIG. 27 also elicited a strong immune response to the C-terminal region of OspA when examined using the Protective ELISA Test described above (FIG. 29).

The above-described techniques are also used to immunize mice and to serologically characterize the immune response against the proteins comprising the altered OspA polypeptides of the present invention.

Tick Challenge of Immunized Mice

Mice, either C3H-J or JCR, that had been immunized as described above, were also challenged with either laboratory-infected nympha or field nympha. The immunized mice were placed in isolation cages and each mouse received 5-10 nymphs. All of the nymphs were collected at counted after 6 days. Four week after challenge, the mice were bled and sera was tested using commercially-available Western blot strips to *Borrelia burgdorferi* sensu stricto strain B31(MarDx strips) and/or *Borrelia garinii* (MRL strips). Eight weeks after challenge, the mice were bled, sera was tested again by Western blot and ear punch and bladder samples were cultured. As a positive control, mice which had been immunized with only aluminum hydroxide adjuvant, as described above, were subjected to the same challenge.

The results of the tick challenge studies (Table IV) demonstrate that while immunization with lipidated OspC protein was unable to protect the mice, as evidenced by a positive Western blot signal (in 4 out of 5 mice), immunization with two different OspC/OspA chimeric proteins (SEQ ID NO:56 and SEQ ID NO:62) did provide protection, as indicated by the absence of Western blot signal (in 0 out of 8 mice and 0 out of 3 mice) (Table IV). The sham positive control showed that the challenge by the ticks was successful in all cases, as evidenced by 100% positive signal in Western blots (Table IV). Results from the tick challenge experiments are shown in Table IV.

TABLE IV

Effect of Vaccination on Transmission of *Borrelia* from Ticks

| Vaccine Candidate | Mouse | Tick-nymph | Seroconversion (Western Blots) Vaccinated | Seroconversion (Western Blots) Sham |
|---|---|---|---|---|
| OspC1-OspAB31 | C3H-J | Long Island | 0+/8 | 8+/8 |
| OspC2-OspAB31 | C3H-J | Long Island | 0+/3 | 4+/4 |
| Lip OspC12 | ICR | Long Island | 4+/5 | 5+15 |

The above-described techniques are also used to measure the ability of mice immunized with proteins comprising the altered OspA polypeptides of the present invention to resist or respond to transmission of *Borrelia* from ticks.

Example 6

Generation of OspA M1, M2, M3, J1, J2 and J3 Constructs Using Site Directed Mutagenesis and PCR All constructs were made using Stratagene's QuikChange site-directed mutagenesis kit. Site-directed mutagenesis was performed using Pfu Turbo DNA polymerase II and a thermal temperature cycler. Pfu Turbo DNA polymerase replicates both plasmid strands with high fidelity and without displacing the mutant oligonucleotide primers. The basic procedure used a supercoiled double-stranded DNA vector (pET 9c for all constructs) with an insert of interest and two synthetic oligonucleotide primers containing the desired mutation(s). The oligonucleotide primers, each complementary to opposite strands of the vector, were extended during the temperature cycling by the Pfu Turbo DNA polymerase. Incorporation of the oligonucleotide primers created a mutated plasmid which contained staggered nicks. Following temperature cycling, the linear product was treated with the restriction enzyme Dpn I, which is specific for methylated DNA. DNA isolated from most *E. coli* strains is dam methylated and therefore is susceptible to Dpn I digestion. Digestion with Dpn I therefore destroyed the original template DNA leaving only the nicked plasmid DNA (which was not methylated) containing the desired mutation(s). This nicked vector DNA (containing the desired mutation(s)) was then transformed into competent *E. coli* which were plated on antibiotic-containing plates. Colonies containing the plasmid (which encodes for antibiotic resistance in addition to the altered OspA polypeptide) were grown and plasmids were purified and sequenced to confirm that they possessed the desired mutation(s).

1) M1, M2 and M3 Mutants

The mutations described herein are made using nucleic acids (e.g., polynucleotides) encoding OspA polypeptides or fragments from any strain of Lyme Disease-causing *Borrelia*, such as *Borrelia burgdorferi* sensu stricto, *Borrelia afzelii* or *Borrelia garinii*. As an example, the generation of the M3 mutations in an OspA chimera, called "BPBP", is described below. The creation of the construct OspA BPBP M3 was as follows. BPBP is a chimeric OspA polypeptide, wherein residues 1-164 are from OspA of B31, residues 165-179 are from OspA of Pko or PGau, residues 180-216 are from OspA of B31 and residues 217-273 are from OspA of Pko (wherein the numbering is as shown in SEQ ID NO:7).

The first step in creating this construct was to make the construct BPBP M1. The M1 mutation consists of a mutation of codon 139 (aga) of OspA from the amino acid arginine to the amino acid methionine (codon atg). A PCR reaction was set up as described above containing a polynucleotide encoding BPBP as the template DNA and the following oligonucleotide primers:

```
a) 5' R139M:
                                    (SEQ ID NO: 117)
5' gaa aaa ata ata aca atg gca gac gga acc 3'.

b) 3' R139M:
                                    (SEQ ID NO: 118)
5' ggt tcc gtc tgc cat tgt tat tat ttt ttc 3'
```

The PCR reaction also contained reaction buffer, 10 ng of the BPBP DNA template, 125 ng of each oligonucleotide primer, and the dNTP mix. The parameters for the PCR were as outlined in Table V.

TABLE V

| Parameters for PCR | | | |
|---|---|---|---|
| Segment | cycles | temp | time |
| 1 | 1 | 95° C. | 30 sec. |
| 2 | 18 | 95° C. | 30 sec. |
| 3 | | 50° C. | 1 min. |
| 4 | | 68° C. | 12 min |

Following PCR, the product was transformed into competent *E. coli* XL1-Blue cells. Colonies formed on the selective agar plates (containing kanamycin) were grown and plasmids were purified and sequenced to confirm that they possessed the desired mutation. The construct BPBP M1 was then used as template to make the plasmid BPBP M2, which in addition to the R139M mutation, also contains a mutation that changes the glutamic acid codon (gag) at position 160 to the codon (tat) which encodes for tyrosine. The oligonucleotide primers used to generate this plasmid were:

```
a) 5' E160Y
                                    (SEQ ID NO: 119)
5' gga aaa gct aaa tat gtt tta aaa ggc 3'

b) 3' E160Y
                                    (SEQ ID NO: 120)
5' gcc ttt taa aac ata ttt agc ttt tcc 3'
```

The parameters for the PCR were as outlined in Table VII. The final mutation, M3, which alters a lysine residue at position 189 to a methionine residue was performed using BPBP M2 as a DNA template. The oligonucleotide primers used to generate this plasmid were:

```
a) 5' K189M
                                    (SEQ ID NO: 121)
5' gtt act tta agc atg aat att tca aaa tc 3'

b) 3' K189M
                                    (SEQ ID NO: 122)
5' ga ttt tga aat att cat gct taa agt aac 3'
```

This final mutation yielded the desired construct, BPBP M3.

2) J1, J2 and J3 Mutants

J1, J2 and J3 mutants were made using the same protocol described for the generation of the M1, M2 and M3 mutants. Such mutants can be made using nucleic acids (e.g., polynucleotides) encoding OspA polypeptides fragments from any strain of Lyme Disease-causing *Borrelia*, such as *Borrelia burgdorferi* sensu stricto, *Borrelia* afzelii or *Borrelia garinii.*

The oligonucleotide primers which were used to generate the J1 mutation (which contains a Y165F mutation (codon tat to ttt) and a V166T mutation (codon gtt to act)) were as follows:

```
a) 5' B31 YV-FT
                                    (SEQ ID NO: 123)
5' gag gtt tta aaa ggc ttt act ctt gaa gga act c 3'

b) 3' B31 YV-FT
                                    (SEQ ID NO: 124)
5' gag ttc ctt caa gag taa agc ctt tta aaa cct g 3'
```

The oligonucleotide primers which were used to generate the J2 mutation (which contains a T170K mutation (codon act to aag)) were as follows:

a) 5' B31 T-K
(SEQ ID NO: 125)
5' tct tga agg aaa gct aac tgc tg 3' b) 3' B31 T-K
(SEQ ID NO: 126)
5' cag cag tta gct ttc ctt caa ga 3'

To generate the J3 mutant (which contains a Y165F mutation (codon tat to ttt), a V166T mutation (codon gtt to act) and a T170K mutation (codon act to aag)), the template containing the J1 mutations was used with the oligonucleotide primers for generating the J2 mutation (5' B31 T-K (SEQ ID NO:125) and 3' B31 T-K (SEQ ID NO:126)).

The altered OspA polypeptides described herein are expressed, used to immunize mice and characterized using ELISA as described in the Experiments above.

While this invention has been particularly shown and described with references to preferred embodiments thereof, it will be understood by those skilled in the art that various changes in form and details may be made therein without departing from the scope of the invention encompassed by the appended claims.

What is claimed is:

1. A purified polypeptide, comprising inclusive and sequentially residue 139 to residue 273 of SEQ ID NO: 7 which is a *Borrelia burgdorferi* OspA protein except that the purified polypeptide has one to three alterations providing increased conformational stability compared to the corresponding unaltered polypeptide, wherein the one to three alterations are selected from the group consisting of the residue 139 being methionine, the residue 160 being tyrosine, the residue 189 being methionine and combinations thereof.

2. The polypeptide of claim 1, wherein residue 160 is tyrosine and residue 189 is methionine.

3. The polypeptide of claim 1, wherein residue 139 is methionine, residue 160 is tyrosine and residue 189 is methionine.

4. The purified polypeptide of claim 1, wherein the purified polypeptide sequence comprises residues 131 through 273 of the *Borrelia burgdorferi* OspA protein, and wherein the sequence includes the one to three alterations and combinations thereof.

5. The purified polypeptide of claim 1, wherein the purified polypeptide sequence comprises residues 17 through 273 of the *Borrelia burgdorferi* OspAprotein, and wherein the sequence includes the one to three alterations, and combinations thereof.

6. A purified polypeptide comprising an OspA protein from a sensu stricto strain of *Borrelia burgdorferi*, wherein the OspA protein comprises SEQ ID NO:7 in which there are alterations consisting of: residue 139 of SEQ ID NO:7 being methionine, residue 160 of SEQ ID NO:7 being tyrosine, and residue 189 of SEQ ID NO:7 being methionine.

* * * * *

UNITED STATES PATENT AND TRADEMARK OFFICE

CERTIFICATE OF CORRECTION

PATENT NO. : 8,992,936 B2
APPLICATION NO. : 13/944078
DATED : March 31, 2015
INVENTOR(S) : Benjamin J. Luft et al.

It is certified that error appears in the above-identified patent and that said Letters Patent is hereby corrected as shown below:

In the specification

Column 1, line 17-22, Government Support paragraph, delete "The invention was supported, in whole or in part, by Grant 2R01AI37256-05A1 from the National Institute of Allergy and Infectious Diseases and Grant NIH GM057215 from the National Institutes of Health."

and insert -- This invention was made with government support under grant numbers AI037256 and GM057215 awarded by the National Institutes of Health. --

Signed and Sealed this
Eighth Day of December, 2015

Michelle K. Lee

Michelle K. Lee
*Director of the United States Patent and Trademark Office*